(12) United States Patent (10) Patent No.: US 12,600,770 B2
Brunner et al. (45) Date of Patent: Apr. 14, 2026

(54) ANTIBODIES TO CONNECTIVE TISSUE GROWTH FACTOR (CTGF) AND USES THEREOF

(71) Applicant: Boehringer Ingelheim International GmbH, Ingelheim am Rhein (DE)

(72) Inventors: Andreas-David Brunner, Mittelbiberach (DE); Lars Dittus, Mittelbiberach (DE); Priyanka Gupta, Newtown, CT (US); Muriel Lize, Ulm (DE); Maria Bonatsakis Myzithras, Sandy Hook, CT (US); Irina Rybina, Sleepy Hollow, NY (US); Julia Sauer, Biberach (DE); Wioletta Anna Skronska-Wasek, Biberach (DE); Heiko Friedrich Stahl, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 19/065,094

(22) Filed: Feb. 27, 2025

(65) Prior Publication Data

US 2025/0277020 A1 Sep. 4, 2025

Related U.S. Application Data

(60) Provisional application No. 63/723,664, filed on Nov. 22, 2024.

(30) Foreign Application Priority Data

Mar. 1, 2024 (EP) ..................................... 24160771

(51) Int. Cl.
C07K 16/22 (2006.01)
(52) U.S. Cl.
CPC .......... C07K 16/22 (2013.01); C07K 2317/24 (2013.01); C07K 2317/76 (2013.01); C07K 2317/92 (2013.01)
(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,816,567 A | 3/1989 | Cabilly et al. | |
| 4,946,778 A | 8/1990 | Ladner et al. | |
| 5,631,144 A | 5/1997 | Lemoine et al. | |
| 6,037,454 A | 3/2000 | Jardieu et al. | |
| 6,054,297 A | 4/2000 | Carter et al. | |
| 6,407,213 B1 | 6/2002 | Carter et al. | |
| 2023/0416352 A1 | 12/2023 | Ma et al. | |

FOREIGN PATENT DOCUMENTS

| | | |
|---|---|---|
| DE | 266710 A3 | 4/1989 |
| EP | 183070 A2 | 6/1986 |
| EP | 244234 A2 | 11/1987 |
| EP | 402226 A1 | 12/1990 |
| EP | 3981787 A1 | 4/2022 |
| EP | 4257603 A1 | 10/2023 |
| WO | 1990005144 A1 | 5/1990 |
| WO | 1990013646 A1 | 11/1990 |
| WO | 1996032478 A1 | 10/1996 |
| WO | 2005077042 A2 | 8/2005 |
| WO | 2012092374 A2 | 7/2012 |
| WO | 2022117060 A1 | 6/2022 |

OTHER PUBLICATIONS

Abdiche, Yasmina Noubia et al. "High-Throughput Epitope Binning Assays on Label-Free Array-Based Biosensors Can Yield Exquisite Epitope Discrimination that Facilitates the Selection of Monoclonal Antibodies with Functional Activity" (2014) PLOS One, vol. 9, Issue 3, e92451, 16 pgs.
Ablexis.com "Alivamab Mouse Platform" (2016) 1 pg.
Almagro, Juan C. et al. "Antibody modeling assessment" (2011) Proteins, vol. 79, 3050-3066.
Almagro, Juan et al. "Humanization of Antibodies" (2008) Frontiers in Bioscience, 13, 1619-1633.
Altschul, Stephen et al. "Gapped BLAST and PSI-BLAST: A new generation of protein database search programs" (1997) Nucleic Acids Research, vol. 25, No. 17, 3389-3402.
Altshul, Stephen et al., "Basic Local Alignment Search Tool" (1990), Journal Molecular Biology, V 215, 403-410.
Bitzer, Sarah, et al. "Application of human iPSC-derived macrophages in a miniaturized high-content-imaging-based efferocytosis assay" (2023) SLAS Discovery, vol. 28, 149-162.
Brennan, M. et al., "Preparation of Bispecific Antibodies by Chemical Recombination of Monoclonal Immunoglobulin G1 Fragments" (1985) Science 229: 81-83.
Brenner et al., "FG-3019, a Human Monoclonal Antibody Recognizing Connective Tissue Growth Factor, is Subject to Target-Mediated Drug Disposition" (2016) Enviromental Science and Pollution Research, vol. 33, No. 8, 1833-1849.
Brown, Michael E. "Assessing the binding properties of the anti-PD-1 antibody landscape using label-free biosensors" (2020) PLOS One, 15(3) e0229206, 21 pgs.
Brüggemann M, et al. "Production of human antibody repertoires in transgenic mice" (1997) Curr Opin Biotechnol. 8 (4):455-458.

(Continued)

*Primary Examiner* — Maher M Haddad
(74) *Attorney, Agent, or Firm* — Kenneth J. Kalafus

(57) ABSTRACT

The present disclosure generally relates to anti-CTGF (connective tissue growth factor) antibodies or antigen-binding fragments thereof. Exemplary anti-CTGF antibodies disclosed herein address the need for treatments of conditions modulated by CTGF signaling. In some aspects, the anti-CTGF antibodies or antigen-binding fragments thereof are for diagnostic and/or therapeutic use, for example in a subject in need thereof, such as a human.

29 Claims, 10 Drawing Sheets

Specification includes a Sequence Listing.

(56)         References Cited

OTHER PUBLICATIONS

Camelo, Ana et al. "The epithelium in idiopathic pulmonary fibrosis: breaking the barrier" (2014) Frontiers in Pharmacology, vol. 4, Article 173, 11 pgs.

Carmen, Sara et al, "Concepts in antibody phage display", (2002) Briefings in Functional Genomics and Proteomics, vol. 1(2):189-203.

Carter, Paul et al. "High Level *Escherichia coli* Expression and Production of a Bivalent Humanized Antibody Fragment" (1992) Biotechnology, 10, 163-167.

Chothia, Cyrus et al. "Canonical Structures for the Hypervariable Regions of Immunoglobulins" (1987) J. Mol. Biol. 196, 901-917.

Chothia, Cyrus et al. "Domain Association in Immunoglobulin Molecules the Packing of Variable Domains" (1985) Journal Molecular Biology, 186, 651-663.

Clackson, Tim et al. "Making antibody fragments using phage display libraries" (1991) Nature, 352, 624-628.

Dahal, Lekh et al. "FcγR requirements leading to successful immunotherapy" (2015) Immunological Reviews, vol. 268, 104-122.

Edge, Albert et al. "Deglycosylation of Glycoproteins by Trifluoromethanesulfonic Acid" (1981) Analytical Biochemistry, 118, 131-197.

Effendi, Wiwin et al. "Connective Tissue Growth Factor in Idiopathic Pulmonary Fibrosis: Breaking the Bridge" (2022) International Journal of Molecular Science, vol. 23, 6064, 19 pgs.

Ge, Yun et al. "Efferocytosis and Its Role in Inflammatory Disorders" (2022) Frontiers in Cell and Developmental Biology, vol. 10, article 839248, 1-15.

Graham, F.L. et al. "Characteristics of a Human Cell Line Transformed by DNA from Human Adenovirus Type 5" (1977) J. Gen. Virol. 36, 59-72.

Higgins, D.G. et al, "Using CLUSTAL for Multiple Sequence Alignments" (1996) Methods in Enzymology, 266, 383-402.

Igawa, Tomoyuki et al. "Engineered Monoclonal Antibody with Novel Antigen-Sweeping Activity In Vivo" (2013) PLOS One, 8(5), e63236, 1-10.

Isshiki, Takuma et al. "Therapeutic strategies to target connective tissue growth factor in fibrotic lung diseases" (2024) Pharmacology & Therapeutics, vol. 253, 108578, 13 pgs.

Johnson, Bryce G. et al. "Connective Tissue Growth Factor Domain 4 Amplifies Fibrotic Kidney Disease through Activation of LDL Receptor-Related Protein 6" (2017) J Am Soc Nephrol, 28, 1769-1782.

Kaasboll, Ole J. et al. "Connective tissue growth factor (CCN2) is a matricellular preproprotein controlled by proteolytic activation" (2018) J Biol. Chem, vol. 293 (46), 17953-17970.

Kabat, et al. "Sequences of Proteins of Immunological Interest" (1991) NIH Publication No. 91-3242, vol. 1, 647-669.

Karlin, S. et al. "Applications and statistics for multiple high-scoring segments in molecular sequences", (1993), Proc. Natl. Acad. Sci. USA, vol. 90, 5873-5877.

Karlin, S. et al. "Methods for assessing the statistical significance of molecular sequence features by using general scoring schemes", (1990) Proc. Natl. Acad. Sci. USA, vol. 87, 2264-2268.

Knappik, Achim et al., "Fully synthetic Human Combinatorial Antibody Libraries (HuCAL) Based on Modular Consensus Frameworks and CDRs Randomized with Trinucleotides" (2000) J. Mol. Biol. 296: 57-86.

Kohler, G. et al. "Continuous cultures of fused cells secreting antibody of predefined specificity" (1975) Nature, vol. 256, 495-497.

Kono, Masato et al. "Plasma CCN2 (connective tissue growth factor; CTGF) is a potential biomarker in idiopathic pulmonary fibrosis (IPF)" (2011) Clin Chim Acta, 412, 2211-2215.

Kulak, Nils et al. "Minimal, encapsulated proteomic-sample processing applied to copy-number estimation in eukaryotic cells" (2014) Nature Methods, vol. 11, No. 3, 319-326.

Lefranc, M. P., "Unique database numbering system for immunogenetic analysis." (1997) Immunology Today, 18 (11), 509.

Liberzon, Arthur et al. "The Molecular Signatures Database Hallmark Gene Set Collection" (2015) Cell Systems, 1, 417-425.

Lonberg, Nils et al. "Human Antibodies from Transgenic Mice" (1995) Intern. Rev. Immunol., vol. 13, 65-93.

Maier, Johannes et al. "Assessment of fully automated antibody homology modeling protocols in molecular operating environment" (2014) Proteins, vol. 82, 1599-1610.

Majewski, Sebastian et al., "Serial Measurements of Circulating KL-6, SP-D, MMP-7, CA19-9, CA-125, CCL18, and Periostin in Patients with Idiopathic Pulmonary Fibrosis Receiving Antifibrotic Therapy: An Exploratory Study" (2021) J Clin Med., 10(17), 3864, 1-23.

Marks, James D. et al. "By-passing Immunization Human Antibodies from V-gene Libraries Displayed on Phage" (1991) J. Mol. Biol., 222, 581-597.

Mather, Jennie et al., "Culture of Testicular Cells in Hormone-Supplemented Serum-Free Medium" (1982), Annals N.Y. Acad. Sci. 383: 44-68.

Mather, Jennie P. "Establishment and Characterization of Two Distinct Mouse Testicular Epithelial Cell Lines" (1980) Biology of Reproduction, 23, 243-252.

Morimoto, Koichi et al. Single-step purification of F(ab')2 fragments of mouse monoclonal antibodies (immunoglobulins G1) by hydrophobic interaction high performance liquid chromatography using TSKgel Phenyl-5PW) (1992) Journal of Biochemical and Biophysical Methods, vol. 24, 107-117.

Morrison, Sherie et al. "Chimeric human antibody molecules: Mouse antigen-binding domains with human constant region domains" (1984) Proc. Natl. Acad. Sci., vol. 81, 6851-6855.

Myers, Eugene et al. "Approximate Matching of Regular Expressions" (1989) Bulletin of Mathematical Biology, vol. 51, No. 1, 5-37.

Myzithras, Maria et al. "Optimizing NBE PK/PD assays using the Gyrolab Affinity Software; conveniently within the bioanalyst's existing workflow" (2018) Bioanalysis, 10(6) 397-406.

NCT06631430, Safety, Tolerability and Pharmacokinetics of Single Rising Doses of BI 3810477 in Healthy Male Subjects(Single-blind, Randomised, Placebo-controlled, Parallel Group Design), Sponsor: Boehringer Ingelheim, Nov. 20, 2024 10 pgs.

North, Benjamin et al. "A New Clustering of Antibody CDR Loop Conformations" (2011) Journal of Molecular Biology, 406, 228-256.

Pearson, William R. et al. "Improved tools for biological sequence comparison" (1988) Prot. Natl. Acad. Sci., vol. 85, 2444-2448.

Pluckthun, A. "Antibodies from *Escherichia coli*" (1994) The Pharmacology of MonoclonalChapter 11, 269-315.

Reichert, Janice M. et al. "Foundation review: The future of antibodies as cancer drugs" (2012) Drug Discovery Today, vol. 17, No. 17/18, 954-963.

Salton, Francesco et al. "Epithelial-Mesenchymal Transition in the Pathogenesis of Idiopathic Pulmonary Fibrosis" (2019) Medicina, 55, 83, 8 pgs.

Schloesser, Daniela et al. "Senescent cells suppress macrophage-mediated corpse removal via upregulation of the CD47-QPCT/L axis" (2022) Journal of Cell Biology, vol. 222, No. 2, e202207097, 1-24.

Schruf, Eva et al., "Recapitulating idiopathic pulmonary fibrosis related alveolar epithelial dysfunction in a human iPSC-derived air-liquid interface model" (2020) FASEB J., vol. 34, 7825-7846.

Sgalla, Giacomo et al. "Pamrevlumab for the treatment of idiopathic pulmonary fibrosis" (2020) Expert Opinion on Investigational Drugs, vol. 29, No. 8, 771-777.

Sgalla, Giacomo et al., "Antibody-based therapies for idiopathic pulmonary fibrosis", (2020) Expert Opinion on Biological Therapy, vol. 20, No. 7, 779-786.

Shi, Lin et al. "Regulatory mechanisms of TGF-β1-induced fibrogenesis of human alveolar epithelial cells" (2016) J Cellular and Molecular Medicine, vol. 20, Issue 11, 2183-2193.

Sojar, Hakimuddin et al. "A Chemical Method for the Deglycosylation of Proteins" (1987) Archives of Biochemistry and Biophysics, 259, 1, 52-57.

(56)                References Cited

OTHER PUBLICATIONS

Song, Lin-lin et al. "A first-in-human phase 1 study of SHR-1906, a humanized monoclonal antibody against connective tissue growth factor, in healthy participants" (2023) Clin Transl Sci. 00, 1-10.

Sonnylal, Sonali, et al. "Connective tissue growth factor causes EMT-like cell fate changes in vivo and in vitro" (2013) J Cell Sci.; vol. 126, Issue 10, 2164-2175.

Sternlicht et al., "Radiation induced pulmonary gene expression changes are attenuated by the CTGF antibody Pamrevlumab", (2018) Respiratory Research, vol. 19, No. 1, 1-16.

Thotakura, Nageswara et al. "[28] Enzymatic deglycosylation of glycoproteins" (1987) Methods of Enzymology, V 138, 350-359.

Torelli, Alberto et al. "Advance and Adam: two algorithms for the analysis of global similarity between homologous informational sequences", (1994), Comput. Appl. Biosci., vol. 10, No. 1, 3-5.

Tyanova, Stefka et al.; "The Perseus computational platform for comprehensive analysis of (prote)omics data" (2016) Nature Methods, vol. 13, No. 9, 731-740.

Urlaub, Gail et al. "Isolation of Chinese hamster cell mutants deficient in dihydrofolate reductase activity" (1980) Proc. Natl. Acad. Sci., vol. 77, No. 7, 4216-4220.

Vargas-Madrazo, Enrique et al. "An improved model of association for VH-VL immunoglobulin domains: Asymmetries between VH and VL in the packing of some interface residues" (2003) Journal of Molecular Recognition, vol. 16, 113-120.

Written Opinion of PCT/EP2025/055309, 6 pgs.

Yang, Danlin et al. "Maximizing in vivo target clearance by design of pH-dependent targeting binding antibodies with altered affinity to FcRn" (2017) MABS, vol. 9, No. 7, 1105-1117.

Yang, Jibing et al. "Activated alveolar epithelial cells initiate fibrosis through autocrine and paracrime secretion of connective tissue growth factor" (2014) Am J Physiol Lung Cell Mol Physiol, 306, L786-L796.

Zapata, Gerardo et al. "Engineering linear F(ab')2 fragments for efficient production in *Escherichia coli* and enhanced antiproliferative activity" (1995) Protein Engineering, vol. 8, No. 10, 1057-1062.

Abreu Jose G, et al. "Connective-tissue growth factor (CTGF) modulates cell signalling by BMP and TGF-beta". Nature Cell Biol. (2002) 4(8):599-604.

Adams Taylor et al, "Alveolar epithelial cell plasticity and injury memory in human pulmonary fibrosis" bioRxiv (2025) 658504. doi:10.1101/2025.06.10.658504.

Adams Taylor S, et al. "Single-cell RNA-seq reveals ectopic and aberrant lung-resident cell populations in idiopathic pulmonary fibrosis" Science Advances (2020) 6(28):eaba1983.

Adler Sharon G, et al. "Phase 1 Study of Anti-CTGF Monoclonal Antibody in Patients with Diabetes and Microalbuminuria" Clinical Journal American Society Nephrology (2010) 5(8):1420-1428.

Akarsu A, et al. "Hypersensitivity reactions to biologicals: from bench to bedside". Curr Treat Options Allergy. (2020) 7:71-83.

Araújo Marcia, et al. "Serum metalloproteinase-7 as a biomarker of progressive pulmonary fibrosis" ERJ Open Research (2024) 10(6):00553-02024.

Arnott John A, et al. "The role of connective tissue growth factor (CTGF/CCN2) in skeletogenesis" Critical Reviews Eukaryotic Gene Express. (2011) 21(1):43-69.

Balci A, et al. "Comprehensive biomarker analysis of patients with idiopathic pulmonary fibrosis and interstitial lung disease with healthy individuals" European Review Medical and Pharmacological Sciences (2023) 27:5468-5479.

Bammert Marie-Therese et al, "A dual role of fibroblast-epithelial crosstalk in acute and chronic lung injury" J Biol Chem (2025) 301:110408.

Baran SW, et al. "Perspectives on the evaluation and adoption of complex in vitro models in drug development: Workshop with the FDA and the pharmaceutical industry (IQ MPS Affiliate)". ALTEX (2022) 39(2):297-314.

Barbe Mary F, et al. "Blocking CTGF/CCN2 reduces established skeletal muscle fibrosis in a rat model of overuse injury" FASEB J (2020) 34:6554-6569.

Basil Maria C, et al. "Human distal airways contain a multipotent secretory cell that can regenerate alveoli" Nature (2022) 604:120-126.

Bauer Yasmina, et al. "MMP-7 is a predictive biomarker of disease progression in patients with idiopathic pulmonary fibrosis" ERJ Open Research (2017) 3:00074-02016.

Bickelhaupt Sebastian, et al. "Effects of CTGF Blockade on Attenuation and Reversal of Radiation-Induced Pulmonary Fibrosis" JNCI: J Natl Cancer Inst (2017) 109:djw339.

Brennan Frank R, et al. "Optimized nonclinical safety assessment strategies supporting clinical development of therapeutic monoclonal antibodies targeting inflammatory diseases" Drug Dev Res. (2014) 75(3): 115-161.

Chen Zihao, et al. "Connective Tissue Growth Factor: From Molecular Understandings to Drug Discovery" Frontiers Cell Development Biology (2020) 8:593269.

Confalonieri Paola, et al. "Regeneration or Repair? The Role of Alveolar Epithelial Cells in the Pathogenesis of Idiopathic Pulmonary Fibrosis (IPF)" Cells (2022) 11(13):2095.

Connolly, Anne M., et al. "Pamrevlumab, a Fully Human Monoclonal Antibody Targeting Connective Tissue Growth Factor, for Non-Ambulatory Patients with Duchenne Muscular Dystrophy" Journal of Neuromuscular Diseases (2023) 10(4):685-699.

Cottin Vincent, et al. "Fibrosing interstitial lung diseases: knowns and unknowns" European Respiratory Review (2019) 28:180100.

European Medicines Agency. Committee for Medicinal Products for Human Use (CHMP) guideline on development, production, characterisation and specifications for monoclonal antibodies and related products. London. Dec. 18, 2008. EMEA/CHMP/BWP/157653/2007.

Flaherty Kevin R, et al. "Design of the PF-ILD trial: a double-blind, randomised, placebo-controlled Phase III trial of nintedanib in patients with progressive fibrosing interstitial lung disease" BMJ Open Respiratory Research (2017) 4(1): e000212.

Garrett Q, et al. "Involvement of CTGF in TGF-$\beta$1-Stimulation of Myofibroblast Differentiation and Collagen Matrix Contraction in the Presence of Mechanical Stress" Investigative Opthalmology Visual Science (2004) 45(4):1109.

George J, et al. "siRNA-mediated knockdown of connective tissue growth factor prevents N-nitrosodimethylamine-induced hepatic fibrosis in rats" Gene Therapy (2007) 14:790-803.

Gerritsen Karin G, et al. "Effect of GFR on Plasma N-Terminal Connective Tissue Growth Factor (CTGF) Concentrations" American Journal Kidney Diseases (2012) 59 (5):619-627.

Gibson Charlisa D, et al. "Advances in targeted therapy for progressive fibrosing interstitial lung disease" Lung (2020) 198(4):597-608.

Hall William C, et al. "Tissue cross-reactivity studies for monoclonal antibodies: predictive value and use for selection of relevant animal species for toxicity testing" Pharmaceutical Sciences Encyclopedia: Drug Discovery, Development, and Manufacturing (2010) 1-34.

Hamai Kosuke, et al. "Comparative Study of Circulating MMP-7, CCL18, KL-6, SP-A, and SP-D as Disease Markers of Idiopathic Pulmonary Fibrosis" Disease Markers (2016) :4759040, 8 pgs.

ICH Expert Working Group. ICH harmonised tripartite guideline: preclinical safety evaluation of biotechnology-derived pharmaceuticals, S6(R1). Jun. 12, 2011, 23 pgs.

Investors and Media: Press Release [Internet]. FibroGen Announces Topline Results from Phase III Zephyrus-I Study of Pamrevlumab for the Treatment of Idiopathic Pulmonary Fibrosis. FibroGen; Jun. 26, 2023 [cited May 17, 2024]. Available from: Website: investor.fibrogen.com/news-releases/news-release-details/fibrogenannounces-topline-results-phase-3-zephyrus-1-study.

Investors and Media: Press Release [Internet]. FibroGen AnnouncesTopline Results from Lelantos-2, a Phase III Clinical Study of Pamrevlumab in Ambulatory Duchenne Muscular Dystrophy. FibroGen; Aug. 29, 2023 [cited May 17, 2024]. Available from: Website: investor.fibrogen.com/news-releases/news-release-details/fibrogenannounces-topline-results-lelantos-2-phase-3-clinical.

(56) References Cited

OTHER PUBLICATIONS

Ito Yasuhiko, et al. "Expression of connective tissue growth factor in human renal fibrosis" Kidney Int (1998) 53:853-861.

Kang S, et al. "RNAi nanotherapy for fibrosis: highly durable knockdown of CTGF/CCN-2 using siRNA-DegradaBALL (LEM-S401) to treat skin fibrotic diseases" Nanoscale (2020) 12:6385-6393.

Khan David A. "Hypersensitivity and immunologic reactions to biologics: opportunities for the allergist." Ann Allergy Asthma Immunol. (2016) 117(2):115-120.

Khan Fasihul A, et al. "A systematic review of blood biomarkers with individual participant data meta-analysis of matrix metalloproteinase-7 in idiopathic pulmonary fibrosis" Eur Respir J (2022) 59:2101612.

King, Talmadge et al. "Idiopathic pulmonary fibrosis" Lancet. (2011) 378 (9807): 1949-1961.

Kolb Martin, et al. "The natural history of progressive fibrosing interstitial lung diseases" Respiratory Research (2019) 20(1):57, 8 pgs.

Koshman, Yevgeniya et al. "Connective tissue growth factor regulates cardiac function and tissue remodeling in a mouse model of dilated cardiomyopathy" Journal of Molecular and Cellular Cardiology, (2015) vol. 89, 214-222.

Lambi Alex G, et al. "The skeletal site-specific role of connective tissue growth factor in prenatal osteogenesis" Developmental Dynamics (2012) 241:(12): 1944-1959.

Lasky, JA "Connective tissue growth factor" Encyclopedia of Respiratory Medicine. Elsevier Ltd. (2006) 553-557.

Leach, Michael, et al. "Use of tissue cross reactivity studies in the development of antibody-based biopharmaceuticals: history, experience, methodology, and future directions." Toxicologic Pathology (2010) 38 (7):1138-1166.

Li Roger M, et al. "Pre-Treatment MMP7 Predicts Progressive Idiopathic Pulmonary Fibrosis in Antifibrotic Treated Patients" Respirology (2025) 30:504-514.

Lipson Kenneth E, et al. "CTGF is a central mediator of tissue remodeling and fibrosis and its inhibition can reverse the process of fibrosis" Fibrogenesis Tissue Repair (2012) 5:S24.

Liu Qing-wei, et al. "Relationship between illness perception, fear of progression and quality of life in interstitial lung disease patients: a cross sectional study" Journal Clinical Nursing (2021) 30(23/24):3493-3505.

Mayr Christoph H, et al. "Spatial Transcriptomic Characterization of Novel Pathologic Niches in IPF" (2024) Science Advances, 10(32), 15 pgs.

Monsen Vivi, et al. "Structural insights into regulation of CCN protein activities and functions" Journal Cell Communication and Signaling (2023) 17:371-390.

Morais Antonio, et al. "Serum metalloproteinases 1 and 7 in the diagnosis of idiopathic pulmonary fibrosis and other interstitial pneumonias" Respiratory Medicine (2015) 109:1063-1068.

Murthy Preetish KL, et al. "Human distal lung maps and lineage hierarchies reveal a bipotent progenitor" Nature (2022) 604:111-119.

Neiens Vanessa, et al. "Preclinical concept studies showing advantage of an inhaled anti-CTGF/CCN2 protein for pulmonary fibrosis treatment" Nature Communications (2025)16(1):3251.

Nishimoto N, et al. "Long-term safety and efficacy of tocilizumab, an anti-IL-6 receptor monoclonal antibody, in monotherapy, in patients with rheumatoid arthritis (the STREAM study): evidence of safety and efficacy in a 5-year extension study" Ann Rheum Dis. (2009) 68(10):1580-1584.

Pan L-H, et al. "Type II alveolar epithelial cells and interstitial fibroblasts express connective tissue growth factor in IPF" Eur Respir J (2001) 17:1220-1227.

Parapuram Sunil K, et al. "Loss of PTEN expression by mouse fibroblasts results in lung fibrosis through a CCN2-dependent mechanism" Matrix Biology (2015) 43:35-41.

PCT/EP2025/055309 International Search Report, mailed Aug. 11, 2025. 9 pgs.

Pichler WJ. "Adverse side-effects to biological agents" Allergy (2006) 61:912-920.

Pintea I, et al. "Hypersensitivity reactions to monoclonal antibodies: classification and treatment approach (review)" Experimental Therapeutic Medicine (2021) 22:949.

Pulito-Cueto Veronica, et al. "Matrix metalloproteinases and their tissue inhibitors as upcoming biomarker signatures of connective tissue diseases-related interstitial lung disease: towards an earlier and accurate diagnosis" Molecular Medicine (2025) 31:70.

Raghu G, et al. "Pamrevlumab for Idiopathic Pulmonary Fibrosis: Results of the Phase 3 Zephyrus-1 Study" C95 N Clin Trial Results Chronic Lung Dis 2024 ; A6613-A6613.doi:10.1164/ajrccm-conference.2024.209.1_meetingabstracts.a6613.

Raghu Ganesh, et al. "An official ATS/ERS/JRS/ALAT statement: idiopathic pulmonary fibrosis: evidence-based guidelines for diagnosis and management" American Journel Respiratory Critical Care Med. (2011) 183(6): 788-824.

Raghu Ganesh, et al. "Diagnosis of idiopathic pulmonary fibrosis: an official ATS/ERS/JRS/ ALAT clinical practice guideline" Am J Respir Crit Care Med. (2018) 198(5) e44-e68.

Raghu Ganesh, et al. "FG-3019 anti-connective tissue growth factor monoclonal antibody: results of an open-label clinical trial in idiopathic pulmonary fibrosis" Eur Respir J. (2016) 47: 1481-1491.

Raghu Ganesh, et al. "Idiopathic Pulmonary Fibrosis (an Update) and Progressive Pulmonary Fibrosis in Adults: An Official ATS/ERS/JRS/ALAT Clinical Practice Guideline" American Journal Respiratory Critical Care Medicine (2022) 205:e18-e47.

Raghu Ganesh, et al. "Pamrevlumab for Idiopathic Pulmonary Fibrosis: The Zephyrus-I Randomized Clinical Trial" JAMA. (2024) 332(5) 380-389.

Raghu, Ganesh et al. "An official ATS/ERS/JRS/ALAT clinical practice guideline: treatment of idiopathic pulmonary fibrosis: executive summary: an update of the 2011 clinical practice guideline" Am J Respir Crit Care Med. (2015) 192 (2):238-248.

Ren Meishen et al. "Connective Tissue Growth Factor: Regulation, Diseases, and Drug Discovery" International Journel Molecular Science (2024) 25:4692.

Richeldi Luca, et al. "Pamrevlumab, an anti-connective tissue growth factor therapy, for idiopathic pulmonary fibrosis (PRAISE): a Phase II, randomised, double-blind, placebo controlled trial" Lancet Respir Med. (2020) 8(1):25-33.

Rojko Jennifer L, et al. "Physiologic IgG biodistribution, transport, and clearance: implications for monoclonal antibody products" Pharmaceutical Sciences Encyclopedia: Drug Discovery, Development, and Manufacturing (2010) 1-36.

Rong M, et al. "Inhibition of b-catenin signaling protects against CTGF-induced alveolar and vascular pathology in neonatal mouse lung" Pediatric Research (2016) 80(1): 136-144.

Rosas Ivan et al. "MMP1 and MMP7 as Potential Peripheral Blood Biomarkers in Idiopathic Pulmonary Fibrosis" PLoS Med (2008) 5(4):e93, 11 pgs.

Safadi Fayez F, et al. "Expression of connective tissue growth factor in bone: its role in osteoblast proliferation and differentiation in vitro and bone formation in vivo" J Cell Physiol. (2003) 196(1):51-62.

Sakai Norihiko, et al. "Inhibition of CTGF ameliorates peritoneal fibrosis through suppression of fibroblast and myofibroblast accumulation and angiogenesis" Scientific Reports (2017) 7:5392.

Sauer Julia et al. "iPSC-derived macrophages: An in vitro model to study human disease-relevant macrophage biology" J Immunol (2025) 00, 1-16.

Song JW, et al. "Biomarkers MMP-7 and SP-A Predictors of Outcome in Idiopathic Pulmonary Fibrosis" Chest (2013) 143:1422-1429.

Strobel B, et al. "Standardized, Scalable, and Timely Flexible Adeno-Associated Virus Vector Production Using Frozen High-Density HEK-293 Cell Stocks and CELLdiscs" Human Gene Therapy Methods (2019) 30:23-33.

Strobel Benjamin, et al. "Modeling Pulmonary Disease Pathways Using Recombinant Adeno-Associated Virus 6.2" Am J Respir Cell Mol Biol (2015) 53:291-302.

(56) References Cited

OTHER PUBLICATIONS

Sung Dong K, et al. "Noncovalenly PEGylated CTGF siRNA/PDMAEMA complex for pulmonary treatment of bleomycin-induced lung fibrosis" Biomaterials (2013) 34:1261-1269.

Tam Angela, et al. "Selective deletion of connective tissue growth factor attenuates experimentally-induced pulmonary fibrosis and pulmonary arterial hypertension" Int J Biochem Cell Biol (2021) 134:105961.

Todd Jamie L, et al. "Circulating matrix metalloproteinases and tissue metalloproteinase inhibitors in patients with idiopathic pulmonary fibrosis in the multicenter IPF-PRO Registry cohort" BMC Pulmonary Medicine (2020) 20:64.

Tsai C-C, et al. "Essential role of connective tissue growth factor (CTGF) in transforming growth factor-$\beta$1 (TGF-$\beta$1)- induced myofibroblast transdifferentiation from Graves' orbital fibroblasts" Scientific Reports (2018) 8:7276.

Tzouvelekis Argyris, et al. "Validation of the prognostic value of MMP-7 in idiopathic pulmonary fibrosis" Respirology (2017) 22:486-493.

Wang Luming, et al. "Complex in vitro model: A transformative model in drug development and precision medicine" Clinical and Translational Science (2023) 17(2):e13695, 17 pgs.

Wang Qingjian, et al. "Cooperative interaction of CTGF and TGF-$\beta$ in animal models of fibrotic disease" Fibrogenesis Tissue Repair (2011) 4:4.

Wei M, et al. "Efficacy and safety of monoclonal antibodies targeting interleukin-17 pathway for inflammatory arthritis: a metaanalysis of randomized controlled clinical trials." Drug Design Development Therapy (2016) 10:2771-2777.

Wells Athol, et al. "What's in a name? That which we call IPF, by any other name would act the same" Eur Respir J. (2018) 51: 1800692.

Wu Dongze, et al. "Efficacy and safety of biologics targeting interleukin-6, -12/23 and -17 pathways for peripheral psoriatic arthritis: a network meta-analysis" Rheumatology (2018) 57(3):563-571.

Yanagihara Toyoshi, et al. "Connective-Tissue Growth Factor (CTGF/CCN2) Contributes to TGF-$\beta$1-Induced Lung Fibrosis" bioRxiv (2020) Jul. 4, 2020 187492.doi:10.1101/2020.07.04.187492.

Yanagihara Toyoshi, et al. "Connective-Tissue Growth Factor Contributes to TGF-$\beta$1-induced Lung Fibrosis" Am J Respir Cell Mol Biol (2022) 66:260-270.

Zheng Caopei et al. "Alveolar epithelial cell dysfunction and epithelial-mesenchymal transition in pulmonary fibrosis pathogenesis" Frontiers Molecular Biosciences (2025) 12:1564176.

| Antibody | - | - | Isotype | A97 | F1 |
|---|---|---|---|---|---|
| MMP7 | - | + | + | + | + |

N-Term CTGF
(McMaster Cohort)

H/V n=12; IPF n=65
Mann-Whitney; $*p \leq 0.05$

+ labelled CTGF 30nM

ANTIBODIES TO CONNECTIVE TISSUE GROWTH FACTOR (CTGF) AND USES THEREOF

CROSS-REFERENCE TO RELATED APPLICATIONS

This application claims priority to European Patent Application No. EP24160771.2, filed Mar. 1, 2024, and U.S. Provisional Patent Application Ser. No. 63/723,664, filed Nov. 22, 2024, each of which is hereby incorporated by reference in its entirety.

SEQUENCE LISTING

This application includes, as part of its disclosure, a "Sequence Listing XML" pursuant to 37 C.F.R. § 1.831(a) which is submitted in XML file format in a file named "09-0753-US-2.xml", created on Feb. 26, 2025 and having a size of 203,519 bytes, which is hereby incorporated by reference herein in its entirety.

FIELD

This disclosure generally relates to anti-CTGF (connective tissue growth factor) antibodies. More specifically, the disclosure relates to anti-CTGF antibodies or antigen-binding fragments thereof and methods of their use for the treatment of various diseases or disorders, for example, respiratory disease, fibrosis, or cancer. Pharmaceutical compositions and kits comprising the anti-CTGF antibodies or antigen-binding fragments thereof are also disclosed.

BACKGROUND

Idiopathic pulmonary fibrosis (IPF) is a chronic, fibrosing interstitial pneumonia of unknown etiology. It is characterized by progressive worsening of dyspnea and lung function, and has a poor prognosis. Standard of care (nintedanib, pirfenidone) can reduce the decline trajectory, nevertheless, life expectancy after diagnosis remains strongly shortened.

Progressive pulmonary fibrosis (PPF), of which IPF is a prototype, is a fatal condition that can develop in a variety of diseases, including inflammatory diseases such as rheumatoid arthritis or scleroderma.

CTGF is a secreted growth factor that modulates many profibrotic processes and is strongly upregulated in IPF and PPF. CTGF is composed of two N-terminal domains (together CTGF-NTF) and two C-terminal domains (together CTGF-CTF) bound by a hinge peptide containing cleavage sequences for matrix metalloproteases (MMP). CTGF is secreted as a full length protein of 38 kDa, and can be rapidly cleaved into CTGF-NTF and CTGF-CTF when exposed to activated matrix metalloproteases. Those proteases are known to be increased in disease.

CTGF has been proposed as prognostic biomarkers of progression in IPF. However, the precise mechanisms by which CTGF or the CTGF fragments may contribute to the pathobiology of pulmonary fibrosis remains unclear.

Current treatment methods in IPF and PPF (nintedanib and pirfenidone) slow progression of pulmonary fibrosis. However, the median treatment duration with both antifibrotics is not much longer than one year. Thus, there is an unmet need for additional therapies for IPF and PPF.

BRIEF SUMMARY

The present disclosure addresses the above need and others by providing agents, in particular antibodies or antigen-binding fragments thereof, which specifically bind to CTGF. In particular, the antibodies or antigen-binding fragments thereof as disclosed herein specifically bind to human CTGF, such as full length CTGF (e.g., having the amino acid sequence of SEQ ID NO: 1 or SEQ ID NO: 2) or CTGF N-terminal fragment (CTGF-NTF) (e.g., having the amino acid sequence of SEQ ID NO: 3). In some aspects, the antibodies or antigen-binding fragments thereof block proteolytic cleavage of CTGF, e.g., by matrix metalloprotease 7 (MMP7). In some aspects, the antibodies or antigen-binding fragments thereof, block the interaction of CTGF with cells that express CTGF receptors, such as alveolar type II cells, fibroblasts and A549 cells. In some aspects, the antibodies or antigen-binding fragments thereof, block the interaction of CTGF-NTF with cells that express CTGF receptors, such as alveolar type II cells, fibroblasts and A549 cells.

The cleavage of CTGF by proteases, such as MMP7, activates the CTGF pathway since the fragments are biologically active. Exemplary anti-CTGF antibodies of the present disclosure bind to CTGF and inhibit this cleavage. They may, thus, reduce the occurrence of fragments. Exemplary anti-CTGF antibodies of the present disclosure additionally specifically bind CTGF-NTF. This inhibition of cleavage and binding of full length CTGF and CTGF-NTF thus reduce fibrogenesis and fibrillar collagen production. Exemplary anti-CTGF antibodies of the present disclosure can reduce levels of the human fibrosis biomarkers such as ProC3.

Macrophages engulfing CTGF fragments show reduced efferocytosis potential. Consequently, dead/senescent cells accumulate and perpetuate profibrotic signaling. Exemplary anti-CTGF antibodies of the present disclosure inhibit the generation of CTGF fragments. Thereby, macrophage homeostasis is promoted.

Alveolar cells undergo epithelial-mesenchymal transition in pulmonary fibrosis leading to a failure of the progenitor cells to repair the alveolus. Exemplary anti-CTGF antibodies of the present disclosure inhibit this epithelial-mesenchymal transition of alveolar cells. Thereby, the maintenance and functionality of the alveolar stem cells and thus repair of the epithelium is promoted.

In some aspects, the anti-CTGF antibody or antigen-binding fragment thereof comprises a light chain variable region comprising a light chain complementarity determining region 1 (L-CDR1) having the amino acid sequence of Y1-SSQSIVHYN-Y2-Y3-TYLE where Y1 is K or R, Y2 is A, E, G, or T and Y3 is K or N (SEQ ID NO: 10), a light chain complementarity determining region 2 (L-CDR2) having the amino acid sequence of KVS-Z1-R-Z2-S where Z1 is N or S and Z2 is A or F (SEQ ID NO: 11), and a light chain complementarity determining region 3 (L-CDR3) having the amino acid sequence of FQGSHFPLT (SEQ ID NO: 12); and a heavy chain variable region comprising a heavy chain complementarity determining region 1 (H-CDR1) having the amino acid sequence of DYYMA (SEQ ID NO: 15), a heavy chain complementarity determining region 2 (H-CDR2) having the amino acid sequence of NINY-X1-GSRTDLL-X2-SLKS where X1 is D, E, or Y and X2 is A, D, or E (SEQ ID NO: 16), and a heavy chain complementarity determining region 3 (H-CDR3) having the amino acid sequence of DTSRGSYFDV (SEQ ID NO: 17).

In some aspects, the anti-CTGF antibody or antigen-binding fragment thereof comprises the six CDRs (L-CDR1, L-CDR2, L-CDR3, H-CDR1, H-CDR2 and H-CDR3) of any one of antibodies A1-A127 as specified in Table 13 (according to Kabat). Preferably, said antibody comprises the six CDRs (L-CDR1, L-CDR2, L-CDR3, H-CDR1, H-CDR2 and H-CDR3) of any one of antibodies A1-A25, A41-A44, A46, A48-A85, or A87-A127 as specified in Table 13 (according to Kabat). Most preferably, said antibody comprises the six CDRs (L-CDR1, L-CDR2, L-CDR3, H-CDR1, H-CDR2 and H-CDR3) of antibody A97 as specified in Table 13 (according to Kabat). While the specific CDR sequences mentioned in Table 13 are according to Kabat, it is understood that the CDR sequences of antibodies A1-A127 of Table 13 may also be determined according to another numbering scheme (e.g., as described herein) based on the sequences of the variable regions or the full-length sequences of the heavy and light chains as outlined for antibodies A1-A127 in Table 13, e.g., by reference to the CDR sequences as shown in Tables 3-8 and the light and heavy chain names corresponding to each antibody as shown in Tables 9-12.

In some aspects, the anti-CTGF antibody or antigen-binding fragment thereof comprises a light chain variable region and a heavy chain variable region each having at least 95% identity to the light chain variable region and the corresponding heavy chain variable region, respectively, of any one of antibodies A1-A127 as specified in Table 13. Preferably, said antibody comprises a light chain variable region and a heavy chain variable region each having at least 95% identity to the light chain variable region and the corresponding heavy chain variable region, respectively, of any one of antibodies A1-A25, A41-A44, A46, A48-A85, or A87-A127 as specified in Table 13. Most preferably, said antibody comprises a light chain variable region and a heavy chain variable region each having at least 95% identity to the light chain variable region and the corresponding heavy chain variable region, respectively, of antibody A97 as specified in Table 13.

In some aspects, the anti-CTGF antibody or antigen-binding fragment thereof comprises the light chain variable region and the corresponding heavy chain variable region of any one of antibodies A1-A127 as specified in Table 13. Preferably, said antibody comprises the light chain variable region and the corresponding heavy chain variable region of any one of antibodies A1-A25, A41-A44, A46, A48-A85, or A87-A127 as specified in Table 13. Most preferably, said antibody comprises the light chain variable region and the corresponding heavy chain variable region of antibody A97 as specified in Table 13.

In some aspects, the anti-CTGF antibody or antigen-binding fragment thereof comprises a light chain and a heavy chain each having at least 95% identity to the light chain and the corresponding heavy chain, respectively, of any one of antibodies A1-A127 as specified in Table 13. Preferably, said antibody comprises a light chain and a heavy chain each having at least 95% identity to the light chain and the corresponding heavy chain, respectively, of any one of antibodies A1-A25, A41-A44, A46, A48-A85, or A87-A127 as specified in Table 13. Most preferably, said antibody comprises a light chain and a heavy chain each having at least 95% identity to the light chain and the corresponding heavy chain, respectively, of antibody A97 as specified in Table 13.

In some aspects, the anti-CTGF antibody or antigen-binding fragment thereof comprises the light chain and the corresponding heavy chain of any one of antibodies A1-A127 as specified in Table 13. Preferably, said antibody comprises the light chain and the corresponding heavy chain of any one of antibodies A1-A25, A41-A44, A46, A48-A85, or A87-A127 as specified in Table 13. Most preferably, said antibody comprises the light chain and the corresponding heavy chain of antibody A97 as specified in Table 13.

In some aspects, the anti-CTGF antibody or antigen-binding fragment thereof as described herein comprises a heavy chain constant region selected from $IgG_1$, $IgG_2$, $IgG_3$, $IgG_4$, IgM, IgA and IgE or a variant thereof. Preferably, the anti-CTGF antibody or antigen-binding fragment thereof as described herein comprises an $IgG_1$ heavy chain constant region.

In some aspects, the anti-CTGF antibody or antigen-binding fragment thereof comprises a heavy chain lacking a C-terminal lysine residue.

In some aspects, the anti-CTGF antibody or antigen-binding fragment thereof comprises a heavy chain constant region wherein the heavy chain constant region is of an $IgG_1$ with L234A and L235A substitutions.

In some aspects, the anti-CTGF antibody or antigen-binding fragment thereof comprises a light chain constant region selected from the group consisting of a kappa and a lambda light chain.

In some aspects, the anti-CTGF antibody or antigen-binding fragment thereof is a monoclonal antibody.

In some aspects, the anti-CTGF antibody or antigen-binding fragment thereof is a monospecific antibody.

In some aspects, the anti-CTGF antibody or antigen-binding fragment thereof binds the full length human CTGF of SEQ ID NO: 2 with a binding affinity of 50 pM or lower, 25 pM or lower, 15 pM or lower, 10 pM or lower, 5 pM or lower, or 2 pM or lower.

In some aspects, the anti-CTGF antibody or antigen-binding fragment thereof binds the human CTGF-NTF of SEQ ID NO: 3 with a binding affinity of 10 nM or lower, 5 nM or lower, 2.5 nM or lower, 1 nM or lower, 0.5 nM or lower, or 0.2 nM or lower.

In some aspects, the anti-CTGF antibody or antigen-binding fragment thereof binds the human CTGF of SEQ ID NO: 2 with a $K_D$ of 5 pM or lower.

In some aspects, the anti-CTGF antibody or antigen-binding fragment thereof binds the N-terminal fragment of human CTGF of SEQ ID NO: 3 with a $K_D$ of 0.5 nM or lower.

In some aspects, the anti-CTGF antibody or antigen-binding fragment thereof decreases or blocks human CTGF binding to primary human fibroblast cells.

In some aspects, the anti-CTGF antibody or antigen-binding fragment thereof decreases or blocks cleavage of human CTGF by MMP7.

In some aspects, the anti-CTGF antibody or antigen-binding fragment thereof blocks or inhibits human TGFbeta-induced increase in COL1A1 expression in lung epithelial cells.

In some aspects, the anti-CTGF antibody or antigen-binding fragment thereof blocks or inhibits CTGF interaction with alveolar type II cells, fibroblasts and/or A549 cells.

In some aspects, the anti-CTGF antibody or antigen-binding fragment thereof blocks or inhibits CTGF-NTF interaction with alveolar type II cells, fibroblasts and/or A549 cells.

In some aspects, the disclosure provides a pharmaceutical composition comprising an anti-CTGF antibody or antigen-binding fragment thereof as disclosed herein, and a pharmaceutically acceptable carrier.

In some aspects, the disclosure provides an anti-CTGF antibody or antigen-binding fragment thereof as disclosed herein for use as a medicament.

In some aspects, the disclosure provides an anti-CTGF antibody or antigen-binding fragment thereof as disclosed herein for use for treating or preventing a CTGF-associated disorder, a fibrotic disease, hypertension, diabetes, myocardial infarction, arthritis, CTGF-related cell proliferative disease, atherosclerosis, glaucoma, or a cancer. Said fibrotic disease may be idiopathic pulmonary fibrosis (IPF), progressive pulmonary fibrosis (PPF), pulmonary fibrosis with interstitial lung disease (PF-ILD), systemic scleroderma (SSc), diabetic nephropathy, diabetic retinopathy, osteoarthritis, scleroderma, chronic heart failure, liver cirrhosis or renal fibrosis. Said cancer may be acute lymphoblastic leukemia, dermatofibroma, breast cancer, angiolipoma, angioleiomyoma, connective tissue-generating cancer, prostate cancer, ovarian cancer, colorectal cancer, pancreatic cancer, gastrointestinal cancer or liver cancer. Said anti-CTGF antibody or antigen-binding fragment thereof may be for parenteral or inhalation administration.

In some aspects, the disclosure provides a method of treating or preventing a CTGF-associated disorder, a fibrotic disease, hypertension, diabetes, myocardial infarction, arthritis, CTGF-related cell proliferative disease, atherosclerosis, glaucoma, or a cancer, comprising administering an effective amount of an anti-CTGF antibody or antigen-binding fragment thereof as disclosed herein to a patient in need thereof. Said fibrotic disease may be idiopathic pulmonary fibrosis (IPF), progressive pulmonary fibrosis (PPF), pulmonary fibrosis with interstitial lung disease (PF-ILD), systemic scleroderma (SSc), diabetic nephropathy, diabetic retinopathy, osteoarthritis, scleroderma, chronic heart failure, liver cirrhosis or renal fibrosis. Said cancer may be acute lymphoblastic leukemia, dermatofibroma, breast cancer, angiolipoma, angioleiomyoma, connective tissue-generating cancer, prostate cancer, ovarian cancer, colorectal cancer, pancreatic cancer, gastrointestinal cancer or liver cancer. Said antibody or antigen-binding fragment thereof may be administered by parenteral or inhalation administration.

In some aspects, the disclosure provides the use of an anti-CTGF antibody or antigen-binding fragment thereof as disclosed herein for the manufacture of a medicament for treating or preventing CTGF-associated disorder, a fibrotic disease, hypertension, diabetes, myocardial infarction, arthritis, CTGF-related cell proliferative disease, atherosclerosis, glaucoma, or a cancer. Said fibrotic disease may be idiopathic pulmonary fibrosis (IPF), progressive pulmonary fibrosis (PPF), pulmonary fibrosis with interstitial lung disease (PF-ILD), systemic scleroderma (SSc), diabetic nephropathy, diabetic retinopathy, osteoarthritis, scleroderma, chronic heart failure, liver cirrhosis or renal fibrosis. Said cancer may be acute lymphoblastic leukemia, dermatofibroma, breast cancer, angiolipoma, angioleiomyoma, connective tissue-generating cancer, prostate cancer, ovarian cancer, colorectal cancer, pancreatic cancer, gastrointestinal cancer or liver cancer. Said anti-CTGF antibody or antigen-binding fragment thereof may be administered by parenteral or inhalation administration.

In some aspects, the disclosure provides an isolated polynucleotide or a plurality of isolated nucleotides that encodes a sequence comprising the heavy chain variable region and/or light chain variable region of an anti-CTGF antibody or antigen-binding fragment thereof as disclosed herein.

In some aspects, the disclosure provides a vector or plurality of vectors comprising a polynucleotide or a plurality of polynucleotides that encode the light chain and/or the heavy chain of an anti-CTGF antibody or antigen-binding fragment thereof as disclosed herein. Said vector may comprise an expression vector or plurality of expression vectors. Said polynucleotide or plurality of polynucleotides may be in functional association with one or more expression control sequences.

In some aspects, the disclosure provides a host cell comprising a polynucleotide or plurality of nucleotides, or a vector or plurality of vectors, that encode the light chain and/or the heavy chain of an anti-CTGF antibody or antigen-binding fragment thereof as disclosed herein.

In some aspects, the disclosure provides a method for the production of an anti-CTGF antibody or antigen-binding fragment thereof as disclosed herein, comprising the steps: (a) cultivating a host cell comprising a polynucleotide or plurality of nucleotides, or a vector or plurality of vectors, that encode the light chain and the heavy chain of said anti-CTGF antibody or antigen-binding fragment thereof, under conditions allowing the expression of said anti-CTGF antibody or antigen-binding fragment thereof; and (b) recovering said anti-CTGF antibody or antigen-binding fragment thereof.

In some aspects, the disclosure provides a method of inhibiting the interaction between human CTGF and a cell, comprising contacting said human CTGF with (an effective amount of) the anti-CTGF antibody or antigen-binding fragment thereof as disclosed herein.

In some aspects, the disclosure provides a method of inhibiting the interaction between human CTGF-NTF and a cell, comprising contacting said human CTGF-NTF with (an effective amount of) the anti-CTGF antibody or antigen-binding fragment thereof as disclosed herein.

NUMBERED STATEMENTS

Figure 1:
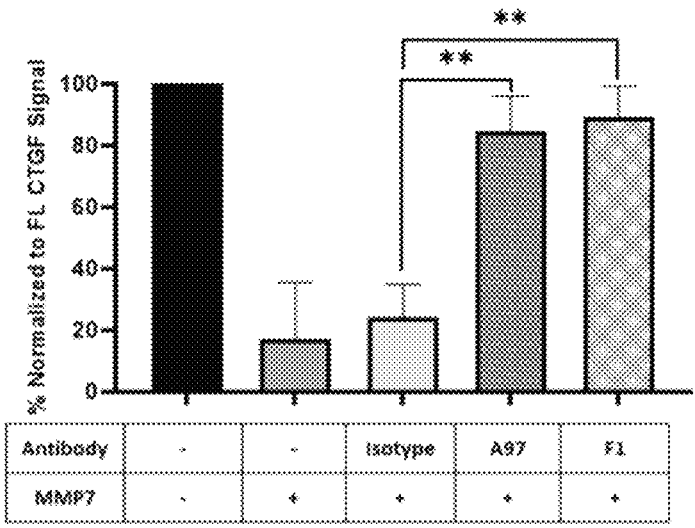
FIG. 1. Normalized full length intact CTGF signal compared to each reaction with addition of MMP7 and MMP7+ antibodies. Antibody 97 compared to isotype control: ($p<0.005$). Antibody F1 compared to isotype control: ($p<0.01$).

The following numbered paragraphs (paras) describe particular aspects and embodiments of the present disclosure:

1. An anti-CTGF antibody or an antigen-binding fragment thereof comprising:
   a light chain variable region comprising a light chain complementarity determining region 1 (L-CDR1) having the amino acid sequence of Y1-SSQSIVHYN-Y2-Y3-TYLE where Y1 is K or R, Y2 is A, E, G, or T and Y3 is K or N (SEQ ID NO: 10), a light chain complementarity determining region 2 (L-CDR2) having the amino acid sequence of KVS-Z1-R-Z2-S where Z1 is N or S and Z2 is A or F (SEQ ID NO: 11), and a light chain complementarity determining region 3 (L-CDR3) having the amino acid sequence of FQGSHFPLT (SEQ ID NO: 12); and
   a heavy chain variable region comprising a heavy chain complementarity determining region 1 (H-CDR1) having the amino acid sequence of DYYMA (SEQ ID NO: 15), a heavy chain complementarity determining region 2 (H-CDR2) having the amino acid sequence of NINY-X1-GSRTDLL-X2-SLKS where X1 is D, E, or Y and X2 is A, D, or E (SEQ ID NO: 16), and a heavy chain complementarity determining region 3 (H-CDR3) having the amino acid sequence of DTSRGSYFDV (SEQ ID NO: 17).

2. The anti-CTGF antibody or an antigen-binding fragment thereof according to para 1, wherein the anti-CTGF antibody or an antigen-binding fragment thereof comprises:
   i. a light chain variable region comprising an L-CDR1 having the amino acid sequence of SEQ ID NO: 220, an L-CDR2 having the amino acid sequence of SEQ ID NO: 221, and an L-CDR3 having the amino acid sequence of SEQ ID NO: 222; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or
   ii. a light chain variable region comprising an L-CDR1 having the amino acid sequence of SEQ ID NO: 100, an L-CDR2 having the amino acid sequence of SEQ ID NO: 101, and an L-CDR3 having the amino acid sequence of SEQ ID NO: 102; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or
   iii. a light chain variable region comprising an L-CDR1 having the amino acid sequence of SEQ ID NO: 110, an L-CDR2 having the amino acid sequence of SEQ ID NO: 111, and an L-CDR3 having the amino acid sequence of SEQ ID NO: 112; and a heavy chain 105, an H-CDR2 having the amino acid sequence of SEQ ID NO: 106, and an H-CDR3 having the amino acid sequence of SEQ ID NO: 107; or
   iv. a light chain variable region comprising an L-CDR1 having the amino acid sequence of SEQ ID NO: 120, an L-CDR2 having the amino acid sequence of SEQ ID NO: 121, and an L-CDR3 having the amino acid sequence of SEQ ID NO: 122; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or v. a light chain variable region comprising an L-CDR1 having the amino acid sequence of SEQ ID NO: 130, an L-CDR2 having the amino acid sequence of SEQ ID NO: 131, and an L-CDR3 having the amino acid sequence of SEQ ID NO: 132; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or vi. a light chain variable region comprising an L-CDR1 having the amino acid sequence of SEQ ID NO: 140, an L-CDR2 having the amino acid sequence of SEQ ID NO: 141, and an L-CDR3 having the amino acid sequence of SEQ ID NO: 142; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or vii. a light chain variable region comprising an L-CDR1 having the amino acid sequence of SEQ ID NO: 150, an L-CDR2 having the amino acid sequence of SEQ ID NO: 151, and an L-CDR3 having the amino acid sequence of SEQ ID NO: 152; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or viii. a light chain variable region comprising an L-CDR1 having the amino acid sequence of SEQ ID NO: 160, an L-CDR2 having the amino acid sequence of SEQ ID NO: 161, and an L-CDR3 having the amino acid sequence of SEQ ID NO: 162; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or ix. a light chain variable region comprising an L-CDR1 having the amino acid sequence of SEQ ID NO: 170, an L-CDR2 having the amino acid sequence of SEQ ID NO: 171, and an L-CDR3 having the amino acid sequence of SEQ ID NO: 172; and a heavy chain 105, an H-CDR2 having the amino acid sequence of SEQ ID NO: 106, and an H-CDR3 having the amino acid sequence of SEQ ID NO: 107; or x. a light chain variable region comprising an L-CDR1 having the amino acid sequence of SEQ ID NO: 180, an L-CDR2 having the amino acid sequence of SEQ ID NO: 181, and an L-CDR3 having the amino acid sequence of SEQ ID NO: 182; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or xi. a light chain variable region comprising an L-CDR1 having the amino acid sequence of SEQ ID NO: 190, an L-CDR2 having the amino acid sequence of SEQ ID NO: 191, and an L-CDR3 having the amino acid sequence of SEQ ID NO: 192; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or xii. a light chain variable region comprising an L-CDR1 having the amino acid sequence of SEQ ID NO: 200, an L-CDR2 having the amino acid sequence of SEQ ID NO: 201, and an L-CDR3 having the amino acid sequence of SEQ ID NO: 202; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or xiii. a light chain variable region comprising an L-CDR1 having the amino acid sequence of SEQ ID NO: 210, an L-CDR2 having the amino acid sequence of SEQ ID NO: 211, and an L-CDR3 having the amino acid sequence of SEQ ID NO: 212; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or xiv. a light chain variable region comprising an L-CDR1 having the amino acid sequence of SEQ ID NO: 230, an L-CDR2 having the amino acid sequence of SEQ ID NO: 231, and an L-CDR3 having the amino acid sequence of SEQ ID NO: 232; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or xv. a light chain variable region comprising an L-CDR1 having the amino acid sequence of SEQ ID NO: 240, an L-CDR2 having the amino acid sequence of SEQ ID NO: 241, and an L-CDR3 having the amino acid sequence of SEQ ID NO: 242; and a heavy chain 105, an H-CDR2 having the amino acid sequence of SEQ ID NO: 106, and an H-CDR3 having the amino acid sequence of SEQ ID NO: 107; or xvi. a light chain variable region comprising an L-CDR1 having the amino acid sequence of SEQ ID NO: 250, an L-CDR2 having the amino acid sequence of SEQ ID NO: 251, and an L-CDR3 having the amino acid sequence of SEQ ID NO: 252; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or xvii. a light chain variable region comprising an L-CDR1 having the amino acid sequence of SEQ ID NO: 100, an L-CDR2 having the amino acid sequence of SEQ ID NO: 101, and an L-CDR3 having the amino acid sequence of SEQ ID NO: 102; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or xviii. a light chain variable region comprising an L-CDR1 having the amino acid sequence of SEQ ID NO: 110, an L-CDR2 having the amino acid sequence of SEQ ID NO: 111, and an L-CDR3 having the amino acid sequence of SEQ ID NO: 112; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or xix. a light chain variable region comprising an L-CDR1 having the amino acid sequence of SEQ ID NO: 120, an L-CDR2 having the amino acid sequence of SEQ ID NO: 121, and an L-CDR3 having the amino acid sequence of SEQ ID NO: 122; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or xx. a light chain variable region comprising an L-CDR1 having the amino acid sequence of SEQ ID NO: 130, an L-CDR2 having the amino acid sequence of SEQ ID NO: 131, and an L-CDR3 having the amino acid sequence of SEQ ID NO: 132; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or xxi. a light chain variable region comprising an L-CDR1 having the amino acid sequence of SEQ ID NO: 140, an L-CDR2 having the amino acid sequence of SEQ ID NO: 141, and an L-CDR3 having the amino acid sequence of SEQ ID NO: 142; and a heavy chain 115, an H-CDR2 having the amino acid sequence of SEQ ID NO: 116, and an H-CDR3 having the amino acid sequence of SEQ ID NO: 117; or xxii. a light chain variable region comprising an L-CDR1 having the amino acid sequence of SEQ ID NO: 150, an L-CDR2 having the amino acid sequence of SEQ ID NO: 151, and an L-CDR3 having the amino acid sequence of SEQ ID NO: 152; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or xxiii. a light chain variable region comprising an L-CDR1 having the amino acid sequence of SEQ ID NO: 160, an L-CDR2 having the amino acid sequence of SEQ ID NO: 161, and an L-CDR3 having the amino acid sequence of SEQ ID NO: 162; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or xxiv. a light chain variable region comprising an L-CDR1 having the amino acid sequence of SEQ ID NO: 170, an L-CDR2 having the amino acid sequence of SEQ ID NO: 171, and an L-CDR3 having the amino acid sequence of SEQ ID NO: 172; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or xxv. a light chain variable region comprising an L-CDR1 having the amino acid sequence of SEQ ID NO: 180, an L-CDR2 having the amino acid sequence of SEQ ID NO: 181, and an L-CDR3 having the amino acid sequence of SEQ ID NO: 182; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or xxvi. a light chain variable region comprising an L-CDR1 having the amino acid sequence of SEQ ID NO: 190, an L-CDR2 having the amino acid sequence of SEQ ID NO: 191, and an L-CDR3 having the amino acid sequence of SEQ ID NO: 192; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or xxvii. a light chain variable region comprising an L-CDR1 having the amino acid sequence of SEQ ID NO: 200, an L-CDR2 having the amino acid sequence of SEQ ID NO: 201, and an L-CDR3 having the amino acid sequence of SEQ ID NO: 202; and a heavy chain 115, an H-CDR2 having the amino acid sequence of SEQ ID NO: 116, and an H-CDR3 having the amino acid sequence of SEQ ID NO: 117; or xxviii. a light chain variable region comprising an L-CDR1 having the amino acid sequence of SEQ ID NO: 210, an L-CDR2 having the amino acid sequence of SEQ ID NO: 211, and an L-CDR3 having the amino acid sequence of SEQ ID NO: 212; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or xxix. a light chain variable region comprising an L-CDR1 having the amino acid sequence of SEQ ID NO: 220, an L-CDR2 having the amino acid sequence of SEQ ID NO: 221, and an L-CDR3 having the amino acid sequence of SEQ ID NO: 222; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or xxx. a light chain variable region comprising an L-CDR1 having the amino acid sequence of SEQ ID NO: 230, an L-CDR2 having the amino acid sequence of SEQ ID NO: 231, and an L-CDR3 having the amino acid sequence of SEQ ID NO: 232; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or xxxi. a light chain variable region comprising an L-CDR1 having the amino acid sequence of SEQ ID NO: 240, an L-CDR2 having the amino acid sequence of SEQ ID NO: 241, and an L-CDR3 having the amino acid sequence of SEQ ID NO: 242; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or xxxii. a light chain variable region comprising an L-CDR1 having the amino acid sequence of SEQ ID NO: 250, an L-CDR2 having the amino acid sequence of SEQ ID NO: 251, and an L-CDR3 having the amino acid sequence of SEQ ID NO: 252; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or xxxiii. a light chain variable region comprising an L-CDR1 having the amino acid sequence of SEQ ID NO: 100, an L-CDR2 having the amino acid sequence of SEQ ID NO: 101, and an L-CDR3 having the amino acid sequence of SEQ ID NO: 102; and a heavy chain 125, an H-CDR2 having the amino acid sequence of SEQ ID NO: 126, and an H-CDR3 having the amino acid sequence of SEQ ID NO: 127; or xxxiv. a light chain variable region comprising an L-CDR1 having the amino acid sequence of SEQ ID NO: 110, an L-CDR2 having the amino acid sequence of SEQ ID NO: 111, and an L-CDR3 having the amino acid sequence of SEQ ID NO: 112; and a heavy chain variable region comprising an H-CDR1 having the amino acid sequence of SEQ ID NO: 125, an H-CDR2 having the amino acid sequence of SEQ ID NO: 126, and an H-CDR3 having the amino acid sequence of SEQ ID NO: 127; or xxxv. a light chain variable region comprising an L-CDR1 having the amino acid sequence of SEQ ID NO: 120, an L-CDR2 having the amino acid sequence of SEQ ID NO: 121, and an L-CDR3 having the amino acid sequence of SEQ ID NO: 122; and a heavy chain variable region comprising an H-CDR1 having the amino acid sequence of SEQ ID NO: 125, an H-CDR2 having the amino acid sequence of SEQ ID NO: 126, and an H-CDR3 having the amino acid sequence of SEQ ID NO: 127; or xxxvi. a light chain variable region comprising an L-CDR1 having the amino acid sequence of SEQ ID NO: 130, an L-CDR2 having the amino acid sequence of SEQ ID NO: 131, and an L-CDR3 having the amino acid sequence of SEQ ID NO: 132; and a heavy chain variable region comprising an H-CDR1 having the amino acid sequence of SEQ ID NO: 125, an H-CDR2 having the amino acid sequence of SEQ ID NO: 126, and an H-CDR3 having the amino acid sequence of SEQ ID NO: 127; or xxxvii. a light chain variable region comprising an L-CDR1 having the amino acid sequence of SEQ ID NO: 140, an L-CDR2 having the amino acid sequence of SEQ ID NO: 141, and an L-CDR3 having the amino acid sequence of SEQ ID NO: 142; and a heavy chain variable region comprising an H-CDR1 having the amino acid sequence of SEQ ID NO: 125, an H-CDR2 having the amino acid sequence of SEQ ID NO: 126, and an H-CDR3 having the amino acid sequence of SEQ ID NO: 127; or xxxviii. a light chain variable region comprising an L-CDR1 having the amino acid sequence of SEQ ID NO: 150, an L-CDR2 having the amino acid sequence of SEQ ID NO: 151, and an L-CDR3 having the amino acid sequence of SEQ ID NO: 152; and a heavy chain variable region comprising an H-CDR1 having the amino acid sequence of SEQ ID NO: 125, an H-CDR2 having the amino acid sequence of SEQ ID NO: 126, and an H-CDR3 having the amino acid sequence of SEQ ID NO: 127; or xxxix. a light chain variable region comprising an L-CDR1 having the amino acid sequence of SEQ ID NO: 160, an L-CDR2 having the amino acid sequence of SEQ ID NO: 161, and an L-CDR3 having the amino acid sequence of SEQ ID NO: 162; and a heavy chain 125, an H-CDR2 having the amino acid sequence of SEQ ID NO: 126, and an H-CDR3 having the amino acid sequence of SEQ ID NO: 127; or xl. a light chain variable region comprising an L-CDR1 having the amino acid sequence of SEQ ID NO: 170, an L-CDR2 having the amino acid sequence of SEQ ID NO: 171, and an L-CDR3 having the amino acid sequence of SEQ ID NO: 172; and a heavy chain variable region comprising an H-CDR1 having the amino acid sequence of SEQ ID NO: 125, an H-CDR2 having the amino acid sequence of SEQ ID NO: 126, and an H-CDR3 having the amino acid sequence of SEQ ID NO: 127; or xli. a light chain variable region comprising an L-CDR1 having the amino acid sequence of SEQ ID NO: 180, an L-CDR2 having the amino acid sequence of SEQ ID NO: 181, and an L-CDR3 having the amino acid sequence of SEQ ID NO: 182; and a heavy chain variable region comprising an H-CDR1 having the amino acid sequence of SEQ ID NO: 125, an H-CDR2 having the amino acid sequence of SEQ ID NO: 126, and an H-CDR3 having the amino acid sequence of SEQ ID NO: 127; or xlii. a light chain variable region comprising an L-CDR1 having the amino acid sequence of SEQ ID NO: 190, an L-CDR2 having the amino acid sequence of SEQ ID NO: 191, and an L-CDR3 having the amino acid sequence of SEQ ID NO: 192; and a heavy chain variable region comprising an H-CDR1 having the amino acid sequence of SEQ ID NO: 125, an H-CDR2 having the amino acid sequence of SEQ ID NO: 126, and an H-CDR3 having the amino acid sequence of SEQ ID NO: 127; or xliii. a light chain variable region comprising an L-CDR1 having the amino acid sequence of SEQ ID NO: 200, an L-CDR2 having the amino acid sequence of SEQ ID NO: 201, and an L-CDR3 having the amino acid sequence of SEQ ID NO: 202; and a heavy chain variable region comprising an H-CDR1 having the amino acid sequence of SEQ ID NO: 125, an H-CDR2 having the amino acid sequence of SEQ ID NO: 126, and an H-CDR3 having the amino acid sequence of SEQ ID NO: 127; or xliv. a light chain variable region comprising an L-CDR1 having the amino acid sequence of SEQ ID NO: 210, an L-CDR2 having the amino acid sequence of SEQ ID NO: 211, and an L-CDR3 having the amino acid sequence of SEQ ID NO: 212; and a heavy chain variable region comprising an H-CDR1 having the amino acid sequence of SEQ ID NO: 125, an H-CDR2 having the amino acid sequence of SEQ ID NO: 126, and an H-CDR3 having the amino acid sequence of SEQ ID NO: 127; or xlv. a light chain variable region comprising an L-CDR1 having the amino acid sequence of SEQ ID NO: 220, an L-CDR2 having the amino acid sequence of SEQ ID NO: 221, and an L-CDR3 having the amino acid sequence of SEQ ID NO: 222; and a heavy chain 125, an H-CDR2 having the amino acid sequence of SEQ ID NO: 126, and an H-CDR3 having the amino acid sequence of SEQ ID NO: 127; or xlvi. a light chain variable region comprising an L-CDR1 having the amino acid sequence of SEQ ID NO: 230, an L-CDR2 having the amino acid sequence of SEQ ID NO: 231, and an L-CDR3 having the amino acid sequence of SEQ ID NO: 232; and a heavy chain variable region comprising an H-CDR1 having the amino acid sequence of SEQ ID NO: 125, an H-CDR2 having the amino acid sequence of SEQ ID NO: 126, and an H-CDR3 having the amino acid sequence of SEQ ID NO: 127; or xlvii. a light chain variable region comprising an L-CDR1 having the amino acid sequence of SEQ ID NO: 240, an L-CDR2 having the amino acid sequence of SEQ ID NO: 241, and an L-CDR3 having the amino acid sequence of SEQ ID NO: 242; and a heavy chain variable region comprising an H-CDR1 having the amino acid sequence of SEQ ID NO: 125, an H-CDR2 having the amino acid sequence of SEQ ID NO: 126, and an H-CDR3 having the amino acid sequence of SEQ ID NO: 127; or xlviii. a light chain variable region comprising an L-CDR1 having the amino acid sequence of SEQ ID NO: 250, an L-CDR2 having the amino acid sequence of SEQ ID NO: 251, and an L-CDR3 having the amino acid sequence of SEQ ID NO: 252; and a heavy chain variable region comprising an H-CDR1 having the amino acid sequence of SEQ ID NO: 125, an H-CDR2 having the amino acid sequence of SEQ ID NO: 126, and an H-CDR3 having the amino acid sequence of SEQ ID NO: 127; or xlix. a light chain variable region comprising an L-CDR1 having the amino acid sequence of SEQ ID NO: 100, an L-CDR2 having the amino acid sequence of SEQ ID NO: 101, and an L-CDR3 having the amino acid sequence of SEQ ID NO: 102; and a heavy chain variable region comprising an H-CDR1 having the amino acid sequence of SEQ ID NO: 135, an H-CDR2 having the amino acid sequence of SEQ ID NO: 136, and an H-CDR3 having the amino acid sequence of SEQ ID NO: 137; or l. a light chain variable region comprising an L-CDR1 having the amino acid sequence of SEQ ID NO: 110, an L-CDR2 having the amino acid sequence of SEQ ID NO: 111, and an L-CDR3 having the amino acid sequence of SEQ ID NO: 112; and a heavy chain variable region comprising an H-CDR1 having the amino acid sequence of SEQ ID NO: 135, an H-CDR2 having the amino acid sequence of SEQ ID NO: 136, and an H-CDR3 having the amino acid sequence of SEQ ID NO: 137; or li. a light chain variable region comprising an L-CDR1 having the amino acid sequence of SEQ ID NO: 120, an L-CDR2 having the amino acid sequence of SEQ ID NO: 121, and an L-CDR3 having the amino acid sequence of SEQ ID NO: 122; and a heavy chain 135, an H-CDR2 having the amino acid sequence of SEQ ID NO: 136, and an H-CDR3 having the amino acid sequence of SEQ ID NO: 137; or lii. a light chain variable region comprising an L-CDR1 having the amino acid sequence of SEQ ID NO: 130, an L-CDR2 having the amino acid sequence of SEQ ID NO: 131, and an L-CDR3 having the amino acid sequence of SEQ ID NO: 132; and a heavy chain variable region comprising an H-CDR1 having the amino acid sequence of SEQ ID NO: 135, an H-CDR2 having the amino acid sequence of SEQ ID NO: 136, and an H-CDR3 having the amino acid sequence of SEQ ID NO: 137; or liii. a light chain variable region comprising an L-CDR1 having the amino acid sequence of SEQ ID NO: 140, an L-CDR2 having the amino acid sequence of SEQ ID NO: 141, and an L-CDR3 having the amino acid sequence of SEQ ID NO: 142; and a heavy chain variable region comprising an H-CDR1 having the amino acid sequence of SEQ ID NO: 135, an H-CDR2 having the amino acid sequence of SEQ ID NO: 136, and an H-CDR3 having the amino acid sequence of SEQ ID NO: 137; or liv. a light chain variable region comprising an L-CDR1 having the amino acid sequence of SEQ ID NO: 150, an L-CDR2 having the amino acid sequence of SEQ ID NO: 151, and an L-CDR3 having the amino acid sequence of SEQ ID NO: 152; and a heavy chain variable region comprising an H-CDR1 having the amino acid sequence of SEQ ID NO: 135, an H-CDR2 having the amino acid sequence of SEQ ID NO: 136, and an H-CDR3 having the amino acid sequence of SEQ ID NO: 137; or lv. a light chain variable region comprising an L-CDR1 having the amino acid sequence of SEQ ID NO: 160, an L-CDR2 having the amino acid sequence of SEQ ID NO: 161, and an L-CDR3 having the amino acid sequence of SEQ ID NO: 162; and a heavy chain variable region comprising an H-CDR1 having the amino acid sequence of SEQ ID NO: 135, an H-CDR2 having the amino acid sequence of SEQ ID NO: 136, and an H-CDR3 having the amino acid sequence of SEQ ID NO: 137; or lvi. a light chain variable region comprising an L-CDR1 having the amino acid sequence of SEQ ID NO: 170, an L-CDR2 having the amino acid sequence of SEQ ID NO: 171, and an L-CDR3 having the amino acid sequence of SEQ ID NO: 172; and a heavy chain variable region comprising an H-CDR1 having the amino acid sequence of SEQ ID NO: 135, an H-CDR2 having the amino acid sequence of SEQ ID NO: 136, and an H-CDR3 having the amino acid sequence of SEQ ID NO: 137; or lvii. a light chain variable region comprising an L-CDR1 having the amino acid sequence of SEQ ID NO: 180, an L-CDR2 having the amino acid sequence of SEQ ID NO: 181, and an L-CDR3 having the amino acid sequence of SEQ ID NO: 182; and a heavy chain 135, an H-CDR2 having the amino acid sequence of SEQ ID NO: 136, and an H-CDR3 having the amino acid sequence of SEQ ID NO: 137; or lviii. a light chain variable region comprising an L-CDR1 having the amino acid sequence of SEQ ID NO: 190, an L-CDR2 having the amino acid sequence of SEQ ID NO: 191, and an L-CDR3 having the amino acid sequence of SEQ ID NO: 192; and a heavy chain variable region comprising an H-CDR1 having the amino acid sequence of SEQ ID NO: 135, an H-CDR2 having the amino acid sequence of SEQ ID NO: 136, and an H-CDR3 having the amino acid sequence of SEQ ID NO: 137; or lix. a light chain variable region comprising an L-CDR1 having the amino acid sequence of SEQ ID NO: 200, an L-CDR2 having the amino acid sequence of SEQ ID NO: 201, and an L-CDR3 having the amino acid sequence of SEQ ID NO: 202; and a heavy chain variable region comprising an H-CDR1 having the amino acid sequence of SEQ ID NO: 135, an H-CDR2 having the amino acid sequence of SEQ ID NO: 136, and an H-CDR3 having the amino acid sequence of SEQ ID NO: 137; or lx. a light chain variable region comprising an L-CDR1 having the amino acid sequence of SEQ ID NO: 210, an L-CDR2 having the amino acid sequence of SEQ ID NO: 211, and an L-CDR3 having the amino acid sequence of SEQ ID NO: 212; and a heavy chain variable region comprising an H-CDR1 having the amino acid sequence of SEQ ID NO: 135, an H-CDR2 having the amino acid sequence of SEQ ID NO: 136, and an H-CDR3 having the amino acid sequence of SEQ ID NO: 137; or lxi. a light chain variable region comprising an L-CDR1 having the amino acid sequence of SEQ ID NO: 220, an L-CDR2 having the amino acid sequence of SEQ ID NO: 221, and an L-CDR3 having the amino acid sequence of SEQ ID NO: 222; and a heavy chain variable region comprising an H-CDR1 having the amino acid sequence of SEQ ID NO: 135, an H-CDR2 having the amino acid sequence of SEQ ID NO: 136, and an H-CDR3 having the amino acid sequence of SEQ ID NO: 137; or lxii. a light chain variable region comprising an L-CDR1 having the amino acid sequence of SEQ ID NO: 230, an L-CDR2 having the amino acid sequence of SEQ ID NO: 231, and an L-CDR3 having the amino acid sequence of SEQ ID NO: 232; and a heavy chain variable region comprising an H-CDR1 having the amino acid sequence of SEQ ID NO: 135, an H-CDR2 having the amino acid sequence of SEQ ID NO: 136, and an H-CDR3 having the amino acid sequence of SEQ ID NO: 137; or lxiii. a light chain variable region comprising an L-CDR1 having the amino acid sequence of SEQ ID NO: 240, an L-CDR2 having the amino acid sequence of SEQ ID NO: 241, and an L-CDR3 having the amino acid sequence of SEQ ID NO: 242; and a heavy chain 135, an H-CDR2 having the amino acid sequence of SEQ ID NO: 136, and an H-CDR3 having the amino acid sequence of SEQ ID NO: 137; or lxiv. a light chain variable region comprising an L-CDR1 having the amino acid sequence of SEQ ID NO: 250, an L-CDR2 having the amino acid sequence of SEQ ID NO: 251, and an L-CDR3 having the amino acid sequence of SEQ ID NO: 252; and a heavy chain variable region comprising an H-CDR1 having the amino acid sequence of SEQ ID NO: 135, an H-CDR2 having the amino acid sequence of SEQ ID NO: 136, and an H-CDR3 having the amino acid sequence of SEQ ID NO: 137; or lxv. a light chain variable region comprising an L-CDR1 having the amino acid sequence of SEQ ID NO: 100, an L-CDR2 having the amino acid sequence of SEQ ID NO: 101, and an L-CDR3 having the amino acid sequence of SEQ ID NO: 102; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or lxvi. a light chain variable region comprising an L-CDR1 having the amino acid sequence of SEQ ID NO: 110, an L-CDR2 having the amino acid sequence of SEQ ID NO: 111, and an L-CDR3 having the amino acid sequence of SEQ ID NO: 112; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or lxvii. a light chain variable region comprising an L-CDR1 having the amino acid sequence of SEQ ID NO: 120, an L-CDR2 having the amino acid sequence of SEQ ID NO: 121, and an L-CDR3 having the amino acid sequence of SEQ ID NO: 122; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or lxviii. a light chain variable region comprising an L-CDR1 having the amino acid sequence of SEQ ID NO: 130, an L-CDR2 having the amino acid sequence of SEQ ID NO: 131, and an L-CDR3 having the amino acid sequence of SEQ ID NO: 132; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or lxix. a light chain variable region comprising an L-CDR1 having the amino acid sequence of SEQ ID NO: 140, an L-CDR2 having the amino acid sequence of SEQ ID NO: 141, and an L-CDR3 having the amino acid sequence of SEQ ID NO: 142; and a heavy chain 145, an H-CDR2 having the amino acid sequence of SEQ ID NO: 146, and an H-CDR3 having the amino acid sequence of SEQ ID NO: 147; or lxx. a light chain variable region comprising an L-CDR1 having the amino acid sequence of SEQ ID NO: 150, an L-CDR2 having the amino acid sequence of SEQ ID NO: 151, and an L-CDR3 having the amino acid sequence of SEQ ID NO: 152; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or lxxi. a light chain variable region comprising an L-CDR1 having the amino acid sequence of SEQ ID NO: 160, an L-CDR2 having the amino acid sequence of SEQ ID NO: 161, and an L-CDR3 having the amino acid sequence of SEQ ID NO: 162; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or lxxii. a light chain variable region comprising an L-CDR1 having the amino acid sequence of SEQ ID NO: 170, an L-CDR2 having the amino acid sequence of SEQ ID NO: 171, and an L-CDR3 having the amino acid sequence of SEQ ID NO: 172; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or lxxiii. a light chain variable region comprising an L-CDR1 having the amino acid sequence of SEQ ID NO: 180, an L-CDR2 having the amino acid sequence of SEQ ID NO: 181, and an L-CDR3 having the amino acid sequence of SEQ ID NO: 182; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or lxxiv. a light chain variable region comprising an L-CDR1 having the amino acid sequence of SEQ ID NO: 190, an L-CDR2 having the amino acid sequence of SEQ ID NO: 191, and an L-CDR3 having the amino acid sequence of SEQ ID NO: 192; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or lxxv. a light chain variable region comprising an L-CDR1 having the amino acid sequence of SEQ ID NO: 200, an L-CDR2 having the amino acid sequence of SEQ ID NO: 201, and an L-CDR3 having the amino acid sequence of SEQ ID NO: 202; and a heavy chain 145, an H-CDR2 having the amino acid sequence of SEQ ID NO: 146, and an H-CDR3 having the amino acid sequence of SEQ ID NO: 147; or lxxvi. a light chain variable region comprising an L-CDR1 having the amino acid sequence of SEQ ID NO: 210, an L-CDR2 having the amino acid sequence of SEQ ID NO: 211, and an L-CDR3 having the amino acid sequence of SEQ ID NO: 212; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or lxxvii. a light chain variable region comprising an L-CDR1 having the amino acid sequence of SEQ ID NO: 220, an L-CDR2 having the amino acid sequence of SEQ ID NO: 221, and an L-CDR3 having the amino acid sequence of SEQ ID NO: 222; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or lxxviii. a light chain variable region comprising an L-CDR1 having the amino acid sequence of SEQ ID NO: 230, an L-CDR2 having the amino acid sequence of SEQ ID NO: 231, and an L-CDR3 having the amino acid sequence of SEQ ID NO: 232; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or lxxix. a light chain variable region comprising an L-CDR1 having the amino acid sequence of SEQ ID NO: 240, an L-CDR2 having the amino acid sequence of SEQ ID NO: 241, and an L-CDR3 having the amino acid sequence of SEQ ID NO: 242; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or lxxx. a light chain variable region comprising an L-CDR1 having the amino acid sequence of SEQ ID NO: 250, an L-CDR2 having the amino acid sequence of SEQ ID NO: 251, and an L-CDR3 having the amino acid sequence of SEQ ID NO: 252; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or lxxxi. a light chain variable region comprising an L-CDR1 having the amino acid sequence of SEQ ID NO: 100, an L-CDR2 having the amino acid sequence of SEQ ID NO: 101, and an L-CDR3 having the amino acid sequence of SEQ ID NO: 102; and a heavy chain 155, an H-CDR2 having the amino acid sequence of SEQ ID NO: 156, and an H-CDR3 having the amino acid sequence of SEQ ID NO: 157; or lxxxii. a light chain variable region comprising an L-CDR1 having the amino acid sequence of SEQ ID NO: 110, an L-CDR2 having the amino acid sequence of SEQ ID NO: 111, and an L-CDR3 having the amino acid sequence of SEQ ID NO: 112; and a heavy chain variable region comprising an H-CDR1 having the amino acid sequence of SEQ ID NO: 155, an H-CDR2 having the amino acid sequence of SEQ ID NO: 156, and an H-CDR3 having the amino acid sequence of SEQ ID NO: 157; or lxxxiii. a light chain variable region comprising an L-CDR1 having the amino acid sequence of SEQ ID NO: 120, an L-CDR2 having the amino acid sequence of SEQ ID NO: 121, and an L-CDR3 having the amino acid sequence of SEQ ID NO: 122; and a heavy chain variable region comprising an H-CDR1 having the amino acid sequence of SEQ ID NO: 155, an H-CDR2 having the amino acid sequence of SEQ ID NO: 156, and an H-CDR3 having the amino acid sequence of SEQ ID NO: 157; or lxxxiv. a light chain variable region comprising an L-CDR1 having the amino acid sequence of SEQ ID NO: 130, an L-CDR2 having the amino acid sequence of SEQ ID NO: 131, and an L-CDR3 having the amino acid sequence of SEQ ID NO: 132; and a heavy chain variable region comprising an H-CDR1 having the amino acid sequence of SEQ ID NO: 155, an H-CDR2 having the amino acid sequence of SEQ ID NO: 156, and an H-CDR3 having the amino acid sequence of SEQ ID NO: 157; or lxxxv. a light chain variable region comprising an L-CDR1 having the amino acid sequence of SEQ ID NO: 140, an L-CDR2 having the amino acid sequence of SEQ ID NO: 141, and an L-CDR3 having the amino acid sequence of SEQ ID NO: 142; and a heavy chain variable region comprising an H-CDR1 having the amino acid sequence of SEQ ID NO: 155, an H-CDR2 having the amino acid sequence of SEQ ID NO: 156, and an H-CDR3 having the amino acid sequence of SEQ ID NO: 157; or lxxxvi. a light chain variable region comprising an L-CDR1 having the amino acid sequence of SEQ ID NO: 150, an L-CDR2 having the amino acid sequence of SEQ ID NO: 151, and an L-CDR3 having the amino acid sequence of SEQ ID NO: 152; and a heavy chain variable region comprising an H-CDR1 having the amino acid sequence of SEQ ID NO: 155, an H-CDR2 having the amino acid sequence of SEQ ID NO: 156, and an H-CDR3 having the amino acid sequence of SEQ ID NO: 157; or lxxxvii. a light chain variable region comprising an L-CDR1 having the amino acid sequence of SEQ ID NO: 160, an L-CDR2 having the amino acid sequence of SEQ ID NO: 161, and an L-CDR3 having the amino acid sequence of SEQ ID NO: 162; and a heavy chain 155, an H-CDR2 having the amino acid sequence of SEQ ID NO: 156, and an H-CDR3 having the amino acid sequence of SEQ ID NO: 157; or lxxxviii. a light chain variable region comprising an L-CDR1 having the amino acid sequence of SEQ ID NO: 170, an L-CDR2 having the amino acid sequence of SEQ ID NO: 171, and an L-CDR3 having the amino acid sequence of SEQ ID NO: 172; and a heavy chain variable region comprising an H-CDR1 having the amino acid sequence of SEQ ID NO: 155, an H-CDR2 having the amino acid sequence of SEQ ID NO: 156, and an H-CDR3 having the amino acid sequence of SEQ ID NO: 157; or lxxxix. a light chain variable region comprising an L-CDR1 having the amino acid sequence of SEQ ID NO: 180, an L-CDR2 having the amino acid sequence of SEQ ID NO: 181, and an L-CDR3 having the amino acid sequence of SEQ ID NO: 182; and a heavy chain variable region comprising an H-CDR1 having the amino acid sequence of SEQ ID NO: 155, an H-CDR2 having the amino acid sequence of SEQ ID NO: 156, and an H-CDR3 having the amino acid sequence of SEQ ID NO: 157; or xc. a light chain variable region comprising an L-CDR1 having the amino acid sequence of SEQ ID NO: 190, an L-CDR2 having the amino acid sequence of SEQ ID NO: 191, and an L-CDR3 having the amino acid sequence of SEQ ID NO: 192; and a heavy chain variable region comprising an H-CDR1 having the amino acid sequence of SEQ ID NO: 155, an H-CDR2 having the amino acid sequence of SEQ ID NO: 156, and an H-CDR3 having the amino acid sequence of SEQ ID NO: 157; or xci. a light chain variable region comprising an L-CDR1 having the amino acid sequence of SEQ ID NO: 200, an L-CDR2 having the amino acid sequence of SEQ ID NO: 201, and an L-CDR3 having the amino acid sequence of SEQ ID NO: 202; and a heavy chain variable region comprising an H-CDR1 having the amino acid sequence of SEQ ID NO: 155, an H-CDR2 having the amino acid sequence of SEQ ID NO: 156, and an H-CDR3 having the amino acid sequence of SEQ ID NO: 157; or xcii. a light chain variable region comprising an L-CDR1 having the amino acid sequence of SEQ ID NO: 210, an L-CDR2 having the amino acid sequence of SEQ ID NO: 211, and an L-CDR3 having the amino acid sequence of SEQ ID NO: 212; and a heavy chain variable region comprising an H-CDR1 having the amino acid sequence of SEQ ID NO: 155, an H-CDR2 having the amino acid sequence of SEQ ID NO: 156, and an H-CDR3 having the amino acid sequence of SEQ ID NO: 157; or xciii. a light chain variable region comprising an L-CDR1 having the amino acid sequence of SEQ ID NO: 220, an L-CDR2 having the amino acid sequence of SEQ ID NO: 221, and an L-CDR3 having the amino acid sequence of SEQ ID NO: 222; and a heavy chain 155, an H-CDR2 having the amino acid sequence of SEQ ID NO: 156, and an H-CDR3 having the amino acid sequence of SEQ ID NO: 157; or xciv. a light chain variable region comprising an L-CDR1 having the amino acid sequence of SEQ ID NO: 230, an L-CDR2 having the amino acid sequence of SEQ ID NO: 231, and an L-CDR3 having the amino acid sequence of SEQ ID NO: 232; and a heavy chain variable region comprising an H-CDR1 having the amino acid sequence of SEQ ID NO: 155, an H-CDR2 having the amino acid sequence of SEQ ID NO: 156, and an H-CDR3 having the amino acid sequence of SEQ ID NO: 157; or xcv. a light chain variable region comprising an L-CDR1 having the amino acid sequence of SEQ ID NO: 240, an L-CDR2 having the amino acid sequence of SEQ ID NO: 241, and an L-CDR3 having the amino acid sequence of SEQ ID NO: 242; and a heavy chain variable region comprising an H-CDR1 having the amino acid sequence of SEQ ID NO: 155, an H-CDR2 having the amino acid sequence of SEQ ID NO: 156, and an H-CDR3 having the amino acid sequence of SEQ ID NO: 157; or xcvi. a light chain variable region comprising an L-CDR1 having the amino acid sequence of SEQ ID NO: 250, an L-CDR2 having the amino acid sequence of SEQ ID NO: 251, and an L-CDR3 having the amino acid sequence of SEQ ID NO: 252; and a heavy chain variable region comprising an H-CDR1 having the amino acid sequence of SEQ ID NO: 155, an H-CDR2 having the amino acid sequence of SEQ ID NO: 156, and an H-CDR3 having the amino acid sequence of SEQ ID NO: 157; or xcvii. a light chain variable region comprising an L-CDR1 having the amino acid sequence of SEQ ID NO: 100, an L-CDR2 having the amino acid sequence of SEQ ID NO: 101, and an L-CDR3 having the amino acid sequence of SEQ ID NO: 102; and a heavy chain variable region comprising an H-CDR1 having the amino acid sequence of SEQ ID NO: 165, an H-CDR2 having the amino acid sequence of SEQ ID NO: 166, and an H-CDR3 having the amino acid sequence of SEQ ID NO: 167; or xcviii. a light chain variable region comprising an L-CDR1 having the amino acid sequence of SEQ ID NO: 110, an L-CDR2 having the amino acid sequence of SEQ ID NO: 111, and an L-CDR3 having the amino acid sequence of SEQ ID NO: 112; and a heavy chain variable region comprising an H-CDR1 having the amino acid sequence of SEQ ID NO: 165, an H-CDR2 having the amino acid sequence of SEQ ID NO: 166, and an H-CDR3 having the amino acid sequence of SEQ ID NO: 167; or xcix. a light chain variable region comprising an L-CDR1 having the amino acid sequence of SEQ ID NO: 120, an L-CDR2 having the amino acid sequence of SEQ ID NO: 121, and an L-CDR3 having the amino acid sequence of SEQ ID NO: 122; and a heavy chain 165, an H-CDR2 having the amino acid sequence of SEQ ID NO: 166, and an H-CDR3 having the amino acid sequence of SEQ ID NO: 167; or c. a light chain variable region comprising an L-CDR1 having the amino acid sequence of SEQ ID NO: 130, an L-CDR2 having the amino acid sequence of SEQ ID NO: 131, and an L-CDR3 having the amino acid sequence of SEQ ID NO: 132; and a heavy chain variable region comprising an H-CDR1 having the amino acid sequence of SEQ ID NO: 165, an H-CDR2 having the amino acid sequence of SEQ ID NO: 166, and an H-CDR3 having the amino acid sequence of SEQ ID NO: 167; or ci. a light chain variable region comprising an L-CDR1 having the amino acid sequence of SEQ ID NO: 140, an L-CDR2 having the amino acid sequence of SEQ ID NO: 141, and an L-CDR3 having the amino acid sequence of SEQ ID NO: 142; and a heavy chain variable region comprising an H-CDR1 having the amino acid sequence of SEQ ID NO: 165, an H-CDR2 having the amino acid sequence of SEQ ID NO: 166, and an H-CDR3 having the amino acid sequence of SEQ ID NO: 167; or cii. a light chain variable region comprising an L-CDR1 having the amino acid sequence of SEQ ID NO: 150, an L-CDR2 having the amino acid sequence of SEQ ID NO: 151, and an L-CDR3 having the amino acid sequence of SEQ ID NO: 152; and a heavy chain variable region comprising an H-CDR1 having the amino acid sequence of SEQ ID NO: 165, an H-CDR2 having the amino acid sequence of SEQ ID NO: 166, and an H-CDR3 having the amino acid sequence of SEQ ID NO: 167; or ciii. a light chain variable region comprising an L-CDR1 having the amino acid sequence of SEQ ID NO: 160, an L-CDR2 having the amino acid sequence of SEQ ID NO: 161, and an L-CDR3 having the amino acid sequence of SEQ ID NO: 162; and a heavy chain variable region comprising an H-CDR1 having the amino acid sequence of SEQ ID NO: 165, an H-CDR2 having the amino acid sequence of SEQ ID NO: 166, and an H-CDR3 having the amino acid sequence of SEQ ID NO: 167; or civ. a light chain variable region comprising an L-CDR1 having the amino acid sequence of SEQ ID NO: 170, an L-CDR2 having the amino acid sequence of SEQ ID NO: 171, and an L-CDR3 having the amino acid sequence of SEQ ID NO: 172; and a heavy chain variable region comprising an H-CDR1 having the amino acid sequence of SEQ ID NO: 165, an H-CDR2 having the amino acid sequence of SEQ ID NO: 166, and an H-CDR3 having the amino acid sequence of SEQ ID NO: 167; or cv. a light chain variable region comprising an L-CDR1 having the amino acid sequence of SEQ ID NO: 180, an L-CDR2 having the amino acid sequence of SEQ ID NO: 181, and an L-CDR3 having the amino acid sequence of SEQ ID NO: 182; and a heavy chain 165, an H-CDR2 having the amino acid sequence of SEQ ID NO: 166, and an H-CDR3 having the amino acid sequence of SEQ ID NO: 167; or cvi. a light chain variable region comprising an L-CDR1 having the amino acid sequence of SEQ ID NO: 190, an L-CDR2 having the amino acid sequence of SEQ ID NO: 191, and an L-CDR3 having the amino acid sequence of SEQ ID NO: 192; and a heavy chain variable region comprising an H-CDR1 having the amino acid sequence of SEQ ID NO: 165, an H-CDR2 having the amino acid sequence of SEQ ID NO: 166, and an H-CDR3 having the amino acid sequence of SEQ ID NO: 167; or cvii. a light chain variable region comprising an L-CDR1 having the amino acid sequence of SEQ ID NO: 200, an L-CDR2 having the amino acid sequence of SEQ ID NO: 201, and an L-CDR3 having the amino acid sequence of SEQ ID NO: 202; and a heavy chain variable region comprising an H-CDR1 having the amino acid sequence of SEQ ID NO: 165, an H-CDR2 having the amino acid sequence of SEQ ID NO: 166, and an H-CDR3 having the amino acid sequence of SEQ ID NO: 167; or cviii. a light chain variable region comprising an L-CDR1 having the amino acid sequence of SEQ ID NO: 210, an L-CDR2 having the amino acid sequence of SEQ ID NO: 211, and an L-CDR3 having the amino acid sequence of SEQ ID NO: 212; and a heavy chain variable region comprising an H-CDR1 having the amino acid sequence of SEQ ID NO: 165, an H-CDR2 having the amino acid sequence of SEQ ID NO: 166, and an H-CDR3 having the amino acid sequence of SEQ ID NO: 167; or cix. a light chain variable region comprising an L-CDR1 having the amino acid sequence of SEQ ID NO: 220, an L-CDR2 having the amino acid sequence of SEQ ID NO: 221, and an L-CDR3 having the amino acid sequence of SEQ ID NO: 222; and a heavy chain variable region comprising an H-CDR1 having the amino acid sequence of SEQ ID NO: 165, an H-CDR2 having the amino acid sequence of SEQ ID NO: 166, and an H-CDR3 having the amino acid sequence of SEQ ID NO: 167; or cx. a light chain variable region comprising an L-CDR1 having the amino acid sequence of SEQ ID NO: 230, an L-CDR2 having the amino acid sequence of SEQ ID NO: 231, and an L-CDR3 having the amino acid sequence of SEQ ID NO: 232; and a heavy chain variable region comprising an H-CDR1 having the amino acid sequence of SEQ ID NO: 165, an H-CDR2 having the amino acid sequence of SEQ ID NO: 166, and an H-CDR3 having the amino acid sequence of SEQ ID NO: 167; or cxi. a light chain variable region comprising an L-CDR1 having the amino acid sequence of SEQ ID NO: 240, an L-CDR2 having the amino acid sequence of SEQ ID NO: 241, and an L-CDR3 having the amino acid sequence of SEQ ID NO: 242; and a heavy chain 165, an H-CDR2 having the amino acid sequence of SEQ ID NO: 166, and an H-CDR3 having the amino acid sequence of SEQ ID NO: 167; or cxii. a light chain variable region comprising an L-CDR1 having the amino acid sequence of SEQ ID NO: 250, an L-CDR2 having the amino acid sequence of SEQ ID NO: 251, and an L-CDR3 having the amino acid sequence of SEQ ID NO: 252; and a heavy chain variable region comprising an H-CDR1 having the amino acid sequence of SEQ ID NO: 165, an H-CDR2 having the amino acid sequence of SEQ ID NO: 166, and an H-CDR3 having the amino acid sequence of SEQ ID NO: 167; or cxiii. a light chain variable region comprising an L-CDR1 having the amino acid sequence of SEQ ID NO: 100, an L-CDR2 having the amino acid sequence of SEQ ID NO: 101, and an L-CDR3 having the amino acid sequence of SEQ ID NO: 102; and a heavy chain variable region comprising an H-CDR1 having the amino acid sequence of SEQ ID NO: 175, an H-CDR2 having the amino acid sequence of SEQ ID NO: 176, and an H-CDR3 having the amino acid sequence of SEQ ID NO: 177; or cxiv. a light chain variable region comprising an L-CDR1 having the amino acid sequence of SEQ ID NO: 110, an L-CDR2 having the amino acid sequence of SEQ ID NO: 111, and an L-CDR3 having the amino acid sequence of SEQ ID NO: 112; and a heavy chain variable region comprising an H-CDR1 having the amino acid sequence of SEQ ID NO: 175, an H-CDR2 having the amino acid sequence of SEQ ID NO: 176, and an H-CDR3 having the amino acid sequence of SEQ ID NO: 177; or cxv. a light chain variable region comprising an L-CDR1 having the amino acid sequence of SEQ ID NO: 120, an L-CDR2 having the amino acid sequence of SEQ ID NO: 121, and an L-CDR3 having the amino acid sequence of SEQ ID NO: 122; and a heavy chain variable region comprising an H-CDR1 having the amino acid sequence of SEQ ID NO: 175, an H-CDR2 having the amino acid sequence of SEQ ID NO: 176, and an H-CDR3 having the amino acid sequence of SEQ ID NO: 177; or cxvi. a light chain variable region comprising an L-CDR1 having the amino acid sequence of SEQ ID NO: 130, an L-CDR2 having the amino acid sequence of SEQ ID NO: 131, and an L-CDR3 having the amino acid sequence of SEQ ID NO: 132; and a heavy chain variable region comprising an H-CDR1 having the amino acid sequence of SEQ ID NO: 175, an H-CDR2 having the amino acid sequence of SEQ ID NO: 176, and an H-CDR3 having the amino acid sequence of SEQ ID NO: 177; or cxvii. a light chain variable region comprising an L-CDR1 having the amino acid sequence of SEQ ID NO: 140, an L-CDR2 having the amino acid sequence of SEQ ID NO: 141, and an L-CDR3 having the amino acid sequence of SEQ ID NO: 142; and a heavy chain 175, an H-CDR2 having the amino acid sequence of SEQ ID NO: 176, and an H-CDR3 having the amino acid sequence of SEQ ID NO: 177; or cxviii. a light chain variable region comprising an L-CDR1 having the amino acid sequence of SEQ ID NO: 150, an L-CDR2 having the amino acid sequence of SEQ ID NO: 151, and an L-CDR3 having the amino acid sequence of SEQ ID NO: 152; and a heavy chain variable region comprising an H-CDR1 having the amino acid sequence of SEQ ID NO: 175, an H-CDR2 having the amino acid sequence of SEQ ID NO: 176, and an H-CDR3 having the amino acid sequence of SEQ ID NO: 177; or cxix. a light chain variable region comprising an L-CDR1 having the amino acid sequence of SEQ ID NO: 160, an L-CDR2 having the amino acid sequence of SEQ ID NO: 161, and an L-CDR3 having the amino acid sequence of SEQ ID NO: 162; and a heavy chain variable region comprising an H-CDR1 having the amino acid sequence of SEQ ID NO: 175, an H-CDR2 having the amino acid sequence of SEQ ID NO: 176, and an H-CDR3 having the amino acid sequence of SEQ ID NO: 177; or cxx. a light chain variable region comprising an L-CDR1 having the amino acid sequence of SEQ ID NO: 170, an L-CDR2 having the amino acid sequence of SEQ ID NO: 171, and an L-CDR3 having the amino acid sequence of SEQ ID NO: 172; and a heavy chain variable region comprising an H-CDR1 having the amino acid sequence of SEQ ID NO: 175, an H-CDR2 having the amino acid sequence of SEQ ID NO: 176, and an H-CDR3 having the amino acid sequence of SEQ ID NO: 177; or cxxi. a light chain variable region comprising an L-CDR1 having the amino acid sequence of SEQ ID NO: 180, an L-CDR2 having the amino acid sequence of SEQ ID NO: 181, and an L-CDR3 having the amino acid sequence of SEQ ID NO: 182; and a heavy chain variable region comprising an H-CDR1 having the amino acid sequence of SEQ ID NO: 175, an H-CDR2 having the amino acid sequence of SEQ ID NO: 176, and an H-CDR3 having the amino acid sequence of SEQ ID NO: 177; or cxxii. a light chain variable region comprising an L-CDR1 having the amino acid sequence of SEQ ID NO: 190, an L-CDR2 having the amino acid sequence of SEQ ID NO: 191, and an L-CDR3 having the amino acid sequence of SEQ ID NO: 192; and a heavy chain variable region comprising an H-CDR1 having the amino acid sequence of SEQ ID NO: 175, an H-CDR2 having the amino acid sequence of SEQ ID NO: 176, and an H-CDR3 having the amino acid sequence of SEQ ID NO: 177; or cxxiii. a light chain variable region comprising an L-CDR1 having the amino acid sequence of SEQ ID NO: 200, an L-CDR2 having the amino acid sequence of SEQ ID NO: 201, and an L-CDR3 having the amino acid sequence of SEQ ID NO: 202; and a heavy chain 175, an H-CDR2 having the amino acid sequence of SEQ ID NO: 176, and an H-CDR3 having the amino acid sequence of SEQ ID NO: 177; or cxxiv. a light chain variable region comprising an L-CDR1 having the amino acid sequence of SEQ ID NO: 210, an L-CDR2 having the amino acid sequence of SEQ ID NO: 211, and an L-CDR3 having the amino acid sequence of SEQ ID NO: 212; and a heavy chain variable region comprising an H-CDR1 having the amino acid sequence of SEQ ID NO: 175, an H-CDR2 having the amino acid sequence of SEQ ID NO: 176, and an H-CDR3 having the amino acid sequence of SEQ ID NO: 177; or cxxv. a light chain variable region comprising an L-CDR1 having the amino acid sequence of SEQ ID NO: 220, an L-CDR2 having the amino acid sequence of SEQ ID NO: 221, and an L-CDR3 having the amino acid sequence of SEQ ID NO: 222; and a heavy chain variable region comprising an H-CDR1 having the amino acid sequence of SEQ ID NO: 175, an H-CDR2 having the amino acid sequence of SEQ ID NO: 176, and an H-CDR3 having the amino acid sequence of SEQ ID NO: 177; or cxxvi. a light chain variable region comprising an L-CDR1 having the amino acid sequence of SEQ ID NO: 230, an L-CDR2 having the amino acid sequence of SEQ ID NO: 231, and an L-CDR3 having the amino acid sequence of SEQ ID NO: 232; and a heavy chain variable region comprising an H-CDR1 having the amino acid sequence of SEQ ID NO: 175, an H-CDR2 having the amino acid sequence of SEQ ID NO: 176, and an H-CDR3 having the amino acid sequence of SEQ ID NO: 177; or cxxvii. a light chain variable region comprising an L-CDR1 having the amino acid sequence of SEQ ID NO: 240, an L-CDR2 having the amino acid sequence of SEQ ID NO: 241, and an L-CDR3 having the amino acid sequence of SEQ ID NO: 242; and a heavy chain variable region comprising an H-CDR1 having the amino acid sequence of SEQ ID NO: 175, an H-CDR2 having the amino acid sequence of SEQ ID NO: 176, and an H-CDR3 having the amino acid sequence of SEQ ID NO: 177.

3. The anti-CTGF antibody or an antigen-binding fragment thereof according to any one of the foregoing paras, wherein the anti-CTGF antibody or an antigen-binding fragment thereof comprises:

i. a light chain variable region comprising an amino acid sequence at least 95% identical to the amino acid sequence of SEQ ID NO: 223, and a heavy chain variable region comprising an amino acid sequence at least 95% identical to the amino acid sequence of SEQ ID NO: 108; or ii. a light chain variable region comprising an amino acid sequence at least 95% identical to the amino acid sequence of SEQ ID NO: 103, and a heavy chain variable region comprising an amino acid sequence at least 95% identical to the amino acid sequence of SEQ ID NO: 108; or iii. a light chain variable region comprising an amino acid sequence at least 95% identical to the amino acid sequence of SEQ ID NO: 113, and a heavy chain variable region comprising an amino acid sequence at least 95% identical to the amino acid sequence of SEQ ID NO: 108; or iv. a light chain variable region comprising an amino acid sequence at least 95% identical to the amino acid sequence of SEQ ID NO: 123, and a heavy chain variable region comprising an amino acid sequence at least 95% identical to the amino acid sequence of SEQ ID NO: 108; or v. a light chain variable region comprising an amino acid sequence at least 95% identical to the amino acid sequence of SEQ ID NO: 133, and a heavy chain variable region comprising an amino acid sequence at least 95% identical to the amino acid sequence of SEQ ID NO: 108; or vi. a light chain variable region comprising an amino acid sequence at least 95% identical to the amino acid sequence of SEQ ID NO: 143, and a heavy chain variable region comprising an amino acid sequence at least 95% identical to the amino acid sequence of SEQ ID NO: 108; or vii. a light chain variable region comprising an amino acid sequence at least 95% identical to the amino acid sequence of SEQ ID NO: 153, and a heavy chain variable region comprising an amino acid sequence at least 95% identical to the amino acid sequence of SEQ ID NO: 108; or viii. a light chain variable region comprising an amino acid sequence at least 95% identical to the amino acid sequence of SEQ ID NO: 163, and a heavy chain variable region comprising an amino acid sequence at least 95% identical to the amino acid sequence of SEQ ID NO: 108; or ix. a light chain variable region comprising an amino acid sequence at least 95% identical to the amino acid sequence of SEQ ID NO: 173, and a heavy chain variable region comprising an amino acid sequence at least 95% identical to the amino acid sequence of SEQ ID NO: 108; or x. a light chain variable region comprising an amino acid sequence at least 95% identical to the amino acid sequence of SEQ ID NO: 183, and a heavy chain variable region comprising an amino acid sequence at least 95% identical to the amino acid sequence of SEQ ID NO: 108; or xi. a light chain variable region comprising an amino acid sequence at least 95% identical to the amino acid sequence of SEQ ID NO: 193, and a heavy chain variable region comprising an amino acid sequence at least 95% identical to the amino acid sequence of SEQ ID NO: 108; or xii. a light chain variable region comprising an amino acid sequence at least 95% identical to the amino acid sequence of SEQ ID NO: 203, and a heavy chain variable region comprising an amino acid sequence at least 95% identical to the amino acid sequence of SEQ ID NO: 108; or xiii. a light chain variable region comprising an amino acid sequence at least 95% identical to the amino acid sequence of SEQ ID NO: 213, and a heavy chain variable region comprising an amino acid sequence at least 95% identical to the amino acid sequence of SEQ ID NO: 108; or xiv. a light chain variable region comprising an amino acid sequence at least 95% identical to the amino acid sequence of SEQ ID NO: 233, and a heavy chain variable region comprising an amino acid sequence at least 95% identical to the amino acid sequence of SEQ ID NO: 108; or xv. a light chain variable region comprising an amino acid sequence at least 95% identical to the amino acid sequence of SEQ ID NO: 243, and a heavy chain variable region comprising an amino acid sequence at least 95% identical to the amino acid sequence of SEQ ID NO: 108; or xvi. a light chain variable region comprising an amino acid sequence at least 95% identical to the amino acid sequence of SEQ ID NO: 253, and a heavy chain variable region comprising an amino acid sequence at least 95% identical to the amino acid sequence of SEQ ID NO: 108; or xvii. a light chain variable region comprising an amino acid sequence at least 95% identical to the amino acid sequence of SEQ ID NO: 103, and a heavy chain variable region comprising an amino acid sequence at least 95% identical to the amino acid sequence of SEQ ID NO: 118; or xviii. a light chain variable region comprising an amino acid sequence at least 95% identical to the amino acid sequence of SEQ ID NO: 113, and a heavy chain variable region comprising an amino acid sequence at least 95% identical to the amino acid sequence of SEQ ID NO: 118; or xix. a light chain variable region comprising an amino acid sequence at least 95% identical to the amino acid sequence of SEQ ID NO: 123, and a heavy chain variable region comprising an amino acid sequence at least 95% identical to the amino acid sequence of SEQ ID NO: 118; or xx. a light chain variable region comprising an amino acid sequence at least 95% identical to the amino acid sequence of SEQ ID NO: 133, and a heavy chain variable region comprising an amino acid sequence at least 95% identical to the amino acid sequence of SEQ ID NO: 118; or xxi. a light chain variable region comprising an amino acid sequence at least 95% identical to the amino acid sequence of SEQ ID NO: 143, and a heavy chain variable region comprising an amino acid sequence at least 95% identical to the amino acid sequence of SEQ ID NO: 118; or xxii. a light chain variable region comprising an amino acid sequence at least 95% identical to the amino acid sequence of SEQ ID NO: 153, and a heavy chain variable region comprising an amino acid sequence at least 95% identical to the amino acid sequence of SEQ ID NO: 118; or xxiii. a light chain variable region comprising an amino acid sequence at least 95% identical to the amino acid sequence of SEQ ID NO: 163, and a heavy chain variable region comprising an amino acid sequence at least 95% identical to the amino acid sequence of SEQ ID NO: 118; or xxiv. a light chain variable region comprising an amino acid sequence at least 95% identical to the amino acid sequence of SEQ ID NO: 173, and a heavy chain variable region comprising an amino acid sequence at least 95% identical to the amino acid sequence of SEQ ID NO: 118; or xxv. a light chain variable region comprising an amino acid sequence at least 95% identical to the amino acid sequence of SEQ ID NO: 183, and a heavy chain variable region comprising an amino acid sequence at least 95% identical to the amino acid sequence of SEQ ID NO: 118; or xxvi. a light chain variable region comprising an amino acid sequence at least 95% identical to the amino acid sequence of SEQ ID NO: 193, and a heavy chain variable region comprising an amino acid sequence at least 95% identical to the amino acid sequence of SEQ ID NO: 118; or xxvii. a light chain variable region comprising an amino acid sequence at least 95% identical to the amino acid sequence of SEQ ID NO: 203, and a heavy chain variable region comprising an amino acid sequence at least 95% identical to the amino acid sequence of SEQ ID NO: 118; or xxviii. a light chain variable region comprising an amino acid sequence at least 95% identical to the amino acid sequence of SEQ ID NO: 213, and a heavy chain variable region comprising an amino acid sequence at least 95% identical to the amino acid sequence of SEQ ID NO: 118; or xxix. a light chain variable region comprising an amino acid sequence at least 95% identical to the amino acid sequence of SEQ ID NO: 223, and a heavy chain variable region comprising an amino acid sequence at least 95% identical to the amino acid sequence of SEQ ID NO: 118; or xxx. a light chain variable region comprising an amino acid sequence at least 95% identical to the amino acid sequence of SEQ ID NO: 233, and a heavy chain variable region comprising an amino acid sequence at least 95% identical to the amino acid sequence of SEQ ID NO: 118; or xxxi. a light chain variable region comprising an amino acid sequence at least 95% identical to the amino acid sequence of SEQ ID NO: 243, and a heavy chain variable region comprising an amino acid sequence at least 95% identical to the amino acid sequence of SEQ ID NO: 118; or xxxii. a light chain variable region comprising an amino acid sequence at least 95% identical to the amino acid sequence of SEQ ID NO: 253, and a heavy chain variable region comprising an amino acid sequence at least 95% identical to the amino acid sequence of SEQ ID NO: 118; or xxxiii. a light chain variable region comprising an amino acid sequence at least 95% identical to the amino acid sequence of SEQ ID NO: 103, and a heavy chain variable region comprising an amino acid sequence at least 95% identical to the amino acid sequence of SEQ ID NO: 128; or xxxiv. a light chain variable region comprising an amino acid sequence at least 95% identical to the amino acid sequence of SEQ ID NO: 113, and a heavy chain variable region comprising an amino acid sequence at least 95% identical to the amino acid sequence of SEQ ID NO: 128; or xxxv. a light chain variable region comprising an amino acid sequence at least 95% identical to the amino acid sequence of SEQ ID NO: 123, and a heavy chain variable region comprising an amino acid sequence at least 95% identical to the amino acid sequence of SEQ ID NO: 128; or xxxvi. a light chain variable region comprising an amino acid sequence at least 95% identical to the amino acid sequence of SEQ ID NO: 133, and a heavy chain variable region comprising an amino acid sequence at least 95% identical to the amino acid sequence of SEQ ID NO: 128; or xxxvii. a light chain variable region comprising an amino acid sequence at least 95% identical to the amino acid sequence of SEQ ID NO: 143, and a heavy chain variable region comprising an amino acid sequence at least 95% identical to the amino acid sequence of SEQ ID NO: 128; or xxxviii. a light chain variable region comprising an amino acid sequence at least 95% identical to the amino acid sequence of SEQ ID NO: 153, and a heavy chain variable region comprising an amino acid sequence at least 95% identical to the amino acid sequence of SEQ ID NO: 128; or xxxix. a light chain variable region comprising an amino acid sequence at least 95% identical to the amino acid sequence of SEQ ID NO: 163, and a heavy chain variable region comprising an amino acid sequence at least 95% identical to the amino acid sequence of SEQ ID NO: 128; or xl. a light chain variable region comprising an amino acid sequence at least 95% identical to the amino acid sequence of SEQ ID NO: 173, and a heavy chain variable region comprising an amino acid sequence at least 95% identical to the amino acid sequence of SEQ ID NO: 128; or xli. a light chain variable region comprising an amino acid sequence at least 95% identical to the amino acid sequence of SEQ ID NO: 183, and a heavy chain variable region comprising an amino acid sequence at least 95% identical to the amino acid sequence of SEQ ID NO: 128; or xlii. a light chain variable region comprising an amino acid sequence at least 95% identical to the amino acid sequence of SEQ ID NO: 193, and a heavy chain variable region comprising an amino acid sequence at least 95% identical to the amino acid sequence of SEQ ID NO: 128; or xliii. a light chain variable region comprising an amino acid sequence at least 95% identical to the amino acid sequence of SEQ ID NO: 203, and a heavy chain variable region comprising an amino acid sequence at least 95% identical to the amino acid sequence of SEQ ID NO: 128; or xliv. a light chain variable region comprising an amino acid sequence at least 95% identical to the amino acid sequence of SEQ ID NO: 213, and a heavy chain variable region comprising an amino acid sequence at least 95% identical to the amino acid sequence of SEQ ID NO: 128; or xlv. a light chain variable region comprising an amino acid sequence at least 95% identical to the amino acid sequence of SEQ ID NO: 223, and a heavy chain variable region comprising an amino acid sequence at least 95% identical to the amino acid sequence of SEQ ID NO: 128; or xlvi. a light chain variable region comprising an amino acid sequence at least 95% identical to the amino acid sequence of SEQ ID NO: 233, and a heavy chain variable region comprising an amino acid sequence at least 95% identical to the amino acid sequence of SEQ ID NO: 128; or xlvii. a light chain variable region comprising an amino acid sequence at least 95% identical to the amino acid sequence of SEQ ID NO: 243, and a heavy chain variable region comprising an amino acid sequence at least 95% identical to the amino acid sequence of SEQ ID NO: 128; or xlviii. a light chain variable region comprising an amino acid sequence at least 95% identical to the amino acid sequence of SEQ ID NO: 253, and a heavy chain variable region comprising an amino acid sequence at least 95% identical to the amino acid sequence of SEQ ID NO: 128; or xlix. a light chain variable region comprising an amino acid sequence at least 95% identical to the amino acid sequence of SEQ ID NO: 103, and a heavy chain variable region comprising an amino acid sequence at least 95% identical to the amino acid sequence of SEQ ID NO: 138; or l. a light chain variable region comprising an amino acid sequence at least 95% identical to the amino acid sequence of SEQ ID NO: 113, and a heavy chain variable region comprising an amino acid sequence at least 95% identical to the amino acid sequence of SEQ ID NO: 138; or li. a light chain variable region comprising an amino acid sequence at least 95% identical to the amino acid sequence of SEQ ID NO: 123, and a heavy chain variable region comprising an amino acid sequence at least 95% identical to the amino acid sequence of SEQ ID NO: 138; or lii. a light chain variable region comprising an amino acid sequence at least 95% identical to the amino acid sequence of SEQ ID NO: 133, and a heavy chain variable region comprising an amino acid sequence at least 95% identical to the amino acid sequence of SEQ ID NO: 138; or liii. a light chain variable region comprising an amino acid sequence at least 95% identical to the amino acid sequence of SEQ ID NO: 143, and a heavy chain variable region comprising an amino acid sequence at least 95% identical to the amino acid sequence of SEQ ID NO: 138; or liv. a light chain variable region comprising an amino acid sequence at least 95% identical to the amino acid sequence of SEQ ID NO: 153, and a heavy chain variable region comprising an amino acid sequence at least 95% identical to the amino acid sequence of SEQ ID NO: 138; or lv. a light chain variable region comprising an amino acid sequence at least 95% identical to the amino acid sequence of SEQ ID NO: 163, and a heavy chain variable region comprising an amino acid sequence at least 95% identical to the amino acid sequence of SEQ ID NO: 138; or lvi. a light chain variable region comprising an amino acid sequence at least 95% identical to the amino acid sequence of SEQ ID NO: 173, and a heavy chain variable region comprising an amino acid sequence at least 95% identical to the amino acid sequence of SEQ ID NO: 138; or lvii. a light chain variable region comprising an amino acid sequence at least 95% identical to the amino acid sequence of SEQ ID NO: 183, and a heavy chain variable region comprising an amino acid sequence at least 95% identical to the amino acid sequence of SEQ ID NO: 138; or lviii. a light chain variable region comprising an amino acid sequence at least 95% identical to the amino acid sequence of SEQ ID NO: 193, and a heavy chain variable region comprising an amino acid sequence at least 95% identical to the amino acid sequence of SEQ ID NO: 138; or lix. a light chain variable region comprising an amino acid sequence at least 95% identical to the amino acid sequence of SEQ ID NO: 203, and a heavy chain variable region comprising an amino acid sequence at least 95% identical to the amino acid sequence of SEQ ID NO: 138; or lx. a light chain variable region comprising an amino acid sequence at least 95% identical to the amino acid sequence of SEQ ID NO: 213, and a heavy chain variable region comprising an amino acid sequence at least 95% identical to the amino acid sequence of SEQ ID NO: 138; or lxi. a light chain variable region comprising an amino acid sequence at least 95% identical to the amino acid sequence of SEQ ID NO: 223, and a heavy chain variable region comprising an amino acid sequence at least 95% identical to the amino acid sequence of SEQ ID NO: 138; or lxii. a light chain variable region comprising an amino acid sequence at least 95% identical to the amino acid sequence of SEQ ID NO: 233, and a heavy chain variable region comprising an amino acid sequence at least 95% identical to the amino acid sequence of SEQ ID NO: 138; or lxiii. a light chain variable region comprising an amino acid sequence at least 95% identical to the amino acid sequence of SEQ ID NO: 243, and a heavy chain variable region comprising an amino acid sequence at least 95% identical to the amino acid sequence of SEQ ID NO: 138; or lxiv. a light chain variable region comprising an amino acid sequence at least 95% identical to the amino acid sequence of SEQ ID NO: 253, and a heavy chain variable region comprising an amino acid sequence at least 95% identical to the amino acid sequence of SEQ ID NO: 138; or lxv. a light chain variable region comprising an amino acid sequence at least 95% identical to the amino acid sequence of SEQ ID NO: 103, and a heavy chain variable region comprising an amino acid sequence at least 95% identical to the amino acid sequence of SEQ ID NO: 148; or lxvi. a light chain variable region comprising an amino acid sequence at least 95% identical to the amino acid sequence of SEQ ID NO: 113, and a heavy chain variable region comprising an amino acid sequence at least 95% identical to the amino acid sequence of SEQ ID NO: 148; or lxvii. a light chain variable region comprising an amino acid sequence at least 95% identical to the amino acid sequence of SEQ ID NO: 123, and a heavy chain variable region comprising an amino acid sequence at least 95% identical to the amino acid sequence of SEQ ID NO: 148; or lxviii. a light chain variable region comprising an amino acid sequence at least 95% identical to the amino acid sequence of SEQ ID NO: 133, and a heavy chain variable region comprising an amino acid sequence at least 95% identical to the amino acid sequence of SEQ ID NO: 148; or lxix. a light chain variable region comprising an amino acid sequence at least 95% identical to the amino acid sequence of SEQ ID NO: 143, and a heavy chain variable region comprising an amino acid sequence at least 95% identical to the amino acid sequence of SEQ ID NO: 148; or lxx. a light chain variable region comprising an amino acid sequence at least 95% identical to the amino acid sequence of SEQ ID NO: 153, and a heavy chain variable region comprising an amino acid sequence at least 95% identical to the amino acid sequence of SEQ ID NO: 148; or lxxi. a light chain variable region comprising an amino acid sequence at least 95% identical to the amino acid sequence of SEQ ID NO: 163, and a heavy chain variable region comprising an amino acid sequence at least 95% identical to the amino acid sequence of SEQ ID NO: 148; or lxxii. a light chain variable region comprising an amino acid sequence at least 95% identical to the amino acid sequence of SEQ ID NO: 173, and a heavy chain variable region comprising an amino acid sequence at least 95% identical to the amino acid sequence of SEQ ID NO: 148; or lxxiii. a light chain variable region comprising an amino acid sequence at least 95% identical to the amino acid sequence of SEQ ID NO: 183, and a heavy chain variable region comprising an amino acid sequence at least 95% identical to the amino acid sequence of SEQ ID NO: 148; or lxxiv. a light chain variable region comprising an amino acid sequence at least 95% identical to the amino acid sequence of SEQ ID NO: 193, and a heavy chain variable region comprising an amino acid sequence at least 95% identical to the amino acid sequence of SEQ ID NO: 148; or lxxv. a light chain variable region comprising an amino acid sequence at least 95% identical to the amino acid sequence of SEQ ID NO: 203, and a heavy chain variable region comprising an amino acid sequence at least 95% identical to the amino acid sequence of SEQ ID NO: 148; or lxxvi. a light chain variable region comprising an amino acid sequence at least 95% identical to the amino acid sequence of SEQ ID NO: 213, and a heavy chain variable region comprising an amino acid sequence at least 95% identical to the amino acid sequence of SEQ ID NO: 148; or lxxvii. a light chain variable region comprising an amino acid sequence at least 95% identical to the amino acid sequence of SEQ ID NO: 223, and a heavy chain variable region comprising an amino acid sequence at least 95% identical to the amino acid sequence of SEQ ID NO: 148; or lxxviii. a light chain variable region comprising an amino acid sequence at least 95% identical to the amino acid sequence of SEQ ID NO: 233, and a heavy chain variable region comprising an amino acid sequence at least 95% identical to the amino acid sequence of SEQ ID NO: 148; or lxxix. a light chain variable region comprising an amino acid sequence at least 95% identical to the amino acid sequence of SEQ ID NO: 243, and a heavy chain variable region comprising an amino acid sequence at least 95% identical to the amino acid sequence of SEQ ID NO: 148; or lxxx. a light chain variable region comprising an amino acid sequence at least 95% identical to the amino acid sequence of SEQ ID NO: 253, and a heavy chain variable region comprising an amino acid sequence at least 95% identical to the amino acid sequence of SEQ ID NO: 148; or lxxxi. a light chain variable region comprising an amino acid sequence at least 95% identical to the amino acid sequence of SEQ ID NO: 103, and a heavy chain variable region comprising an amino acid sequence at least 95% identical to the amino acid sequence of SEQ ID NO: 158; or lxxxii. a light chain variable region comprising an amino acid sequence at least 95% identical to the amino acid sequence of SEQ ID NO: 113, and a heavy chain variable region comprising an amino acid sequence at least 95% identical to the amino acid sequence of SEQ ID NO: 158; or lxxxiii. a light chain variable region comprising an amino acid sequence at least 95% identical to the amino acid sequence of SEQ ID NO: 123, and a heavy chain variable region comprising an amino acid sequence at least 95% identical to the amino acid sequence of SEQ ID NO: 158; or lxxxiv. a light chain variable region comprising an amino acid sequence at least 95% identical to the amino acid sequence of SEQ ID NO: 133, and a heavy chain variable region comprising an amino acid sequence at least 95% identical to the amino acid sequence of SEQ ID NO: 158; or lxxxv. a light chain variable region comprising an amino acid sequence at least 95% identical to the amino acid sequence of SEQ ID NO: 143, and a heavy chain variable region comprising an amino acid sequence at least 95% identical to the amino acid sequence of SEQ ID NO: 158; or lxxxvi. a light chain variable region comprising an amino acid sequence at least 95% identical to the amino acid sequence of SEQ ID NO: 153, and a heavy chain variable region comprising an amino acid sequence at least 95% identical to the amino acid sequence of SEQ ID NO: 158; or lxxxvii. a light chain variable region comprising an amino acid sequence at least 95% identical to the amino acid sequence of SEQ ID NO: 163, and a heavy chain variable region comprising an amino acid sequence at least 95% identical to the amino acid sequence of SEQ ID NO: 158; or lxxxviii. a light chain variable region comprising an amino acid sequence at least 95% identical to the amino acid sequence of SEQ ID NO: 173, and a heavy chain variable region comprising an amino acid sequence at least 95% identical to the amino acid sequence of SEQ ID NO: 158; or lxxxix. a light chain variable region comprising an amino acid sequence at least 95% identical to the amino acid sequence of SEQ ID NO: 183, and a heavy chain variable region comprising an amino acid sequence at least 95% identical to the amino acid sequence of SEQ ID NO: 158; or xc. a light chain variable region comprising an amino acid sequence at least 95% identical to the amino acid sequence of SEQ ID NO: 193, and a heavy chain variable region comprising an amino acid sequence at least 95% identical to the amino acid sequence of SEQ ID NO: 158; or xci. a light chain variable region comprising an amino acid sequence at least 95% identical to the amino acid sequence of SEQ ID NO: 203, and a heavy chain variable region comprising an amino acid sequence at least 95% identical to the amino acid sequence of SEQ ID NO: 158; or xcii. a light chain variable region comprising an amino acid sequence at least 95% identical to the amino acid sequence of SEQ ID NO: 213, and a heavy chain variable region comprising an amino acid sequence at least 95% identical to the amino acid sequence of SEQ ID NO: 158; or xciii. a light chain variable region comprising an amino acid sequence at least 95% identical to the amino acid sequence of SEQ ID NO: 223, and a heavy chain variable region comprising an amino acid sequence at least 95% identical to the amino acid sequence of SEQ ID NO: 158; or xciv. a light chain variable region comprising an amino acid sequence at least 95% identical to the amino acid sequence of SEQ ID NO: 233, and a heavy chain variable region comprising an amino acid sequence at least 95% identical to the amino acid sequence of SEQ ID NO: 158; or xcv. a light chain variable region comprising an amino acid sequence at least 95% identical to the amino acid sequence of SEQ ID NO: 243, and a heavy chain variable region comprising an amino acid sequence at least 95% identical to the amino acid sequence of SEQ ID NO: 158; or xcvi. a light chain variable region comprising an amino acid sequence at least 95% identical to the amino acid sequence of SEQ ID NO: 253, and a heavy chain variable region comprising an amino acid sequence at least 95% identical to the amino acid sequence of SEQ ID NO: 158; or xcvii. a light chain variable region comprising an amino acid sequence at least 95% identical to the amino acid sequence of SEQ ID NO: 103, and a heavy chain variable region comprising an amino acid sequence at least 95% identical to the amino acid sequence of SEQ ID NO: 168; or xcviii. a light chain variable region comprising an amino acid sequence at least 95% identical to the amino acid sequence of SEQ ID NO: 113, and a heavy chain variable region comprising an amino acid sequence at least 95% identical to the amino acid sequence of SEQ ID NO: 168; or xcix. a light chain variable region comprising an amino acid sequence at least 95% identical to the amino acid sequence of SEQ ID NO: 123, and a heavy chain variable region comprising an amino acid sequence at least 95% identical to the amino acid sequence of SEQ ID NO: 168; or c. a light chain variable region comprising an amino acid sequence at least 95% identical to the amino acid sequence of SEQ ID NO: 133, and a heavy chain variable region comprising an amino acid sequence at least 95% identical to the amino acid sequence of SEQ ID NO: 168; or ci. a light chain variable region comprising an amino acid sequence at least 95% identical to the amino acid sequence of SEQ ID NO: 143, and a heavy chain variable region comprising an amino acid sequence at least 95% identical to the amino acid sequence of SEQ ID NO: 168; or cii. a light chain variable region comprising an amino acid sequence at least 95% identical to the amino acid sequence of SEQ ID NO: 153, and a heavy chain variable region comprising an amino acid sequence at least 95% identical to the amino acid sequence of SEQ ID NO: 168; or ciii. a light chain variable region comprising an amino acid sequence at least 95% identical to the amino acid sequence of SEQ ID NO: 163, and a heavy chain variable region comprising an amino acid sequence at least 95% identical to the amino acid sequence of SEQ ID NO: 168; or civ. a light chain variable region comprising an amino acid sequence at least 95% identical to the amino acid sequence of SEQ ID NO: 173, and a heavy chain variable region comprising an amino acid sequence at least 95% identical to the amino acid sequence of SEQ ID NO: 168; or cv. a light chain variable region comprising an amino acid sequence at least 95% identical to the amino acid sequence of SEQ ID NO: 183, and a heavy chain variable region comprising an amino acid sequence at least 95% identical to the amino acid sequence of SEQ ID NO: 168; or cvi. a light chain variable region comprising an amino acid sequence at least 95% identical to the amino acid sequence of SEQ ID NO: 193, and a heavy chain variable region comprising an amino acid sequence at least 95% identical to the amino acid sequence of SEQ ID NO: 168; or cvii. a light chain variable region comprising an amino acid sequence at least 95% identical to the amino acid sequence of SEQ ID NO: 203, and a heavy chain variable region comprising an amino acid sequence at least 95% identical to the amino acid sequence of SEQ ID NO: 168; or cviii. a light chain variable region comprising an amino acid sequence at least 95% identical to the amino acid sequence of SEQ ID NO: 213, and a heavy chain variable region comprising an amino acid sequence at least 95% identical to the amino acid sequence of SEQ ID NO: 168; or cix. a light chain variable region comprising an amino acid sequence at least 95% identical to the amino acid sequence of SEQ ID NO: 223, and a heavy chain variable region comprising an amino acid sequence at least 95% identical to the amino acid sequence of SEQ ID NO: 168; or cx. a light chain variable region comprising an amino acid sequence at least 95% identical to the amino acid sequence of SEQ ID NO: 233, and a heavy chain variable region comprising an amino acid sequence at least 95% identical to the amino acid sequence of SEQ ID NO: 168; or cxi. a light chain variable region comprising an amino acid sequence at least 95% identical to the amino acid sequence of SEQ ID NO: 243, and a heavy chain variable region comprising an amino acid sequence at least 95% identical to the amino acid sequence of SEQ ID NO: 168; or cxii. a light chain variable region comprising an amino acid sequence at least 95% identical to the amino acid sequence of SEQ ID NO: 253, and a heavy chain variable region comprising an amino acid sequence at least 95% identical to the amino acid sequence of SEQ ID NO: 168; or cxiii. a light chain variable region comprising an amino acid sequence at least 95% identical to the amino acid sequence of SEQ ID NO: 103, and a heavy chain variable region comprising an amino acid sequence at least 95% identical to the amino acid sequence of SEQ ID NO: 178; or cxiv. a light chain variable region comprising an amino acid sequence at least 95% identical to the amino acid sequence of SEQ ID NO: 113, and a heavy chain variable region comprising an amino acid sequence at least 95% identical to the amino acid sequence of SEQ ID NO: 178; or cxv. a light chain variable region comprising an amino acid sequence at least 95% identical to the amino acid sequence of SEQ ID NO: 123, and a heavy chain variable region comprising an amino acid sequence at least 95% identical to the amino acid sequence of SEQ ID NO: 178; or cxvi. a light chain variable region comprising an amino acid sequence at least 95% identical to the amino acid sequence of SEQ ID NO: 133, and a heavy chain variable region comprising an amino acid sequence at least 95% identical to the amino acid sequence of SEQ ID NO: 178; or cxvii. a light chain variable region comprising an amino acid sequence at least 95% identical to the amino acid sequence of SEQ ID NO: 143, and a heavy chain variable region comprising an amino acid sequence at least 95% identical to the amino acid sequence of SEQ ID NO: 178; or cxviii. a light chain variable region comprising an amino acid sequence at least 95% identical to the amino acid sequence of SEQ ID NO: 153, and a heavy chain variable region comprising an amino acid sequence at least 95% identical to the amino acid sequence of SEQ ID NO: 178; or cxix. a light chain variable region comprising an amino acid sequence at least 95% identical to the amino acid sequence of SEQ ID NO: 163, and a heavy chain variable region comprising an amino acid sequence at least 95% identical to the amino acid sequence of SEQ ID NO: 178; or cxx. a light chain variable region comprising an amino acid sequence at least 95% identical to the amino acid sequence of SEQ ID NO: 173, and a heavy chain variable region comprising an amino acid sequence at least 95% identical to the amino acid sequence of SEQ ID NO: 178; or cxxi. a light chain variable region comprising an amino acid sequence at least 95% identical to the amino acid sequence of SEQ ID NO: 183, and a heavy chain variable region comprising an amino acid sequence at least 95% identical to the amino acid sequence of SEQ ID NO: 178; or cxxii. a light chain variable region comprising an amino acid sequence at least 95% identical to the amino acid sequence of SEQ ID NO: 193, and a heavy chain variable region comprising an amino acid sequence at least 95% identical to the amino acid sequence of SEQ ID NO: 178; or cxxiii. a light chain variable region comprising an amino acid sequence at least 95% identical to the amino acid sequence of SEQ ID NO: 203, and a heavy chain variable region comprising an amino acid sequence at least 95% identical to the amino acid sequence of SEQ ID NO: 178; or cxxiv. a light chain variable region comprising an amino acid sequence at least 95% identical to the amino acid sequence of SEQ ID NO: 213, and a heavy chain variable region comprising an amino acid sequence at least 95% identical to the amino acid sequence of SEQ ID NO: 178; or cxxv. a light chain variable region comprising an amino acid sequence at least 95% identical to the amino acid sequence of SEQ ID NO: 223, and a heavy chain variable region comprising an amino acid sequence at least 95% identical to the amino acid sequence of SEQ ID NO: 178; or cxxvi. a light chain variable region comprising an amino acid sequence at least 95% identical to the amino acid sequence of SEQ ID NO: 233, and a heavy chain variable region comprising an amino acid sequence at least 95% identical to the amino acid sequence of SEQ ID NO: 178; or cxxvii. a light chain variable region comprising an amino acid sequence at least 95% identical to the amino acid sequence of SEQ ID NO: 243, and a heavy chain variable region comprising an amino acid sequence at least 95% identical to the amino acid sequence of SEQ ID NO: 178.

4. The anti-CTGF antibody or an antigen-binding fragment thereof according to any one of the foregoing paras, wherein the anti-CTGF antibody or an antigen-binding fragment thereof comprises:

i. a light chain variable region comprising the amino acid sequence of SEQ ID NO: 223, and a heavy chain variable region comprising the amino acid sequence of SEQ ID NO: 108; or ii. a light chain variable region comprising the amino acid sequence of SEQ ID NO: 103, and a heavy chain variable region comprising the amino acid sequence of SEQ ID NO: 108; or iii. a light chain variable region comprising the amino acid sequence of SEQ ID NO: 113, and a heavy chain variable region comprising the amino acid sequence of SEQ ID NO: 108; or iv. a light chain variable region comprising the amino acid sequence of SEQ ID NO: 123, and a heavy chain variable region comprising the amino acid sequence of SEQ ID NO: 108; or v. a light chain variable region comprising the amino acid sequence of SEQ ID NO: 133, and a heavy chain variable region comprising the amino acid sequence of SEQ ID NO: 108; or vi. a light chain variable region comprising the amino acid sequence of SEQ ID NO: 143, and a heavy chain variable region comprising the amino acid sequence of SEQ ID NO: 108; or vii. a light chain variable region comprising the amino acid sequence of SEQ ID NO: 153, and a heavy chain variable region comprising the amino acid sequence of SEQ ID NO: 108; or viii. a light chain variable region comprising the amino acid sequence of SEQ ID NO: 163, and a heavy chain variable region comprising the amino acid sequence of SEQ ID NO: 108; or ix. a light chain variable region comprising the amino acid sequence of SEQ ID NO: 173, and a heavy chain variable region comprising the amino acid sequence of SEQ ID NO: 108; or x. a light chain variable region comprising the amino acid sequence of SEQ ID NO: 183, and a heavy chain variable region comprising the amino acid sequence of SEQ ID NO: 108; or xi. a light chain variable region comprising the amino acid sequence of SEQ ID NO: 193, and a heavy chain variable region comprising the amino acid sequence of SEQ ID NO: 108; or xii. a light chain variable region comprising the amino acid sequence of SEQ ID NO: 203, and a heavy chain variable region comprising the amino acid sequence of SEQ ID NO: 108; or xiii. a light chain variable region comprising the amino acid sequence of SEQ ID NO: 213, and a heavy chain variable region comprising the amino acid sequence of SEQ ID NO: 108; or xiv. a light chain variable region comprising the amino acid sequence of SEQ ID NO: 233, and a heavy chain variable region comprising the amino acid sequence of SEQ ID NO: 108; or xv. a light chain variable region comprising the amino acid sequence of SEQ ID NO: 243, and a heavy chain variable region comprising the amino acid sequence of SEQ ID NO: 108; or xvi. a light chain variable region comprising the amino acid sequence of SEQ ID NO: 253, and a heavy chain variable region comprising the amino acid sequence of SEQ ID NO: 108; or xvii. a light chain variable region comprising the amino acid sequence of SEQ ID NO: 103, and a heavy chain variable region comprising the amino acid sequence of SEQ ID NO: 118; or xviii. a light chain variable region comprising the amino acid sequence of SEQ ID NO: 113, and a heavy chain variable region comprising the amino acid sequence of SEQ ID NO: 118; or xix. a light chain variable region comprising the amino acid sequence of SEQ ID NO: 123, and a heavy chain variable region comprising the amino acid sequence of SEQ ID NO: 118; or xx. a light chain variable region comprising the amino acid sequence of SEQ ID NO: 133, and a heavy chain variable region comprising the amino acid sequence of SEQ ID NO: 118; or xxi. a light chain variable region comprising the amino acid sequence of SEQ ID NO: 143, and a heavy chain variable region comprising the amino acid sequence of SEQ ID NO: 118; or xxii. a light chain variable region comprising the amino acid sequence of SEQ ID NO: 153, and a heavy chain variable region comprising the amino acid sequence of SEQ ID NO: 118; or xxiii. a light chain variable region comprising the amino acid sequence of SEQ ID NO: 163, and a heavy chain variable region comprising the amino acid sequence of SEQ ID NO: 118; or xxiv. a light chain variable region comprising the amino acid sequence of SEQ ID NO: 173, and a heavy chain variable region comprising the amino acid sequence of SEQ ID NO: 118; or xxv. a light chain variable region comprising the amino acid sequence of SEQ ID NO: 183, and a heavy chain variable region comprising the amino acid sequence of SEQ ID NO: 118; or xxvi. a light chain variable region comprising the amino acid sequence of SEQ ID NO: 193, and a heavy chain variable region comprising the amino acid sequence of SEQ ID NO: 118; or xxvii. a light chain variable region comprising the amino acid sequence of SEQ ID NO: 203, and a heavy chain variable region comprising the amino acid sequence of SEQ ID NO: 118; or xxviii. a light chain variable region comprising the amino acid sequence of SEQ ID NO: 213, and a heavy chain variable region comprising the amino acid sequence of SEQ ID NO: 118; or xxix. a light chain variable region comprising the amino acid sequence of SEQ ID NO: 223, and a heavy chain variable region comprising the amino acid sequence of SEQ ID NO: 118; or xxx. a light chain variable region comprising the amino acid sequence of SEQ ID NO: 233, and a heavy chain variable region comprising the amino acid sequence of SEQ ID NO: 118; or xxxi. a light chain variable region comprising the amino acid sequence of SEQ ID NO: 243, and a heavy chain variable region comprising the amino acid sequence of SEQ ID NO: 118; or xxxii. a light chain variable region comprising the amino acid sequence of SEQ ID NO: 253, and a heavy chain variable region comprising the amino acid sequence of SEQ ID NO: 118; or xxxiii. a light chain variable region comprising the amino acid sequence of SEQ ID NO: 103, and a heavy chain variable region comprising the amino acid sequence of SEQ ID NO: 128; or xxxiv. a light chain variable region comprising the amino acid sequence of SEQ ID NO: 113, and a heavy chain variable region comprising the amino acid sequence of SEQ ID NO: 128; or xxxv. a light chain variable region comprising the amino acid sequence of SEQ ID NO: 123, and a heavy chain variable region comprising the amino acid sequence of SEQ ID NO: 128; or xxxvi. a light chain variable region comprising the amino acid sequence of SEQ ID NO: 133, and a heavy chain variable region comprising the amino acid sequence of SEQ ID NO: 128; or xxxvii. a light chain variable region comprising the amino acid sequence of SEQ ID NO: 143, and a heavy chain variable region comprising the amino acid sequence of SEQ ID NO: 128; or xxxviii. a light chain variable region comprising the amino acid sequence of SEQ ID NO: 153, and a heavy chain variable region comprising the amino acid sequence of SEQ ID NO: 128; or xxxix. a light chain variable region comprising the amino acid sequence of SEQ ID NO: 163, and a heavy chain variable region comprising the amino acid sequence of SEQ ID NO: 128; or xl. a light chain variable region comprising the amino acid sequence of SEQ ID NO: 173, and a heavy chain variable region comprising the amino acid sequence of SEQ ID NO: 128; or xli. a light chain variable region comprising the amino acid sequence of SEQ ID NO: 183, and a heavy chain variable region comprising the amino acid sequence of SEQ ID NO: 128; or xlii. a light chain variable region comprising the amino acid sequence of SEQ ID NO: 193, and a heavy chain variable region comprising the amino acid sequence of SEQ ID NO: 128; or xliii. a light chain variable region comprising the amino acid sequence of SEQ ID NO: 203, and a heavy chain variable region comprising the amino acid sequence of SEQ ID NO: 128; or xliv. a light chain variable region comprising the amino acid sequence of SEQ ID NO: 213, and a heavy chain variable region comprising the amino acid sequence of SEQ ID NO: 128; or xlv. a light chain variable region comprising the amino acid sequence of SEQ ID NO: 223, and a heavy chain variable region comprising the amino acid sequence of SEQ ID NO: 128; or xlvi. a light chain variable region comprising the amino acid sequence of SEQ ID NO: 233, and a heavy chain variable region comprising the amino acid sequence of SEQ ID NO: 128; or xlvii. a light chain variable region comprising the amino acid sequence of SEQ ID NO: 243, and a heavy chain variable region comprising the amino acid sequence of SEQ ID NO: 128; or xlviii. a light chain variable region comprising the amino acid sequence of SEQ ID NO: 253, and a heavy chain variable region comprising the amino acid sequence of SEQ ID NO: 128; or xlix. a light chain variable region comprising the amino acid sequence of SEQ ID NO: 103, and a heavy chain variable region comprising the amino acid sequence of SEQ ID NO: 138; or l. a light chain variable region comprising the amino acid sequence of SEQ ID NO: 113, and a heavy chain variable region comprising the amino acid sequence of SEQ ID NO: 138; or li. a light chain variable region comprising the amino acid sequence of SEQ ID NO: 123, and a heavy chain variable region comprising the amino acid sequence of SEQ ID NO: 138; or lii. a light chain variable region comprising the amino acid sequence of SEQ ID NO: 133, and a heavy chain variable region comprising the amino acid sequence of SEQ ID NO: 138; or liii. a light chain variable region comprising the amino acid sequence of SEQ ID NO: 143, and a heavy chain variable region comprising the amino acid sequence of SEQ ID NO: 138; or liv. a light chain variable region comprising the amino acid sequence of SEQ ID NO: 153, and a heavy chain variable region comprising the amino acid sequence of SEQ ID NO: 138; or lv. a light chain variable region comprising the amino acid sequence of SEQ ID NO: 163, and a heavy chain variable region comprising the amino acid sequence of SEQ ID NO: 138; or lvi. a light chain variable region comprising the amino acid sequence of SEQ ID NO: 173, and a heavy chain variable region comprising the amino acid sequence of SEQ ID NO: 138; or lvii. a light chain variable region comprising the amino acid sequence of SEQ ID NO: 183, and a heavy chain variable region comprising the amino acid sequence of SEQ ID NO: 138; or lviii. a light chain variable region comprising the amino acid sequence of SEQ ID NO: 193, and a heavy chain variable region comprising the amino acid sequence of SEQ ID NO: 138; or lix. a light chain variable region comprising the amino acid sequence of SEQ ID NO: 203, and a heavy chain variable region comprising the amino acid sequence of SEQ ID NO: 138; or lx. a light chain variable region comprising the amino acid sequence of SEQ ID NO: 213, and a heavy chain variable region comprising the amino acid sequence of SEQ ID NO: 138; or lxi. a light chain variable region comprising the amino acid sequence of SEQ ID NO: 223, and a heavy chain variable region comprising the amino acid sequence of SEQ ID NO: 138; or lxii. a light chain variable region comprising the amino acid sequence of SEQ ID NO: 233, and a heavy chain variable region comprising the amino acid sequence of SEQ ID NO: 138; or lxiii. a light chain variable region comprising the amino acid sequence of SEQ ID NO: 243, and a heavy chain variable region comprising the amino acid sequence of SEQ ID NO: 138; or lxiv. a light chain variable region comprising the amino acid sequence of SEQ ID NO: 253, and a heavy chain variable region comprising the amino acid sequence of SEQ ID NO: 138; or lxv. a light chain variable region comprising the amino acid sequence of SEQ ID NO: 103, and a heavy chain variable region comprising the amino acid sequence of SEQ ID NO: 148; or lxvi. a light chain variable region comprising the amino acid sequence of SEQ ID NO: 113, and a heavy chain variable region comprising the amino acid sequence of SEQ ID NO: 148; or lxvii. a light chain variable region comprising the amino acid sequence of SEQ ID NO: 123, and a heavy chain variable region comprising the amino acid sequence of SEQ ID NO: 148; or lxviii. a light chain variable region comprising the amino acid sequence of SEQ ID NO: 133, and a heavy chain variable region comprising the amino acid sequence of SEQ ID NO: 148; or lxix. a light chain variable region comprising the amino acid sequence of SEQ ID NO: 143, and a heavy chain variable region comprising the amino acid sequence of SEQ ID NO: 148; or lxx. a light chain variable region comprising the amino acid sequence of SEQ ID NO: 153, and a heavy chain variable region comprising the amino acid sequence of SEQ ID NO: 148; or lxxi. a light chain variable region comprising the amino acid sequence of SEQ ID NO: 163, and a heavy chain variable region comprising the amino acid sequence of SEQ ID NO: 148; or lxxii. a light chain variable region comprising the amino acid sequence of SEQ ID NO: 173, and a heavy chain variable region comprising the amino acid sequence of SEQ ID NO: 148; or lxxiii. a light chain variable region comprising the amino acid sequence of SEQ ID NO: 183, and a heavy chain variable region comprising the amino acid sequence of SEQ ID NO: 148; or lxxiv. a light chain variable region comprising the amino acid sequence of SEQ ID NO: 193, and a heavy chain variable region comprising the amino acid sequence of SEQ ID NO: 148; or lxxv. a light chain variable region comprising the amino acid sequence of SEQ ID NO: 203, and a heavy chain variable region comprising the amino acid sequence of SEQ ID NO: 148; or lxxvi. a light chain variable region comprising the amino acid sequence of SEQ ID NO: 213, and a heavy chain variable region comprising the amino acid sequence of SEQ ID NO: 148; or lxxvii. a light chain variable region comprising the amino acid sequence of SEQ ID NO: 223, and a heavy chain variable region comprising the amino acid sequence of SEQ ID NO: 148; or lxxviii. a light chain variable region comprising the amino acid sequence of SEQ ID NO: 233, and a heavy chain variable region comprising the amino acid sequence of SEQ ID NO: 148; or lxxix. a light chain variable region comprising the amino acid sequence of SEQ ID NO: 243, and a heavy chain variable region comprising the amino acid sequence of SEQ ID NO: 148; or lxxx. a light chain variable region comprising the amino acid sequence of SEQ ID NO: 253, and a heavy chain variable region comprising the amino acid sequence of SEQ ID NO: 148; or lxxxi. a light chain variable region comprising the amino acid sequence of SEQ ID NO: 103, and a heavy chain variable region comprising the amino acid sequence of SEQ ID NO: 158; or lxxxii. a light chain variable region comprising the amino acid sequence of SEQ ID NO: 113, and a heavy chain variable region comprising the amino acid sequence of SEQ ID NO: 158; or lxxxiii. a light chain variable region comprising the amino acid sequence of SEQ ID NO: 123, and a heavy chain variable region comprising the amino acid sequence of SEQ ID NO: 158; or lxxxiv. a light chain variable region comprising the amino acid sequence of SEQ ID NO: 133, and a heavy chain variable region comprising the amino acid sequence of SEQ ID NO: 158; or lxxxv. a light chain variable region comprising the amino acid sequence of SEQ ID NO: 143, and a heavy chain variable region comprising the amino acid sequence of SEQ ID NO: 158; or lxxxvi. a light chain variable region comprising the amino acid sequence of SEQ ID NO: 153, and a heavy chain variable region comprising the amino acid sequence of SEQ ID NO: 158; or lxxxvii. a light chain variable region comprising the amino acid sequence of SEQ ID NO: 163, and a heavy chain variable region comprising the amino acid sequence of SEQ ID NO: 158; or lxxxviii. a light chain variable region comprising the amino acid sequence of SEQ ID NO: 173, and a heavy chain variable region comprising the amino acid sequence of SEQ ID NO: 158; or lxxxix. a light chain variable region comprising the amino acid sequence of SEQ ID NO: 183, and a heavy chain variable region comprising the amino acid sequence of SEQ ID NO: 158; or xc. a light chain variable region comprising the amino acid sequence of SEQ ID NO: 193, and a heavy chain variable region comprising the amino acid sequence of SEQ ID NO: 158; or xci. a light chain variable region comprising the amino acid sequence of SEQ ID NO: 203, and a heavy chain variable region comprising the amino acid sequence of SEQ ID NO: 158; or xcii. a light chain variable region comprising the amino acid sequence of SEQ ID NO: 213, and a heavy chain variable region comprising the amino acid sequence of SEQ ID NO: 158; or xciii. a light chain variable region comprising the amino acid sequence of SEQ ID NO: 223, and a heavy chain variable region comprising the amino acid sequence of SEQ ID NO: 158; or xciv. a light chain variable region comprising the amino acid sequence of SEQ ID NO: 233, and a heavy chain variable region comprising the amino acid sequence of SEQ ID NO: 158; or xcv. a light chain variable region comprising the amino acid sequence of SEQ ID NO: 243, and a heavy chain variable region comprising the amino acid sequence of SEQ ID NO: 158; or xcvi. a light chain variable region comprising the amino acid sequence of SEQ ID NO: 253, and a heavy chain variable region comprising the amino acid sequence of SEQ ID NO: 158; or xcvii. a light chain variable region comprising the amino acid sequence of SEQ ID NO: 103, and a heavy chain variable region comprising the amino acid sequence of SEQ ID NO: 168; or xcviii. a light chain variable region comprising the amino acid sequence of SEQ ID NO: 113, and a heavy chain variable region comprising the amino acid sequence of SEQ ID NO: 168; or xcix. a light chain variable region comprising the amino acid sequence of SEQ ID NO: 123, and a heavy chain variable region comprising the amino acid sequence of SEQ ID NO: 168; or c. a light chain variable region comprising the amino acid sequence of SEQ ID NO: 133, and a heavy chain variable region comprising the amino acid sequence of SEQ ID NO: 168; or ci. a light chain variable region comprising the amino acid sequence of SEQ ID NO: 143, and a heavy chain variable region comprising the amino acid sequence of SEQ ID NO: 168; or cii. a light chain variable region comprising the amino acid sequence of SEQ ID NO: 153, and a heavy chain variable region comprising the amino acid sequence of SEQ ID NO: 168; or ciii. a light chain variable region comprising the amino acid sequence of SEQ ID NO: 163, and a heavy chain variable region comprising the amino acid sequence of SEQ ID NO: 168; or civ. a light chain variable region comprising the amino acid sequence of SEQ ID NO: 173, and a heavy chain variable region comprising the amino acid sequence of SEQ ID NO: 168; or cv. a light chain variable region comprising the amino acid sequence of SEQ ID NO: 183, and a heavy chain variable region comprising the amino acid sequence of SEQ ID NO: 168; or cvi. a light chain variable region comprising the amino acid sequence of SEQ ID NO: 193, and a heavy chain variable region comprising the amino acid sequence of SEQ ID NO: 168; or cvii. a light chain variable region comprising the amino acid sequence of SEQ ID NO: 203, and a heavy chain variable region comprising the amino acid sequence of SEQ ID NO: 168; or cviii. a light chain variable region comprising the amino acid sequence of SEQ ID NO: 213, and a heavy chain variable region comprising the amino acid sequence of SEQ ID NO: 168; or cix. a light chain variable region comprising the amino acid sequence of SEQ ID NO: 223, and a heavy chain variable region comprising the amino acid sequence of SEQ ID NO: 168; or cx. a light chain variable region comprising the amino acid sequence of SEQ ID NO: 233, and a heavy chain variable region comprising the amino acid sequence of SEQ ID NO: 168; or cxi. a light chain variable region comprising the amino acid sequence of SEQ ID NO: 243, and a heavy chain variable region comprising the amino acid sequence of SEQ ID NO: 168; or cxii. a light chain variable region comprising the amino acid sequence of SEQ ID NO: 253, and a heavy chain variable region comprising the amino acid sequence of SEQ ID NO: 168; or cxiii. a light chain variable region comprising the amino acid sequence of SEQ ID NO: 103, and a heavy chain variable region comprising the amino acid sequence of SEQ ID NO: 178; or cxiv. a light chain variable region comprising the amino acid sequence of SEQ ID NO: 113, and a heavy chain variable region comprising the amino acid sequence of SEQ ID NO: 178; or cxv. a light chain variable region comprising the amino acid sequence of SEQ ID NO: 123, and a heavy chain variable region comprising the amino acid sequence of SEQ ID NO: 178; or cxvi. a light chain variable region comprising the amino acid sequence of SEQ ID NO: 133, and a heavy chain variable region comprising the amino acid sequence of SEQ ID NO: 178; or cxvii. a light chain variable region comprising the amino acid sequence of SEQ ID NO: 143, and a heavy chain variable region comprising the amino acid sequence of SEQ ID NO: 178; or cxviii. a light chain variable region comprising the amino acid sequence of SEQ ID NO: 153, and a heavy chain variable region comprising the amino acid sequence of SEQ ID NO: 178; or cxix. a light chain variable region comprising the amino acid sequence of SEQ ID NO: 163, and a heavy chain variable region comprising the amino acid sequence of SEQ ID NO: 178; or cxx. a light chain variable region comprising the amino acid sequence of SEQ ID NO: 173, and a heavy chain variable region comprising the amino acid sequence of SEQ ID NO: 178; or cxxi. a light chain variable region comprising the amino acid sequence of SEQ ID NO: 183, and a heavy chain variable region comprising the amino acid sequence of SEQ ID NO: 178; or cxxii. a light chain variable region comprising the amino acid sequence of SEQ ID NO: 193, and a heavy chain variable region comprising the amino acid sequence of SEQ ID NO: 178; or cxxiii. a light chain variable region comprising the amino acid sequence of SEQ ID NO: 203, and a heavy chain variable region comprising the amino acid sequence of SEQ ID NO: 178; or cxxiv. a light chain variable region comprising the amino acid sequence of SEQ ID NO: 213, and a heavy chain variable region comprising the amino acid sequence of SEQ ID NO: 178; or cxxv. a light chain variable region comprising the amino acid sequence of SEQ ID NO: 223, and a heavy chain variable region comprising the amino acid sequence of SEQ ID NO: 178; or cxxvi. a light chain variable region comprising the amino acid sequence of SEQ ID NO: 233, and a heavy chain variable region comprising the amino acid sequence of SEQ ID NO: 178; or cxxvii. a light chain variable region comprising the amino acid sequence of SEQ ID NO: 243, and a heavy chain variable region comprising the amino acid sequence of SEQ ID NO: 178.

5. The anti-CTGF antibody or antigen-binding fragment thereof according to any one of the foregoing paras, comprising:

i. a light chain comprising an amino acid sequence at least 95% identical to the amino acid sequence of SEQ ID NO: 224, and a heavy chain comprising an amino acid sequence at least 95% identical to the amino acid sequence of SEQ ID NO: 109; or ii. a light chain comprising an amino acid sequence at least 95% identical to the amino acid sequence of SEQ ID NO: 104, and a heavy chain comprising an amino acid sequence at least 95% identical to the amino acid sequence of SEQ ID NO: 109; or iii. a light chain comprising an amino acid sequence at least 95% identical to the amino acid sequence of SEQ ID NO: 114, and a heavy chain comprising an amino acid sequence at least 95% identical to the amino acid sequence of SEQ ID NO: 109; or iv. a light chain comprising an amino acid sequence at least 95% identical to the amino acid sequence of SEQ ID NO: 124, and a heavy chain comprising an amino acid sequence at least 95% identical to the amino acid sequence of SEQ ID NO: 109; or v. a light chain comprising an amino acid sequence at least 95% identical to the amino acid sequence of SEQ ID NO: 134, and a heavy chain comprising an amino acid sequence at least 95% identical to the amino acid sequence of SEQ ID NO: 109; or vi. a light chain comprising an amino acid sequence at least 95% identical to the amino acid sequence of SEQ ID NO: 144, and a heavy chain comprising an amino acid sequence at least 95% identical to the amino acid sequence of SEQ ID NO: 109; or vii. a light chain comprising an amino acid sequence at least 95% identical to the amino acid sequence of SEQ ID NO: 154, and a heavy chain comprising an amino acid sequence at least 95% identical to the amino acid sequence of SEQ ID NO: 109; or viii. a light chain comprising an amino acid sequence at least 95% identical to the amino acid sequence of SEQ ID NO: 164, and a heavy chain comprising an amino acid sequence at least 95% identical to the amino acid sequence of SEQ ID NO: 109; or ix. a light chain comprising an amino acid sequence at least 95% identical to the amino acid sequence of SEQ ID NO: 174, and a heavy chain comprising an amino acid sequence at least 95% identical to the amino acid sequence of SEQ ID NO: 109; or x. a light chain comprising an amino acid sequence at least 95% identical to the amino acid sequence of SEQ ID NO: 184, and a heavy chain comprising an amino acid sequence at least 95% identical to the amino acid sequence of SEQ ID NO: 109; or xi. a light chain comprising an amino acid sequence at least 95% identical to the amino acid sequence of SEQ ID NO: 194, and a heavy chain comprising an amino acid sequence at least 95% identical to the amino acid sequence of SEQ ID NO: 109; or xii. a light chain comprising an amino acid sequence at least 95% identical to the amino acid sequence of SEQ ID NO: 204, and a heavy chain comprising an amino acid sequence at least 95% identical to the amino acid sequence of SEQ ID NO: 109; or xiii. a light chain comprising an amino acid sequence at least 95% identical to the amino acid sequence of SEQ ID NO: 214, and a heavy chain comprising an amino acid sequence at least 95% identical to the amino acid sequence of SEQ ID NO: 109; or xiv. a light chain comprising an amino acid sequence at least 95% identical to the amino sequence at least 95% identical to the amino acid sequence of SEQ ID NO: 109; or xv. a light chain comprising an amino acid sequence at least 95% identical to the amino acid sequence of SEQ ID NO: 244, and a heavy chain comprising an amino acid sequence at least 95% identical to the amino acid sequence of SEQ ID NO: 109; or xvi. a light chain comprising an amino acid sequence at least 95% identical to the amino acid sequence of SEQ ID NO: 254, and a heavy chain comprising an amino acid sequence at least 95% identical to the amino acid sequence of SEQ ID NO: 109; or xvii. a light chain comprising an amino acid sequence at least 95% identical to the amino acid sequence of SEQ ID NO: 104, and a heavy chain comprising an amino acid sequence at least 95% identical to the amino acid sequence of SEQ ID NO: 119; or xviii. a light chain comprising an amino acid sequence at least 95% identical to the amino acid sequence of SEQ ID NO: 114, and a heavy chain comprising an amino acid sequence at least 95% identical to the amino acid sequence of SEQ ID NO: 119; or xix. a light chain comprising an amino acid sequence at least 95% identical to the amino acid sequence of SEQ ID NO: 124, and a heavy chain comprising an amino acid sequence at least 95% identical to the amino acid sequence of SEQ ID NO: 119; or xx. a light chain comprising an amino acid sequence at least 95% identical to the amino acid sequence of SEQ ID NO: 134, and a heavy chain comprising an amino acid sequence at least 95% identical to the amino acid sequence of SEQ ID NO: 119; or xxi. a light chain comprising an amino acid sequence at least 95% identical to the amino acid sequence of SEQ ID NO: 144, and a heavy chain comprising an amino acid sequence at least 95% identical to the amino acid sequence of SEQ ID NO: 119; or xxii. a light chain comprising an amino acid sequence at least 95% identical to the amino acid sequence of SEQ ID NO: 154, and a heavy chain comprising an amino acid sequence at least 95% identical to the amino acid sequence of SEQ ID NO: 119; or xxiii. a light chain comprising an amino acid sequence at least 95% identical to the amino acid sequence of SEQ ID NO: 164, and a heavy chain comprising an amino acid sequence at least 95% identical to the amino acid sequence of SEQ ID NO: 119; or xxiv. a light chain comprising an amino acid sequence at least 95% identical to the amino acid sequence of SEQ ID NO: 174, and a heavy chain comprising an amino acid sequence at least 95% identical to the amino acid sequence of SEQ ID NO: 119; or xxv. a light chain comprising an amino acid sequence at least 95% identical to the amino acid sequence of SEQ ID NO: 184, and a heavy chain comprising an amino acid sequence at least 95% identical to the amino acid sequence of SEQ ID NO: 119; or xxvi. a light chain comprising an amino acid sequence at least 95% identical to the amino sequence at least 95% identical to the amino acid sequence of SEQ ID NO: 119; or xxvii. a light chain comprising an amino acid sequence at least 95% identical to the amino acid sequence of SEQ ID NO: 204, and a heavy chain comprising an amino acid sequence at least 95% identical to the amino acid sequence of SEQ ID NO: 119; or xxviii. a light chain comprising an amino acid sequence at least 95% identical to the amino acid sequence of SEQ ID NO: 214, and a heavy chain comprising an amino acid sequence at least 95% identical to the amino acid sequence of SEQ ID NO: 119; or xxix. a light chain comprising an amino acid sequence at least 95% identical to the amino acid sequence of SEQ ID NO: 224, and a heavy chain comprising an amino acid sequence at least 95% identical to the amino acid sequence of SEQ ID NO: 119; or xxx. a light chain comprising an amino acid sequence at least 95% identical to the amino acid sequence of SEQ ID NO: 234, and a heavy chain comprising an amino acid sequence at least 95% identical to the amino acid sequence of SEQ ID NO: 119; or xxxi. a light chain comprising an amino acid sequence at least 95% identical to the amino acid sequence of SEQ ID NO: 244, and a heavy chain comprising an amino acid sequence at least 95% identical to the amino acid sequence of SEQ ID NO: 119; or xxxii. a light chain comprising an amino acid sequence at least 95% identical to the amino acid sequence of SEQ ID NO: 254, and a heavy chain comprising an amino acid sequence at least 95% identical to the amino acid sequence of SEQ ID NO: 119; or xxxiii. a light chain comprising an amino acid sequence at least 95% identical to the amino acid sequence of SEQ ID NO: 104, and a heavy chain comprising an amino acid sequence at least 95% identical to the amino acid sequence of SEQ ID NO: 129; or xxxiv. a light chain comprising an amino acid sequence at least 95% identical to the amino acid sequence of SEQ ID NO: 114, and a heavy chain comprising an amino acid sequence at least 95% identical to the amino acid sequence of SEQ ID NO: 129; or xxxv. a light chain comprising an amino acid sequence at least 95% identical to the amino acid sequence of SEQ ID NO: 124, and a heavy chain comprising an amino acid sequence at least 95% identical to the amino acid sequence of SEQ ID NO: 129; or xxxvi. a light chain comprising an amino acid sequence at least 95% identical to the amino acid sequence of SEQ ID NO: 134, and a heavy chain comprising an amino acid sequence at least 95% identical to the amino acid sequence of SEQ ID NO: 129; or xxxvii. a light chain comprising an amino acid sequence at least 95% identical to the amino acid sequence of SEQ ID NO: 144, and a heavy chain comprising an amino acid sequence at least 95% identical to the amino acid sequence of SEQ ID NO: 129; or xxxviii. a light chain comprising an amino acid sequence at least 95% identical to the amino acid sequence of SEQ ID NO: 154, and a heavy chain comprising an amino acid sequence at least 95% identical to the amino acid sequence of SEQ ID NO: 129; or xxxix. a light chain comprising an amino acid sequence at least 95% identical to the amino acid sequence of SEQ ID NO: 164, and a heavy chain comprising an amino acid sequence at least 95% identical to the amino acid sequence of SEQ ID NO: 129; or xl. a light chain comprising an amino acid sequence at least 95% identical to the amino acid sequence of SEQ ID NO: 174, and a heavy chain comprising an amino acid sequence at least 95% identical to the amino acid sequence of SEQ ID NO: 129; or xli. a light chain comprising an amino acid sequence at least 95% identical to the amino acid sequence of SEQ ID NO: 184, and a heavy chain comprising an amino acid sequence at least 95% identical to the amino acid sequence of SEQ ID NO: 129; or xlii. a light chain comprising an amino acid sequence at least 95% identical to the amino acid sequence of SEQ ID NO: 194, and a heavy chain comprising an amino acid sequence at least 95% identical to the amino acid sequence of SEQ ID NO: 129; or xliii. a light chain comprising an amino acid sequence at least 95% identical to the amino acid sequence of SEQ ID NO: 204, and a heavy chain comprising an amino acid sequence at least 95% identical to the amino acid sequence of SEQ ID NO: 129; or xliv. a light chain comprising an amino acid sequence at least 95% identical to the amino acid sequence of SEQ ID NO: 214, and a heavy chain comprising an amino acid sequence at least 95% identical to the amino acid sequence of SEQ ID NO: 129; or xlv. a light chain comprising an amino acid sequence at least 95% identical to the amino acid sequence of SEQ ID NO: 224, and a heavy chain comprising an amino acid sequence at least 95% identical to the amino acid sequence of SEQ ID NO: 129; or xlvi. a light chain comprising an amino acid sequence at least 95% identical to the amino acid sequence of SEQ ID NO: 234, and a heavy chain comprising an amino acid sequence at least 95% identical to the amino acid sequence of SEQ ID NO: 129; or xlvii. a light chain comprising an amino acid sequence at least 95% identical to the amino acid sequence of SEQ ID NO: 244, and a heavy chain comprising an amino acid sequence at least 95% identical to the amino acid sequence of SEQ ID NO: 129; or xlviii. a light chain comprising an amino acid sequence at least 95% identical to the amino acid sequence of SEQ ID NO: 254, and a heavy chain comprising an amino acid sequence at least 95% identical to the amino acid sequence of SEQ ID NO: 129; or xlix. a light chain comprising an amino acid sequence at least 95% identical to the amino acid sequence of SEQ ID NO: 104, and a heavy chain comprising an amino acid sequence at least 95% identical to the amino acid sequence of SEQ ID NO: 139; or l. a light chain comprising an amino acid sequence at least 95% identical to the amino acid sequence of SEQ ID NO: 114, and a heavy chain comprising an amino acid sequence at least 95% identical to the amino acid sequence of SEQ ID NO: 139; or li. a light chain comprising an amino acid sequence at least 95% identical to the amino acid sequence of SEQ ID NO: 124, and a heavy chain comprising an amino acid sequence at least 95% identical to the amino acid sequence of SEQ ID NO: 139; or lii. a light chain comprising an amino acid sequence at least 95% identical to the amino acid sequence of SEQ ID NO: 134, and a heavy chain comprising an amino acid sequence at least 95% identical to the amino acid sequence of SEQ ID NO: 139; or liii. a light chain comprising an amino acid sequence at least 95% identical to the amino acid sequence of SEQ ID NO: 144, and a heavy chain comprising an amino acid sequence at least 95% identical to the amino acid sequence of SEQ ID NO: 139; or liv. a light chain comprising an amino acid sequence at least 95% identical to the amino acid sequence of SEQ ID NO: 154, and a heavy chain comprising an amino acid sequence at least 95% identical to the amino acid sequence of SEQ ID NO: 139; or lv. a light chain comprising an amino acid sequence at least 95% identical to the amino acid sequence of SEQ ID NO: 164, and a heavy chain comprising an amino acid sequence at least 95% identical to the amino acid sequence of SEQ ID NO: 139; or lvi. a light chain comprising an amino acid sequence at least 95% identical to the amino acid sequence of SEQ ID NO: 174, and a heavy chain comprising an amino acid sequence at least 95% identical to the amino acid sequence of SEQ ID NO: 139; or lvii. a light chain comprising an amino acid sequence at least 95% identical to the amino acid sequence of SEQ ID NO: 184, and a heavy chain comprising an amino acid sequence at least 95% identical to the amino acid sequence of SEQ ID NO: 139; or lviii. a light chain comprising an amino acid sequence at least 95% identical to the amino acid sequence of SEQ ID NO: 194, and a heavy chain comprising an amino acid sequence at least 95% identical to the amino acid sequence of SEQ ID NO: 139; or lix. a light chain comprising an amino acid sequence at least 95% identical to the amino acid sequence of SEQ ID NO: 204, and a heavy chain comprising an amino acid sequence at least 95% identical to the amino acid sequence of SEQ ID NO: 139; or lx. a light chain comprising an amino acid sequence at least 95% identical to the amino acid sequence of SEQ ID NO: 214, and a heavy chain comprising an amino acid sequence at least 95% identical to the amino acid sequence of SEQ ID NO: 139; or lxi. a light chain comprising an amino acid sequence at least 95% identical to the amino acid sequence of SEQ ID NO: 224, and a heavy chain comprising an amino acid sequence at least 95% identical to the amino acid sequence of SEQ ID NO: 139; or lxii. a light chain comprising an amino acid sequence at least 95% identical to the amino sequence at least 95% identical to the amino acid sequence of SEQ ID NO: 139; or lxiii. a light chain comprising an amino acid sequence at least 95% identical to the amino acid sequence of SEQ ID NO: 244, and a heavy chain comprising an amino acid sequence at least 95% identical to the amino acid sequence of SEQ ID NO: 139; or lxiv. a light chain comprising an amino acid sequence at least 95% identical to the amino acid sequence of SEQ ID NO: 254, and a heavy chain comprising an amino acid sequence at least 95% identical to the amino acid sequence of SEQ ID NO: 139; or lxv. a light chain comprising an amino acid sequence at least 95% identical to the amino acid sequence of SEQ ID NO: 104, and a heavy chain comprising an amino acid sequence at least 95% identical to the amino acid sequence of SEQ ID NO: 149; or lxvi. a light chain comprising an amino acid sequence at least 95% identical to the amino acid sequence of SEQ ID NO: 114, and a heavy chain comprising an amino acid sequence at least 95% identical to the amino acid sequence of SEQ ID NO: 149; or lxvii. a light chain comprising an amino acid sequence at least 95% identical to the amino acid sequence of SEQ ID NO: 124, and a heavy chain comprising an amino acid sequence at least 95% identical to the amino acid sequence of SEQ ID NO: 149; or lxviii. a light chain comprising an amino acid sequence at least 95% identical to the amino acid sequence of SEQ ID NO: 134, and a heavy chain comprising an amino acid sequence at least 95% identical to the amino acid sequence of SEQ ID NO: 149; or lxix. a light chain comprising an amino acid sequence at least 95% identical to the amino acid sequence of SEQ ID NO: 144, and a heavy chain comprising an amino acid sequence at least 95% identical to the amino acid sequence of SEQ ID NO: 149; or lxx. a light chain comprising an amino acid sequence at least 95% identical to the amino acid sequence of SEQ ID NO: 154, and a heavy chain comprising an amino acid sequence at least 95% identical to the amino acid sequence of SEQ ID NO: 149; or lxxi. a light chain comprising an amino acid sequence at least 95% identical to the amino acid sequence of SEQ ID NO: 164, and a heavy chain comprising an amino acid sequence at least 95% identical to the amino acid sequence of SEQ ID NO: 149; or lxxii. a light chain comprising an amino acid sequence at least 95% identical to the amino acid sequence of SEQ ID NO: 174, and a heavy chain comprising an amino acid sequence at least 95% identical to the amino acid sequence of SEQ ID NO: 149; or lxxiii. a light chain comprising an amino acid sequence at least 95% identical to the amino acid sequence of SEQ ID NO: 184, and a heavy chain comprising an amino acid sequence at least 95% identical to the amino acid sequence of SEQ ID NO: 149; or lxxiv. a light chain comprising an amino acid sequence at least 95% identical to the amino sequence at least 95% identical to the amino acid sequence of SEQ ID NO: 149; or lxxv. a light chain comprising an amino acid sequence at least 95% identical to the amino acid sequence of SEQ ID NO: 204, and a heavy chain comprising an amino acid sequence at least 95% identical to the amino acid sequence of SEQ ID NO: 149; or lxxvi. a light chain comprising an amino acid sequence at least 95% identical to the amino acid sequence of SEQ ID NO: 214, and a heavy chain comprising an amino acid sequence at least 95% identical to the amino acid sequence of SEQ ID NO: 149; or lxxvii. a light chain comprising an amino acid sequence at least 95% identical to the amino acid sequence of SEQ ID NO: 224, and a heavy chain comprising an amino acid sequence at least 95% identical to the amino acid sequence of SEQ ID NO: 149; or lxxviii. a light chain comprising an amino acid sequence at least 95% identical to the amino acid sequence of SEQ ID NO: 234, and a heavy chain comprising an amino acid sequence at least 95% identical to the amino acid sequence of SEQ ID NO: 149; or lxxix. a light chain comprising an amino acid sequence at least 95% identical to the amino acid sequence of SEQ ID NO: 244, and a heavy chain comprising an amino acid sequence at least 95% identical to the amino acid sequence of SEQ ID NO: 149; or lxxx. a light chain comprising an amino acid sequence at least 95% identical to the amino acid sequence of SEQ ID NO: 254, and a heavy chain comprising an amino acid sequence at least 95% identical to the amino acid sequence of SEQ ID NO: 149; or lxxxi. a light chain comprising an amino acid sequence at least 95% identical to the amino acid sequence of SEQ ID NO: 104, and a heavy chain comprising an amino acid sequence at least 95% identical to the amino acid sequence of SEQ ID NO: 159; or lxxxii. a light chain comprising an amino acid sequence at least 95% identical to the amino acid sequence of SEQ ID NO: 114, and a heavy chain comprising an amino acid sequence at least 95% identical to the amino acid sequence of SEQ ID NO: 159; or lxxxiii. a light chain comprising an amino acid sequence at least 95% identical to the amino acid sequence of SEQ ID NO: 124, and a heavy chain comprising an amino acid sequence at least 95% identical to the amino acid sequence of SEQ ID NO: 159; or lxxxiv. a light chain comprising an amino acid sequence at least 95% identical to the amino acid sequence of SEQ ID NO: 134, and a heavy chain comprising an amino acid sequence at least 95% identical to the amino acid sequence of SEQ ID NO: 159; or lxxxv. a light chain comprising an amino acid sequence at least 95% identical to the amino acid sequence of SEQ ID NO: 144, and a heavy chain comprising an amino acid sequence at least 95% identical to the amino acid sequence of SEQ ID NO: 159; or lxxxvi. a light chain comprising an amino acid sequence at least 95% identical to the amino acid sequence of SEQ ID NO: 154, and a heavy chain comprising an amino acid sequence at least 95% identical to the amino acid sequence of SEQ ID NO: 159; or lxxxvii. a light chain comprising an amino acid sequence at least 95% identical to the amino acid sequence of SEQ ID NO: 164, and a heavy chain comprising an amino acid sequence at least 95% identical to the amino acid sequence of SEQ ID NO: 159; or lxxxviii. a light chain comprising an amino acid sequence at least 95% identical to the amino acid sequence of SEQ ID NO: 174, and a heavy chain comprising an amino acid sequence at least 95% identical to the amino acid sequence of SEQ ID NO: 159; or lxxxix. a light chain comprising an amino acid sequence at least 95% identical to the amino acid sequence of SEQ ID NO: 184, and a heavy chain comprising an amino acid sequence at least 95% identical to the amino acid sequence of SEQ ID NO: 159; or xc. a light chain comprising an amino acid sequence at least 95% identical to the amino acid sequence of SEQ ID NO: 194, and a heavy chain comprising an amino acid sequence at least 95% identical to the amino acid sequence of SEQ ID NO: 159; or xci. a light chain comprising an amino acid sequence at least 95% identical to the amino acid sequence of SEQ ID NO: 204, and a heavy chain comprising an amino acid sequence at least 95% identical to the amino acid sequence of SEQ ID NO: 159; or xcii. a light chain comprising an amino acid sequence at least 95% identical to the amino acid sequence of SEQ ID NO: 214, and a heavy chain comprising an amino acid sequence at least 95% identical to the amino acid sequence of SEQ ID NO: 159; or xciii. a light chain comprising an amino acid sequence at least 95% identical to the amino acid sequence of SEQ ID NO: 224, and a heavy chain comprising an amino acid sequence at least 95% identical to the amino acid sequence of SEQ ID NO: 159; or xciv. a light chain comprising an amino acid sequence at least 95% identical to the amino acid sequence of SEQ ID NO: 234, and a heavy chain comprising an amino acid sequence at least 95% identical to the amino acid sequence of SEQ ID NO: 159; or xcv. a light chain comprising an amino acid sequence at least 95% identical to the amino acid sequence of SEQ ID NO: 244, and a heavy chain comprising an amino acid sequence at least 95% identical to the amino acid sequence of SEQ ID NO: 159; or xcvi. a light chain comprising an amino acid sequence at least 95% identical to the amino acid sequence of SEQ ID NO: 254, and a heavy chain comprising an amino acid sequence at least 95% identical to the amino acid sequence of SEQ ID NO: 159; or xcvii. a light chain comprising an amino acid sequence at least 95% identical to the amino acid sequence of SEQ ID NO: 104, and a heavy chain comprising an amino acid sequence at least 95% identical to the amino acid sequence of SEQ ID NO: 169; or xcviii. a light chain comprising an amino acid sequence at least 95% identical to the amino acid sequence of SEQ ID NO: 114, and a heavy chain comprising an amino acid sequence at least 95% identical to the amino acid sequence of SEQ ID NO: 169; or xcix. a light chain comprising an amino acid sequence at least 95% identical to the amino acid sequence of SEQ ID NO: 124, and a heavy chain comprising an amino acid sequence at least 95% identical to the amino acid sequence of SEQ ID NO: 169; or c. a light chain comprising an amino acid sequence at least 95% identical to the amino acid sequence of SEQ ID NO: 134, and a heavy chain comprising an amino acid sequence at least 95% identical to the amino acid sequence of SEQ ID NO: 169; or ci. a light chain comprising an amino acid sequence at least 95% identical to the amino acid sequence of SEQ ID NO: 144, and a heavy chain comprising an amino acid sequence at least 95% identical to the amino acid sequence of SEQ ID NO: 169; or cii. a light chain comprising an amino acid sequence at least 95% identical to the amino acid sequence of SEQ ID NO: 154, and a heavy chain comprising an amino acid sequence at least 95% identical to the amino acid sequence of SEQ ID NO: 169; or ciii. a light chain comprising an amino acid sequence at least 95% identical to the amino acid sequence of SEQ ID NO: 164, and a heavy chain comprising an amino acid sequence at least 95% identical to the amino acid sequence of SEQ ID NO: 169; or civ. a light chain comprising an amino acid sequence at least 95% identical to the amino acid sequence of SEQ ID NO: 174, and a heavy chain comprising an amino acid sequence at least 95% identical to the amino acid sequence of SEQ ID NO: 169; or cv. a light chain comprising an amino acid sequence at least 95% identical to the amino acid sequence of SEQ ID NO: 184, and a heavy chain comprising an amino acid sequence at least 95% identical to the amino acid sequence of SEQ ID NO: 169; or cvi. a light chain comprising an amino acid sequence at least 95% identical to the amino acid sequence of SEQ ID NO: 194, and a heavy chain comprising an amino acid sequence at least 95% identical to the amino acid sequence of SEQ ID NO: 169; or cvii. a light chain comprising an amino acid sequence at least 95% identical to the amino acid sequence of SEQ ID NO: 204, and a heavy chain comprising an amino acid sequence at least 95% identical to the amino acid sequence of SEQ ID NO: 169; or cviii. a light chain comprising an amino acid sequence at least 95% identical to the amino acid sequence of SEQ ID NO: 214, and a heavy chain comprising an amino acid sequence at least 95% identical to the amino acid sequence of SEQ ID NO: 169; or cix. a light chain comprising an amino acid sequence at least 95% identical to the amino acid sequence of SEQ ID NO: 224, and a heavy chain comprising an amino acid sequence at least 95% identical to the amino acid sequence of SEQ ID NO: 169; or cx. a light chain comprising an amino acid sequence at least 95% identical to the amino sequence at least 95% identical to the amino acid sequence of SEQ ID NO: 169; or cxi. a light chain comprising an amino acid sequence at least 95% identical to the amino acid sequence of SEQ ID NO: 244, and a heavy chain comprising an amino acid sequence at least 95% identical to the amino acid sequence of SEQ ID NO: 169; or cxii. a light chain comprising an amino acid sequence at least 95% identical to the amino acid sequence of SEQ ID NO: 254, and a heavy chain comprising an amino acid sequence at least 95% identical to the amino acid sequence of SEQ ID NO: 169; or cxiii. a light chain comprising an amino acid sequence at least 95% identical to the amino acid sequence of SEQ ID NO: 104, and a heavy chain comprising an amino acid sequence at least 95% identical to the amino acid sequence of SEQ ID NO: 179; or cxiv. a light chain comprising an amino acid sequence at least 95% identical to the amino acid sequence of SEQ ID NO: 114, and a heavy chain comprising an amino acid sequence at least 95% identical to the amino acid sequence of SEQ ID NO: 179; or cxv. a light chain comprising an amino acid sequence at least 95% identical to the amino acid sequence of SEQ ID NO: 124, and a heavy chain comprising an amino acid sequence at least 95% identical to the amino acid sequence of SEQ ID NO: 179; or cxvi. a light chain comprising an amino acid sequence at least 95% identical to the amino acid sequence of SEQ ID NO: 134, and a heavy chain comprising an amino acid sequence at least 95% identical to the amino acid sequence of SEQ ID NO: 179; or cxvii. a light chain comprising an amino acid sequence at least 95% identical to the amino acid sequence of SEQ ID NO: 144, and a heavy chain comprising an amino acid sequence at least 95% identical to the amino acid sequence of SEQ ID NO: 179; or cxviii. a light chain comprising an amino acid sequence at least 95% identical to the amino acid sequence of SEQ ID NO: 154, and a heavy chain comprising an amino acid sequence at least 95% identical to the amino acid sequence of SEQ ID NO: 179; or cxix. a light chain comprising an amino acid sequence at least 95% identical to the amino acid sequence of SEQ ID NO: 164, and a heavy chain comprising an amino acid sequence at least 95% identical to the amino acid sequence of SEQ ID NO: 179; or cxx. a light chain comprising an amino acid sequence at least 95% identical to the amino acid sequence of SEQ ID NO: 174, and a heavy chain comprising an amino acid sequence at least 95% identical to the amino acid sequence of SEQ ID NO: 179; or cxxi. a light chain comprising an amino acid sequence at least 95% identical to the amino acid sequence of SEQ ID NO: 184, and a heavy chain comprising an amino acid sequence at least 95% identical to the amino acid sequence of SEQ ID NO: 179; or cxxii. a light chain comprising an amino acid sequence at least 95% identical to the amino sequence at least 95% identical to the amino acid sequence of SEQ ID NO: 179; or cxxiii. a light chain comprising an amino acid sequence at least 95% identical to the amino acid sequence of SEQ ID NO: 204, and a heavy chain comprising an amino acid sequence at least 95% identical to the amino acid sequence of SEQ ID NO: 179; or cxxiv. a light chain comprising an amino acid sequence at least 95% identical to the amino acid sequence of SEQ ID NO: 214, and a heavy chain comprising an amino acid sequence at least 95% identical to the amino acid sequence of SEQ ID NO: 179; or cxxv. a light chain comprising an amino acid sequence at least 95% identical to the amino acid sequence of SEQ ID NO: 224, and a heavy chain comprising an amino acid sequence at least 95% identical to the amino acid sequence of SEQ ID NO: 179; or cxxvi. a light chain comprising an amino acid sequence at least 95% identical to the amino acid sequence of SEQ ID NO: 234, and a heavy chain comprising an amino acid sequence at least 95% identical to the amino acid sequence of SEQ ID NO: 179; or cxxvii. a light chain comprising an amino acid sequence at least 95% identical to the amino acid sequence of SEQ ID NO: 244, and a heavy chain comprising an amino acid sequence at least 95% identical to the amino acid sequence of SEQ ID NO: 179.

6. The anti-CTGF antibody or antigen-binding fragment thereof according to any one of the foregoing paras, comprising:

i. a light chain comprising the amino acid sequence of SEQ ID NO: 224, and a heavy chain comprising the amino acid sequence of SEQ ID NO: 109; or ii. a light chain comprising the amino acid sequence of SEQ ID NO: 104, and a heavy chain comprising the amino acid sequence of SEQ ID NO: 109; or iii. a light chain comprising the amino acid sequence of SEQ ID NO: 114, and a heavy chain comprising the amino acid sequence of SEQ ID NO: 109; or iv. a light chain comprising the amino acid sequence of SEQ ID NO: 124, and a heavy chain comprising the amino acid sequence of SEQ ID NO: 109; or v. a light chain comprising the amino acid sequence of SEQ ID NO: 134, and a heavy chain comprising the amino acid sequence of SEQ ID NO: 109; or vi. a light chain comprising the amino acid sequence of SEQ ID NO: 144, and a heavy chain comprising the amino acid sequence of SEQ ID NO: 109; or vii. a light chain comprising the amino acid sequence of SEQ ID NO: 154, and a heavy chain comprising the amino acid sequence of SEQ ID NO: 109; or viii. a light chain comprising the amino acid sequence of SEQ ID NO: 164, and a heavy chain comprising the amino acid sequence of SEQ ID NO: 109; or ix. a light chain comprising the amino acid sequence of SEQ ID NO: 174, and a heavy chain comprising the amino acid sequence of SEQ ID NO: 109; or x. a light chain comprising the amino acid sequence of SEQ ID NO: 184, and a heavy chain comprising the amino acid sequence of SEQ ID NO: 109; or xi. a light chain comprising the amino acid sequence of SEQ ID NO: 194, and a heavy chain comprising the amino acid sequence of SEQ ID NO: 109; or xii. a light chain comprising the amino acid sequence of SEQ ID NO: 204, and a heavy chain comprising the amino acid sequence of SEQ ID NO: 109; or xiii. a light chain comprising the amino acid sequence of SEQ ID NO: 214, and a heavy chain comprising the amino acid sequence of SEQ ID NO: 109; or xiv. a light chain comprising the amino acid sequence of SEQ ID NO: 234, and a heavy chain comprising the amino acid sequence of SEQ ID NO: 109; or xv. a light chain comprising the amino acid sequence of SEQ ID NO: 244, and a heavy chain comprising the amino acid sequence of SEQ ID NO: 109; or xvi. a light chain comprising the amino acid sequence of SEQ ID NO: 254, and a heavy chain comprising the amino acid sequence of SEQ ID NO: 109; or xvii. a light chain comprising the amino acid sequence of SEQ ID NO: 104, and a heavy chain comprising the amino acid sequence of SEQ ID NO: 119; or xviii. a light chain comprising the amino acid sequence of SEQ ID NO: 114, and a heavy chain comprising the amino acid sequence of SEQ ID NO: 119; or xix. a light chain comprising the amino acid sequence of SEQ ID NO: 124, and a heavy chain comprising the amino acid sequence of SEQ ID NO: 119; or xx. a light chain comprising the amino acid sequence of SEQ ID NO: 134, and a heavy chain comprising the amino acid sequence of SEQ ID NO: 119; or xxi. a light chain comprising the amino acid sequence of SEQ ID NO: 144, and a heavy chain comprising the amino acid sequence of SEQ ID NO: 119; or xxii. a light chain comprising the amino acid sequence of SEQ ID NO: 154, and a heavy chain comprising the amino acid sequence of SEQ ID NO: 119; or xxiii. a light chain comprising the amino acid sequence of SEQ ID NO: 164, and a heavy chain comprising the amino acid sequence of SEQ ID NO: 119; or xxiv. a light chain comprising the amino acid sequence of SEQ ID NO: 174, and a heavy chain comprising the amino acid sequence of SEQ ID NO: 119; or xxv. a light chain comprising the amino acid sequence of SEQ ID NO: 184, and a heavy chain comprising the amino acid sequence of SEQ ID NO: 119; or xxvi. a light chain comprising the amino acid sequence of SEQ ID NO: 194, and a heavy chain comprising the amino acid sequence of SEQ ID NO: 119; or xxvii. a light chain comprising the amino acid sequence of SEQ ID NO: 204, and a heavy chain comprising the amino acid sequence of SEQ ID NO: 119; or xxviii. a light chain comprising the amino acid sequence of SEQ ID NO: 214, and a heavy chain comprising the amino acid sequence of SEQ ID NO: 119; or xxix. a light chain comprising the amino acid sequence of SEQ ID NO: 224, and a heavy chain comprising the amino acid sequence of SEQ ID NO: 119; or xxx. a light chain comprising the amino acid sequence of SEQ ID NO: 234, and a heavy chain comprising the amino acid sequence of SEQ ID NO: 119; or xxxi. a light chain comprising the amino acid sequence of SEQ ID NO: 244, and a heavy chain comprising the amino acid sequence of SEQ ID NO: 119; or xxxii. a light chain comprising the amino acid sequence of SEQ ID NO: 254, and a heavy chain comprising the amino acid sequence of SEQ ID NO: 119; or xxxiii. a light chain comprising the amino acid sequence of SEQ ID NO: 104, and a heavy chain comprising the amino acid sequence of SEQ ID NO: 129; or xxxiv. a light chain comprising the amino acid sequence of SEQ ID NO: 114, and a heavy chain comprising the amino acid sequence of SEQ ID NO: 129; or xxxv. a light chain comprising the amino acid sequence of SEQ ID NO: 124, and a heavy chain comprising the amino acid sequence of SEQ ID NO: 129; or xxxvi. a light chain comprising the amino acid sequence of SEQ ID NO: 134, and a heavy chain comprising the amino acid sequence of SEQ ID NO: 129; or xxxvii. a light chain comprising the amino acid sequence of SEQ ID NO: 144, and a heavy chain comprising the amino acid sequence of SEQ ID NO: 129; or xxxviii. a light chain comprising the amino acid sequence of SEQ ID NO: 154, and a heavy chain comprising the amino acid sequence of SEQ ID NO: 129; or xxxix. a light chain comprising the amino acid sequence of SEQ ID NO: 164, and a heavy chain comprising the amino acid sequence of SEQ ID NO: 129; or xl. a light chain comprising the amino acid sequence of SEQ ID NO: 174, and a heavy chain comprising the amino acid sequence of SEQ ID NO: 129; or xli. a light chain comprising the amino acid sequence of SEQ ID NO: 184, and a heavy chain comprising the amino acid sequence of SEQ ID NO: 129; or xlii. a light chain comprising the amino acid sequence of SEQ ID NO: 194, and a heavy chain comprising the amino acid sequence of SEQ ID NO: 129; or xliii. a light chain comprising the amino acid sequence of SEQ ID NO: 204, and a heavy chain comprising the amino acid sequence of SEQ ID NO: 129; or xliv. a light chain comprising the amino acid sequence of SEQ ID NO: 214, and a heavy chain comprising the amino acid sequence of SEQ ID NO: 129; or xlv. a light chain comprising the amino acid sequence of SEQ ID NO: 224, and a heavy chain comprising the amino acid sequence of SEQ ID NO: 129; or xlvi. a light chain comprising the amino acid sequence of SEQ ID NO: 234, and a heavy chain comprising the amino acid sequence of SEQ ID NO: 129; or xlvii. a light chain comprising the amino acid sequence of SEQ ID NO: 244, and a heavy chain comprising the amino acid sequence of SEQ ID NO: 129; or xlviii. a light chain comprising the amino acid sequence of SEQ ID NO: 254, and a heavy chain comprising the amino acid sequence of SEQ ID NO: 129; or xlix. a light chain comprising the amino acid sequence of SEQ ID NO: 104, and a heavy chain comprising the amino acid sequence of SEQ ID NO: 139; or l. a light chain comprising the amino acid sequence of SEQ ID NO: 114, and a heavy chain comprising the amino acid sequence of SEQ ID NO: 139; or li. a light chain comprising the amino acid sequence of SEQ ID NO: 124, and a heavy chain comprising the amino acid sequence of SEQ ID NO: 139; or lii. a light chain comprising the amino acid sequence of SEQ ID NO: 134, and a heavy chain comprising the amino acid sequence of SEQ ID NO: 139; or liii. a light chain comprising the amino acid sequence of SEQ ID NO: 144, and a heavy chain comprising the amino acid sequence of SEQ ID NO: 139; or liv. a light chain comprising the amino acid sequence of SEQ ID NO: 154, and a heavy chain comprising the amino acid sequence of SEQ ID NO: 139; or lv. a light chain comprising the amino acid sequence of SEQ ID NO: 164, and a heavy chain comprising the amino acid sequence of SEQ ID NO: 139; or lvi. a light chain comprising the amino acid sequence of SEQ ID NO: 174, and a heavy chain comprising the amino acid sequence of SEQ ID NO: 139; or lvii. a light chain comprising the amino acid sequence of SEQ ID NO: 184, and a heavy chain comprising the amino acid sequence of SEQ ID NO: 139; or lviii. a light chain comprising the amino acid sequence of SEQ ID NO: 194, and a heavy chain comprising the amino acid sequence of SEQ ID NO: 139; or lix. a light chain comprising the amino acid sequence of SEQ ID NO: 204, and a heavy chain comprising the amino acid sequence of SEQ ID NO: 139; or lx. a light chain comprising the amino acid sequence of SEQ ID NO: 214, and a heavy chain comprising the amino acid sequence of SEQ ID NO: 139; or lxi. a light chain comprising the amino acid sequence of SEQ ID NO: 224, and a heavy chain comprising the amino acid sequence of SEQ ID NO: 139; or lxii. a light chain comprising the amino acid sequence of SEQ ID NO: 234, and a heavy chain comprising the amino acid sequence of SEQ ID NO: 139; or lxiii. a light chain comprising the amino acid sequence of SEQ ID NO: 244, and a heavy chain comprising the amino acid sequence of SEQ ID NO: 139; or lxiv. a light chain comprising the amino acid sequence of SEQ ID NO: 254, and a heavy chain comprising the amino acid sequence of SEQ ID NO: 139; or lxv. a light chain comprising the amino acid sequence of SEQ ID NO: 104, and a heavy chain comprising the amino acid sequence of SEQ ID NO: 149; or lxvi. a light chain comprising the amino acid sequence of SEQ ID NO: 114, and a heavy chain comprising the amino acid sequence of SEQ ID NO: 149; or lxvii. a light chain comprising the amino acid sequence of SEQ ID NO: 124, and a heavy chain comprising the amino acid sequence of SEQ ID NO: 149; or lxviii. a light chain comprising the amino acid sequence of SEQ ID NO: 134, and a heavy chain comprising the amino acid sequence of SEQ ID NO: 149; or lxix. a light chain comprising the amino acid sequence of SEQ ID NO: 144, and a heavy chain comprising the amino acid sequence of SEQ ID NO: 149; or lxx. a light chain comprising the amino acid sequence of SEQ ID NO: 154, and a heavy chain comprising the amino acid sequence of SEQ ID NO: 149; or lxxi. a light chain comprising the amino acid sequence of SEQ ID NO: 164, and a heavy chain comprising the amino acid sequence of SEQ ID NO: 149; or lxxii. a light chain comprising the amino acid sequence of SEQ ID NO: 174, and a heavy chain comprising the amino acid sequence of SEQ ID NO: 149; or lxxiii. a light chain comprising the amino acid sequence of SEQ ID NO: 184, and a heavy chain comprising the amino acid sequence of SEQ ID NO: 149; or lxxiv. a light chain comprising the amino acid sequence of SEQ ID NO: 194, and a heavy chain comprising the amino acid sequence of SEQ ID NO: 149; or lxxv. a light chain comprising the amino acid sequence of SEQ ID NO: 204, and a heavy chain comprising the amino acid sequence of SEQ ID NO: 149; or lxxvi. a light chain comprising the amino acid sequence of SEQ ID NO: 214, and a heavy chain comprising the amino acid sequence of SEQ ID NO: 149; or lxxvii. a light chain comprising the amino acid sequence of SEQ ID NO: 224, and a heavy chain comprising the amino acid sequence of SEQ ID NO: 149; or lxxviii. a light chain comprising the amino acid sequence of SEQ ID NO: 234, and a heavy chain comprising the amino acid sequence of SEQ ID NO: 149; or lxxix. a light chain comprising the amino acid sequence of SEQ ID NO: 244, and a heavy chain comprising the amino acid sequence of SEQ ID NO: 149; or lxxx. a light chain comprising the amino acid sequence of SEQ ID NO: 254, and a heavy chain comprising the amino acid sequence of SEQ ID NO: 149; or lxxxi. a light chain comprising the amino acid sequence of SEQ ID NO: 104, and a heavy chain comprising the amino acid sequence of SEQ ID NO: 159; or lxxxii. a light chain comprising the amino acid sequence of SEQ ID NO: 114, and a heavy chain comprising the amino acid sequence of SEQ ID NO: 159; or lxxxiii. a light chain comprising the amino acid sequence of SEQ ID NO: 124, and a heavy chain comprising the amino acid sequence of SEQ ID NO: 159; or lxxxiv. a light chain comprising the amino acid sequence of SEQ ID NO: 134, and a heavy chain comprising the amino acid sequence of SEQ ID NO: 159; or lxxxv. a light chain comprising the amino acid sequence of SEQ ID NO: 144, and a heavy chain comprising the amino acid sequence of SEQ ID NO: 159; or lxxxvi. a light chain comprising the amino acid sequence of SEQ ID NO: 154, and a heavy chain comprising the amino acid sequence of SEQ ID NO: 159; or lxxxvii. a light chain comprising the amino acid sequence of SEQ ID NO: 164, and a heavy chain comprising the amino acid sequence of SEQ ID NO: 159; or lxxxviii. a light chain comprising the amino acid sequence of SEQ ID NO: 174, and a heavy chain comprising the amino acid sequence of SEQ ID NO: 159; or lxxxix. a light chain comprising the amino acid sequence of SEQ ID NO: 184, and a heavy chain comprising the amino acid sequence of SEQ ID NO: 159; or xc. a light chain comprising the amino acid sequence of SEQ ID NO: 194, and a heavy chain comprising the amino acid sequence of SEQ ID NO: 159; or xci. a light chain comprising the amino acid sequence of SEQ ID NO: 204, and a heavy chain comprising the amino acid sequence of SEQ ID NO: 159; or xcii. a light chain comprising the amino acid sequence of SEQ ID NO: 214, and a heavy chain comprising the amino acid sequence of SEQ ID NO: 159; or xciii. a light chain comprising the amino acid sequence of SEQ ID NO: 224, and a heavy chain comprising the amino acid sequence of SEQ ID NO: 159; or xciv. a light chain comprising the amino acid sequence of SEQ ID NO: 234, and a heavy chain comprising the amino acid sequence of SEQ ID NO: 159; or xcv. a light chain comprising the amino acid sequence of SEQ ID NO: 244, and a heavy chain comprising the amino acid sequence of SEQ ID NO: 159; or xcvi. a light chain comprising the amino acid sequence of SEQ ID NO: 254, and a heavy chain comprising the amino acid sequence of SEQ ID NO: 159; or xcvii. a light chain comprising the amino acid sequence of SEQ ID NO: 104, and a heavy chain comprising the amino acid sequence of SEQ ID NO: 169; or xcviii. a light chain comprising the amino acid sequence of SEQ ID NO: 114, and a heavy chain comprising the amino acid sequence of SEQ ID NO: 169; or xcix. a light chain comprising the amino acid sequence of SEQ ID NO: 124, and a heavy chain comprising the amino acid sequence of SEQ ID NO: 169; or c. a light chain comprising the amino acid sequence of SEQ ID NO: 134, and a heavy chain comprising the amino acid sequence of SEQ ID NO: 169; or ci. a light chain comprising the amino acid sequence of SEQ ID NO: 144, and a heavy chain comprising the amino acid sequence of SEQ ID NO: 169; or cii. a light chain comprising the amino acid sequence of SEQ ID NO: 154, and a heavy chain comprising the amino acid sequence of SEQ ID NO: 169; or ciii. a light chain comprising the amino acid sequence of SEQ ID NO: 164, and a heavy chain comprising the amino acid sequence of SEQ ID NO: 169; or civ. a light chain comprising the amino acid sequence of SEQ ID NO: 174, and a heavy chain comprising the amino acid sequence of SEQ ID NO: 169; or cv. a light chain comprising the amino acid sequence of SEQ ID NO: 184, and a heavy chain comprising the amino acid sequence of SEQ ID NO: 169; or cvi. a light chain comprising the amino acid sequence of SEQ ID NO: 194, and a heavy chain comprising the amino acid sequence of SEQ ID NO: 169; or cvii. a light chain comprising the amino acid sequence of SEQ ID NO: 204, and a heavy chain comprising the amino acid sequence of SEQ ID NO: 169; or cviii. a light chain comprising the amino acid sequence of SEQ ID NO: 214, and a heavy chain comprising the amino acid sequence of SEQ ID NO: 169; or cix. a light chain comprising the amino acid sequence of SEQ ID NO: 224, and a heavy chain comprising the amino acid sequence of SEQ ID NO: 169; or cx. a light chain comprising the amino acid sequence of SEQ ID NO: 234, and a heavy chain comprising the amino acid sequence of SEQ ID NO: 169; or cxi. a light chain comprising the amino acid sequence of SEQ ID NO: 244, and a heavy chain comprising the amino acid sequence of SEQ ID NO: 169; or cxii. a light chain comprising the amino acid sequence of SEQ ID NO: 254, and a heavy chain comprising the amino acid sequence of SEQ ID NO: 169; or cxiii. a light chain comprising the amino acid sequence of SEQ ID NO: 104, and a heavy chain comprising the amino acid sequence of SEQ ID NO: 179; or cxiv. a light chain comprising the amino acid sequence of SEQ ID NO: 114, and a heavy chain comprising the amino acid sequence of SEQ ID NO: 179; or cxv. a light chain comprising the amino acid sequence of SEQ ID NO: 124, and a heavy chain comprising the amino acid sequence of SEQ ID NO: 179; or cxvi. a light chain comprising the amino acid sequence of SEQ ID NO: 134, and a heavy chain comprising the amino acid sequence of SEQ ID NO: 179; or cxvii. a light chain comprising the amino acid sequence of SEQ ID NO: 144, and a heavy chain comprising the amino acid sequence of SEQ ID NO: 179; or cxviii. a light chain comprising the amino acid sequence of SEQ ID NO: 154, and a heavy chain comprising the amino acid sequence of SEQ ID NO: 179; or cxix. a light chain comprising the amino acid sequence of SEQ ID NO: 164, and a heavy chain comprising the amino acid sequence of SEQ ID NO: 179; or cxx. a light chain comprising the amino acid sequence of SEQ ID NO: 174, and a heavy chain comprising the amino acid sequence of SEQ ID NO: 179; or cxxi. a light chain comprising the amino acid sequence of SEQ ID NO: 184, and a heavy chain comprising the amino acid sequence of SEQ ID NO: 179; or cxxii. a light chain comprising the amino acid sequence of SEQ ID NO: 194, and a heavy chain comprising the amino acid sequence of SEQ ID NO: 179; or cxxiii. a light chain comprising the amino acid sequence of SEQ ID NO: 204, and a heavy chain comprising the amino acid sequence of SEQ ID NO: 179; or cxxiv. a light chain comprising the amino acid sequence of SEQ ID NO: 214, and a heavy chain comprising the amino acid sequence of SEQ ID NO: 179; or cxxv. a light chain comprising the amino acid sequence of SEQ ID NO: 224, and a heavy chain comprising the amino acid sequence of SEQ ID NO: 179; or cxxvi. a light chain comprising the amino acid sequence of SEQ ID NO: 234, and a heavy chain comprising the amino acid sequence of SEQ ID NO: 179; or cxxvii. a light chain comprising the amino acid sequence of SEQ ID NO: 244, and a heavy chain comprising the amino acid sequence of SEQ ID NO: 179.

7. The anti-CTGF antibody or an antigen-binding fragment thereof according to any one of the foregoing paras, comprising a light chain variable region comprising an L-CDR1 having the amino acid sequence of SEQ ID NO: 220, an L-CDR2 having the amino acid sequence of SEQ ID NO: 221, and an L-CDR3 having the amino acid sequence of SEQ ID NO: 222; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107.

8. The anti-CTGF antibody or an antigen-binding fragment thereof according to any one of the foregoing paras, comprising a light chain variable region comprising the amino acid sequence of SEQ ID NO: 223, and a heavy chain variable region comprising the amino acid sequence of SEQ ID NO: 108.

9. The anti-CTGF antibody or antigen-binding fragment thereof according to any one of the foregoing paras, comprising a light chain comprising the amino acid sequence of SEQ ID NO: 224, and a heavy chain comprising the amino acid sequence of SEQ ID NO: 109.

10. The anti-CTGF antibody of any one of the foregoing paras, wherein (a) said antibody comprises a heavy chain constant region selected from IgG1, IgG2, IgG3, IgG4, IgM, IgA and IgE or a variant thereof; (b) the antibody is a monoclonal antibody; and/or (c) the antibody is a human, humanized, or chimeric antibody, preferably a humanized antibody.

11. The anti-CTGF antibody of any one of the foregoing paras, wherein said antibody (a) binds human CTGF with a $K_D$ of 5 pM or lower; (b) binds the N-terminal fragment of human CTGF with a $K_D$ of 0.5 nM or lower; (c) decreases or blocks human CTGF binding to primary human fibroblast cells; (d) decreases or blocks cleavage of human CTGF by MMP7; (e) blocks or inhibits human TGFbeta-induced increase in COL1A1 expression in lung epithelial cells; (f) blocks or inhibits CTGF interaction with alveolar type II cells, fibroblasts and A549 cells; and/or (g) blocks or inhibits CTGF-NTF interaction with alveolar type II cells, fibroblasts and A549 cells.

12. A pharmaceutical composition comprising the antibody or an antigen-binding fragment thereof according to any of the foregoing paras and a pharmaceutically acceptable carrier.

13. The antibody or an antigen-binding fragment thereof according to any one of paras 1 to 11 or the composition according to para 12 for use as a medicament.

14. The antibody or an antigen-binding fragment thereof according to any one of paras 1 to 11 or the composition according to para 12 for use in treating or preventing a CTGF-associated disorder, a fibrotic disease, hypertension, diabetes, myocardial infarction, arthritis, CTGF-related cell proliferative disease, atherosclerosis, glaucoma, or a cancer.

15. The antibody, or an antigen-binding fragment thereof, or the composition for use according to para 13 or 14, wherein said fibrotic disease is idiopathic pulmonary fibrosis (IPF), progressive pulmonary fibrosis (PPF), pulmonary fibrosis with interstitial lung disease (PF-ILD), systemic scleroderma (SSc), Duchenne muscular dystrophy, diabetic nephropathy, diabetic retinopathy, osteoarthritis, scleroderma, chronic heart failure, liver cirrhosis or renal fibrosis, or wherein said cancer is acute lymphoblastic leukemia, dermatofibroma, breast cancer, angiolipoma, angioleiomyoma, connective tissue-generating cancer, prostate cancer, ovarian cancer, colorectal cancer, pancreatic cancer, gastrointestinal cancer, or liver cancer.

16. An isolated polynucleotide or a plurality of isolated polynucleotides that encodes a sequence comprising the heavy chain variable region and/or light chain variable region of the antibody or an antigen-binding fragment thereof according to any one of paras 1 to 11.

17. A vector or plurality of vectors comprising the polynucleotide or the plurality of polynucleotides according to para 16, preferably an expression vector or plurality of expression vectors, more preferably a vector or plurality of vectors comprising said polynucleotide or plurality of polynucleotides in functional association with one or more expression control sequences.

18. A host cell comprising the polynucleotide or plurality of nucleotides according to para 17.

19. A method for the production of an anti-CTGF antibody or antigen-binding fragment thereof according to any one of paras 1 to 11, comprising the steps:

(a) cultivating a host cell according to para 18 under conditions allowing the expression of the anti-CTGF antibody or antigen-binding fragment thereof; and (b) recovering said anti-CTGF antibody or antigen-binding fragment thereof.

20. A method of inhibiting the interaction between human CTGF or human CTGF-NTF and a cell, comprising contacting said human CTGF with an effective amount of the anti-CTGF antibody or antigen-binding fragment thereof according to any one of paras 1 to 11.

DETAILED DESCRIPTION

This disclosure generally relates to anti-CTGF antibodies or antigen-binding fragments thereof. Exemplary anti-CTGF antibodies disclosed herein address the need for treatments of conditions modulated by CTGF signaling. In some aspects, the anti-CTGF antibodies or antigen-binding fragments thereof are for diagnostic and/or therapeutic use, for example in a subject in need thereof, such as a human.

In some aspects, the present disclosure provides an anti-CTGF antibody, in particular, a monoclonal anti-CTGF antibody, for example a human or humanized monoclonal anti-CTGF antibody, having one or more of the properties described herein.

In some aspects, the anti-CTGF-antibody or antigen-binding fragment thereof decreases or prevents the cleavage of full length CTGF by a protease, such as MMP7.

In some aspects, the anti-CTGF-antibody or antigen-binding fragment thereof decreases or blocks the interaction between CTGF and cells that express one or more receptors for CTGF, such as alveolar type II cells, fibroblasts and A549 cells.

In some aspects, the anti-CTGF-antibody or antigen-binding fragment thereof decreases or prevents the inhibition of macrophage efferocytosis by CTGF-NTF.

In some aspects, the anti-CTGF-antibody or antigen-binding fragment thereof decreases or prevents fibrotic progression in human small airway cells raised at an air-liquid interface and exposed to pro-fibrotic cytokines, such as the IPF cytokine cocktail (IPF-RC) described in Example 5 herein.

In some aspects, the anti-CTGF-antibody or antigen-binding fragment thereof exhibits a binding affinity ($K_D$) for full length human CTGF of lower than 50 pM, lower than 25 pM, lower than 15 pM, lower than 10 pM, lower than 5 pM, or lower than 2 pM, preferably when measured by surface plasmon resonance at 25° C.

In some aspects, the anti-CTGF-antibody or antigen-binding fragment thereof exhibits a binding affinity ($K_D$) for human CTGF-NTF of lower than 10 nM, lower than 5 nM, lower than 2.5 nM, lower than 1 nM, lower than 0.5 nM, or lower than 0.2 nM, preferably when measured by surface plasmon resonance at 25° C.

In some aspects, the anti-CTGF antibody or antigen-binding fragment thereof of the present disclosure has favorable pharmacokinetic properties. In some aspects, the anti-CTGF antibody of the present disclosure has favorable biophysical properties, for example yield, quality, stability, or solubility.

In the present detailed description, numerous specific details are set forth to provide a full understanding of the subject technology. It will be apparent, however, to one of ordinary skill in the art that the subject technology may be practiced without some of these specific details. In other instances, well-known structures and techniques have not been shown in detail so as not to obscure the subject technology. Preferences and options for a given aspect, feature, embodiment, or parameter should, unless the context indicates otherwise, be regarded as having been disclosed in combination with any and all preferences and options for all other aspects, features, embodiments and parameters of the invention.

Antibodies

The generalized structure of antibodies or immunoglobulin is well known to those of skill in the art, these molecules are heterotetrametric glycoproteins, typically of about 150,000 daltons, composed of two identical light (L) chains and two identical heavy (H) chains. Each light chain is covalently linked to a heavy chain by one disulfide bond to form a heterodimer, and the heterotrimeric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain ($V_H$ is the variable heavy chain), followed by three or four constant domains ($C_H1$, $C_H2$, $C_H3$, and optionally $C_H4$), as well as a hinge region between $C_H1$ and $C_H2$. Each light chain has two domains, an amino-terminal variable domain ($V_L$ is the variable light chain) and a carboxy-terminal constant domain ($C_L$). The $V_L$ domain associates non-covalently with the $V_H$ domain, whereas the $C_L$ domain is commonly covalently linked to the $C_H1$ domain via a disulfide bond. Particular amino acid residues are believed to form an interface between the light and heavy chain variable domains (Chothia et al., 1985, J. Mol. Biol. 186:651-663, Vargas-Madrazo E, Paz-García E. J Mol Recognit. 2003; 16 (3): 113-120). The variable domains are also referred herein as variable regions, and the constant domains as constant regions.

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5th Ed. Public Health Service, National Institutes of Health, Bethesda, Md., whereas HVLs are structurally defined according to the three-dimensional structure of the variable domain, as described by Chothia and Lesk, 1987, J. Mol. Biol. 196:901-917. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain. Unless indicated otherwise, references to CDR sequences herein refer to the CDR sequences defined by Kabat. IMGT and NORTH provide alternative definitions of the CDRs (see, Lefranc M P. Unique database numbering system for immunogenetic analysis. Immunol Today (1997) 18:509; and North B, Lehmann A, Dunbrack R L J. A new clustering of antibody CDR loop conformations. J Mol Biol. (2011) 406:228-56). Additionally, CDRs may be defined per the Chemical Computing Group (CCG) numbering (Almagro et al., Proteins 2011; 79:3050-3066 and Maier et al, Proteins 2014; 82:1599-1610). The CDR1, CDR2, CDR3 of the heavy and light chains therefore define the unique and functional properties specific for a given antibody. The skilled person is able to determine the CDR sequences according to aforementioned numbering schemes from a specified VH and/or VL sequences. Except where indicated otherwise, the present invention has been disclosed with reference to the CDRs defined according to Kabat, though it is to be understood that the invention could likewise be determined with reference to other CDR numbering schemes, such as those CDRs disclosed in Tables 3-8 herein (e.g., Chothia, CCG, IMGT, or Aho).

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding. Those skilled in the art can routinely determine which residues comprise a particular CDR given the variable region amino acid sequence of the antibody. The CDR1, CDR2, CDR3 of the heavy and light chains therefore define the unique and functional properties specific for a given antibody.

FR residues and Ig constant domains are generally not directly involved in antigen binding but contribute to antigen binding and/or mediate antibody effector function. Some FR residues are thought to have a significant effect on antigen binding in at least three ways: by noncovalently binding directly to an epitope, by interacting with one or more CDR residues, and by affecting the interface between the heavy and light chains. The constant domains are not directly involved in antigen binding but mediate various Ig effector functions, such as participation of the antibody in antibody-dependent cellular cytotoxicity (ADCC), complement-dependent cytotoxicity (CDC) and antibody-dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, $IgG_4$, $IgA_1$, and $IgA_2$, respectively. The antibodies, as described herein, may be of any one these classes or subclasses. Preferably, the antibody is of the IgG-type, more preferably IgG1. The heavy chain constant domains that correspond to the different classes of immunoglobulins are called α, δ, ε, γ, and μ, respectively. The subunit structures and three-dimensional configurations of the classes of native immunoglobulins are well known.

Definitions

The terms, "antibody", and "anti-CTGF antibody", are used herein interchangeably and encompass monoclonal antibodies (including full length monoclonal antibodies), multispecific antibodies (e.g., bispecific antibodies), antibodies with minor modifications such as N- or C-terminal truncations and antibody fragments such as variable domains and other portions of antibodies that exhibit a desired biological activity, e.g., CTGF binding.

The term "monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation that may be present. Monoclonal antibodies typically bind one antigenic epitope. A bispecific monoclonal antibody binds two distinct antigenic epitopes. A monoclonal antibody may be monospecific or multispecific such as bispecific, monovalent, bivalent or multivalent. It should be understood that monoclonal antibodies can be made by any technique or methodology known in the art; including e.g., the hybridoma method (Kohler et al., 1975, Nature 256:495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222:581-597.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g. human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus or germline sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81:6851-6855).

The terms "antibody fragment", "antigen-binding fragment", "anti-CTGF antibody fragment", "anti-CTGF antibody fragment", "engineered anti-CTGF antibody fragment" refer to a portion of a full length anti-CTGF antibody, in which a variable region or a functional capability is retained, for example, CTGF binding. Examples of antibody fragments include, but are not limited to, a Fab, Fab', F(ab')₂, Fd, Fv, scFv and scFv-Fc fragment, a diabody, a linear antibody, a single-chain antibody, a minibody, a diabody formed from antibody fragments, and multispecific antibodies formed from antibody fragments.

Antibody fragments can be obtained for example by treating full length antibodies treated with enzymes such as papain or pepsin to generate useful antibody fragments. Papain digestion is used to produce two identical antigen-binding antibody fragments called "Fab" fragments, each with a single antigen-binding site, and a residual "Fc" fragment. The Fab fragment also contains the constant domain of the light chain and the $C_H1$ domain of the heavy chain. Pepsin treatment yields a F(ab')$_2$ fragment that has two antigen-binding sites and is still capable of cross-linking antigen.

An example of antibody fragments according to the present disclosure are Fab' fragments. Fab' fragments differ from Fab fragments by the presence of additional residues including one or more cysteines from the antibody hinge region at the C-terminus of the C$_H$1 domain. F(ab')$_2$ antibody fragments are pairs of Fab' fragments linked by cysteine residues in the hinge region. Other chemical couplings of antibody fragments are also known.

A "Fv" fragment contains a complete antigen-recognition and binding site consisting of a dimer of one heavy and one light chain variable domain in tight, non-covalent association. In this configuration, the three CDRs of each variable domain interact to define an antigen-biding site on the surface of the V$_H$-V$_L$ dimer. Collectively, the six CDRs confer antigen-binding specificity to the antibody.

Antibody fragments may also include "single-chain Fv" or "scFv" fragments. A "single-chain Fv" or "scFv" antibody fragment is a single chain Fv variant comprising the V$_H$ and V$_L$ domains of an antibody where the domains are present in a single polypeptide chain. The single chain Fv is capable of recognizing and binding antigen. The scFv polypeptide may optionally also contain a polypeptide linker positioned between the V$_H$ and V$_L$ domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

Antibody fragments may also form tandem Fd segments, which comprise a pair of tandem Fd segments (V$_H$-C$_H$1-V$_H$-C$_H$1) to form a pair of antigen binding regions. These "linear antibodies" can be bispecific or monospecific as described in, for example, Zapata et al. 1995, Protein Eng. 8(10):1057-1062.

The term "human antibody" as used herein includes antibodies or fragments thereof derived from human germline immunoglobulin sequences. The term "human antibody" is not intended to include antibodies in which CDR sequences derived from the germline of another (mammalian) species, such as a mouse, rat or rabbit, have been grafted onto human framework sequences. Thus, as used herein, the term "human antibody" refers to an antibody or fragment thereof in which every part of the protein (e.g., CDR, framework, C$_L$, C$_H$ domains (e.g., C$_H$1, C$_H$2, C$_H$3), hinge, V$_L$, V$_H$) is substantially non-immunogenic in humans, with only minor sequence changes or variations as further described herein below.

Technologies for creating such a "human antibody" have been described and include without being limiting phage display or use of transgenic animals (www.Ablexis.com/technology-alivamab.php; WO 90/05144; D. Marks, H. R. Hoogenboom, T. P. Bonnert, J. McCafferty, A. D. Griffiths and G. Winter (1991) "By-passing immunisation. Human antibodies from V-gene libraries displayed on phage." J. Mol. Biol., 222, 581-597; Knappik et al., J. Mol. Biol. 296:57-86, 2000; S. Carmen and L. Jermutus, "Concepts in antibody phage display". Briefings in Functional Genomics and Proteomics 2002 1(2):189-203; Lonberg N, Huszar D. "Human antibodies from transgenic mice". Int Rev Immunol. 1995; 13(1):65-93; Brüggemann M, Taussig M J. "Production of human antibody repertoires in transgenic mice". Curr Opin Biotechnol. 1997 August; 8(4):455-8).

Thus, a human antibody is distinct from e.g., a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes.

In some aspects, an anti-CTGF antibody is a humanized antibody or antibody fragment thereof. A humanized antibody or a humanized antibody fragment is a specific type of chimeric antibody which includes an immunoglobulin amino acid sequence variant, or fragment thereof, which is capable of binding to a predetermined antigen and which, comprises one or more FRs having substantially the amino acid sequence of a human immunoglobulin and one or more CDRs having substantially the amino acid sequence of a non-human immunoglobulin. This non-human amino acid sequence often referred to as an "import" sequence is typically taken from an "import" antibody domain, particularly a variable domain. In general, a humanized antibody includes at least the CDRs or HVLs of a non-human antibody, inserted between the FRs of a human heavy or light chain variable domain. Methods of humanization of antibodies are for example described by Almagro et al., (2008) Frontiers in Bioscience 13, 1619-1633, or in WO12092374 A2.

The chimeric, humanized or human antibodies or antigen-binding fragments thereof of the present disclosure may further be engineered. Such engineering includes without limitation the removal or exchange of undesired amino acids, for example to reduce immunogenicity in humans, or to avoid deamidation, undesirable charges or lipophilicity or non-specific binding. Such removal or exchange of undesired amino acids can, for example, be introduced by random or site-specific mutagenesis in vitro or by somatic mutation in vivo. Moreover, in connection with chimeric or humanized antibodies, it will be understood that certain mouse FR residues may be retained in an antibody or fragment thereof.

In some aspects, an anti-CTGF antibody comprises substantially all of at least one, and typically two, variable domains (such as contained, for example, in Fab, Fab', F(ab')$_2$, ScFv, and Fv fragments). In some aspects, the anti-CTGF antibody also includes at least a portion of an immunoglobulin Fc region, typically that of a human immunoglobulin. Ordinarily, the antibody will contain both the light chain as well as at least the variable domain of a heavy chain. The antibody also may include one or more of the C$_H$1, hinge, C$_H$2, C$_H$3, and/or C$_H$4 regions of the heavy chain, as appropriate.

In some aspects, an anti-CTGF antibody can be selected from any class of immunoglobulins, including IgM, IgG, IgD, IgA and IgE, and any isotype, including IgG$_1$, IgG$_2$, IgG$_3$, IgG$_4$, IgA$_1$ and IgA$_2$. An alternative anti-CTGF antibody can comprise sequences from more than one immunoglobulin class or isotype, and selecting particular modified or unmodified constant domains to optimize desired effector functions is within the ordinary skill in the art.

For example, the Fc region of an antibody mediates its serum half-life and effector functions, such as complement-dependent cytotoxicity (CDC), antibody-dependent cellular cytotoxicity (ADCC) and antibody-dependent cell phagocytosis (ADCP). Fc engineering can be employed to optimize antibody properties suited to the pharmacology activity required of them. Where such cytotoxic activity is not desirable, such as targeting an immune cell in the treatment of cancer, the constant domain may be of isotype with reduced effector function, such as IgG4, and/or be modified with known modifications that reduce effector function. Where such cytotoxic activity is desirable, such as for destruction of a targeted tumor cell, the constant domain may be of isotype with increased effector function and/or be modified with known modifications to increase effector function. Several mutations are known to either reduce or increase effector function. See, e.g., "*The future of antibodies as cancer drugs*" Janice M Reichert, Eugen Dhimolea, Drug Discov Today (2012) September; 17(17-18):954-63; PMID: 22561895, "*Antibody Drug Discovery*" (Volume 4 of Molecular medicine and medicinal chemistry) Clive R. Wood, World Scientific, 2012 ISBN 1848166281, 9781848166288; "*FcγR requirements leading to successful immunotherapy*" Immunol Rev. (2015) November; 268(1): 104-22; PMID: 26497516.

In some aspects, the constant domain of an antibody of the present disclosure is human IgG1 having two modifications in the constant region, Leu234Ala and Leu235Ala. Said modifications in the constant region reduce effector function.

The FRs and CDRs, or HVLs, of an engineered anti-CTGF antibody or antigen-binding fragment thereof need not correspond precisely to the parental sequences, i.e., the sequences of the antibody as isolated prior to engineering. For example, a parental sequence may be altered (e.g., mutagenized) by substitution, insertion or deletion such that the resulting amino acid residue is no longer identical to the original residue in the corresponding position in either parental sequence but the antibody nevertheless retains the function of binding to CTGF. Such alteration typically will not be extensive. Such alterations typically will be conservative alterations. Usually, at least 75% of the engineered antibody residues will correspond to those of the parental sequences, more often at least 90%, and most frequently greater than 95%, or greater than 98% or greater than 99%.

Immunoglobulin residues that affect the interface between heavy and light chain variable regions ("the $V_L$-$V_H$ interface") are those that affect the proximity or orientation of the two chains with respect to one another. Certain residues that may be involved in interchain interactions include $V_L$ residues 34, 36, 38, 44, 46, 87, 89, 91, 96, and 98 and $V_H$ residues 35, 37, 39, 45, 47, 91, 93, 95, 100, and 103 (utilizing the numbering system set forth in Kabat et al., Sequences of Proteins of Immunological Interest (National Institutes of Health, Bethesda, Md., 1987)). U.S. Pat. No. 6,407,213 also discusses that residues such as $V_L$ residues 43 and 85, and $V_H$ residues 43 and 60 also may be involved in this interaction. While these residues are indicated for human IgG only, they are applicable across species. Important antibody residues that are reasonably expected to be involved in interchain interactions are selected for substitution into the consensus sequence.

The terms "consensus sequence" and "consensus antibody" refer to an amino acid sequence which comprises the most frequently occurring amino acid residue at each location in all immunoglobulins of any particular class, isotype, or subunit structure, e.g., a human immunoglobulin variable domain. The consensus sequence may be based on immunoglobulins of a particular species or of many species. A "consensus" sequence, structure, or antibody is understood to encompass a consensus human sequence as described in certain embodiments, and to refer to an amino acid sequence which comprises the most frequently occurring amino acid residues at each location in all human immunoglobulins of any particular class, isotype, or subunit structure. Thus, the consensus sequence contains an amino acid sequence having at each position an amino acid that is present in one or more known immunoglobulins, but which may not exactly duplicate the entire amino acid sequence of any single immunoglobulin. The variable region consensus sequence is not obtained from any naturally produced antibody or immunoglobulin. Kabat et al., 1991, Sequences of Proteins of Immunological Interest, 5th Ed. Public Health Service, National Institutes of Health, Bethesda, Md., and variants thereof. The FRs of heavy and light chain consensus sequences, and variants thereof, provide useful sequences for the preparation of human or humanized anti-CTGF antibodies. See, for example, U.S. Pat. Nos. 6,037,454 and 6,054,297.

An "isolated" antibody is one that has been identified and separated and/or recovered from a component of its natural environment or from a cell culture from which it was expressed. An isolated antibody or antibody fragment may have one or more co- or post-translational modifications that arise during production, purification, and/or storage of the antibody or antibody fragment. Contaminant components of the antibody's natural environment are those materials that may interfere with diagnostic or therapeutic uses of the antibody, and can be enzymes, hormones, or other proteinaceous or non-proteinaceous solutes. In some aspects, the antibody will be purified to at least greater than 95% isolation by weight of antibody, for example purified to at least greater than 95%, 96%, 97%, 98%, or 99%.

An isolated antibody includes an antibody in situ within recombinant cells in which it is produced, since at least one component of the antibody's natural environment will not be present. Ordinarily however, an isolated antibody will be prepared by at least one purification step in which the recombinant cellular material is removed.

"Multispecific" refers to a protein, such as an antibody, that specifically binds two or more distinct antigens or two or more distinct epitopes within the same antigen.

"Bispecific" refers to a protein, such as an antibody, that specifically binds two distinct antigens or two distinct epitopes within the same antigen.

In some embodiments, the antibody that specifically binds CTGF or the antigen-binding fragment thereof is a monospecific antibody. In some embodiments, the antibody that specifically binds CTGF or the antigen-binding fragment thereof is a bispecific antibody. In some embodiments, the antibody or the antigen-binding fragment thereof is a multispecific antibody. The monospecific antibodies that specifically bind CTGF provided herein may be engineered into bispecific antibodies, which are also encompassed within the scope of the present disclosure.

Full length bispecific antibodies may be generated for example using Fab arm exchange (e.g., half-molecule exchange, exchanging one heavy chain-light chain pair) between two monospecific bivalent antibodies by introducing substitutions at the heavy chain $C_H3$ interface in each half molecule to favor heterodimer formation of two antibody half molecules having distinct specificity either in vitro in cell-free environment or using co-expression. The Fab arm exchange reaction is the result of a disulfide-bond.

Bispecific antibodies may also be generated using designs such as the Triomab/Quadroma (Trion Pharma/Fresenius Biotech), Knob-in-Hole (Genentech), CrossMAbs (Roche) and the electrostatically-induced $C_H3$ interaction (Chugai, Amgen, NovoNordisk, Oncomed), the LUZ-Y (Genentech), the Strand Exchange Engineered Domain body (SEEDbody) (EMD Serono), the Biclonic (Merus) and as DuoBody® Products (Genmab A/S).

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

For diagnostic as well as therapeutic monitoring purposes, the antibodies or antigen-binding fragment thereof of the invention also may be conjugated to a label, either a label alone or a label and an additional second agent (prodrug, chemotherapeutic agent and the like). A label, as distinguished from the other second agents refers to an agent that is a detectable compound or composition and it may be conjugated directly or indirectly to an anti-CTGF antibody or antigen-binding fragment thereof of the present invention. The label may itself be detectable (e.g., radioisotope labels or fluorescent labels) or, in the case of an enzymatic label, may catalyze chemical alteration of a substrate compound or composition that is detectable. Labeled anti-CTGF antibodies or antigen-binding fragments thereof can be prepared and used in various applications including in vitro and in vivo diagnostics.

In various aspects of the present invention one or more domains of the anti-CTGF antibodies or antigen-binding fragments thereof will be recombinantly expressed. Such recombinant expression may employ one or more control sequences, i.e., polynucleotide sequences necessary for expression of an operably linked coding sequence in a particular host organism. The control sequences suitable for use in prokaryotic cells include, for example, promoter, operator, and ribosome binding site sequences. Eukaryotic control sequences include, but are not limited to, promoters, polyadenylation signals, and enhancers. These control sequences can be utilized for expression and production of anti-CTGF antibodies or antigen-binding fragments thereof in prokaryotic and eukaryotic host cells.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers are optionally contiguous. Linking can be accomplished by ligation at convenient restriction sites. If such sites do not exist, synthetic oligonucleotide adaptors or linkers can be used.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers, which may for example have been transfected with one or more expression vectors encoding one or more amino acids sequences of an antibody or antigen-binding fragment thereof of the present invention.

The term "mammal" for purposes of treatment according to the invention refers to any animal classified as a mammal, including humans, domesticated and farm animals, and zoo, sports, or companion animals, such as dogs, horses, cats, cows, and the like. Preferably, the mammal is a human.

A "disorder", as used herein, is any condition that would benefit from treatment with an anti-CTGF antibody or antigen-binding fragment thereof described herein. This includes chronic and acute disorders or diseases including those pathological conditions that predispose the mammal to the disorder in question. Non-limiting examples or disorders to be treated herein include CTGF-associated disorders.

As used herein, the term "CTGF-associated disorder" or "CTGF-associated disease" refers to a condition, which can be alleviated by inhibiting the CTGF cleavage and/or by inhibiting CTGF signaling, e.g., CTGF-NTF signaling. The terms "CTGF-associated disorder" or "CTGF-associated disease" include inflammatory disease, respiratory disease, or fibrotic disorders. CTGF-associated disorders include progressive pulmonary fibrosis, idiopathic pulmonary fibrosis, arthritis, atherosclerosis, cardiac fibrosis, connective tissue fibrosis, Duchenne muscular dystrophy, diabetic nephropathy, diabetic retinopathy, diffuse scleroderma, endothelial fibrosis, epithelial fibrosis, fibrotic disorders, glaucoma, joint fibrosis, kidney fibrosis, limited scleroderma, liver fibrosis, macular degeneration, ocular fibrosis, osteoarthritis, proliferative vitreoretinopathy, pulmonary fibrosis, and systemic fibrosis. CTGF-associated disorders include cancers including acute lymphoblastic leukemia, dermatofibromas, breast cancer, breast carcinoma, glioma and glioblastoma, rhabdomyosarcoma and fibrosarcoma, desmoplasia, angiolipoma, angioleiomyoma, desmoplastic cancers, and prostate, ovarian, colorectal, pancreatic, gastrointestinal, and liver cancer and other tumor growth and metastases.

The terms "specifically binds" or "specific binding" in the context of a binding agent, e.g., an antibody or antigen-binding fragment thereof, refers to a binding agent that associates more frequently, more rapidly, with greater duration, with greater affinity, with greater avidity or with some combination of the above, to an antigen or an epitope within the antigen than with an unrelated antigen. In certain embodiments, an antibody or antigen-binding fragment thereof specifically binds to an antigen or epitope within an antigen with a $K_D$ of about 0.1 mM or less, preferably less than about 1 μM. Because of the sequence identity between homologous proteins in different species, or variants of a protein within a single species, specific binding can include an antibody or antigen-binding fragment thereof that recognizes a protein in more than one species. It is understood that, in certain embodiments, an antibody or antigen-binding fragment thereof that specifically binds a first protein may or may not specifically bind a second protein. As such, "specific binding" does not necessarily require (although it can include) exclusive binding, i.e. binding to a single protein. Thus, an antibody or antigen-binding fragment thereof may, in certain embodiments, specifically bind more than one protein.

Methods for determining whether two molecules specifically bind a protein are described herein or a known in the art and include, for example, equilibrium dialysis, surface plasmon resonance, and the like. In one embodiment, specific binding is characterized by a $K_D$ of about $1 \times 10^{-7}$ M (100 nM) or less according to the affinity binding method described in the Examples section herein. In some embodiments, specific binding is characterized by a $K_D$ of about $5 \times 10^{-8}$ M (50 nM) or less according to the affinity binding method described in the Examples section herein. In some embodiments, specific binding is characterized by a $K_D$ of about $1 \times 10^{-8}$ M (10 nM) or less according to the affinity binding method described in the Examples section herein. In some embodiments, specific binding is characterized by a $K_D$ of about $5 \times 10^{-9}$ M (5 nM) or less according to the affinity binding method described in the Examples section herein.

The term "subcutaneous administration" refers to introduction of a drug, for example an anti-CTGF antibody or antigen-binding fragment thereof of the invention, under the skin of a subject such as an animal or human patient. Subcutaneous administration may be performed within a pocket between the skin and underlying tissue. Subcutaneous administration may be performed by relatively slow, sustained delivery from a drug receptacle. Pinching or drawing the skin up and away from underlying tissue may create the pocket.

The term "subcutaneous infusion" refers to introduction of a drug, for example an anti-CTGF antibody or antigen-binding fragment thereof of the invention, under the skin of a subject, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the subject, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of a subject, where bolus drug delivery is less than approximately 15 minutes; in some aspects, less than 5 minutes, and some aspects aspect, less than 60 seconds. In some aspects, administration is within a pocket between the skin and underlying tissue, where the pocket may be created by pinching or drawing the skin up and away from underlying tissue. For example, "subcutaneous bolus" refers to the administration of an anti-CTGF antibody or antigen-binding fragment thereof of the invention to a subject in less than approximately 15 minutes; in some aspects, less than 5 minutes, and in some aspects, less than 60 seconds The term "therapeutically effective amount" is used to refer to an amount of an anti-CTGF antibody or antigen-binding fragment thereof that relieves or ameliorates one or more of the symptoms of the disorder being treated. In doing so, it is that amount that has a beneficial patient outcome. Efficacy can be measured in conventional ways, depending on the condition to be treated.

The terms "treatment" and "therapy" and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an anti-CTGF antibody or antigen-binding fragment thereof prior to or following the onset of a symptom of a disease or disorder thereby preventing or removing one or more signs of the disease or disorder. As an example, the term includes the administration of an anti-CTGF antibody or antigen-binding fragment thereof after clinical manifestation of the disease to combat the symptoms of the disease. Further, administration of an anti-CTGF antibody or antigen-binding fragment thereof after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein. Moreover, as long as the compositions of the invention either alone or in combination with another therapeutic agent alleviate or ameliorate at least one symptom of a disorder being treated as compared to that symptom in the absence of use of the anti-CTGF antibody or antigen-binding fragment thereof composition or antigen-binding fragment thereof, the result should be considered an effective treatment of the underlying disorder regardless of whether all the symptoms of the disorder are alleviated or not.

To "prevent" refers to prophylactic or preventative measures that prevent and/or slow the development of a targeted pathologic condition or disorder. Thus, those in need of prevention include those prone to have or susceptible to the disorder. In some embodiments, a disease or disorder (preferably a CTGF-associated disorder) is successfully prevented according to the methods provided herein if the patient develops, transiently or permanently, e.g., fewer or less severe symptoms associated with the disease or disorder, or a later onset of symptoms associated with the disease or disorder, than a patient who has not been subject to the methods of the invention.

An "effective amount" of an agent, e.g., a pharmaceutical composition, refers to an amount effective, at dosages and for periods of time necessary, to achieve the desired therapeutic or prophylactic result.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present disclosure, the term "comprise" encompasses the term "consist of". The term "comprising" thus encompasses "including" as well as "consisting" e.g., a composition "comprising" X may consist exclusively of X or may include something additional e.g., X+Y. For example, unless the context requires otherwise, an antibody chain disclosed as "comprising" a specified amino acid sequence encompasses an antibody chain "consisting of" that amino acid sequence. Optionally, said antibody chain may be glycosylated at one or more sites and/or may have one or more post-translational modifications.

The term "about" in relation to a numerical value x means x plus or minus (±) 10%, for example, x±1%, or x±2%, or x±3%, or x±4%, or x±5%, or x±6%, or x±7%, or x±8%, or x±9%, or x±10%.

Antibody Preparation

In further aspects, the present invention provides a method of producing anti-CTGF antibodies of the invention and antigen-binding fragments thereof, comprising culturing a recombinant host cell expressing the heavy and light chains and isolating the antibody or antigen-binding fragment thereof produced by the cell.

Preferably, the method for producing an antibody or antigen-binding fragment thereof comprises (a) culturing the host cell and (b) isolating the antibody or antigen-binding fragment thereof expressed from the cell. In addition, the method may optionally contain the step (c) of purifying the antibody or antigen-binding fragment thereof.

An antibody of the invention can be produced by transfecting a host cell with one or more vectors comprising polynucleotides encoding the respective antibodies or fragments, culturing the host cell (in particular under conditions that allow synthesis of said antibody molecule); and recovering said antibody molecule from said culture. It is understood that the heavy and the light chain of an antibody may be encoded by separate polynucleotides. Accordingly, provided herein is also a plurality of polynucleotides encoding the (heavy and light chain of) the antibodies or antigen-binding fragments thereof as described herein (by separate polynucleotides). Such a plurality of polynucleotides may be comprised in a (single) vector or in a plurality of vectors.

The antibody or antigen-binding fragment thereof (e.g. as monoclonal antibodies) can be made using recombinant DNA methods as described in U.S. Pat. No. 4,816,567, which is incorporated by reference herein.

The (isolated) polynucleotides encoding the heavy and light chains may be transfected into host cells such as *E. coli* cells, simian COS cells, Chinese hamster ovary (CHO) cells, or myeloma cells that do not otherwise produce immunoglobulin protein, monoclonal antibodies are generated by the host cells. For example, isolated polynucleotides encoding the heavy and light chains may be stably transfected into a suitable host cell, e.g., a CHO cell, for antibody production.

Various techniques are known for the production of antibody fragments. Traditionally, these fragments are derived via proteolytic digestion of intact antibodies, as described, for example, by Morimoto et al., J. Biochem. Biophys. Meth. 24:107-117 (1993) and Brennan et al., Science 229:81 (1985). In some embodiments, anti-CTGF antibody fragments are produced recombinantly. Fab, Fv, and scFv antibody fragments can all be expressed in and secreted from *E. coli* or other host cells, thus allowing the production of large amounts of these fragments. Other techniques for the production of antibody fragments will be apparent to the skilled practitioner. For example, antibody fragments can be produced by techniques known in the art including, but not limited to: F(ab')2 fragment produced by pepsin digestion of an antibody molecule; Fab fragment generated by reducing the disulfide bridges of an F(ab')2 fragment; Fab fragment generated by the treatment of the antibody molecule with papain and a reducing agent. According to the present invention, techniques can be adapted for the production of single-chain antibodies specific to CTGF (see, e.g., U.S. Pat. No. 4,946,778).

Exemplary Anti-CTGF Antibodies of the Disclosure

Described and disclosed herein are anti-CTGF antibodies, in particular human anti-CTGF antibodies, as well as compositions and articles of manufacture comprising anti-CTGF antibodies of the present invention. Also described are antigen-binding fragments of an anti-CTGF antibody. The anti-CTGF antibodies and antigen-binding fragments thereof can be used in the treatment of a variety of diseases or disorders, in particular, CTGF-associated disorders. An anti-CTGF antibody and an antigen-binding fragment thereof each include at least a portion that specifically binds to CTGF, or a fragment thereof, e.g., CTGF-NTF, preferably human CTGF or human CTGF-NTF.

The generation of anti-CTGF antibodies and their characterization is described in the Examples. CDRs of representative anti-CTGF antibodies of the present invention are disclosed in Tables 1-8 below. Heavy Chain CDR-1, CDR-2, CDR3 (H-CDR1-3) and Light Chain CDR-1, CDR-2, CDR3 (L-CDR1-3) are provided according to the numbering systems according to Kabat, Aho, CCG, and Chothia.

77

TABLE 1

Light chain CDRs according to Kabat

| Antibody Chain | CDR1 | SEQ ID NO: | CDR2 | SEQ ID NO: | CDR3 | SEQ ID NO: |
|---|---|---|---|---|---|---|
| L1 | KSSQSIVHYNEKTYLE | 100 | KVSSRFS | 101 | FQGSHFPLT | 102 |
| L2 | KSSQSIVHYNEKTYLE | 110 | KVSSRAS | 111 | FQGSHFPLT | 112 |
| L3 | KSSQSIVHYNGKTYLE | 120 | KVSSRFS | 121 | FQGSHFPLT | 122 |
| L4 | KSSQSIVHYNGKTYLE | 130 | KVSSRAS | 131 | FQGSHFPLT | 132 |
| L5 | KSSQSIVHYNENTYLE | 140 | KVSSRFS | 141 | FQGSHFPLT | 142 |
| L6 | KSSQSIVHYNENTYLE | 150 | KVSSRAS | 151 | FQGSHFPLT | 152 |
| L7 | RSSQSIVHYNENTYLE | 160 | KVSNRFS | 161 | FQGSHFPLT | 162 |
| L8 | RSSQSIVHYNANTYLE | 170 | KVSNRFS | 171 | FQGSHFPLT | 172 |
| L9 | RSSQSIVHYNTNTYLE | 180 | KVSNRFS | 181 | FQGSHFPLT | 182 |
| L10 | RSSQSIVHYNGKTYLE | 190 | KVSNRFS | 191 | FQGSHFPLT | 192 |
| L11 | RSSQSIVHYNEKTYLE | 200 | KVSNRFS | 201 | FQGSHFPLT | 202 |
| L12 | KSSQSIVHYNGNTYLE | 210 | KVSSRFS | 211 | FQGSHFPLT | 212 |
| L13 | KSSQSIVHYNGNTYLE | 220 | KVSSRAS | 221 | FQGSHFPLT | 222 |
| L14 | KSSQSIVHYNGNTYLE | 230 | KVSSRAS | 231 | FQGSHFPLT | 232 |
| L15 | KSSQSIVHYNEKTYLE | 240 | KVSSRAS | 241 | FQGSHFPLT | 242 |
| L16 | RSSQSIVHYNGNTYLE | 250 | KVSNRDS | 251 | FQGSHFPLT | 252 |

TABLE 2

Heavy chain CDRs according to Kabat

| Antibody Chain | CDR1 | SEQ ID NO: | CDR2 | SEQ ID NO: | CDR3 | SEQ ID NO: |
|---|---|---|---|---|---|---|
| H1 | DYYMA | 105 | NINYEGSRTDLLESLKS | 106 | DTSRGSYFDV | 107 |
| H2 | DYYMA | 115 | NINYYGSRTDLLESLKS | 116 | DTSRGSYFDV | 117 |
| H3 | DYYMA | 125 | NINYEGSRTDLLASLKS | 126 | DTSRGSYFDV | 127 |
| H4 | DYYMA | 135 | NINYYGSRTDLLASLKS | 136 | DTSRGSYFDV | 137 |
| H5 | DYYMA | 145 | NINYDGSRTDLLDSLKS | 146 | DTSRGSYFDV | 147 |
| H6 | DYYMA | 155 | NINYEGSRTDLLDSLKS | 156 | DTSRGSYFDV | 157 |
| H7 | DYYMA | 165 | NINYDGSRTDLLESLKS | 166 | DTSRGSYFDV | 167 |
| H8 | DYYMA | 175 | NINYDGSRTDLLDSLKS | 176 | DTSRGSYFDV | 177 |

TABLE 3

Light chain CDRs according to Aho

| Antibody chain | CDR1 | SEQ ID NO: | CDR2 | SEQ ID NO: | CDR3 | SEQ ID NO: |
|---|---|---|---|---|---|---|
| L1 | QSIVHYNEKTY | 310 | KVS | 320 | FQGSHFPLT | 321 |
| L2 | QSIVHYNEKTY | 310 | KVS | 320 | FQGSHFPLT | 321 |
| L3 | QSIVHYNGKTY | 311 | KVS | 320 | FQGSHFPLT | 321 |

78

TABLE 3-continued

Light chain CDRs according to Aho

| Antibody chain | CDR1 | SEQ ID NO: | CDR2 | SEQ ID NO: | CDR3 | SEQ ID NO: |
|---|---|---|---|---|---|---|
| L4 | QSIVHYNGKTY | 311 | KVS | 320 | FQGSHFPLT | 321 |
| L5 | QSIVHYNENTY | 312 | KVS | 320 | FQGSHFPLT | 321 |
| L6 | QSIVHYNENTY | 312 | KVS | 320 | FQGSHFPLT | 321 |
| L7 | QSIVHYNENTY | 312 | KVS | 320 | FQGSHFPLT | 321 |
| L8 | QSIVHYNANTY | 313 | KVS | 320 | FQGSHFPLT | 321 |
| L9 | QSIVHYNTNTY | 314 | KVS | 320 | FQGSHFPLT | 321 |
| L10 | QSIVHYNGKTY | 311 | KVS | 320 | FQGSHFPLT | 321 |
| L11 | QSIVHYNEKTY | 310 | KVS | 320 | FQGSHFPLT | 321 |
| L12 | QSIVHYNGNTY | 315 | KVS | 320 | FQGSHFPLT | 321 |
| L13 | QSIVHYNGNTY | 315 | KVS | 320 | FQGSHFPLT | 321 |
| L14 | QSIVHYNGNTY | 315 | KVS | 320 | FQGSHFPLT | 321 |
| L15 | QSIVHYNEKTY | 310 | KVS | 320 | FQGSHFPLT | 321 |
| L16 | QSIVHYNGNTY | 315 | KVS | 320 | FQGSHFPLT | 321 |

TABLE 4

Heavy chain CDRs according to Aho

| Antibody chain | CDR1 | SEQ ID NO: | CDR2 | SEQ ID NO: | CDR3 | SEQ ID NO: |
|---|---|---|---|---|---|---|
| H1 | GFTFSDYY | 331 | INYEGSRT | 341 | ARDTSRGSYFDV | 348 |
| H2 | GFTFSDYY | 331 | INYYGSRT | 342 | ARDTSRGSYFDV | 348 |
| H3 | GFTFSDYY | 331 | INYEGSRT | 341 | ARDTSRGSYFDV | 348 |
| H4 | GFTFSDYY | 331 | INYYGSRT | 342 | ARDTSRGSYFDV | 348 |
| H5 | GFTFSDYY | 331 | INYDGSRT | 343 | ARDTSRGSYFDV | 348 |
| H6 | GFTFSDYY | 331 | INYEGSRT | 341 | ARDTSRGSYFDV | 348 |
| H7 | GFTFSDYY | 331 | INYDGSRT | 343 | ARDTSRGSYFDV | 348 |
| H8 | GFTFSDYY | 331 | INYDGSRT | 343 | ARDTSRGSYFDV | 348 |

TABLE 5

Light chain CDRs according to CCG

| Antibody chain | CDR1 | SEQ ID NO: | CDR2 | SEQ ID NO: | CDR3 | SEQ ID NO: |
|---|---|---|---|---|---|---|
| L1 | KSSQSIVHYNEKTYLE | 300 | KVSSRFS | 316 | FQGSHFPLT | 321 |
| L2 | KSSQSIVHYNEKTYLE | 300 | KVSSRAS | 317 | FQGSHFPLT | 321 |
| L3 | KSSQSIVHYNGKTYLE | 301 | KVSSRFS | 316 | FQGSHFPLT | 321 |
| L4 | KSSQSIVHYNGKTYLE | 301 | KVSSRAS | 317 | FQGSHFPLT | 321 |
| L5 | KSSQSIVHYNENTYLE | 302 | KVSSRFS | 316 | FQGSHFPLT | 321 |

TABLE 5-continued

Light chain CDRs according to CCG

| Antibody chain | CDR1 | SEQ ID NO:CDR2 | | SEQ ID NO:CDR3 | | SEQ ID NO: |
|---|---|---|---|---|---|---|
| L6 | KSSQSIVHYNENTYLE | 302 | KVSSRAS | 317 | FQGSHFPLT | 321 |
| L7 | RSSQSIVHYNENTYLE | 303 | KVSNRFS | 318 | FQGSHFPLT | 321 |
| L8 | RSSQSIVHYNANTYLE | 304 | KVSNRFS | 318 | FQGSHFPLT | 321 |
| L9 | RSSQSIVHYNTNTYLE | 305 | KVSNRFS | 318 | FQGSHFPLT | 321 |
| L10 | RSSQSIVHYNGKTYLE | 306 | KVSNRFS | 318 | FQGSHFPLT | 321 |
| L11 | RSSQSIVHYNEKTYLE | 307 | KVSNRFS | 318 | FQGSHFPLT | 321 |
| L12 | KSSQSIVHYNGNTYLE | 308 | KVSSRFS | 316 | FQGSHFPLT | 321 |
| L13 | KSSQSIVHYNGNTYLE | 308 | KVSSRAS | 317 | FQGSHFPLT | 321 |
| L14 | KSSQSIVHYNGNTYLE | 308 | KVSSRAS | 317 | FQGSHFPLT | 321 |
| L15 | KSSQSIVHYNEKTYLE | 300 | KVSSRAS | 317 | FQGSHFPLT | 321 |
| L16 | RSSQSIVHYNGNTYLE | 309 | KVSNRDS | 319 | FQGSHFPLT | 321 |

TABLE 7-continued

Light chain CDRs according to Chothia

| Antibody chain | CDR1 | SEQ ID NO:CDR2 | | SEQ ID NO:CDR3 | | SEQ ID NO: |
|---|---|---|---|---|---|---|
| L9 | RSSQSIVHYNTNTYLE | 305 | KVSNRFS | 318 | FQGSHFPLT | 321 |
| L10 | RSSQSIVHYNGKTYLE | 306 | KVSNRFS | 318 | FQGSHFPLT | 321 |
| L11 | RSSQSIVHYNEKTYLE | 307 | KVSNRFS | 318 | FQGSHFPLT | 321 |
| L12 | KSSQSIVHYNGNTYLE | 308 | KVSSRFS | 316 | FQGSHFPLT | 321 |
| L13 | KSSQSIVHYNGNTYLE | 308 | KVSSRAS | 317 | FQGSHFPLT | 321 |
| L14 | KSSQSIVHYNGNTYLE | 308 | KVSSRAS | 317 | FQGSHFPLT | 321 |
| L15 | KSSQSIVHYNEKTYLE | 300 | KVSSRAS | 317 | FQGSHFPLT | 321 |
| L16 | RSSQSIVHYNGNTYLE | 309 | KVSNRDS | 319 | FQGSHFPLT | 321 |

TABLE 6

Heavy chain CDRs according to CCG

| Antibody chain | CDR1 | SEQ ID NO: | CDR2 | SEQ ID NO: | CDR3 | SEQ ID NO: |
|---|---|---|---|---|---|---|
| H1 | GFTFSDYYMA | 332 | NINYEGSRTDLLESLKS | 334 | DTSRGSYFDV | 347 |
| H2 | GFTFSDYYMA | 332 | NINYYGSRTDLLESLKS | 335 | DTSRGSYFDV | 347 |
| H3 | GFTFSDYYMA | 332 | NINYEGSRTDLLASLKS | 336 | DTSRGSYFDV | 347 |
| H4 | GFTFSDYYMA | 332 | NINYYGSRTDLLASLKS | 337 | DTSRGSYFDV | 347 |
| H5 | GFTFSDYYMA | 332 | NINYDGSRTDLLDSLKS | 338 | DTSRGSYFDV | 347 |
| H6 | GFTFSDYYMA | 332 | NINYEGSRTDLLDSLKS | 339 | DTSRGSYFDV | 347 |
| H7 | GFTFSDYYMA | 332 | NINYDGSRTDLLESLKS | 340 | DTSRGSYFDV | 347 |
| H8 | GFTFSDYYMA | 332 | NINYDGSRTDLLDSLKS | 338 | DTSRGSYFDV | 347 |

TABLE 7

Light chain CDRs according to Chothia

| Antibody chain | CDR1 | SEQ ID NO:CDR2 | | SEQ ID NO:CDR3 | | SEQ ID NO: |
|---|---|---|---|---|---|---|
| L1 | KSSQSIVHYNEKTYLE | 300 | KVSSRFS | 316 | FQGSHFPLT | 321 |
| L2 | KSSQSIVHYNEKTYLE | 300 | KVSSRAS | 317 | FQGSHFPLT | 321 |
| L3 | KSSQSIVHYNGKTYLE | 301 | KVSSRFS | 316 | FQGSHFPLT | 321 |
| L4 | KSSQSIVHYNGKTYLE | 301 | KVSSRAS | 317 | FQGSHFPLT | 321 |
| L5 | KSSQSIVHYNENTYLE | 302 | KVSSRFS | 316 | FQGSHFPLT | 321 |
| L6 | KSSQSIVHYNENTYLE | 302 | KVSSRAS | 317 | FQGSHFPLT | 321 |
| L7 | RSSQSIVHYNENTYLE | 303 | KVSNRFS | 318 | FQGSHFPLT | 321 |
| L8 | RSSQSIVHYNANTYLE | 304 | KVSNRFS | 318 | FQGSHFPLT | 321 |

TABLE 8

Heavy chain CDRs according to Chothia

| Antibody chain | CDR1 | SEQ ID NO: | CDR2 | SEQ ID NO: | CDR3 | SEQ ID NO: |
|---|---|---|---|---|---|---|
| H1 | GFTFSDY | 333 | NYEGSR | 344 | TSRGSYFD | 349 |
| H2 | GFTFSDY | 333 | NYYGSR | 345 | TSRGSYFD | 349 |
| H3 | GFTFSDY | 333 | NYEGSR | 344 | TSRGSYFD | 349 |
| H4 | GFTFSDY | 333 | NYYGSR | 345 | TSRGSYFD | 349 |
| H5 | GFTFSDY | 333 | NYDGSR | 346 | TSRGSYFD | 349 |
| H6 | GFTFSDY | 333 | NYEGSR | 344 | TSRGSYFD | 349 |
| H7 | GFTFSDY | 333 | NYDGSR | 346 | TSRGSYFD | 349 |
| H8 | GFTFSDY | 333 | NYDGSR | 346 | TSRGSYFD | 349 |

Amino Acid Sequence Variants

Variant anti-CTGF antibodies and antibody fragments thereof can be engineered based on a set of CDRs depicted in Tables 1-8. It is to be understood that in the variant anti-CTGF antibodies and antibody fragments the amino acid sequence of the CDRs remain unchanged or have minimal changes (e.g., 1-5 changes), but the surrounding regions, e.g., FR regions can be engineered. Amino acid sequence variants of the anti-CTGF antibody can be prepared by introducing appropriate nucleotide changes into the anti-CTGF antibody DNA, or by peptide synthesis. Such variants include, for example, deletions from, and/or insertions into and/or substitutions of, residues within the amino acid sequences of the anti-CTGF antibodies of the examples herein. Any combination of deletions, insertions, and substitutions is made to arrive at the final construct, provided that the final construct possesses the desired characteristics. The amino acid changes also may alter post-translational processes of the human or variant anti-CTGF antibody, such as changing the number or position of glycosylation sites.

In some embodiments, the present invention includes anti-CTGF antibodies or antibody fragments thereof having a variable heavy chain (also referred to as "heavy chain variable region") and a variable light chain (also referred to as "light chain variable region"), wherein the variable heavy chain amino acid sequence and the variable light chain amino acid sequence are at least at least 90%, preferably at least 92.5%, more preferably at least 95%, still more preferably at least 98%, or even more preferably at least 99% identical to the amino acid sequences disclosed in Tables 9-10 provided that the antibody or fragments thereof retain binding to CTGF.

TABLE 9

| Anti-CTGF antibody light chain variable region sequences | | | |
|---|---|---|---|
| Antibody Chain Name | Light Chain Variable Region Sequence | SEQ ID NO | Antibodies That Contain This Chain |
| L1 | VVMTQTPLSLSVSLGDQASISCKSSQSIVHYNEK TYLEWYLQKPGQSPQLLIYKVSSRFSGVPDRFSG SGSGTDFTLKISRVEAEDLGVYYCFQGSHFPLTF GQGTKLEIK | 103 | A1, A2, A3, A4, A5, A6, A7, A8 |
| L2 | VVMTQTPLSLSVSLGDQASISCKSSQSIVHYNEK TYLEWYLQKPGQSPQLLIYKVSSRASGVPDRFSG SGSGTDFTLKISRVEAEDLGVYYCFQGSHFPLTF GQGTKLEIK | 113 | A9, A10, A11, A12, A13, A14, A15, A16 |
| L3 | VVMTQTPLSLSVSLGDQASISCKSSQSIVHYNGK TYLEWYLQKPGQSPQLLIYKVSSRFSGVPDRFSG SGSGTDFTLKISRVEAEDLGVYYCFQGSHFPLTF GQGTKLEIK | 123 | A17, A18, A19, A20, A21, A22, A23, A24 |
| L4 | VVMTQTPLSLSVSLGDQASISCKSSQSIVHYNGK TYLEWYLQKPGQSPQLLIYKVSSRASGVPDRFSG SGSGTDFTLKISRVEAEDLGVYYCFQGSHFPLTF GQGTKLEIK | 133 | A25, A26, A27, A28, A29, A30, A31, A32 |
| L5 | VVMTQTPLSLSVSLGDQASISCKSSQSIVHYNEN TYLEWYLQKPGQSPQLLIYKVSSRFSGVPDRFSG SGSGTDFTLKISRVEAEDLGVYYCFQGSHFPLTF GQGTKLEIK | 143 | A33, A34, A35, A36, A37, A38, A39, A40 |
| L6 | VVMTQTPLSLSVSLGDQASISCKSSQSIVHYNEN TYLEWYLQKPGQSPQLLIYKVSSRASGVPDRFSG SGSGTDFTLKISRVEAEDLGVYYCFQGSHFPLTF GQGTKLEIK | 153 | A41, A42, A43, A44, A45, A46, A47, A48 |
| L7 | VVMTQTPLSLPVSLGDQASISCRSSQSIVHYNEN TYLEWYLQKPGQSPQLLIYKVSNRFSGVPDRFSG SGSGTDFTLKISRVEAEDLGVYYCFQGSHFPLTF GQGTKLEIK | 163 | A49, A50, A51, A52, A53, A54, A55, A56 |
| L8 | VVMTQTPLSLPVSLGDQASISCRSSQSIVHYNAN TYLEWYLQKPGQSPQLLIYKVSNRFSGVPDRFSG SGSGTDFTLKISRVEAEDLGVYYCFQGSHFPLTF GQGTKLEIK | 173 | A57, A58, A59, A60, A61, A62, A63, A64 |
| L9 | VVMTQTPLSLPVSLGDQASISCRSSQSIVHYNTN TYLEWYLQKPGQSPQLLIYKVSNRFSGVPDRFSG SGSGTDFTLKISRVEAEDLGVYYCFQGSHFPLTF GQGTKLEIK | 183 | A65, A66, A67, A68, A69, A70, A71, A72 |
| L10 | VVMTQTPLSLPVSLGDQASISCRSSQSIVHYNGK TYLEWYLQKPGQSPQLLIYKVSNRFSGVPDRFSG SGSGTDFTLKISRVEAEDLGVYYCFQGSHFPLTF GQGTKLEIK | 193 | A73, A74, A75, A76, A77, A78, A79, A80 |
| L11 | VVMTQTPLSLPVSLGDQASISCRSSQSIVHYNEK TYLEWYLQKPGQSPQLLIYKVSNRFSGVPDRFSG SGSGTDFTLKISRVEAEDLGVYYCFQGSHFPLTF GQGTKLEIK | 203 | A81, A82, A83, A84, A85, A86, A87, A88 |

TABLE 9-continued

| | Anti-CTGF antibody light chain variable region sequences | | |
|---|---|---|---|
| Antibody Chain Name | Light Chain Variable Region Sequence | SEQ ID NO | Antibodies That Contain This Chain |
| L12 | VVMTQTPLSLSVSLGDQASISCKSSQSIVHYNGN TYLEWYLQKPGQSPQLLIYKVSSRFSGVPDRFSG SGSGTDFTLKISRVEAEDLGVYYCFQGSHFPLTF GQGTKLEIK | 213 | A89, A90, A91, A92, A93, A94, A95, A96 |
| L13 | VVMTQTPLSLSVSLGDQASISCKSSQSIVHYNGN TYLEWYLQKPGQSPQLLIYKVSSRASGVPDRFSG SGSGTDFTLKISRVEAEDLGVYYCFQGSHFPLTF GQGTKLEIK | 223 | A97, A98, A99, A100, A101, A102, A103, A104 |
| L14 | DIVMTQTPLSLSVSLGDQASISCKSSQSIVHYNG NTYLEWYLQKPGQSPQLLIYKVSSRASGVPDRES GSGSGTDFTLKISRVEAEDLGVYYCFQGSHFPLT FGQGTKLEIK | 233 | A105, A106, A107, A108, A109, A110, A111, A112 |
| L15 | DIVMTQTPLSLSVSLGDQASISCKSSQSIVHYNE KTYLEWYLQKPGQSPQLLIYKVSSRASGVPDRES GSGSGTDFTLKISRVEAEDLGVYYCFQGSHFPLT FGQGTKLEIK | 243 | A113, A114, A115, A116, A117, A118, A119, A120 |
| L16 | VVMTQTPLSLPVSLGDQASISCRSSQSIVHYNGN TYLEWYLQKPGQSPQLLIYKVSNRDSGVPDRFSG SGSGTDFTLKISRVEAEDLGVYYCFQGSHFPLTF GQGTKLEIK | 253 | A121, A122, A123, A124, A125, A126, A127, A128 |

TABLE 10

| | Anti-CTGF antibody heavy chain variable region sequences | | |
|---|---|---|---|
| Antibody Chain Name | Heavy Chain Variable Region Sequence | SEQ ID NO | Antibodies That Contain This Chain |
| H1 | EVQLVESGGGLVQPGGSLRLSCAASGFTFSDYYM AWVRQAPGKGLEWVANINYEGSRTDLLESLKSRF TISRDNAKNSVYLQMNSLRAEDTAVYYCARDTSR GSYFDVWGAGTTVTVSS | 108 | A1, A9, A17, A25, A33, A41, A49, A57, A65, A73, A81, A89, A97, A105, A113, A121 |
| H2 | EVQLVESGGGLVQPGGSLRLSCAASGFTFSDYYM AWVRQAPGKGLEWVANINYYGSRTDLLESLKSRF TISRDNAKNSVYLQMNSLRAEDTAVYYCARDTSR GSYFDVWGAGTTVTVSS | 118 | A2, A10, A18, A26, A34, A42, A50, A58, A66, A74, A82, A90, A98, A106, A114, A122 |
| H3 | EVQLVESGGGLVQPGGSLRLSCAASGFTFSDYYM AWVRQAPGKGLEWVANINYEGSRTDLLASLKSRF TISRDNAKNSVYLQMNSLRAEDTAVYYCARDTSR GSYFDVWGAGTTVTVSS | 128 | A3, A11, A19, A27, A35, A43, A51, A59, A67, A75, A83, A91, A99, A107, A115, A123 |
| H4 | EVQLVESGGGLVQPGGSLRLSCAASGFTFSDYYM AWVRQAPGKGLEWVANINYYGSRTDLLASLKSRF TISRDNAKNSVYLQMNSLRAEDTAVYYCARDTSR GSYFDVWGAGTTVTVSS | 138 | A4, A12, A20, A28, A36, A44, A52, A60, A68, A76, A84, A92, A100, A108, A116, A124 |
| H5 | EVQLVESGGGLVQPGGSLRLSCAASGFTFSDYYM AWVRQAPGKGLEWVANINYDGSRTDLLDSLKSRF TISRDNAKNSVYLQMNSLRAEDTAVYYCARDTSR GSYFDVWGAGTTVTVSS | 148 | A5, A13, A21, A29, A37, A45, A53, A61, A69, A77, A85, A93, A101, A109, A117, A125 |
| H6 | EVQLVESGGGLVQPGGSLRLSCAASGFTFSDYYM AWVRQAPGKGLEWVANINYEGSRTDLLDSLKSRF TISRDNAKNSVYLQMNSLRAEDTAVYYCARDTSR GSYFDVWGAGTTVTVSS | 158 | A6, A14, A22, A30, A38, A46, A54, A62, A70, A78, A86, A94, A102, A110, A118, A126 |
| H7 | EVQLVESGGGLVQPGGSLRLSCAASGFTFSDYYM AWVRQAPGKGLEWVANINYDGSRTDLLESLKSRF TISRDNAKNSVYLQMNSLRAEDTAVYYCARDTSR GSYFDVWGAGTTVTVSS | 168 | A7, A15, A23, A31, A39, A47, A55, A63, A71, A79, A87, A95, A103, A111, A119, A127 |

TABLE 10-continued

| Anti-CTGF antibody heavy chain variable region sequences | | | |
| --- | --- | --- | --- |
| Antibody Chain Name | Heavy Chain Variable Region Sequence | SEQ ID NO | Antibodies That Contain This Chain |
| H8 | EVKLVESGGGLVQPGGSLRLSCAASGFTFSDYYM AWVRQAPGKGLEWVANINYDGSRTDLLDSLKSRF TISRDNAKNSVYLQMNSLRAEDTAVYYCARDTSR GSYFDVWGAGTTVTVSS | 178 | A8, A16, A24, A32, A40, A48, A56, A64, A72, A80, A88, A96, A104, A112, A120, A128 |

TABLE 11

| Anti-CTGF antibody light chain sequences | | | |
| --- | --- | --- | --- |
| Antibody Chain Name | Light Chain Sequence | SEQ ID NO | Antibodies That Contain This Chain |
| L1 | VVMTQTPLSLSVSLGDQASISCKSSQSIVHYNEKTYLEW YLQKPGQSPQLLIYKVSSRFSGVPDRFSGSGSGTDFTLK ISRVEAEDLGVYYCFQGSHFPLTFGQGTKLEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 104 | A1, A2, A3, A4, A5, A6, A7, A8 |
| L2 | VVMTQTPLSLSVSLGDQASISCKSSQSIVHYNEKTYLEW YLQKPGQSPQLLIYKVSSRASGVPDRFSGSGSGTDFTLK ISRVEAEDLGVYYCFQGSHFPLTFGQGTKLEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 114 | A9, A10, A11, A12, A13, A14, A15, A16 |
| L3 | VVMTQTPLSLSVSLGDQASISCKSSQSIVHYNGKTYLEW YLQKPGQSPQLLIYKVSSRFSGVPDRFSGSGSGTDFTLK ISRVEAEDLGVYYCFQGSHFPLTFGQGTKLEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 124 | A17, A18, A19, A20, A21, A22, A23, A24 |
| L4 | VVMTQTPLSLSVSLGDQASISCKSSQSIVHYNGKTYLEW YLQKPGQSPQLLIYKVSSRASGVPDRFSGSGSGTDFTLK ISRVEAEDLGVYYCFQGSHFPLTFGQGTKLEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 134 | A25, A26, A27, A28, A29, A30, A31, A32 |
| L5 | VVMTQTPLSLSVSLGDQASISCKSSQSIVHYNENTYLEW YLQKPGQSPQLLIYKVSSRFSGVPDRFSGSGSGTDFTLK ISRVEAEDLGVYYCFQGSHFPLTFGQGTKLEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 144 | A33, A34, A35, A36, A37, A38, A39, A40 |
| L6 | VVMTQTPLSLSVSLGDQASISCKSSQSIVHYNENTYLEW YLQKPGQSPQLLIYKVSSRASGVPDRFSGSGSGTDFTLK ISRVEAEDLGVYYCFQGSHFPLTFGQGTKLEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 154 | A41, A42, A43, A44, A45, A46, A47, A48 |
| L7 | VVMTQTPLSLPVSLGDQASISCRSSQSIVHYNENTYLEW YLQKPGQSPQLLIYKVSNRFSGVPDRFSGSGSGTDFTLK ISRVEAEDLGVYYCFQGSHFPLTFGQGTKLEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 164 | A49, A50, A51, A52, A53, A54, A55, A56 |
| L8 | VVMTQTPLSLPVSLGDQASISCRSSQSIVHYNANTYLEW YLQKPGQSPQLLIYKVSNRFSGVPDRFSGSGSGTDFTLK ISRVEAEDLGVYYCFQGSHFPLTFGQGTKLEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 174 | A57, A58, A59, A60, A61, A62, A63, A64 |
| L9 | VVMTQTPLSLPVSLGDQASISCRSSQSIVHYNTNTYLEW YLQKPGQSPQLLIYKVSNRFSGVPDRFSGSGSGTDFTLK ISRVEAEDLGVYYCFQGSHFPLTFGQGTKLEIKRTVAAP | 184 | A65, A66, A67, A68, A69, A70, A71, A72 |

TABLE 11-continued

| Antibody Chain Name | Light Chain Sequence | SEQ ID NO | Antibodies That Contain This Chain |
|---|---|---|---|
| | SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | | |
| L10 | VVMTQTPLSLPVSLGDQASISCRSSQSIVHYNGKTYLEW YLQKPGQSPQLLIYKVSNRFSGVPDRFSGSGSGTDFTLK ISRVEAEDLGVYYCFQGSHFPLTFGQGTKLEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 194 | A73, A74, A75, A76, A77, A78, A79, A80 |
| L11 | VVMTQTPLSLPVSLGDQASISCRSSQSIVHYNEKTYLEW YLQKPGQSPQLLIYKVSNRFSGVPDRFSGSGSGTDFTLK ISRVEAEDLGVYYCFQGSHFPLTFGQGTKLEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 204 | A81, A82, A83, A84, A85, A86, A87, A88 |
| L12 | VVMTQTPLSLSVSLGDQASISCKSSQSIVHYNGNTYLEW YLQKPGQSPQLLIYKVSSRFSGVPDRFSGSGSGTDFTLK ISRVEAEDLGVYYCFQGSHFPLTFGQGTKLEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 214 | A89, A90, A91, A92, A93, A94, A95, A96 |
| L13 | VVMTQTPLSLSVSLGDQASISCKSSQSIVHYNGNTYLEW YLQKPGQSPQLLIYKVSSRASGVPDRFSGSGSGTDFTLK ISRVEAEDLGVYYCFQGSHFPLTFGQGTKLEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 224 | A97, A98, A99, A100, A101, A102, A103, A104 |
| L14 | DIVMTQTPLSLSVSLGDQASISCKSSQSIVHYNGNTYLE WYLQKPGQSPQLLIYKVSSRASGVPDRFSGSGSGTDFTL KISRVEAEDLGVYYCFQGSHFPLTFGQGTKLEIKRTVAA PSVFIFPPSDEQLKSGTASVVCLLNNFYPREAKVQWKVD NALQSGNSQESVTEQDSKDSTYSLSSTLTLSKADYEKHK VYACEVTHQGLSSPVTKSFNRGEC | 234 | A105, A106, A107, A108, A109, A110, A111, A112 |
| L15 | DIVMTQTPLSLSVSLGDQASISCKSSQSIVHYNEKTYLE WYLQKPGQSPQLLIYKVSSRASGVPDRFSGSGSGTDFTL KISRVEAEDLGVYYCFQGSHFPLTFGQGTKLEIKRTVAA PSVFIFPPSDEQLKSGTASVVCLLNNFYPREAKVQWKVD NALQSGNSQESVTEQDSKDSTYSLSSTLTLSKADYEKHK VYACEVTHQGLSSPVTKSFNRGEC | 244 | A113, A114, A115, A116, A117, A118, A119, A120 |
| L16 | VVMTQTPLSLPVSLGDQASISCRSSQSIVHYNGNTYLEW YLQKPGQSPQLLIYKVSNRDSGVPDRFSGSGSGTDFTLK ISRVEAEDLGVYYCFQGSHFPLTFGQGTKLEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 254 | A121, A122, A123, A124, A125, A126, A127, A128 |

TABLE 12

| Antibody Chain Name | Heavy Chain Sequence | SEQ ID NO | Antibodies That Contain This Chain |
|---|---|---|---|
| H1 | EVQLVESGGGLVQPGGSLRLSCAASGFTFSDYYMAWVRQ APGKGLEWVANINYEGSRTDLLESLKSRFTISRDNAKNS VYLQMNSLRAEDTAVYYCARDTSRGSYFDVWGAGTTVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKRVEPKSCDKTHTCPPCPAP EAAGGPSVFLFPPKPKDTLMISRTPEVTCVVVDVSHEDP EVKENWYVDGVEVHNAKTKPREEQYNSTYRVVSVLTVLH QDWLNGKEYKCKVSNKALPAPIEKTISKAKGQPREPQVY | 109 | A1, A9, A17, A25, A33, A41, A49, A57, A65, A73, A81, A89, A97, A105, A113, A121 |

TABLE 12-continued

Anti-CTGF antibody heavy chain sequences

| Antibody Chain Name | Heavy Chain Sequence | SEQ ID NO | Antibodies That Contain This Chain |
|---|---|---|---|
| | TLPPSRFEMTKNQVSLTCLVKGFYPSDIAVEWESNGQPE NNYKTTPPVLDSDGSFFLYSKLTVDKSRWQQGNVESCSV MHEALHNHYTQKSLSLSPG | | |
| H2 | EVQLVESGGGLVQPGGSLRLSCAASGFTFSDYYMAWVRQ APGKGLEWVANINYYGSRTDLLESLKSRFTISRDNAKNS VYLQMNSLRAEDTAVYYCARDTSRGSYFDVWGAGTTVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKRVEPKSCDKTHTCPPCPAP EAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAKGQPREPQVY TLPPSRFEMTKNQVSLTCLVKGFYPSDIAVEWESNGQPE NNYKTTPPVLDSDGSFFLYSKLTVDKSRWQQGNVFSCSV MHEALHNHYTQKSLSLSPG | 119 | A2, A10, A18, A26, A34, A42, A50, A58, A66, A74, A82, A90, A98, A106, A114, A122 |
| H3 | EVQLVESGGGLVQPGGSLRLSCAASGFTFSDYYMAWVRQ APGKGLEWVANINYEGSRTDLLASLKSRFTISRDNAKNS VYLQMNSLRAEDTAVYYCARDTSRGSYFDVWGAGTTVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKRVEPKSCDKTHTCPPCPAP EAAGGPSVFLFPPKPKDTLMISRTPEVTCVVVDVSHEDP EVKENWYVDGVEVHNAKTKPREEQYNSTYRVVSVLTVLH QDWLNGKEYKCKVSNKALPAPIEKTISKAKGQPREPQVY TLPPSRFEMTKNQVSLTCLVKGFYPSDIAVEWESNGQPE NNYKTTPPVLDSDGSFFLYSKLTVDKSRWQQGNVFSCSV MHEALHNHYTQKSLSLSPG | 129 | A3, A11, A19, A27, A35, A43, A51, A59, A67, A75, A83, A91, A99, A107, A115, A123 |
| H4 | EVQLVESGGGLVQPGGSLRLSCAASGFTFSDYYMAWVRQ APGKGLEWVANINYYGSRTDLLASLKSRFTISRDNAKNS VYLQMNSLRAEDTAVYYCARDTSRGSYFDVWGAGTTVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKRVEPKSCDKTHTCPPCPAP EAAGGPSVFLFPPKPKDTLMISRTPEVTCVVVDVSHEDP EVKENWYVDGVEVHNAKTKPREEQYNSTYRVVSVLTVLH QDWLNGKEYKCKVSNKALPAPIEKTISKAKGQPREPQVY TLPPSRFEMTKNQVSLTCLVKGFYPSDIAVEWESNGQPE NNYKTTPPVLDSDGSFFLYSKLTVDKSRWQQGNVFSCSV MHEALHNHYTQKSLSLSPG | 139 | A4, A12, A20, A28, A36, A44, A52, A60, A68, A76, A84, A92, A100, A108, A116, A124 |
| H5 | EVQLVESGGGLVQPGGSLRLSCAASGFTFSDYYMAWVRQ APGKGLEWVANINYDGSRTDLLDSLKSRFTISRDNAKNS VYLQMNSLRAEDTAVYYCARDTSRGSYFDVWGAGTTVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKRVEPKSCDKTHTCPPCPAP EAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAKGQPREPQVY TLPPSRFEMTKNQVSLTCLVKGFYPSDIAVEWESNGQPE NNYKTTPPVLDSDGSFFLYSKLTVDKSRWQQGNVESCSV MHEALHNHYTQKSLSLSPG | 149 | A5, A13, A21, A29, A37, A45, A53, A61, A69, A77, A85, A93, A101, A109, A117, A125 |
| H6 | EVQLVESGGGLVQPGGSLRLSCAASGFTFSDYYMAWVRQ APGKGLEWVANINYEGSRTDLLDSLKSRFTISRDNAKNS VYLQMNSLRAEDTAVYYCARDTSRGSYFDVWGAGTTVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKRVEPKSCDKTHTCPPCPAP EAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAKGQPREPQVY TLPPSRFEMTKNQVSLTCLVKGFYPSDIAVEWESNGQPE NNYKTTPPVLDSDGSFFLYSKLTVDKSRWQQGNVESCSV MHEALHNHYTQKSLSLSPG | 159 | A6, A14, A22, A30, A38, A46, A54, A62, A70, A78, A86, A94, A102, A110, A118, A126 |
| H7 | EVQLVESGGGLVQPGGSLRLSCAASGFTFSDYYMAWVRQ APGKGLEWVANINYDGSRTDLLESLKSRFTISRDNAKNS VYLQMNSLRAEDTAVYYCARDTSRGSYFDVWGAGTTVTV SSASTKGPSVFPLAPSSKSTSGGTAALGCLVKDYFPEPV TVSWNSGALTSGVHTFPAVLQSSGLYSLSSVVTVPSSSL | 169 | A7, A15, A23, A31, A39, A47, A55, A63, A71, A79, A87, A95, A103, A111, |

TABLE 12-continued

| | Anti-CTGF antibody heavy chain sequences | | |
|---|---|---|---|
| Antibody<br>Chain Name | Heavy Chain Sequence | SEQ<br>ID NO | Antibodies<br>That Contain<br>This Chain |
| | GTQTYICNVNHKPSNTKVDKRVEPKSCDKTHTCPPCPAP<br>EAAGGPSVELFPPKPKDTLMISRTPEVTCVVVDVSHEDP<br>EVKFNWYVDGVEVHNAKTKPREEQYNSTYRVVSVLTVLH<br>QDWLNGKEYKCKVSNKALPAPIEKTISKAKGQPREPQVY<br>TLPPSRFEMTKNQVSLTCLVKGFYPSDIAVEWESNGQPE<br>NNYKTTPPVLDSDGSFFLYSKLTVDKSRWQQGNVESCSV<br>MHEALHNHYTQKSLSLSPG | | A119, A127 |
| H8 | EVKLVESGGGLVQPGGSLRLSCAASGFTFSDYYMAWVRQ<br>APGKGLEWVANINYDGSRTDLLDSLKSRFTISRDNAKNS<br>VYLQMNSLRAEDTAVYYCARDTSRGSYFDVWGAGTTVTV<br>SSASTKGPSVFPLAPSSKSTSGGTAALGCLVKDYFPEPV<br>TVSWNSGALTSGVHTFPAVLQSSGLYSLSSVVTVPSSSL<br>GTQTYICNVNHKPSNTKVDKRVEPKSCDKTHTCPPCPAP<br>EAAGGPSVFLFPPKPKDTLMISRTPEVTCVVVDVSHEDP<br>EVKFNWYVDGVEVHNAKTKPREEQYNSTYRVVSVLTVLH<br>QDWLNGKEYKCKVSNKALPAPIEKTISKAKGQPREPQVY<br>TLPPSRFEMTKNQVSLTCLVKGFYPSDIAVEWESNGQPE<br>NNYKTTPPVLDSDGSFFLYSKLTVDKSRWQQGNVFSCSV<br>MHEALHNHYTQKSLSLSPG | 179 | A8, A16, A24,<br>A32, A40, A48,<br>A56, A64, A72,<br>A80, A88, A96,<br>A104, A112,<br>A120, A128 |

25

Combinations of light chain variable regions and heavy chain variable regions shown in Tables 9 and 10, or of light chains and heavy chains shown in Tables 11 and 12, result in certain antibodies of the present disclosure shown in Table 13.

TABLE 13

| | | | | | SEQ ID NOs of exemplary antibodies according to the disclosure. | | | | | |
|---|---|---|---|---|---|---|---|---|---|---|
| Antibody<br>Name | Light<br>Chain<br>SEQ ID<br>NO: | Heavy<br>Chain<br>SEQ ID<br>NO: | VL<br>SEQ ID<br>NO: | VH<br>SEQ ID<br>NO: | VL<br>CDR1<br>SEQ ID<br>NO: | VL<br>CDR2<br>SEQ ID<br>NO: | VL<br>CDR3<br>SEQ ID<br>NO: | VH<br>CDR1<br>SEQ ID<br>NO: | VH<br>CDR2<br>SEQ ID<br>NO: | VH<br>CDR3<br>SEQ ID<br>NO: |
| A1 | 104 | 109 | 103 | 108 | 100 | 101 | 102 | 105 | 106 | 107 |
| A2 | 104 | 119 | 103 | 118 | 100 | 101 | 102 | 115 | 116 | 117 |
| A3 | 104 | 129 | 103 | 128 | 100 | 101 | 102 | 125 | 126 | 127 |
| A4 | 104 | 139 | 103 | 138 | 100 | 101 | 102 | 135 | 136 | 137 |
| A5 | 104 | 149 | 103 | 148 | 100 | 101 | 102 | 145 | 146 | 147 |
| A6 | 104 | 159 | 103 | 158 | 100 | 101 | 102 | 155 | 156 | 157 |
| A7 | 104 | 169 | 103 | 168 | 100 | 101 | 102 | 165 | 166 | 167 |
| A8 | 104 | 179 | 103 | 178 | 100 | 101 | 102 | 175 | 176 | 177 |
| A9 | 114 | 109 | 113 | 108 | 110 | 111 | 112 | 105 | 106 | 107 |
| A10 | 114 | 119 | 113 | 118 | 110 | 111 | 112 | 115 | 116 | 117 |
| A11 | 114 | 129 | 113 | 128 | 110 | 111 | 112 | 125 | 126 | 127 |
| A12 | 114 | 139 | 113 | 138 | 110 | 111 | 112 | 135 | 136 | 137 |
| A13 | 114 | 149 | 113 | 148 | 110 | 111 | 112 | 145 | 146 | 147 |
| A14 | 114 | 159 | 113 | 158 | 110 | 111 | 112 | 155 | 156 | 157 |
| A15 | 114 | 169 | 113 | 168 | 110 | 111 | 112 | 165 | 166 | 167 |
| A16 | 114 | 179 | 113 | 178 | 110 | 111 | 112 | 175 | 176 | 177 |
| A17 | 124 | 109 | 123 | 108 | 120 | 121 | 122 | 105 | 106 | 107 |
| A18 | 124 | 119 | 123 | 118 | 120 | 121 | 122 | 115 | 116 | 117 |
| A19 | 124 | 129 | 123 | 128 | 120 | 121 | 122 | 125 | 126 | 127 |
| A20 | 124 | 139 | 123 | 138 | 120 | 121 | 122 | 135 | 136 | 137 |
| A21 | 124 | 149 | 123 | 148 | 120 | 121 | 122 | 145 | 146 | 147 |
| A22 | 124 | 159 | 123 | 158 | 120 | 121 | 122 | 155 | 156 | 157 |
| A23 | 124 | 169 | 123 | 168 | 120 | 121 | 122 | 165 | 166 | 167 |
| A24 | 124 | 179 | 123 | 178 | 120 | 121 | 122 | 175 | 176 | 177 |
| A25 | 134 | 109 | 133 | 108 | 130 | 131 | 132 | 105 | 106 | 107 |
| A26 | 134 | 119 | 133 | 118 | 130 | 131 | 132 | 115 | 116 | 117 |
| A27 | 134 | 129 | 133 | 128 | 130 | 131 | 132 | 125 | 126 | 127 |
| A28 | 134 | 139 | 133 | 138 | 130 | 131 | 132 | 135 | 136 | 137 |
| A29 | 134 | 149 | 133 | 148 | 130 | 131 | 132 | 145 | 146 | 147 |
| A30 | 134 | 159 | 133 | 158 | 130 | 131 | 132 | 155 | 156 | 157 |
| A31 | 134 | 169 | 133 | 168 | 130 | 131 | 132 | 165 | 166 | 167 |
| A32 | 134 | 179 | 133 | 178 | 130 | 131 | 132 | 175 | 176 | 177 |
| A33 | 144 | 109 | 143 | 108 | 140 | 141 | 142 | 105 | 106 | 107 |
| A34 | 144 | 119 | 143 | 118 | 140 | 141 | 142 | 115 | 116 | 117 |
| A35 | 144 | 129 | 143 | 128 | 140 | 141 | 142 | 125 | 126 | 127 |

TABLE 13-continued

SEQ ID NOs of exemplary antibodies according to the disclosure.

| Antibody Name | Light Chain SEQ ID NO: | Heavy Chain SEQ ID NO: | VL SEQ ID NO: | VH SEQ ID NO: | VL CDR1 SEQ ID NO: | VL CDR2 SEQ ID NO: | VL CDR3 SEQ ID NO: | VH CDR1 SEQ ID NO: | VH CDR2 SEQ ID NO: | VH CDR3 SEQ ID NO: |
|---|---|---|---|---|---|---|---|---|---|---|
| A36 | 144 | 139 | 143 | 138 | 140 | 141 | 142 | 135 | 136 | 137 |
| A37 | 144 | 149 | 143 | 148 | 140 | 141 | 142 | 145 | 146 | 147 |
| A38 | 144 | 159 | 143 | 158 | 140 | 141 | 142 | 155 | 156 | 157 |
| A39 | 144 | 169 | 143 | 168 | 140 | 141 | 142 | 165 | 166 | 167 |
| A40 | 144 | 179 | 143 | 178 | 140 | 141 | 142 | 175 | 176 | 177 |
| A41 | 154 | 109 | 153 | 108 | 150 | 151 | 152 | 105 | 106 | 107 |
| A42 | 154 | 119 | 153 | 118 | 150 | 151 | 152 | 115 | 116 | 117 |
| A43 | 154 | 129 | 153 | 128 | 150 | 151 | 152 | 125 | 126 | 127 |
| A44 | 154 | 139 | 153 | 138 | 150 | 151 | 152 | 135 | 136 | 137 |
| A45 | 154 | 149 | 153 | 148 | 150 | 151 | 152 | 145 | 146 | 147 |
| A46 | 154 | 159 | 153 | 158 | 150 | 151 | 152 | 155 | 156 | 157 |
| A47 | 154 | 169 | 153 | 168 | 150 | 151 | 152 | 165 | 166 | 167 |
| A48 | 154 | 179 | 153 | 178 | 150 | 151 | 152 | 175 | 176 | 177 |
| A49 | 164 | 109 | 163 | 108 | 160 | 161 | 162 | 105 | 106 | 107 |
| A50 | 164 | 119 | 163 | 118 | 160 | 161 | 162 | 115 | 116 | 117 |
| A51 | 164 | 129 | 163 | 128 | 160 | 161 | 162 | 125 | 126 | 127 |
| A52 | 164 | 139 | 163 | 138 | 160 | 161 | 162 | 135 | 136 | 137 |
| A53 | 164 | 149 | 163 | 148 | 160 | 161 | 162 | 145 | 146 | 147 |
| A54 | 164 | 159 | 163 | 158 | 160 | 161 | 162 | 155 | 156 | 157 |
| A55 | 164 | 169 | 163 | 168 | 160 | 161 | 162 | 165 | 166 | 167 |
| A56 | 164 | 179 | 163 | 178 | 160 | 161 | 162 | 175 | 176 | 177 |
| A57 | 174 | 109 | 173 | 108 | 170 | 171 | 172 | 105 | 106 | 107 |
| A58 | 174 | 119 | 173 | 118 | 170 | 171 | 172 | 115 | 116 | 117 |
| A59 | 174 | 129 | 173 | 128 | 170 | 171 | 172 | 125 | 126 | 127 |
| A60 | 174 | 139 | 173 | 138 | 170 | 171 | 172 | 135 | 136 | 137 |
| A61 | 174 | 149 | 173 | 148 | 170 | 171 | 172 | 145 | 146 | 147 |
| A62 | 174 | 159 | 173 | 158 | 170 | 171 | 172 | 155 | 156 | 157 |
| A63 | 174 | 169 | 173 | 168 | 170 | 171 | 172 | 165 | 166 | 167 |
| A64 | 174 | 179 | 173 | 178 | 170 | 171 | 172 | 175 | 176 | 177 |
| A65 | 184 | 109 | 183 | 108 | 180 | 181 | 182 | 105 | 106 | 107 |
| A66 | 184 | 119 | 183 | 118 | 180 | 181 | 182 | 115 | 116 | 117 |
| A67 | 184 | 129 | 183 | 128 | 180 | 181 | 182 | 125 | 126 | 127 |
| A68 | 184 | 139 | 183 | 138 | 180 | 181 | 182 | 135 | 136 | 137 |
| A69 | 184 | 149 | 183 | 148 | 180 | 181 | 182 | 145 | 146 | 147 |
| A70 | 184 | 159 | 183 | 158 | 180 | 181 | 182 | 155 | 156 | 157 |
| A71 | 184 | 169 | 183 | 168 | 180 | 181 | 182 | 165 | 166 | 167 |
| A72 | 184 | 179 | 183 | 178 | 180 | 181 | 182 | 175 | 176 | 177 |
| A73 | 194 | 109 | 193 | 108 | 190 | 191 | 192 | 105 | 106 | 107 |
| A74 | 194 | 119 | 193 | 118 | 190 | 191 | 192 | 115 | 116 | 117 |
| A75 | 194 | 129 | 193 | 128 | 190 | 191 | 192 | 125 | 126 | 127 |
| A76 | 194 | 139 | 193 | 138 | 190 | 191 | 192 | 135 | 136 | 137 |
| A77 | 194 | 149 | 193 | 148 | 190 | 191 | 192 | 145 | 146 | 147 |
| A78 | 194 | 159 | 193 | 158 | 190 | 191 | 192 | 155 | 156 | 157 |
| A79 | 194 | 169 | 193 | 168 | 190 | 191 | 192 | 165 | 166 | 167 |
| A80 | 194 | 179 | 193 | 178 | 190 | 191 | 192 | 175 | 176 | 177 |
| A81 | 204 | 109 | 203 | 108 | 200 | 201 | 202 | 105 | 106 | 107 |
| A82 | 204 | 119 | 203 | 118 | 200 | 201 | 202 | 115 | 116 | 117 |
| A83 | 204 | 129 | 203 | 128 | 200 | 201 | 202 | 125 | 126 | 127 |
| A84 | 204 | 139 | 203 | 138 | 200 | 201 | 202 | 135 | 136 | 137 |
| A85 | 204 | 149 | 203 | 148 | 200 | 201 | 202 | 145 | 146 | 147 |
| A86 | 204 | 159 | 203 | 158 | 200 | 201 | 202 | 155 | 156 | 157 |
| A87 | 204 | 169 | 203 | 168 | 200 | 201 | 202 | 165 | 166 | 167 |
| A88 | 204 | 179 | 203 | 178 | 200 | 201 | 202 | 175 | 176 | 177 |
| A89 | 214 | 109 | 213 | 108 | 210 | 211 | 212 | 105 | 106 | 107 |
| A90 | 214 | 119 | 213 | 118 | 210 | 211 | 212 | 115 | 116 | 117 |
| A91 | 214 | 129 | 213 | 128 | 210 | 211 | 212 | 125 | 126 | 127 |
| A92 | 214 | 139 | 213 | 138 | 210 | 211 | 212 | 135 | 136 | 137 |
| A93 | 214 | 149 | 213 | 148 | 210 | 211 | 212 | 145 | 146 | 147 |
| A94 | 214 | 159 | 213 | 158 | 210 | 211 | 212 | 155 | 156 | 157 |
| A95 | 214 | 169 | 213 | 168 | 210 | 211 | 212 | 165 | 166 | 167 |
| A96 | 214 | 179 | 213 | 178 | 210 | 211 | 212 | 175 | 176 | 177 |
| A97 | 224 | 109 | 223 | 108 | 220 | 221 | 222 | 105 | 106 | 107 |
| A98 | 224 | 119 | 223 | 118 | 220 | 221 | 222 | 115 | 116 | 117 |
| A99 | 224 | 129 | 223 | 128 | 220 | 221 | 222 | 125 | 126 | 127 |
| A100 | 224 | 139 | 223 | 138 | 220 | 221 | 222 | 135 | 136 | 137 |
| A101 | 224 | 149 | 223 | 148 | 220 | 221 | 222 | 145 | 146 | 147 |
| A102 | 224 | 159 | 223 | 158 | 220 | 221 | 222 | 155 | 156 | 157 |
| A103 | 224 | 169 | 223 | 168 | 220 | 221 | 222 | 165 | 166 | 167 |
| A104 | 224 | 179 | 223 | 178 | 220 | 221 | 222 | 175 | 176 | 177 |
| A105 | 234 | 109 | 233 | 108 | 230 | 231 | 232 | 105 | 106 | 107 |
| A106 | 234 | 119 | 233 | 118 | 230 | 231 | 232 | 115 | 116 | 117 |
| A107 | 234 | 129 | 233 | 128 | 230 | 231 | 232 | 125 | 126 | 127 |
| A108 | 234 | 139 | 233 | 138 | 230 | 231 | 232 | 135 | 136 | 137 |

TABLE 13-continued

| | | | | | | | | | |
|---|---|---|---|---|---|---|---|---|---|
| SEQ ID NOs of exemplary antibodies according to the disclosure. | | | | | | | | | |
| Antibody Name | Light Chain SEQ ID NO: | Heavy Chain SEQ ID NO: | VL SEQ ID NO: | VH SEQ ID NO: | VL CDR1 SEQ ID NO: | VL CDR2 SEQ ID NO: | VL CDR3 SEQ ID NO: | VH CDR1 SEQ ID NO: | VH CDR2 SEQ ID NO: | VH CDR3 SEQ ID NO: |
| A109 | 234 | 149 | 233 | 148 | 230 | 231 | 232 | 145 | 146 | 147 |
| A110 | 234 | 159 | 233 | 158 | 230 | 231 | 232 | 155 | 156 | 157 |
| A111 | 234 | 169 | 233 | 168 | 230 | 231 | 232 | 165 | 166 | 167 |
| A112 | 234 | 179 | 233 | 178 | 230 | 231 | 232 | 175 | 176 | 177 |
| A113 | 244 | 109 | 243 | 108 | 240 | 241 | 242 | 105 | 106 | 107 |
| A114 | 244 | 119 | 243 | 118 | 240 | 241 | 242 | 115 | 116 | 117 |
| A115 | 244 | 129 | 243 | 128 | 240 | 241 | 242 | 125 | 126 | 127 |
| A116 | 244 | 139 | 243 | 138 | 240 | 241 | 242 | 135 | 136 | 137 |
| A117 | 244 | 149 | 243 | 148 | 240 | 241 | 242 | 145 | 146 | 147 |
| A118 | 244 | 159 | 243 | 158 | 240 | 241 | 242 | 155 | 156 | 157 |
| A119 | 244 | 169 | 243 | 168 | 240 | 241 | 242 | 165 | 166 | 167 |
| A120 | 244 | 179 | 243 | 178 | 240 | 241 | 242 | 175 | 176 | 177 |
| A121 | 254 | 109 | 253 | 108 | 250 | 251 | 252 | 105 | 106 | 107 |
| A122 | 254 | 119 | 253 | 118 | 250 | 251 | 252 | 115 | 116 | 117 |
| A123 | 254 | 129 | 253 | 128 | 250 | 251 | 252 | 125 | 126 | 127 |
| A124 | 254 | 139 | 253 | 138 | 250 | 251 | 252 | 135 | 136 | 137 |
| A125 | 254 | 149 | 253 | 148 | 250 | 251 | 252 | 145 | 146 | 147 |
| A126 | 254 | 159 | 253 | 158 | 250 | 251 | 252 | 155 | 156 | 157 |
| A127 | 254 | 169 | 253 | 168 | 250 | 251 | 252 | 165 | 166 | 167 |
| A128 | 254 | 179 | 253 | 178 | 250 | 251 | 252 | 175 | 176 | 177 |

In some embodiments, the present invention includes anti-CTGF antibodies or antibody fragments thereof having a variable heavy chain and a variable light chain, wherein the variable heavy chain amino acid sequence are at least 80% or at least 85%, preferably at least 90%, more preferably at least 92.5%, still more preferably at least 95%, even more preferably at least 98%, or most preferably at least 99% identical to the amino acid sequences of SEQ ID NO: 108, 118, 128, 138, 148, 158, 168, or 178 and the variable light chain amino acid sequence are at least 80% or at least 85%, preferably at least 90%, more preferably at least 92.5%, still more preferably at least 95%, even more preferably at least 98%, or most preferably at least 99% identical to the amino acid sequences of SEQ ID NO: 103, 113, 123, 133, 143, 153, 163, 173, 183, 193, 203, 213, 223, 233, 243, or 253.

In some embodiments, the present invention includes anti-CTGF antibodies having a heavy chain and a light chain, wherein the heavy chain amino acid sequence and the light chain amino acid sequence are at least 95%, preferably at least 98%, or more preferably at least 99% identical to the amino acid sequences disclosed in Tables 11 and 12 provided that the antibody or fragments thereof retain binding to CTGF.

In some embodiments, the anti-CTGF antibodies or antibody fragments thereof comprise a variable heavy chain sequence that comprises an amino acid sequence with at least about 95%, preferably about 96%, more preferably about 97%, still more preferably about 98%, or even more preferably about 99%, sequence identity to the amino acid sequence set forth in SEQ ID NOs: 100, 101, 102, 103, 110, 111, 112, 113, 114, 115, 116, 117, 104, 118, 119, 120, 121, 122, 123, 124, or 221. Preferably, the anti-CTGF antibodies or antibody fragments thereof retains the binding and/or functional activity of an anti-CTGF antibody or antibody fragment thereof that comprises the variable heavy chain sequence of SEQ ID NOs: 100, 101, 102, 103, 110, 111, 112, 113, 114, 115, 116, 117, 104, 118, 119, 120, 121, 122, 123, 124, or 221. In some embodiments, the anti-CTGF antibodies or antibody fragments thereof comprise the variable heavy chain sequence of SEQ ID NOs: 108, 118, 128, 138, 148, 158, 168, or 178 and have one or more conservative amino acid substitutions, e.g., 1, 2, 3, 4, 5, 1-2, 1-3, 1-4 or 1-5 conservative amino acid substitutions in the heavy chain variable sequence. In some embodiments, the one or more conservative amino acid substitutions fall within one or more framework regions in SEQ ID NOs: 108, 118, 128, 138, 148, 158, 168, or 178 (based on the numbering system of Kabat).

In some embodiments, the anti-CTGF antibody or antibody fragment thereof comprises a variable heavy chain sequence with at least about 95%, preferably about 96%, more preferably about 97%, still more preferably about 98%, or even more preferably about 99% sequence identity to the anti-CTGF heavy chain variable region sequence set forth in 108, 118, 128, 138, 148, 158, 168, or 178 comprises one or more conservative amino acid substitutions in a framework region (based on the numbering system of Kabat), and retains the binding and/or functional activity of an anti-CTGF antibody or antibody fragment thereof that comprises a variable heavy chain sequence as set forth in SEQ ID NOs: 108, 118, 128, 138, 148, 158, 168, or 178 and a variable light chain sequence as set forth in SEQ ID NOs: 103, 113, 123, 133, 143, 153, 163, 173, 183, 193, 203, 213, 223, 233, 243, or 253.

In some embodiments, the anti-CTGF antibodies or antibody fragments thereof comprise a variable light chain sequence that comprises an amino acid sequence with at least about 95%, preferably about 96%, more preferably about 97%, still more preferably about 98%, or even more preferably about 99%, sequence identity to the amino acid sequence set forth in SEQ ID NOs: 103, 113, 123, 133, 143, 153, 163, 173, 183, 193, 203, 213, 223, 233, 243, or 253. Preferably, the anti-CTGF antibodies or antibody fragments thereof retains the binding and/or functional activity of an anti-CTGF antibody or antibody fragment thereof that comprises the variable light chain sequence of SEQ ID NOs: 103, 113, 123, 133, 143, 153, 163, 173, 183, 193, 203, 213, 223, 233, 243, or 253. In some embodiments, the anti-CTGF antibodies or antibody fragments thereof comprise the variable light chain sequence of SEQ ID NOs: 103, 113, 123, 133, 143, 153, 163, 173, 183, 193, 203, 213, 223, 233, 243, or 253 and have one or more conservative amino acid substitutions, e.g., 1, 2, 3, 4, 5, 1-2, 1-3, 1-4 or 1-5 conservative amino acid substitutions in the light chain variable sequence. In some embodiments, the one or more conservative amino acid substitutions fall within one or more framework regions in SEQ ID NOS: 103, 113, 123, 133, 143, 153, 163, 173, 183, 193, 203, 213, 223, 233, 243, or 253 (based on the numbering system of Kabat).

In some embodiments, the anti-CTGF antibody or antibody fragment thereof comprises a variable light chain sequence with at least about 95%, preferably about 96%, more preferably about 97%, still more preferably about 98%, or even more preferably about 99% sequence identity to the anti-CTGF light chain variable region sequence set forth in SEQ ID NOs: 103, 113, 123, 133, 143, 153, 163, 173, 183, 193, 203, 213, 223, 233, 243, or 253 comprises one or more conservative amino acid substitutions in a framework region (based on the numbering system of Kabat), and retains the binding and/or functional activity of an anti-CTGF antibody or antibody fragment thereof that comprises a variable heavy chain sequence as set forth in SEQ ID NOs: 108, 118, 128, 138, 148, 158, 168, or 178 and a variable light chain sequence as set forth in SEQ ID NOs: 103, 113, 123, 133, 143, 153, 163, 173, 183, 193, 203, 213, 223, 233, 243, or 253.

In some embodiments, the present invention includes anti-CTGF antibodies or antigen-binding fragments thereof having an amino acid substitution. These variants have at least one amino acid residue in the anti-CTGF antibody or antigen-binding fragment thereof removed and a different residue inserted in its place. The sites of greatest interest for substitutional mutagenesis include the hypervariable regions, but FR alterations are also contemplated. Conservative substitutions are shown in Table 14 under the heading of "preferred substitutions". If such substitutions result in a change in biological activity, then more substantial changes, denominated "exemplary substitutions", or as further described below in reference to amino acid classes, may be introduced and the products screened.

TABLE 14

| Exemplary amino acid substitutions | | |
| --- | --- | --- |
| Original Residue | Exemplary Substitutions | Preferred Substitutions |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | arg; asn; gln; lys; | arg |
| Ile (I) | leu; val; met; ala; phe; norleucine | leu |
| Leu (L) | ile; norleucine; val; met; ala; phe | ile |
| Lys (K) | arg; gln; asn | arg |
| Met (M) | leu; phe; ile | leu |
| Phe (F) | tyr; leu; val; ile; ala; | tyr |
| Pro (P) | ala | ala |
| Ser (S) | thr | thr |
| Thr (T) | ser | ser |
| Trp (W) | tyr; phe | tyr |
| Tyr (Y) | phe;trp; thr; ser | phe |
| Val (V) | leu; ile; met; phe ala; norleucine; | leu |

Naturally occurring amino acid residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.
Conservative substitutions will entail exchanging a member of one of these classes for another member of the same class. Non-conservative substitutions will entail exchanging a member of one of these classes for another class.

Any cysteine residue not involved in maintaining the proper conformation of the anti-CTGF antibody or antigen-binding fragment thereof also may be substituted, generally with serine, to improve the oxidative stability of the molecule, prevent aberrant crosslinking, or provide for established points of conjugation to a cytotoxic or cytostatic compound. Conversely, cysteine bond(s) may be added to the antibody or antigen-binding fragment thereof to improve its stability (particularly where the antibody is an antibody fragment such as an Fv fragment).

Another type of variant of the antibody involves altering the original glycosylation pattern of the antibody. The term "altering" in this context means deleting one or more carbohydrate moieties found in the antibody, and/or adding one or more glycosylation sites that were not previously present in the antibody. For example, an antibody may comprise an amino acid substitution at position 297 of the human IgG₁ heavy chain to abrogate oligosaccharyltransferase enzyme complex-mediated glycosylation by replacing the asparagine 297 (e.g. N297A, N297G).

In some aspects, the present invention includes nucleic acid molecules that encode the amino acid sequence variants of the anti-CTGF antibodies or antigen-binding fragments thereof described herein. Nucleic acid molecules encoding amino acid sequence variants of an anti-CTGF antibody or antigen-binding fragment thereof are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-CTGF antibody or antigen-binding fragment thereof. For example, nucleic acid molecules according to the invention also encompass nucleic acid molecules which hybridize under stringent conditions to nucleic acid molecules as disclosed herein, whereby the term "stringent conditions" within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C.

In certain embodiments, the anti-CTGF antibody is an antibody fragment. There are techniques that have been developed for the production of antibody fragments. Fragments can be derived via proteolytic digestion of intact antibodies (see, e.g., Morimoto et al., 1992, Journal of Biochemical and Biophysical Methods 24:107-117; and Brennan et al., 1985, Science 229:81). Alternatively, the fragments can be produced directly in recombinant host cells. For example, Fab'-SH fragments can be directly recovered from E. coli and chemically coupled to form F(ab')₂ fragments (see, e.g., Carter et al., 1992, Bio/Technology 10:163-167). By another approach, F(ab')₂ fragments can be isolated directly from recombinant host cell culture. Other techniques for the production of antibody fragments will be apparent to a skilled practitioner.

In some aspects, the anti-CTGF antibodies and antigen-binding fragments thereof can include modifications, such as glycosylation, oxidation, or deamidation.

In certain embodiments, it may be desirable to use an anti-CTGF antibody fragment, rather than an intact antibody. It may be desirable to modify the antibody fragment in order to increase its serum half-life. This can be achieved, for example, by incorporation of a salvage receptor binding epitope into the antibody fragment. In one method, the appropriate region of the antibody fragment can be altered (e.g., mutated), or the epitope can be incorporated into a peptide tag that is then fused to the antibody fragment at either end or in the middle, for example, by DNA or peptide synthesis (see, e.g., WO 96/32478). For example, antibody fragments of the invention may also be fused to human serum albumin to increase the serum half-life, if the use of a full length IgG scaffold is undesirable. Such fusion proteins of the antibody fragment with human serum albumin may be advantageous in situations in which two different antibody fragments need to be fused to increase avidity, or to generate a bispecific binding protein with extended serum half-life (see e.g. WO 05/077042 A2).

Removal of any carbohydrate moieties present on the antibody can be accomplished chemically or enzymatically. Chemical deglycosylation is described by Hakimuddin et al., 1987, Arch. Biochem. Biophys. 259:52 and by Edge et al., 1981, Anal. Biochem., 118:131. Enzymatic cleavage of carbohydrate moieties on antibodies can be achieved by the use of a variety of endo- and exo-glycosidases as described by Thotakura et al., 1987, Meth. Enzymol 138:350.

A type of useful modification comprises linking the antibody to one of a variety of nonproteinaceous polymers, e.g., polyethylene glycol, polypropylene glycol, or polyoxy-alkylenes, in the manner set forth in one or more of U.S. Pat. Nos. 4,640,835, 4,496,689, 4,301,144, 4,670,417, 4,791,192 and 4,179,337.

The present invention also provides the anti-CTGF antibody or antigen-binding fragment thereof that competes for binding to CTGF with an anti-CTGF antibody according to the present invention. In one embodiment, the present invention provides an anti-CTGF antibody or antigen-binding fragment thereof that competes for binding to CTGF with antibodies A1-A128. Competition assays may be conducted for example as described in PLOS One. 2014; 9(3): e92451 using a biosensor, or PLOS One 2020 Mar. 5; 15(3): e0229206, or by a method disclosed herein.

Therapeutic Uses

In one embodiment, the anti-CTGF antibodies of the invention or antigen-binding fragments thereof are useful for treating and/or preventing CTGF-associated disorders. In some embodiments, the anti-CTGF antibodies of the invention or antigen-binding fragments thereof are useful as a medicament.

The present invention provides antibodies for treatment (use in) of various diseases and disorders associated with CTGF. The antibodies of the invention reduce the deleterious effects of CTGF production or activity in several disorders. Further, the antibodies show favorable pharmacokinetics and/or pharmacodynamics, making them superior therapeutic agents for the treatment of disorders associated with CTGF.

The anti-CTGF antibodies of the present invention inhibit development of fibrosis. The present disclosure contemplates treating patients with a CTGF-associated disorder with an anti-CTGF antibody to improve or stabilize the pathology, restore organ function, improve the quality of life, and extend survival.

The antibodies of the invention are useful in therapeutic applications to prevent or treat CTGF-associated disorders involving fibrosis. In some aspects, the antibodies of the invention are administered to a subject to prevent or treat a CTGF-associated disorder including, but are not limited to, disorders exhibiting altered expression and deposition of extracellular matrix-associated proteins, e.g., fibrotic disorders. In various aspects, the fibrosis may be localized to a particular tissue, such as epithelial, endothelial, or connective tissue; or to an organ, such as kidney, lung, or liver. Fibrosis can also occur in the eye and joints. In other aspects, the fibrosis may be systemic and involve multiple organ and tissue systems. CTGF-associated disorders include, for example, atherosclerosis, arthritis, retinopathies such as diabetic retinopathy; nephropathies such as diabetic nephropathy; Duchenne muscular dystrophy, cardiac, pulmonary, liver, and kidney fibrosis, and diseases associated with chronic inflammation and/or infection.

Additionally, the antibodies of the invention are useful in therapeutic applications, to prevent or treat CTGF-associated disorders in a subject. Such disorders include, but are not limited to, disorders characterized by angiogenesis and other processes which play a central role in conditions such as atherosclerosis, glaucoma, etc.; and in cancer, including acute lymphoblastic leukemia, dermatofibromas, breast cancer, breast carcinoma, glioma and glioblastoma, rhabdomyosarcoma and fibrosarcoma, desmoplasia, angiolipoma, angioleiomyoma, desmoplastic cancers, and prostate, ovarian, colorectal, pancreatic, gastrointestinal, and liver cancer and other tumor growth and metastases.

In some aspects, the invention provides antibodies for reducing the incidence of or preventing a CTGF-associated disorder in a subject having a predisposition to develop such a disorder. A predisposition may include, e.g., hyperglycemia, hypertension, or obesity in the subject. Such disorders may occur, e.g., due to diabetes, obesity, etc., and include diabetic nephropathy, retinopathy, and cardiovascular disease. Additionally, a predisposition may be suspected due to an event, e.g., a myocardial infarction, surgery, peritoneal dialysis, chronic and acute transplant rejection, chemotherapy, radiation therapy, trauma, orthopedic or paralytic immobilization, congestive heart failure, pregnancy, or varicosities in the subject.

In particular embodiments, as exemplified herein, the antibodies of the present invention are administered to a subject to treat fibrosis of an organ, e.g., lung or kidney. In additional embodiments, the antibodies are administered to a subject to treat or prevent ocular disorders such as proliferative vitreoretinopathy, diabetic retinopathy, or macular degeneration. Because CTGF is implicated in a wide variety of disorders, the invention contemplates treating patients having a CTGF-associated disorder using an antibody of the invention to improve or stabilize pathology and organ function, improve the quality of life, and extend survival.

For therapeutic applications, the antibodies of the invention are administered to a mammal, preferably a human, in a pharmaceutically acceptable dosage form. The antibodies may be administered intravenously. The antibodies may be administered intravenously as a bolus or by continuous infusion over a period of time. The antibodies may be administered by intramuscular, subcutaneous, intra-articular, intrasynovial, intrathecal, intravitreal, intracranial, oral, topical, or inhalation routes. The antibodies may be administered subcutaneously. When the antibody possesses the suitable activity, intratumoral, peritumoral, intralesional, or perilesional routes of administration can also be utilized to exert local as well as systemic therapeutic effects.

Such dosage forms encompass pharmaceutically acceptable carriers that are nontoxic and nontherapeutic. When present in an aqueous dosage form, rather than being lyophilized, the antibody typically will be formulated at a concentration of about 0.1 mg/ml to 100 mg/ml, although wide variation outside of these ranges is permitted.

For the prevention or treatment of disease, the appropriate dosage of antibody will depend on the type of disease to be treated, as defined above, the severity and course of the disease, whether the antibodies are administered for preventive or therapeutic purposes, the course of previous therapy, the patient's clinical history and response to the antibody, and the discretion of the attending physician. The antibody is suitably administered to the patient at one time or over a series of treatments.

Depending on the type and severity of the disease, about 0.015 to 25 mg of antibody/kg of patient weight is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens may be useful and are not excluded from the present invention.

According to some embodiments of the invention, the effectiveness of the antibody in preventing or treating disease may be improved by administering the antibody serially or in combination with another agent that is effective for the same clinical objective, such as another antibody directed against a different epitope than the principal antibody, or one or more conventional therapeutic agents known for the intended therapeutic indication, e.g. prevention or treatment of conditions associated with excessive extracellular matrix production such as fibrosis or sclerosis, inhibition of tumor cell growth or metastasis, inhibition of neovascularization, or reduction of inflammation. Such agents may ameliorate symptoms or improve outcome via a similar mechanism of action, e.g., anti-TGFβ antibodies, or by a different mechanism, e.g., interferon-γ. Such agents may additionally ameliorate symptoms directly or indirectly associated with a CTGF-associated disorder or a predisposition to develop a CTGF-associated disorder, e.g., angiotensin-converting enzyme (ACE) inhibitors and angiotensin receptor blockers (Arbs).

Non-Therapeutic Uses

The antibodies described herein are useful as affinity purification agents. In this process, the antibodies are immobilized on a solid phase such a Protein A resin, using methods well known in the art. The immobilized antibody is contacted with a sample containing the CTGF protein (or fragment thereof, such as CTGF-NTF) to be purified, and thereafter the support is washed with a suitable solvent that will remove substantially all the material in the sample except the CTGF protein, which is bound to the immobilized antibody. Finally, the support is washed with another suitable solvent that will release the CTGF protein from the antibody.

The CTGF antibodies and fragments thereof of the invention as disclosed herein are also useful in diagnostic assays to detect and/or quantify CTGF protein, for example, detecting CTGF expression in specific cells, tissues, or plasma.

It will be advantageous in some embodiments, for example, for diagnostic purposes to label the antibody with a detectable moiety. Numerous detectable labels are available, including radioisotopes, fluorescent labels, enzyme substrate labels, quantum dots and the like. The label may be indirectly conjugated with the antibody using various known techniques. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody can be conjugated with a small hapten (such as digoxin) and one of the different types of labels mentioned above is conjugated with an anti-hapten antibody (e.g., anti-digoxin antibody). Thus, indirect conjugation of the label with the antibody can be achieved.

Diagnostic Kits

An anti-CTGF antibody or fragment thereof can be used in a diagnostic kit, i.e., a packaged combination of reagents in predetermined amounts with instructions for performing the diagnostic assay, such as an assay for the detection of full length CTGF and CTGF-NTF, e.g., in plasma. Accordingly, also provided herein is the use of the antibody or antigen-binding fragment thereof as described herein for diagnosis of a CTGF-associated disorder. Where the antibody is labeled with an enzyme, the kit may include substrates and cofactors required by the enzyme such as a substrate precursor that provides the detectable chromophore or fluorophore. In addition, other additives may be included such as stabilizers, buffers (for example a block buffer or lysis buffer), and the like. The relative amounts of the various reagents may be varied widely to provide for concentrations in solution of the reagents that substantially optimize the sensitivity of the assay. The reagents may be provided as dry powders, usually lyophilized, including excipients that on dissolution will provide a reagent solution having the appropriate concentration.

Compositions, Combinations and Administration Thereof

A composition comprising an anti-CTGF antibody or an antigen-binding fragment thereof according to the invention can be administered to a subject having or at risk of the CTGF-associated diseases and/or disorders described herein. The invention provides for the use of an anti-CTGF antibody or an antigen-binding fragment thereof in the manufacture of a medicament for prevention or treatment of a CTGF-associated disease or disorder. The term "subject" as used herein means any mammalian patient to which an anti-CTGF antibody or an antigen-binding fragment thereof can be administered, including, e.g., humans and certain non-human mammals, such as domesticated animals (e.g., cows, sheep, pigs, cats, dogs, and horses), primates (e.g., humans and non-human primates such as monkeys), rabbits, and rodents (e.g., mice and rats). Subjects specifically intended for treatment using the methods described herein include humans.

An anti-CTGF antibody or an antigen-binding fragment thereof may be administered on their own or in combination with one or more additional therapeutic agents, such as state-of-the-art or standard-of-care compounds, such as e.g., anti-fibrotic agents, steroids, immune modulators, checkpoint inhibitors, cell proliferation inhibitors, anti-angiogenic substances, cytostatic or cytotoxic substances, and the like.

In some aspects, the present invention also provides pharmaceutical compositions administered as pharmaceutical compositions comprising a therapeutically effective amount of the anti-CTGF antibody or an antigen-binding fragment thereof, and optionally one or more additional therapeutic agents.

Some aspects of the invention provide a binding molecule of the invention for use in the therapy of a CTGF-associated disease, wherein said therapy comprises one or more pharmacologically active substances.

Some aspects of the invention provide the use of one or more active ingredients in the manufacture of a medicament for the therapy of CTGF-associated disease, wherein said medicament comprises the binding molecule of the invention.

In some aspects of the invention, the anti-CTGF antibody or antigen-binding fragment thereof is optionally administered in combination with an additional therapeutic agent. The additional therapeutic agent may be a phosphodiesterase 4 inhibitor, a tyrosine kinase inhibitor, a lysophosphatidic acid receptor 1 (LPA1) antagonist, an inhibitor of Src and Abl kinases, a prostacyclin vasodilator, an angiotensin II type 2 receptor agonist (ATRAG), a c-Jun N-terminal kinase inhibitor, an analgesic, an opioid, a P2X3 homotrimeric receptor antagonist, an N-methyl-D-aspartate (NMDA) receptor inhibitor, an additional CTGF inhibitor, an anxiolytic, a proton pump inhibitor, an antifibrotic agent, or any combination thereof. The additional therapeutic agent may be 9MW3811 (Mabwell Shanghai Bioscience Co., Ltd.), ANG-3070 (Angion Biomedica Corp), AP01 (Avalyn Pharma Inc.), autoantibody reductive therapy, autologous lung spheroid stem cells (University of North Carolina, Chapel Hill), AZD5055 (AstraZeneca), AZD8965 (AstraZeneca), BBT-877 (Bridge Biotherapeutics), belumosudil (KD025, Kadmon), BG00011 (Biogen, STX-100), BI 1819479 (Boehringer Ingelheim), BI 1839100 (Boehringer Ingelheim), BLD-0409 (Blade Therapeutics), BLD-2660 (Blade), BLU-5937, BMS-986020 (Bristol Myers Squibb), BMS-986278 (Bristol-Myers Squibb), BNC 1021 (BONAC/Toray, TRK-250, PK-7010), bosentan, buloxibutid (Vicore Pharma AB, C21), buspirone, C106 (Vicore Pharma AB), CAL 101 (Calluna Pharma AS), carlumab (Janssen, CNTO-888), CC-90001 (Celgene), clonazepam, CMR316 (Calibr), codeine, dasatinib, dectrekumab (Novartis, QAX576), desvenlafaxine, deupirfenidone (PureTech, LYT-100), DWN12088 (Daewoong Pharmaceutical Co. LTD.), Taladegib (Endeavor Biomedicines, Inc., ENV-101), epigallocatechin-3-gallate (University of California, San Francisco), fipaxalparant (Horizon Therapeutics, HZN-825), fluoxetine, gabapentin, garadacimab (CSL, CSL312), GB 2064 (Galecto, PAT-1251), GB0139 (Galecto), gefapixant, GLPG1690 (Galapagos), GSK3915393 (GlaxoSmithKline), HEC 68498 (HEC Pharm), HEC-866 (HEC Pharm), HSK44459 (Haisco Pharmaceutical Group Co., Ltd.), HuL001 (HuniLife Biotechnology, Inc.), human umbilical cord mesenchymal stem cell injection (Shanghai Life Science & Technology), ifenprodil, ifetroban (Cumberland Pharmaceuticals), imatinib, indolinone, ISM001-055 (In-Silico Medicine Hong Kong Limited, INS018_055), IW001 (ImmuneWorks), lanalumab (Novartis), lebrikizumab, leramistat (Modern Biosciences Ltd), letemovir, lorazepam, LTI-03 (Lung Therapeutics, Inc), LTP001 (Novartis), macitentan, minocycline, N-acetylcysteine (NAC), nalbuphine (Trevi Therapeutics), ND-L02-50201 (Nitto Denko), nerandomilast (Boehringer Ingelheim, BI 1015550), nintedanib (Boehringer Ingelheim), NIP292 (CR Pharma, The National Institutes of Pharmaceutical R&D Co. Ltd, China), olokizumab (R-Pharm International, LLC), omeprazole, ORIN1001 (Fosun, Orinove), orvepitant, pamrevlumab (FibroGen), pantoprazole, pirfenidone, PLN-74809 (Pliant Therapeutics, bexotegrast), prednisone, pregabalin, PRM-151 (recombinant human pentraxin-2 protein, Genetech, Promedior), PRS-220 (Pieris Australia Pty Ltd), quercetin, rabeprazole, rituximab, RSN0402 (Shenzhen Resproly Bio-pharmaceutical Co., Ltd), saracatinib, SB17170 (SPARK Biopharma), setanaxib (Genkyotex, GKT137831), setogepram (ProMetic, PBI-4050), SHR-1906 (Hengrui Pharmaceuticals Co., Ltd), sildenafil, simtuzumab (Gilead, GS-6624), sirolimus, SM-04646 (Samumed), tanzisertib (Celgene, CC-930), thalidomide, tipelukast (MediciNova, MN-001), treprostinil (United Therapeutics), TRK-250 (Toray, BNC-1021), TTI-101 (Tvardi Therapeutics), valganciclovir, vixarelimab (Genentech), voxelotor (GBT446), zileuton, zinc and nicotinamide riboside (Cedars-Sinai Medical Center), or any combination thereof. The additional therapeutic agent is preferably nintedanib, nerandomilast, pirfenidone, or any combination thereof.

Various delivery systems are known and can be used to administer the anti-CTGF antibody or an antigen-binding fragment thereof. Methods of introduction include but are not limited to intravitreal, eye drops, intradermal, intramuscular, intraperitoneal, intravenous, subcutaneous, intranasal, epidural, and oral routes. The anti-CTGF antibody or an antigen-binding fragment thereof can be administered, for example by infusion, bolus or injection, and can be administered together with other biologically active agents. Administration can be systemic or local. Formulations for such injections may be prepared in, for example, prefilled syringes. As such in an aspect of the invention, pre-filled syringes are provided that include an anti-CTGF antibody or an antigen-binding fragment thereof.

To be used in therapy, the anti-CTGF antibody of the invention is formulated into pharmaceutical compositions appropriate to facilitate administration to animals or humans. Typical formulations of the binding molecule or antibody molecule described herein can be prepared by mixing the binding molecule or antibody molecule with physiologically acceptable carriers, excipients or stabilizers, in the form of lyophilized or otherwise dried formulations or aqueous solutions or aqueous or non-aqueous suspensions. Carriers, excipients, modifiers or stabilizers are nontoxic at the dosages and concentrations employed.

In typical embodiments, the pharmaceutical composition is formulated in accordance with routine procedures as a pharmaceutical composition adapted for intravenous or subcutaneous administration to a subject. Typically, compositions for administration by injection are solutions in sterile isotonic aqueous buffer. Where necessary, the pharmaceutical composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing an anti-CTGF antibody or an antigen-binding fragment thereof in lyophilized form and (b) a second container containing a pharmaceutically acceptable diluent (e.g., sterile water) for injection. The pharmaceutically acceptable diluent can be used for reconstitution or dilution of the lyophilized anti-CTGF antibody or antigen-binding fragment thereof. Optionally associated with such container(s)

can be a notice in the form prescribed by a governmental agency regulating the manufacture, use or sale of pharmaceuticals or biological products, which notice reflects approval by the agency of manufacture, use or sale for human administration.

In some embodiments, antibodies of the invention can be formulated to doses, which include for example a dose of 1 mg/kg to 200 mg/kg. including, for example, 1 mg/kg to 25 mg/kg, 25 mg/kg to 50 mg/kg, 50 mg/kg to 75 mg/kg, 75 mg/kg to 100 mg/kg, 100 mg/kg to 125 mg/kg, 125 mg/kg to 150 mg/kg, 150 mg/kg to 175 mg/kg, or 175 mg/kg to 200 mg/kg. With respect to therapeutic regimens for combinatorial administration, in a specific embodiment, an anti-CTGF antibody or antigen-binding fragment thereof is administered concurrently with a second and/or third therapeutic agent. In some embodiments, the second and/or third therapeutic agent is administered prior or subsequent to administration of the anti-CTGF antibody or antigen-binding fragment thereof.

Polynucleotides, Vectors, and Host Cells

The present invention relates to (isolated) polynucleotides that comprise a sequence encoding an anti-CTGF antibody or antigen-binding fragment thereof, vectors, and host cells comprising the polynucleotides, and recombinant techniques for production of the antibody. As described above, the antibody or antigen-binding fragment thereof, as described herein, may be encoded on a single or on a plurality of polynucleotides (e.g., with heavy and light chain encoded on separate polynucleotides). The (isolated) polynucleotides can encode any desired form of the anti-CTGF antibody including, for example, full length monoclonal antibodies, Fab, Fab', F(ab')$_2$, and Fv fragments, diabodies, linear antibodies, single-chain antibody molecules, and multispecific antibodies formed from antibody fragments.

The polynucleotide(s) that comprise a sequence encoding an anti-CTGF antibody or a fragment or chain thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The anti-CTGF antibodies can also be produced as fusion polypeptides, in which the antibody is fused with a heterologous polypeptide, such as a signal sequence or other polypeptide having a specific cleavage site at the amino terminus of the mature protein or polypeptide. The heterologous signal sequence selected is typically one that is recognized and processed (e.g., cleaved by a signal peptidase) by the host cell. For prokaryotic host cells that do not recognize and process the anti-CTGF antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO 90/13646. In mammalian cells, mammalian signal sequences as well as viral secretory leaders, for example, the herpes simplex gD signal, can be used. The DNA for such precursor region is ligated in reading frame to DNA encoding the anti-CTGF antibody.

Anti-CTGF antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-CTGF antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia* pastors (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated anti-CTGF antibody are derived from multicellular organisms. Examples of invertebrate cells include plant and insect cells, including, e.g., numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk worm). A variety of viral strains for transfection are publicly available, e.g., the L-1 variant of *Autographa californica* NPV and the Bm-5 strain of *Bombyx mori* NPV, and such viruses may be used, particularly for transfection of *Spodoptera frugiperda* cells.

Plant cell cultures of cotton, corn, potato, soybean, *petunia*, tomato, and tobacco can also be utilized as hosts.

The anti-CTGF antibodies or antigen-binding fragments thereof can also be incorporated in viral vectors, e.g. the polynucleotide encoding for the anti-CTGF antibody or antigen-binding fragment thereof is introduced into the viral vector and then expressed in the body of the subject after infection with the virus.

In some aspects, expression of the anti-CTGF antibody or antigen-binding fragment thereof is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, J. Gen Virol. 36:59), baby hamster kidney cells (BHK, ATCC CCL 10), Chinese hamster ovary cells/-DHFR1 (CHO, Urlaub et al., 1980, Proc. Natl. Acad. Sci. USA 77:4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, Annals N.Y. Acad. Sci. 383:44-68), MRC 5 cells, FS4 cells, and human hepatoma line (Hep G2).

Also included are nucleic acids that hybridize under low, moderate, and high stringency conditions, in particular under high stringency conditions, as defined herein, to all or a portion (e.g., the portion encoding the variable region) of the nucleotide sequence represented by isolated polynucleotide sequence(s) that encode an anti-CTGF antibody or antibody fragment. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, at least 98%, or at least 99% identical to the sequence of a portion or all of a nucleic acid encoding an anti-CTGF polypeptide (e.g., a heavy chain or light chain variable region), or its complement. Hybridizing nucleic acids of the type described herein can be used, for example, as a cloning probe, a primer, e.g., a PCR primer, or a diagnostic probe. In some aspects, "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

In one embodiment, the present invention relates to an isolated polynucleotide comprising a nucleotide sequence encoding a heavy chain variable region comprising the amino acid sequence of any one of SEQ ID NOs: 108, 118, 128, 138, 148, 158, 168, or 178.

In one embodiment, the present invention relates to an isolated polynucleotide comprising a nucleotide sequence encoding a light chain variable region comprising the amino acid sequence of any one of SEQ ID NOs: 103, 113, 123, 133, 143, 153, 163, 173, 183, 193, 203, 213, 223, 233, 243, or 253.

In one embodiment, the present invention relates to an isolated polynucleotide comprising a nucleotide sequence encoding a heavy chain region comprising the amino acid sequence of any one of SEQ NO: 109, 119, 129, 139, 149, 159, 169, or 179.

In one embodiment, the present invention relates to an isolated polynucleotide comprising the nucleotide sequence encoding of a light chain region comprising the amino acid sequence of any one any one of SEQ NO: 104, 114, 124, 134, 144, 154, 164, 174, 184, 194, 204, 214, 224, 234, 244, or 254.

Articles of Manufacture

In some aspects, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition is the anti-CTGF antibody or the antigen-binding fragment thereof. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

Additional Exemplary Anti-CTGF Antibody and Compound Sequences

The sequences of certain exemplary anti-CTGF antibodies and compounds used in the working examples herein are provided as follows.

```
Antibody F1 light chain:
                                    (SEQ ID NO: 20)
DIQMTQSPSSLSASVGDRVTITCRASQGISSWLAWYQQKPEKAPKSLIYA

ASSLQSGVPSRFSGSGSGTDFTLTISSLQPEDFATYYCQQYNSYPPTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

Antibody F1 heavy chain:
                                    (SEQ ID NO: 21)
EGQLVQSGGGLVHPGGSLRLSCAGSGFTFSSYGMHWVRQAPGKGLEWVSG

IGTGGGTYSTDSVKGRFTISRDNAKNSLYLQMNSLRAEDMAVYYCARGDY

YGSGSFFDCWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRFEMTKNQVSLTCLVKGFYPSDIAVEWESNGQPENNYKTTPPV

LDSDGSFFLYSKLTVDKSRWQQGNVFSCSVMHEALHNHYTQKSLSLSPGK.
```

-continued

Antibody H1 light chain:
(SEQ ID NO: 22)
ETVVTQEPSLTVSPGGTVTLTCRSSIGAVTTSNYANWVQQKPGQAFRGLI

GGTSNRAPWTPARFSGSLLGGKAALTLSGVQPEDEAEYYCALWYSTHYVF

GGGTKLTVLGQPKANPTVTLFPPSSEELQANKATLVCLISDFYPGAVTVA

WKADGSPVKAGVETTKPSKQSNNKYAASSYLSLTPEQWKSHRSYSCQVTH

EGSTVEKTVAPTECS.

Antibody H1 heavy chain:
(SEQ ID NO: 23)
EVTLKESGPVLVKPTETLTLTCTVSGFSLSTFGVHWIRQPPGKGLEWLGV

IWRRGGTDYNAAFMSRLTISKDTSKSQVVFTMTNMDPVDTATYYCARDGG

FDYWGQGTTVTVSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSCDKTHTCPPCPAPELLGGPSVFLFPPKPKDTLYI

TREPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPP

SRDELTKNQVSLTCLVKGFYPSDIAVEWESNGQPENNYKTTPPVLDSDGS

FFLYSKLTVDKSRWQQGNVFSCSVMHEALHNHYTQKSLSLSPGK.

Antibody H2 light chain:
(SEQ ID NO: 24)
EIVLTQSPATLSLSPGERATLSCSASSSVSYMHWFQQKPGQSPKLWIYST

SNLASGVPARFSGSGSGTDYTLTISSLEPEDFAVYYCQQRSSYPLTFGQG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC.

Antibody H2 heavy chain:
(SEQ ID NO: 25)
EVQLVESGGGLVQPGGSLRLSCAASGFSFNTYAMNWVRQAPGKGLEWVAR

IRTKSNNYATYYADSVKDRFTISRDDSESSLYLQMNSLKTEDTAVYYCVE

TGFAYWDQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

Compound P1:
(SEQ ID NO: 26)
QDSTSDLIPAPPLSKVPLQQNFQDNQFQGKWYVVGVAGNAILRPDKQPAK

MFATIYELKEDKSYDVTSVRFEAKSCKYTIKTFVPGSQPGEFTSGQIKSA

PGQTSTLVRVVSTNYNQHAMVFFKHVSQNREIFVITLYGRTKELTSELKE

NFIRFSKSLGLPENHIVFPVPIDQCIDGHHHHHHHHHH.

Human CTGF and CTGF-NTF Sequences

A wild-type human CTGF sequence is available as NCBI Accession No. NP_001892.2 having the following amino acid sequence (with the signal peptide included): MTAA-SMGPVRVAFVVLLALCSRPAVGQNCSGPCRCPDEPA-PRCPAGVSL VLDGCGCCRVCAKQLGELCTERDPCD- PHKGLFCHFGSPANRKIGVCTAKDGAPCIFGGTVYR SGESFQSSCKYQCTCLDGAVGCMPLCSMDVRLPSP-DCPFPRRVKLPGKCCEEWVCDEPKDQTVVGPALAA YRLEDTFGPDPTMIRANCLVQTTEWSACSKTCGM-GISTRVTNDNASCRLEKQSR LCMVRPCEADLEENIK-KGKKCIRTPKISKPIKFELSGCTSMKTYRAKFCG-VCTDGRCCTPHRTT TLPVEFKCPDGEVMKKNMMFI-KTCACHYNCPGDNDIFESLYYRKMYGDMA (SEQ ID NO: 1).

Full-length human CTGF used in the working examples herein has the following amino acid sequence, corresponding to NCBI Accession No. NP_001892.1 (with the signal peptide omitted): QNCSGPCRCPDEPAPRCPAGVSL-VLDGCGCCRVCAKQLGELCTERDPCD PHKGLFC-DFGSPANRKIGVCTAKDGAPCIFGGTVYRSGESFQSS-CKYQCTCLDGAVGCMPLC SMDVRLPSPDCPFPRRV-KLPGKCCEEWVCDEPKDQTVVGPALAAYRLEDTFG-PDPTMIRANC LVQTTEWSACSKTCGMGISTRVTND-NASCRLEKQSRLCMVRPCEADLEENIKKGKKCIRTP-KIS KPIKFELSGCTSMKTYRAKFCGVCTDGR-CCTPHRTTTLPVEFKCPDGEVMKKNMMFIKTCACH YNCPGDNDIFESLYYRKMYGDMA (SEQ ID NO:2), which was purchased from R&D Systems (catalog no. 9190-CC).

The human N-terminal fragment of CTGF (CTGF-NTF) used in the working examples herein has the following amino acid sequence: QNCSGPCRCPDEPAPRCPAGV-SLVLDGCGC CRVCAKQLGELCTERDPCDPHKGL-FCDFGSPANRKIGVCTAKDGAPCIFGGTVYRSGE-SFQS SCKYQCTCLDGAVGCMPLCSMDVRLPSPDC-PFPRRVKLPGKCCEEWVCDEPKDQTVVGPAL AEN-LYFQ (SEQ ID NO: 3), which was recombinantly expressed. The final 6 amino acids at the C-terminus of the CTGF-NTF sequence are a partial TEV protease cleavage site that remains following purification.

EXAMPLES

Example 1. Generation of Anti-CTGF Antibodies

Methods

Mice are immunized with a human N-terminal fragment of CTGF (CTGF-NTF). B cells are harvested and used to produce hybridomas by fusion with PAI myeloma cells. The resulting antibodies are screened for binding to recombinant human, cynomolgus monkey, and mouse CTGF-NTF. Antibodies are purified from serum-free hybridoma supernatants using MabSelectSuRe resin (GE Healthcare). Binding of the purified antibodies human and cynomolgus CTGF-NTF are assayed on an Octet QK system (ForteBio) equipped with streptavidin (SA) biosensor tips (ForteBio). Variable gene sequences are recovered from hybridomas, and chimeric antibodies are generated containing these variable gene sequences.

Results

The two clones were obtained having binding affinity to human CTGF-NTF of 15 pM and 40 pM respectively. These clones were observed to have similar sequences to one another. The antibody having binding affinity to human CTGF-NTF of 15 pM was selected for humanization, resulting in the humanized antibody A128, having the light chain variable region of SEQ ID NO: 253 and the heavy chain variable region of SEQ ID NO: 178.

Example 2. Production and Characterization of
Humanized Antibodies

This example describes production and testing of variants of humanized antibody A128 described in Example 1. In total, eight variants of the heavy chain variable region and sixteen variants of the light chain variable region were produced. Each heavy chain variable region variant is coexpressed with each light chain variable region variant in CHO cells, resulting in 128 different combinations.

Percentage humanness of the heavy- and light-chain variable regions, expression titer, and binding affinity for full length CTGF determined by surface plasmon resonance (SPR) were determined. Results are shown in Table 15 below.

TABLE 15

| Antibody Name | VL SEQ ID NO: | VH SEQ ID NO: | VL % Humanness | VH % Humanness | Titer (mg/mL) | $K_D$ (pM) |
|---|---|---|---|---|---|---|
| A1 | 103 | 108 | 83.838 | 84.694 | 43.7 | 290 |
| A2 | 103 | 118 | 83.838 | 84.694 | 46.6 | 250 |
| A3 | 103 | 128 | 83.838 | 84.694 | 45.7 | 230 |
| A4 | 103 | 138 | 83.838 | 84.694 | 50.3 | 220 |
| A5 | 103 | 148 | 83.838 | 86.735 | 49.4 | 320 |
| A6 | 103 | 158 | 83.838 | 85.714 | 32.9 | 320 |
| A7 | 103 | 168 | 83.838 | 85.714 | 52.8 | 330 |
| A8 | 103 | 178 | 83.838 | 85.714 | 60.2 | 340 |
| A9 | 113 | 108 | 82.828 | 84.694 | 63.5 | 210 |
| A10 | 113 | 118 | 82.828 | 84.694 | 80.3 | 190 |
| A11 | 113 | 128 | 82.828 | 84.694 | 69.9 | 170 |
| A12 | 113 | 138 | 82.828 | 84.694 | 80.2 | 170 |
| A13 | 113 | 148 | 82.828 | 86.735 | 70.1 | 250 |
| A14 | 113 | 158 | 82.828 | 85.714 | 49.7 | 220 |
| A15 | 113 | 168 | 82.828 | 85.714 | 74.9 | 260 |
| A16 | 113 | 178 | 82.828 | 85.714 | 83.8 | 240 |
| A17 | 123 | 108 | 84.848 | 84.694 | 58.5 | 200 |
| A18 | 123 | 118 | 84.848 | 84.694 | 73.6 | 190 |
| A19 | 123 | 128 | 84.848 | 84.694 | 67.3 | 170 |
| A20 | 123 | 138 | 84.848 | 84.694 | 75.8 | 180 |
| A21 | 123 | 148 | 84.848 | 86.735 | 68.8 | 250 |
| A22 | 123 | 158 | 84.848 | 85.714 | 45.4 | 210 |
| A23 | 123 | 168 | 84.848 | 85.714 | 70.6 | 230 |
| A24 | 123 | 178 | 84.848 | 85.714 | 80.4 | 230 |
| A25 | 133 | 108 | 83.838 | 84.694 | 64 | 150 |
| A26 | 133 | 118 | 83.838 | 84.694 | Too Low | No capture |
| A27 | 133 | 128 | 83.838 | 84.694 | Too Low | No capture |
| A28 | 133 | 138 | 83.838 | 84.694 | Too Low | No capture |
| A29 | 133 | 148 | 83.838 | 86.735 | 1.26 | No capture |
| A30 | 133 | 158 | 83.838 | 85.714 | 0.7835 | No capture |
| A31 | 133 | 168 | 83.838 | 85.714 | 0.6562 | No capture |
| A32 | 133 | 178 | 83.838 | 85.714 | Too Low | No capture |
| A33 | 143 | 108 | 82.828 | 84.694 | 4.66 | No binding |
| A34 | 143 | 118 | 82.828 | 84.694 | 6.26 | No binding |
| A35 | 143 | 128 | 82.828 | 84.694 | 2.5 | No binding |
| A36 | 143 | 138 | 82.828 | 84.694 | 4.98 | No binding |
| A37 | 143 | 148 | 82.828 | 86.735 | 2.88 | No binding |
| A38 | 143 | 158 | 82.828 | 85.714 | 1.57 | No capture |
| A39 | 143 | 168 | 82.828 | 85.714 | 0.2674 | No capture |
| A40 | 143 | 178 | 82.828 | 85.714 | 2.59 | No capture |
| A41 | 153 | 108 | 81.818 | 84.694 | 37 | 190 |
| A42 | 153 | 118 | 81.818 | 84.694 | 43.9 | 150 |
| A43 | 153 | 128 | 81.818 | 84.694 | 42.6 | 150 |
| A44 | 153 | 138 | 81.818 | 84.694 | 45.8 | 160 |
| A45 | 153 | 148 | 81.818 | 86.735 | 11.4 | No binding |
| A46 | 153 | 158 | 81.818 | 85.714 | 28 | 200 |
| A47 | 153 | 168 | 81.818 | 85.714 | 7.1 | No binding |
| A48 | 153 | 178 | 81.818 | 85.714 | 46.4 | 230 |
| A49 | 163 | 108 | 80.808 | 84.694 | 16.7 | 300 |
| A50 | 163 | 118 | 80.808 | 84.694 | 20.7 | 260 |
| A51 | 163 | 128 | 80.808 | 84.694 | 21.3 | 250 |
| A52 | 163 | 138 | 80.808 | 84.694 | 22.5 | 270 |
| A53 | 163 | 148 | 80.808 | 86.735 | 21.9 | 360 |
| A54 | 163 | 158 | 80.808 | 85.714 | 14.8 | 310 |
| A55 | 163 | 168 | 80.808 | 85.714 | 23.1 | 350 |
| A56 | 163 | 178 | 80.808 | 85.714 | 19.4 | 310 |
| A57 | 173 | 108 | 80.808 | 84.694 | 51.7 | 350 |
| A58 | 173 | 118 | 80.808 | 84.694 | 57.9 | 300 |
| A59 | 173 | 128 | 80.808 | 84.694 | 61.3 | 270 |
| A60 | 173 | 138 | 80.808 | 84.694 | 66.1 | 300 |
| A61 | 173 | 148 | 80.808 | 86.735 | 61.2 | 350 |
| A62 | 173 | 158 | 80.808 | 85.714 | 36.9 | 350 |
| A63 | 173 | 168 | 80.808 | 85.714 | 63.1 | 340 |
| A64 | 173 | 178 | 80.808 | 85.714 | 78.3 | 320 |
| A65 | 183 | 108 | 80.808 | 84.694 | 42.7 | 270 |

TABLE 15-continued

| Antibody Name | VL SEQ ID NO: | VH SEQ ID NO: | VL % Humanness | VH % Humanness | Titer (mg/mL) | $K_D$ (pM) |
|---|---|---|---|---|---|---|
| A66 | 183 | 118 | 80.808 | 84.694 | 56 | 250 |
| A67 | 183 | 128 | 80.808 | 84.694 | 53.9 | 240 |
| A68 | 183 | 138 | 80.808 | 84.694 | 62.5 | 150 |
| A69 | 183 | 148 | 80.808 | 86.735 | 56.2 | 280 |
| A70 | 183 | 158 | 80.808 | 85.714 | 36.1 | 270 |
| A71 | 183 | 168 | 80.808 | 85.714 | 55.5 | 280 |
| A72 | 183 | 178 | 80.808 | 85.714 | 73.6 | 270 |
| A73 | 193 | 108 | 81.818 | 84.694 | 73.7 | 580 |
| A74 | 193 | 118 | 81.818 | 84.694 | 95 | 200 |
| A75 | 193 | 128 | 81.818 | 84.694 | 83.3 | 170 |
| A76 | 193 | 138 | 81.818 | 84.694 | 103.9 | 180 |
| A77 | 193 | 148 | 81.818 | 86.735 | 80.9 | 230 |
| A78 | 193 | 158 | 81.818 | 85.714 | 57.1 | 230 |
| A79 | 193 | 168 | 81.818 | 85.714 | 87.7 | 160 |
| A80 | 193 | 178 | 81.818 | 85.714 | 98.8 | 250 |
| A81 | 203 | 108 | 80.808 | 84.694 | 25.1 | 290 |
| A82 | 203 | 118 | 80.808 | 84.694 | 29.1 | 360 |
| A83 | 203 | 128 | 80.808 | 84.694 | 30 | 260 |
| A84 | 203 | 138 | 80.808 | 84.694 | 32.4 | 290 |
| A85 | 203 | 148 | 80.808 | 86.735 | 31 | 280 |
| A86 | 203 | 158 | 80.808 | 85.714 | 0.2403 | No capture |
| A87 | 203 | 168 | 80.808 | 85.714 | 31 | 340 |
| A88 | 203 | 178 | 80.808 | 85.714 | 38.7 | 320 |
| A89 | 213 | 108 | 83.838 | 84.694 | 38.1 | 160 |
| A90 | 213 | 118 | 83.838 | 84.694 | 49.5 | 170 |
| A91 | 213 | 128 | 83.838 | 84.694 | 44.6 | 130 |
| A92 | 213 | 138 | 83.838 | 84.694 | 48.3 | 160 |
| A93 | 213 | 148 | 83.838 | 86.735 | 45.4 | 180 |
| A94 | 213 | 158 | 83.838 | 85.714 | 28.8 | 190 |
| A95 | 213 | 168 | 83.838 | 85.714 | 44.2 | 190 |
| A96 | 213 | 178 | 83.838 | 85.714 | 55.2 | 190 |
| A97 | 223 | 108 | 82.828 | 84.694 | 70.7 | 140 |
| A98 | 223 | 118 | 82.828 | 84.694 | 83.2 | 120 |
| A99 | 223 | 128 | 82.828 | 84.694 | 79.7 | 110 |
| A100 | 223 | 138 | 82.828 | 84.694 | 83.1 | 130 |
| A101 | 223 | 148 | 82.828 | 86.735 | 78.3 | 170 |
| A102 | 223 | 158 | 82.828 | 85.714 | 58.4 | 150 |
| A103 | 223 | 168 | 82.828 | 85.714 | 86.9 | 150 |
| A104 | 223 | 178 | 82.828 | 85.714 | 88.1 | 170 |
| A105 | 233 | 108 | 84 | 84.694 | 98.3 | 420 |
| A106 | 233 | 118 | 84 | 84.694 | 60.7 | 430 |
| A107 | 233 | 128 | 84 | 84.694 | 107.9 | 370 |
| A108 | 233 | 138 | 84 | 84.694 | 116.2 | 420 |
| A109 | 233 | 148 | 84 | 86.735 | 106.3 | 440 |
| A110 | 233 | 158 | 84 | 85.714 | 81.5 | 450 |
| A111 | 233 | 168 | 84 | 85.714 | 107.4 | 510 |
| A112 | 233 | 178 | 84 | 85.714 | 108.8 | 480 |
| A113 | 243 | 108 | 84 | 84.694 | 78.3 | 760 |
| A114 | 243 | 118 | 84 | 84.694 | 89.2 | 750 |
| A115 | 243 | 128 | 84 | 84.694 | 94.2 | 660 |
| A116 | 243 | 138 | 84 | 84.694 | 91.3 | 690 |
| A117 | 243 | 148 | 84 | 86.735 | 89.3 | 810 |
| A118 | 243 | 158 | 84 | 85.714 | 65.4 | 810 |
| A119 | 243 | 168 | 84 | 85.714 | 91.1 | 910 |
| A120 | 243 | 178 | 84 | 85.714 | 97 | 840 |
| A121 | 253 | 108 | 82.828 | 84.694 | 74.3 | 240 |
| A122 | 253 | 118 | 82.828 | 84.694 | 73.7 | 230 |
| A123 | 253 | 128 | 82.828 | 84.694 | 81.3 | 210 |
| A124 | 253 | 138 | 82.828 | 84.694 | 83.9 | 250 |
| A125 | 253 | 148 | 82.828 | 86.735 | 87.4 | 260 |
| A126 | 253 | 158 | 82.828 | 85.714 | 58.2 | 270 |
| A127 | 253 | 168 | 82.828 | 85.714 | 81.9 | 280 |
| A128 | 253 | 178 | 82.828 | 85.714 | 101.7 | 270 |

115 116

Antibody A97 was selected for further characterization. Unless indicated otherwise, antibodies used in the following examples are full length antibodies, e.g., full length Antibody A97 having the heavy chain of SEQ ID NO: 109 and the light chain of SEQ ID NO: 224.

Example 3. Effects of Anti-CTGF Antibodies on Cleavage of CTGF

This example tests the ability of anti-CTGF antibodies to prevent the cleavage of CTGF by MMP7 in vitro.
Methods Samples are prepared in Diluent A (Quanterix) by separately mixing each anti-CTGF antibody (Antibody A97 or Antibody F1, having the light chain of SEQ ID NO: 20 and the heavy chain of SEQ ID NO: 21) and isotype human IgG control with full length human CTGF (R&D Systems 9190-CC) in microcentrifuge tubes with or without the addition of MMP7 (R&D Systems 907-MP-010 and Millipore 444270100UG, 100 to 1000:1 MMP7 to anti-CTGF molar ratios). Full length CTGF only control samples are prepared with or without MMP7 for signal normalization and assay verification. Samples are incubated for 2 hours at 37° C. to activate MMP7, which cleaves full length CTGF at the hinge region connecting N-terminal and C-terminal domains. After two hours, samples are analyzed (neat) on a sandwich immunoassay (Homebrew methods for Planar Array SP-X by Quantertix, 100-0461), utilizing 1 µg/ml N-terminal capture (rat clone ZX-9B6 anti-human CTGF monoclonal antibody, conjugated to Quanterix antibody Homebrew tag) and 1 µg/ml C-terminal antibody detection (R&D systems anti-human CTGF mAb9190 or AF660, biotinylated following Quanterix protocol) and utilizing all consumables, reagents and assay protocols according to the manufacturer (Quanterix SP-X Homebrew methods and kit 100-0461). After reading the plate on SP-X Imager at short (20 s) and long (300 s) exposures, raw signals are compared (IV units; dual imaging chemiluminescent signal with high resolution CCD camera) and normalized to the signal of full length (intact) CTGF without MMPs as baseline. As the assay methods are stepwise, utilizing an N-terminal specific CTGF capture (binds to non-competing epitope to both Antibody 97 and Antibody F1) with a C-terminal specific CTGF detection can only detect intact CTGF, as any cleaved fragment alone either will not bind during capture step (washed away) or will not produce signal during detection step.
Results As shown in FIG. 1, the addition of Antibody 97 (p<0.005) or Antibody F1 (p<0.01) significantly protected in vitro MMP7-mediated cleavage when compared to isotype control incubated with MMP7 (averaged multiple runs and MMP7 concentrations) with normalized signal approaching full length CTGF normalized signal control without addition of MMP7.

Example 4. N-Terminal and Full Length CTGF Measurement in Patient Samples

To assess the concentration of N-Terminal and full length CTGF in patient plasma samples, antibodies that bind to the N- and C-Terminal regions of CTGF are labeled with Homebrew and Biotin tags according to the manufacturer's protocol (Simoa Planar Array Homebrew, 100-0461, Quanterix). The N-Terminal CTGF Assay uses a rat clone ZX-9B6 anti-Human CTGF monoclonal antibody with Homebrew antibody tag for the capture and Antibody 97 labeled with Biotin for the detection. The full length CTGF assay uses Millipore pAb (ABS1628) to CTGF C-Terminus labeled with Homebrew antibody tag for capture and Antibody F1 labeled with Biotin for detection. The immunoassay procedure is followed according to the manufacturer's protocol (Simoa Planar Array Homebrew, 100-0461, Quanterix). Samples and standards are prepared in the kit-provided sample diluent A, with the full length standard (Recombinant Human CTGF, 9190-CC, R&D Systems) starting at 138 ng/ml and serially diluted 1:4. The N-terminal standard is an N-terminal fragment consisting of the first two domains of CTGF through the hinge region, starting at 200 ng/ml and serially diluted 1:4. Samples are diluted 1:4 for the N-terminal assay and used without dilution for the full length assay. Samples are read on the SP-X imager, optimizing the exposure times to the top standard concentration on the respective plates and reported as picomolar (pM) concentrations.

Total MMP7 levels are assessed with in patient plasma samples by immuno-assay (U-Plex Human MMP7, K151AHEK, Meso Scale Discovery) following the manufacturer's protocol. Samples are diluted 1:4 and results are reported as ng/mL.

Figure 2A:
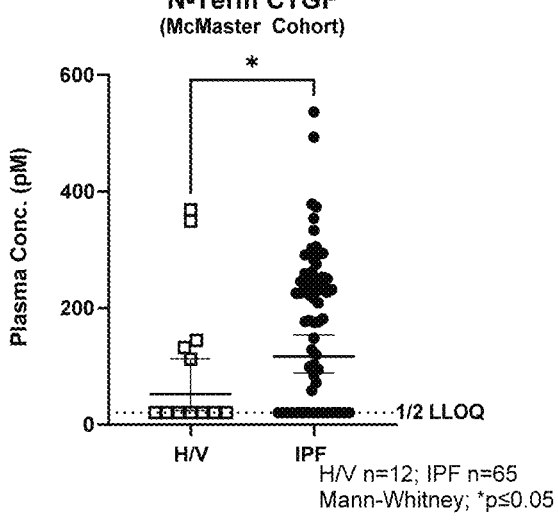
FIG. 2A-2B. Measurement of N-terminal CTGF (FIG. 2A) and full length CTGF (FIG. 2B) in samples from healthy volunteers ("H/V") and IPF patients ("IPF"). N-terminal CTGF concentration was significantly elevated in IPF patients ($p \leq 0.05$).
Figure 2B:
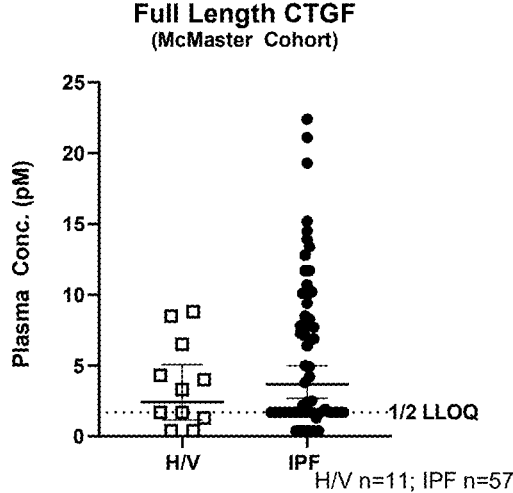
Figure 3:
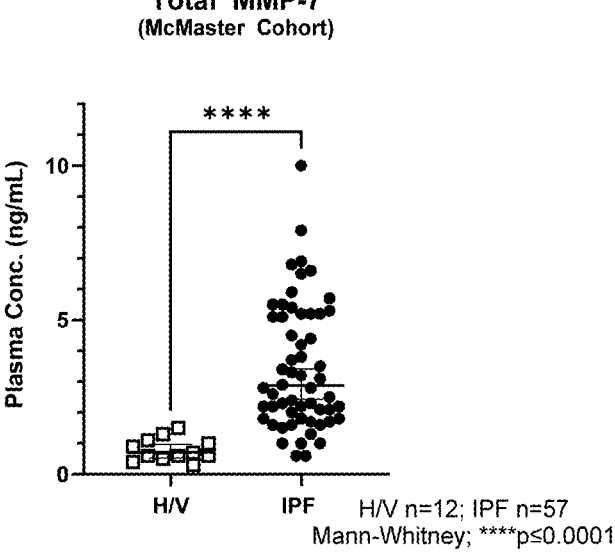
FIG. 3. Measurement of MMP7 in samples from healthy volunteers ("H/V") and IPF patients ("IPF"). MMP7 concentration was significantly elevated in IPF patients ($p \leq 0.0001$).

Results are shown for measurement of N-terminal CTGF (FIG. 2A), full length CTGF (FIG. 2B) and MMP7 (FIG. 3) in healthy volunteers ("H/V") and IPF patients ("IPF"). N-terminal CTGF concentration was significantly elevated in IPF patients (p≤0.05). Full length CTGF concentration was not significantly different between IPF patients and healthy volunteers. MMP7 concentration was significantly elevated in IPF patients (p≤0.0001).

Example 5. Alpha Smooth Muscle Actin Effects in Patient-Derived Multicellular Systems To test the efficacy of a blocking anti-CTGF antibody in reducing fibrotic progression, primary progenitor basal cells isolated from IPF patient lungs are cultured for four weeks under air-liquid interphase (ALI) transwell condition to fully differentiated small airway epithelium. The differentiated lung epithelium is then cocultured with primary human fibroblasts isolated from IPF patients in the basolateral compartment of the transwell culture.

During a 72 hour stimulation with an IPF cytokine cocktail (IPF-RC, Schruf et al., FASEB J. 2020 June; 34(6):7825-7846), the upper epithelium layer starts to produce and secrete metalloproteases (MMPs, including MMP7) and CTGF. The activated fibroblasts underneath further produce large amounts of CTGF which then are cleaved by MMP7 into its active fragments (N-term and C-term fragments) which induce pro-fibrotic stimulation and transition of fibroblasts into myofibroblast cells (FMT). The fibrotic transitioning phase can be quantified by measuring alpha smooth muscle actin (a-SMA) in fibroblast lysates or by measuring the release of matrix modulating collagen components (e.g., COL1A1) in the coculture supernatant. A treatment of the IPF coculture with an anti-CTGF antibody after a 24 hour IPF cocktail pre-stimulation time was tested for its ability reduce fibrotic progression.

Figure 4A:
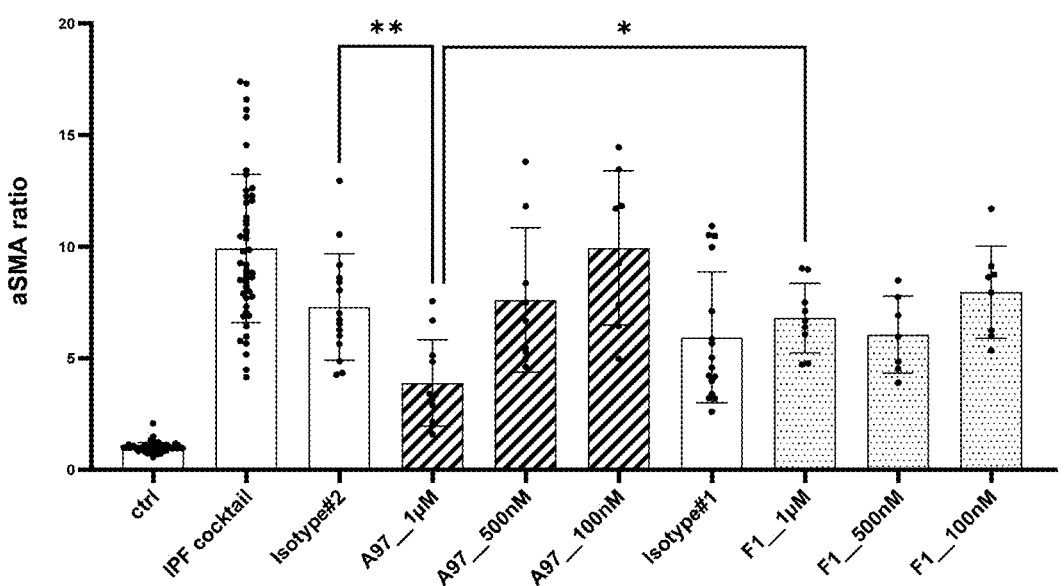
FIG. 4A and FIG. 4B. MSD-ELISA analysis of smooth muscle actin (a-SMA) in the IPF small airway epithelial cell (SAEC) air liquid interface (ALI) co-culture system. Fold change expression values are shown, normalized to untreated control fibroblast lysate samples. Note elevated levels of profibrotic marker a-SMA in the IPF cocktail-treated co-culture after 72 h. The anti-CTGF Antibodies and isotype controls were added 24 hours after IPF cocktail stimulation. Antibody A97 (FIG. 4A) and antibody A13 (FIG. 4B) each show a dose-dependent reduction of a-SMA expression, whereas antibody F1 and corresponding isotype control antibodies does not show significant effects. (n=3 biological replicates performed in n=3 individual experiments). Each assay point represents a technical co-culture well. (*$p<0.001$, $p<0.01$, *$p<0.05$; one-way ANOVA).
Figure 4B:
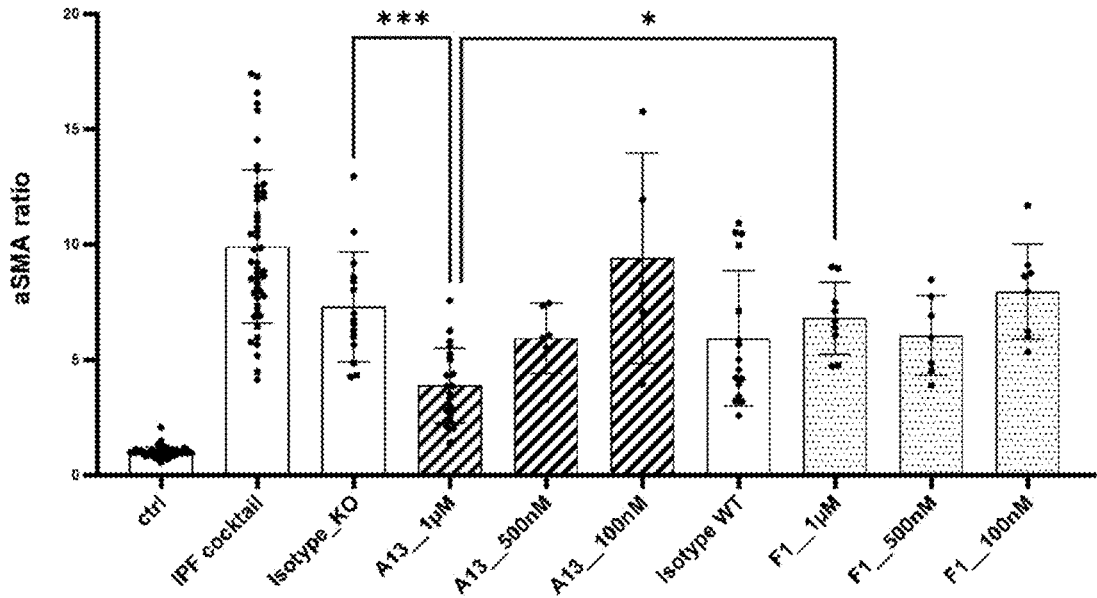

The IPF cocktail treatment induced a 10×-fold increase of a-SMA expression in fibroblasts, which represents the pro-fibrotic FMT transition (FIG. 4A and FIG. 4B). The anti-CTGF antibody A97 (FIG. 4A) and antibody A13 (FIG. 4B) each significantly reduced the a-SMA expression in a dose dependent manner, while isotype controls and antibody F1 were not able to lower the a-SMA expression. Thus, anti- CTGF antibody A97 and A13 reduced fibrotic signaling and fibrotic progression in a patient-derived multicellular system.

Example 6. Blockade of CTGF-Induced EMT in Primary Alveolar Cells

CTGF has been proposed to induce epithelial-to-mesenchymal transition (EMT) in alveolar stem cells, which contributes to the blockage of human alveolar type I epithelial cells (AT1) differentiation observed in disease. Alveolar cells undergo epithelial-mesenchymal transition in pulmonary fibrosis leading to a failure of the progenitor cells to repair alveoli and increased signal to the fibroblasts to produce matrix. CTGF has been involved in this process. As AT1 stem from human alveolar type II epithelial cells (AT2) and build the gas-exchange surface, this is an important hallmark of the pathogenesis in pulmonary fibrosis, leading to insufficient oxygenation.

In order to address this experimentally, we set up the isolation of the alveolar cells from explanted lungs, and assayed the ability of antibody A97 to block induction of EMT.

Primary human AT2 are seeded in 2D culture plates, then starved in minimal medium overnight before treatment for 24 hours or 72 hours with TGFß1 to induce a pro-fibrotic epithelial to mesenchymal cell transition (EMT). Antibody A97, antibody F1, or isotype control antibody (dose range 0.1-1 µM) is added simultaneously with TGFß1. Blocking CTGF cleavage and/or inhibiting the N-terminal CTGF fragment effects were hypothesized to inhibit/reduce the TGFß1 induced EMT effect and help to stabilize the alveolar epithelium to maintain its biological function (mainly differentiation into AT1). The progression of alveolar to mesenchymal cell transition is measured via intracellular Vimentin staining (cytoskeletal modulation during EMT), and by collagen release quantification measured by ELISA (COL1A1 in AT2 cell lysates and supernatant) ELISA.

Figure 5:
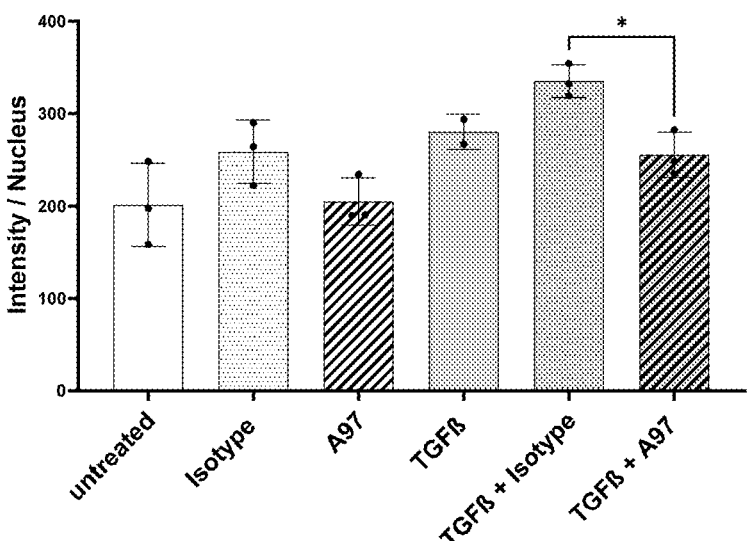
FIG. 5. Vimentin staining intensity per nucleus in 2D cultured alveolar EMT assay following AT2 cell culture treatment with TGFß1. (*$p<0.05$)
Figure 6:
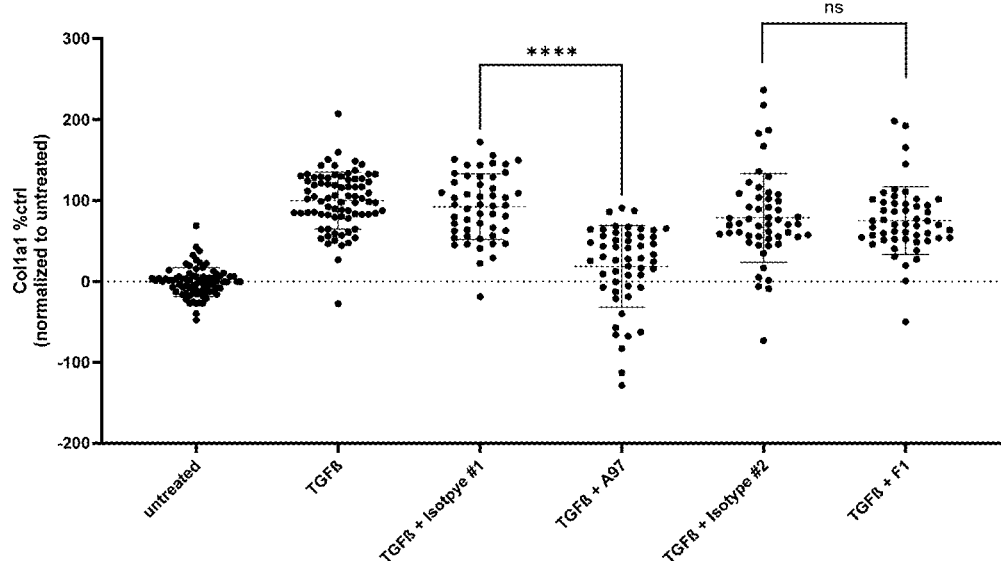
FIG. 6. COL1A1 expression levels in 2D cultured AT2 EMT assay. MSD-ELISA analysis of Collagen1a1 in 2D cultured AT2 EMT system. Fold change expression values shown, normalized to untreated control AT2 cell lysate samples. TGFß1 treatment induces increased COL1A1 expression. Antibody A97 significantly inhibits collagen production compared to corresponding isotype control. (n=2 donors measured as 3 individual replicates. Each assay point represents a lysate sample of a technical well (***p<0.001; one-way ANOVA; ns: not significant).

Treatment with Antibody A97 reduced Vimentin upregulation 72 hours after TGFß1 stimulation (FIG. 5) and reduced the level of collagen 1A1 to unstimulated control levels 24 hours after TGFß1 treatment (FIG. 6). Treatment with Antibody F1 did not significantly reduce the level of collagen 1A1 (FIG. 6). These results support the use of antibody A97 to promote the maintenance and functionality of the alveolar epithelial stem cells.

Example 7. Proteomic Analysis

Introduction

CTGF is a secreted growth factor that modulates many profibrotic processes and is strongly up-regulated in idiopathic pulmonary fibrosis (IPF). It is composed of two N-terminal domains (together NTF) and two C-terminal domains (together CTF) bound by a hinge peptide containing cleavage sequences for matrix metalloproteases (MMP), especially MMP7. The cleavage of CTGF by MMP7 activates the pathway since the fragments are biologically active. Anti-CTGF antibody A97 binds CTGF and inhibits its cleavage (see Example 3 above) and thus reduces the occurrence of fragments, and also binds the N-terminal fragment, thus potentially reducing fibrogenesis and fibrillar collagen production.

This example utilizes a patient-derived system containing the identified fibrotic niche. We isolate primary small airway epithelial cells from IPF donors as well as pulmonary fibroblasts. The small airways are then raised at the air-liquid-interface for five weeks in an organotypic culture. After priming with TGFb, a pro-fibrotic factor upstream of CTGF, the small airways and the fibroblast are put in cocultures and treated with the IPF cocktail (Schruf et al, 2020). This results in the induction of CTGF and MMP7, resulting in fibrogenesis. In this experimental setup, we test the modulation of fibrosis protein biomarkers in cells treated with the IPF cocktail by anti-CTGF antibodies A13, A97 or F1.

Co-culture supernatant proteomes are analyzed by liquid chromatography coupled to mass spectrometry (LC-MS) to quantify protein expression values that are modulated by the tested antibodies. Quantification includes the fibrosis PoCP biomarker Pro-Collagen III (ProC3), which, among other proteins, represents the production of the fibrillar collagen III, a major constituent of fibrotic extracellular matrix and tissue stiffening biomarker. We furthermore quantify additional proteins that are related to fibrosis and tested their relation to CTGF expression values.

Methods

Sample preparation is performed in a 96-well format (twin.tec PCR Plate 96 LoBind, Eppendorf) following the in-StageTip protocol (Kulak et. Al; doi: 10.1038/nmeth.2834) (PreOmics IST-Kit catalogue number P.O.00027). 100 µl of each cell culture supernatant is dried (Concentrator plus, Eppendorf). 50 µl of PreOmics lysis buffer is added per well followed by a boiling step at 95° C., 1200 rpm (ThermoMixer C, Eppendorf) for 20 min to solubilize proteins, reduce disulfide bridges, and alkylate free cysteines. After a 5 min cool down of the samples, the PreOmics digestion mix is added in the recommended amount followed by overnight digestion at 37° C., 1200 rpm (ThermoMixer C, Eppendorf). Digestion is stopped adding a 1:1 volume of PreOmics stopping buffer, followed by a sample clean-up utilizing the PreOmics iST protocol. After elution, clean peptides are dried (Concentrator plus, Eppendorf) and resuspended in 25 µl of PreOmics LC-buffer with a 30 min incubation step at 30° C., 1200 rpm (ThermoMixer C, Eppendorf). The peptide concentration per well is quantified utilizing a colorimetric quantitative peptide assay (catalogue number 23275, Pierce, Quantitative Peptide Assay, Thermo Fisher Scientific).

Proteome analysis is performed utilizing the Vanquish Neo system (Thermo Fisher Scientific) coupled to an Orbitrap Eclipse mass spectrometer (Thermo Fisher Scientific) with a nano-electrospray source. 500 ng of each sample is injected and separated with a 15 cm Easy-Spray PepMap Neo column (75 µm ID, 150 mm length, PN ES75150PN, Thermo Fisher Scientific) heated to 40° C. and run at a 450 nl/min flow rate. The chromatography gradient is set to 45 min total, separating peptides by hydrophobicity for 37 minutes starting with 1% Buffer B (80% ACN™, 19.9% ddH2O, 0.1% FA), 99% Buffer A (99.9% ddH2O, 0.1% FA) and ending with 35% Buffer B and 65% Buffer A. For column wash and regeneration, Buffer B is ramped up to 95% in 4 minutes and kept for 4 minutes at 95% Buffer B until the end of the gradient. Column regeneration is performed automatically before sample pickup for the next run. Electrospray voltage is set to 1900V in positive ion mode.

Mass spectrometry analysis is performed using a data independent acquisition (DIA) scan mode. One full scan event (MS1) is followed by 33 MS2 (MSMS) scans covering a 300-1650 m/z range. MS1 resolution is set to 120,000, AGC target to 2E6 with a maximum injection time of 60 ms. MS2 resolution is set to 15,000, AGC target to 2E6 with a maximum injection time of 22 ms.

Mass spectrometry raw data are processed within the Spectronaut software suite (v17.4, Biognosys AG, Schlieren, Switzerland) utilizing the directDIA search algorithm with standard settings. Searches are performed against the human UniProt reference proteome of canonical and isoform sequences (UP000005640_9606.fa, UP000005640_9606_additional.fa).

Data analysis is performed in the Perseus environment (Tyanova et al.; doi: 10.1038/nmeth.3901) and GraphPad Prism. COL3A1 quantification events are transferred into GraphPad Prism and visualized as column bar plot highlighting mean and standard deviation. Statistical analysis is performed using a one-way ANOVA for all groups against the positive control (IPF-cocktail treatment). For global protein correlation analysis, the data matrix is filtered for at least 50% protein quantification events across the experiment. Missing values are imputed from 1.8 standard deviations downshifted normal distribution with a spread of 0.3 standard deviations. The data matrix is transposed by genes, followed by protein profile expression correlation across samples by Pearson. The resulting protein profile correlation matrix is clustered hierarchically by column and row to identify co-regulated protein clusters. Zooming into the cluster containing the CTGF (CCN2 gene), proteins are identified whose expression correlates with CTGF protein levels.

Results

Antibody A97 prevents CTGF activation by cleavage inhibition and thus reduces the occurrence of fragments (see Example 3) and hinders the N-terminal fragment binding to fibroblasts (see Example 9), thus reducing fibrogenesis and fibrillar collagen production.

Figure 7:
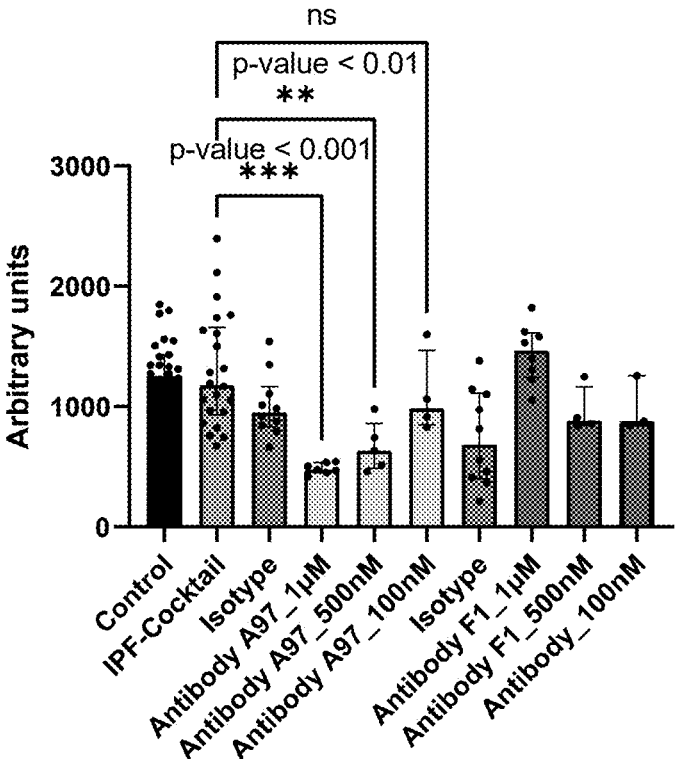
FIG. 7. Results of collagen III (ProC3) production inhibition in the supernatant of an air-liquid-interface cell culture, shown in arbitrary units. Fibrosis and collagen III production is stimulated by IPF-cocktail. Anti-CTGF antibodies A97 or F1 were used in concentrations of 1 uM, 500 nM, or 100 nM as shown. (*p<0.001; p<0.01; ns: not significant).

Procollagen 3 (ProC3) is a prognostic biomarker for disease progression in IPF and PPF. The results in this example demonstrate that A97 significantly modulated ProC3 levels in cells treated with the IPF cocktail (FIG. 7) (*p<0.001; p<0.01). This effect appeared to be dose-dependent. By contrast, Antibody F1 showed no significant effect on Procollagen 3 production in cells treated with the IPF cocktail (FIG. 7).

Figure 8:
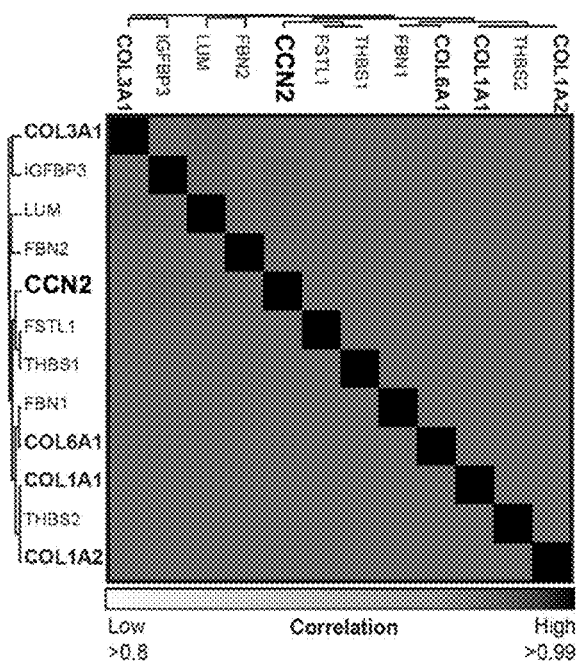
FIG. 8. Global protein expression correlation analysis of air-liquid-interface supernatant. Zooming into the protein cluster containing CTGF (Gene name: CCN2) shows a strong correlation to collagen proteins and other extracellular markers. All proteins highlighted in this cluster have a very high protein expression profile correlation with each other with >0.8 according to Pearson. Note that the black coloring on the diagonal only reflects that each protein has a Pearson correlation of 1 with itself.

Furthermore, the global correlation of protein expression profiles across experimental groups revealed that CTGF (Gene: CCN2) protein expression levels in the co-culture supernatant are strongly correlated to the production of other fibrillar collagens such as COL6A1, COL1A1 and COL1A2 besides the already presented COL3A1 (FIG. 8). In addition to collagens, additional potential biomarkers were modulated. All proteins highlighted in this cluster have a very high protein expression profile correlation with each other with >0.8 according to Pearson.

The results showed that CTGF expression levels were tightly correlated to fibrosis progression in this system, and antibody A97 was an effective inhibitor of collagen production, thereby modulating fibrosis progression.

Functional analysis of proteomic data revealed differences between the F1 and A97 antibodies in modulating collagen production using Hallmark protein annotations (Liberzon et al., The Molecular Signatures Database (MSigDB) hallmark gene set collection. Cell Syst. 2015 Dec. 23; 1(6):417-425.). Results are shown in Table 16. The term "Odds Ratio" indicates the over-representation of the protein set. For example, an odds ratio of 2 means that the protein annotation is twice as frequent as expected by random chance. The term "FDR-adjusted p-value" represents the Bonferroni correction for multiple testing applied to the enrichment p-value of "hallmark" protein set annotations. It indicates the probability of observing the enrichment by chance after adjusting for multiple comparisons. The term "Combined Score" is the natural logarithm of the p-value multiplied by the z-score, where the z-score is the deviation from the expected rank, providing a comprehensive measure of the significance and effect size of the enrichment. The results show that proteins whose values were significantly higher in the F1-treated sample compared to the A97-treated sample were enriched in for the hallmark annotation "Epithelial to mesenchymal transition". Protein annotated as "Epithelial to mesenchymal" transition were not enriched for samples treated with A13 or A97, but were enriched for "IPF cocktail". The results show that antibodies A13 and A97 were each able to prevent the increase in epithelial to mesenchymal transition gene expression induced by the IPF cocktail. By contrast, antibody F1 was not able to prevent the statistically significant increase in epithelial to mesenchymal transition gene expression.

TABLE 16

Functional enrichment analysis for the Hallmark term: "Epithelial mesenchymal transition".

|  | Odds ratio | FDR p-value | Combined score |
|---|---|---|---|
| IPF cocktail | 11.53 | 2.35E−16 | 456.18 |
| F1 1 uM | 11.65 | 2.54E−09 | 270.14 |
| A13 1 uM | 4.91 | 0.10 | 20.12 |
| Ctrl | 1.80 | 1.00 | 5.06 |
| A97 1 uM | 1.12 | 0.89 | 0.48 |

Example 8. Free CTGF Measurement

The purpose of this bioanalysis was to determine target engagement of the antibodies A13, A97 and F1 from a small airway epithelial cell (SAEC) co-culture study to correlate functional effects with target binding. For this, CTGF is quantified using a competitive ligand binding assay approach. Full target engagement by an antibody under the applied assay conditions ("conditional target engagement") is expected to result in no quantifiable free CTGF. Lower target engagement will result in the detection of free CTGF levels.

Samples from cell co-culture experiments described in Example 5 are used for measurement of human CTGF levels. Cell co-culture samples are taken and concentrations of human CTGF are determined on the Gyrolab immunoassay platform using an assay targeting two different epitopes of the protein. As shown in Example 12, antibodies A97 and A13 do not compete with F1 for binding to CTGF. Using Antibody F1 and Antibody A97 as capturing and detection reagents, respectively, allows discrimination between free CTGF and CTGF engaged by one or the other antibody at the applied assay conditions ("conditional target engagement"). In this assay, CTGF is only detected if not bound by either A97, A13 or F1. Therefore, reduced levels in detected free CTGF are a measure for target engagement by the antibodies in these samples.

Human CTGF concentrations are determined using a semi-automated ligand binding assay (LBA) platform (Gyros Protein Technologies AB, xPand). For the measurement, the samples are measured as 1:100 dilution in Rexxip AN buffer (Gyros Protein Technologies AB, #P0004994). The analyte, human CTGF, is immobilized on streptavidin-coated Gyrolab Bioaffy 1000 CDs (Gyros Protein Technologies AB, #P0004253) using a biotin-tagged (Thermo Scientific, #21335) derivative of Antibody F1 (100 µg/ml in PBS/0.01% Tween 20) and is detected by recording the fluorescence of a fluorophore-labeled (Thermo Scientific, #A20006) derivative of Antibody A97 used at 20 nM in Rexxip F buffer (Gyros Protein Technologies AB, #P0004825). Biotinylation and fluorophore-conjugation of the unlabeled antibodies is performed for 1 hour at room temperature after mixing 1.67 UM antibody, 16.7 UM label reagent, and 0.1 M NaHCO₃, all dissolved in PBS.

For the absolute quantification of the analyte, calibration curves are generated in 1% matrix in Rexxip AN buffer. From these curves a lower limit of quantification (LLOQ) is derived for each individual CD by multiplying the concentration at three-fold blank response (limit of detection) with the applied dilution factor (100), resulting in a value of 0.32 nM. Response signals achieved from unknown samples are matched against the calibration curves to derive the corresponding analyte concentration.

Figure 9A:
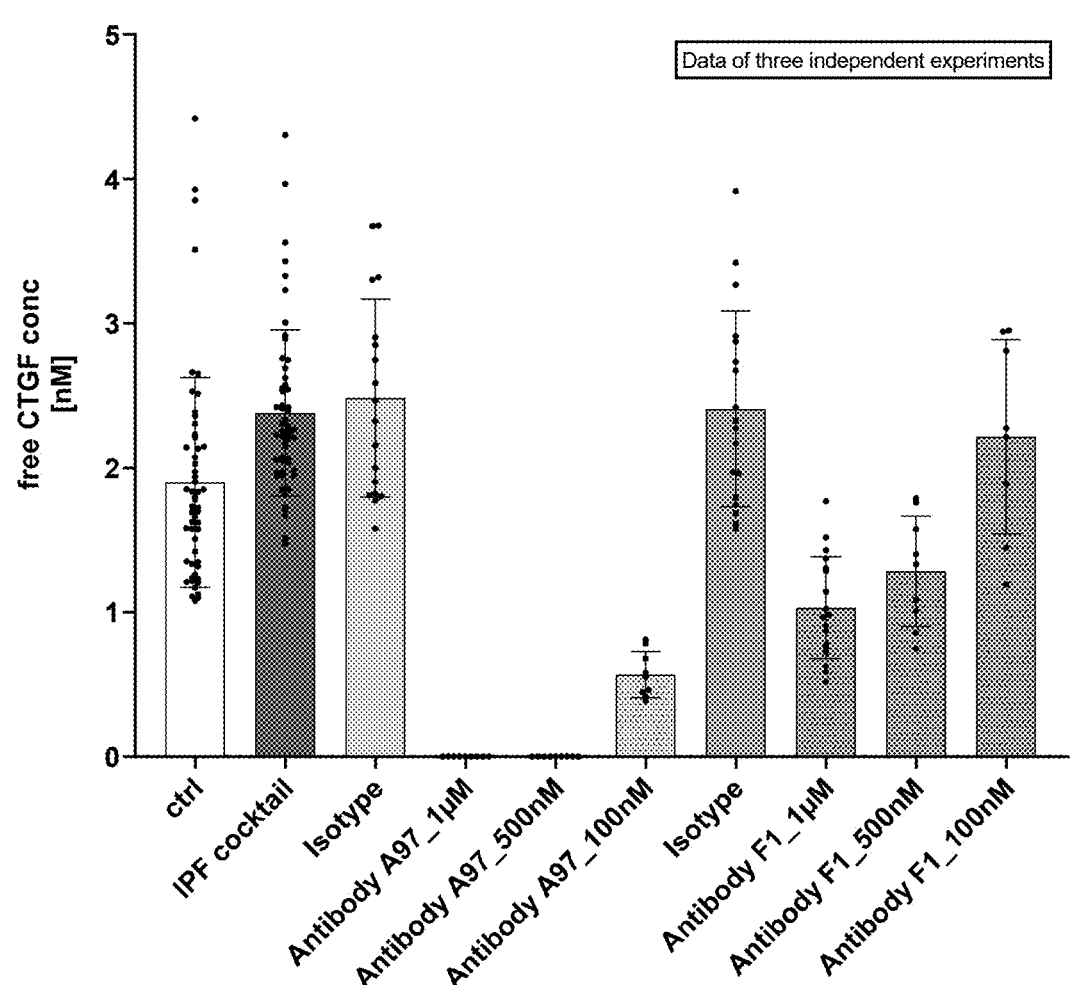
FIG. 9A and FIG. 9B. Free CTGF concentrations determined in samples from an IPF SAEC ALI coculture assay using a ligand binding assay on the Gyrolab platform. CTGF levels are determined using a biotinylated derivative of F1 for immobilization of CTGF and an Alexa-Fluor conjugate of A97 binding to a complementary epitope. Comparing A97 (FIG. 9A) and A13 (FIG. 9B), respectively, with F1 at equal concentrations shows significantly stronger binding of CTGF by the A97 and A13 in this assay. The bars show mean values of up to 54 individual datapoints and error bars represent the standard deviation. Samples shown on the x-axis (y-value=0) have values at or below the lower quantification limit.
Figure 9B:
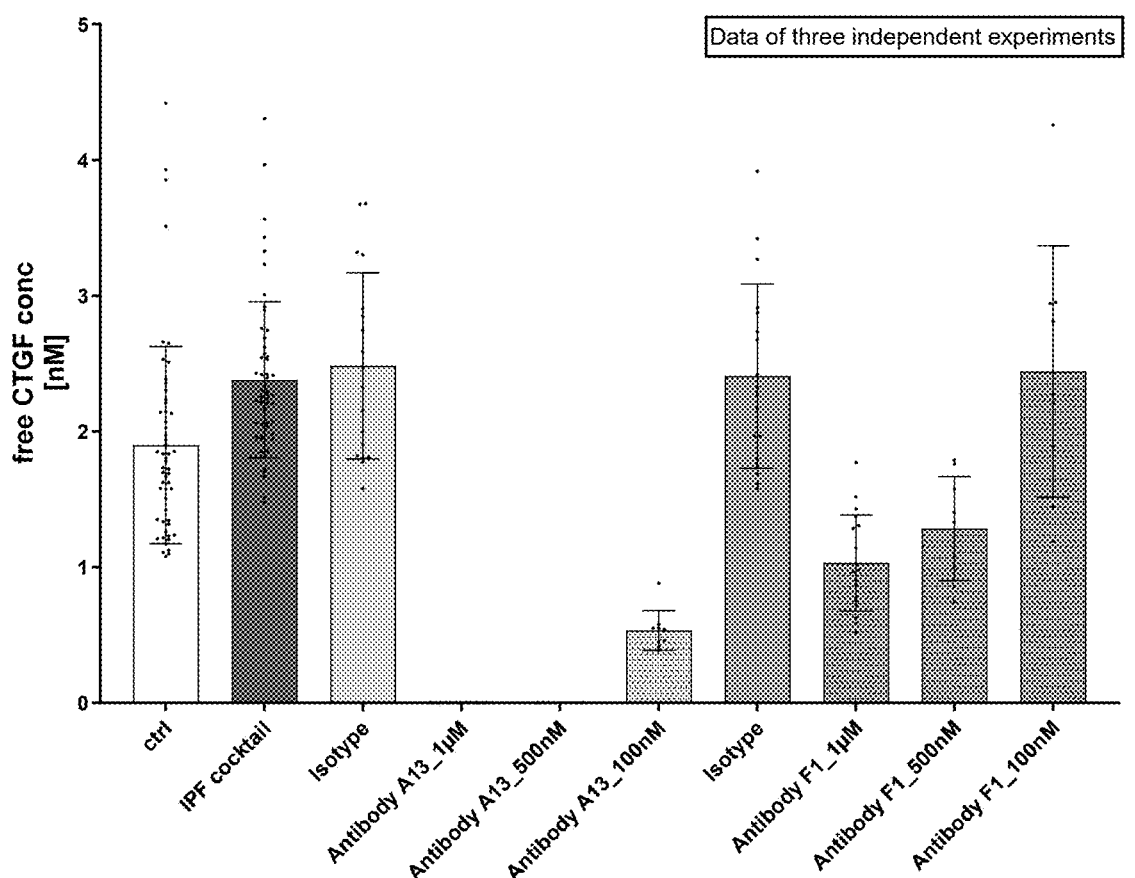

The quantification of free CTGF in the samples recovered from the IPF SAEC ALI coculture assay showed increased levels of CTGF upon treatment with IPF ("IPF cocktail") with or without isotype control antibodies ("isotype") compared with non-treated controls ("ctrl") (FIG. 9A and FIG. 9B). Results are shown from three independent experiments. For the isotype controls ("isotype"), similar levels of free CTGF were determined as for the respective control sample ("IPF cocktail").

For the anti-CTGF antibodies A13, A97 and F1, a dose-dependent decrease in free CTGF levels was observed, with no detectable levels for 1 μM and 500 nM with both A13 and A97. Comparing the determined concentrations of free CTGF between anti-CTGF antibodies A13, A97 and F1 at equal concentrations, we conclude that A13 and A97 engaged CTGF more effectively than F1, with F1 being unable to fully engage CTGF (i.e., free CTGF was detected) even at the highest antibody concentration tested.

Example 9. Cell Binding Assay

CTGF and fragments thereof have been proposed to signal through multiple receptors, however, over 200 receptors have been proposed and little evidence on the actual interaction has been shown. We aimed to assess whether an antibody against CTGF could abrogate binding to the cell surface of multiple cell types in order to understand the ability of the antibody to reduce CTGF signaling. For that a binding assay was developed and applied to several cell types, specifically, alveolar type II cells, fibroblasts and A549 cells.

To assess the impact of the CTGF antibodies on the binding of the CTGF to the cell membrane, recombinant CTGF is labeled with R-Phycoerythrin (RPE) according to the manufacturer's protocol (LYNX Rapid RPE Antibody Conjugation Kit™®, LNK024RPE, Bio-Rad) and pre-incubated with either Isotype control ("Iso Ctrl") or anti-CTGF antibodies A97, F1, H1, or H2, or compound P1 (30 nM CTGF labeled protein and 1 μM of respective antibody or compound) for 1 hour (A549 cells and primary human fibroblasts (phFb)) or 4 hours (primary human alveolar type II cells (phAT2)). Cells are seeded 24 hours prior to the experiment, in 96 well plate: 8000 phFb cells/well in Dulbecco's Modified Eagle Medium (DMEM) containing GlutaMAX Supplement™ (Thermo Fisher Scientific), with the addition of 10% fetal bovine serum (FCS), 1% Penicillin/Streptomycin (P/S) and 1% non-essential amino acids; 10000 AT2 cells/well in basal media (Stemcell #100-0848) with addition of 10× supplements (Stemcell #100-0849) and Antibiotic-Antimycotic (Gibco #15240062); 10000 A549 cells/well in DMEM supplemented with 10% FCS and 1% PS. The prepared mixture of RPE-labeled CTGF and antibodies is added to the cell cultures and incubated for the indicated time at 37° C. Afterwards, cells are washed 3 times with PBS and the fresh media is added. Finally, cells are scanned with IncuCyte and the RPE signal, indicating CTGF binding to the cell membrane, is measured. Values are normalized to the cell density (brightfield image) and shown relatively to control (media with labeled CTGF).

Figure 10:
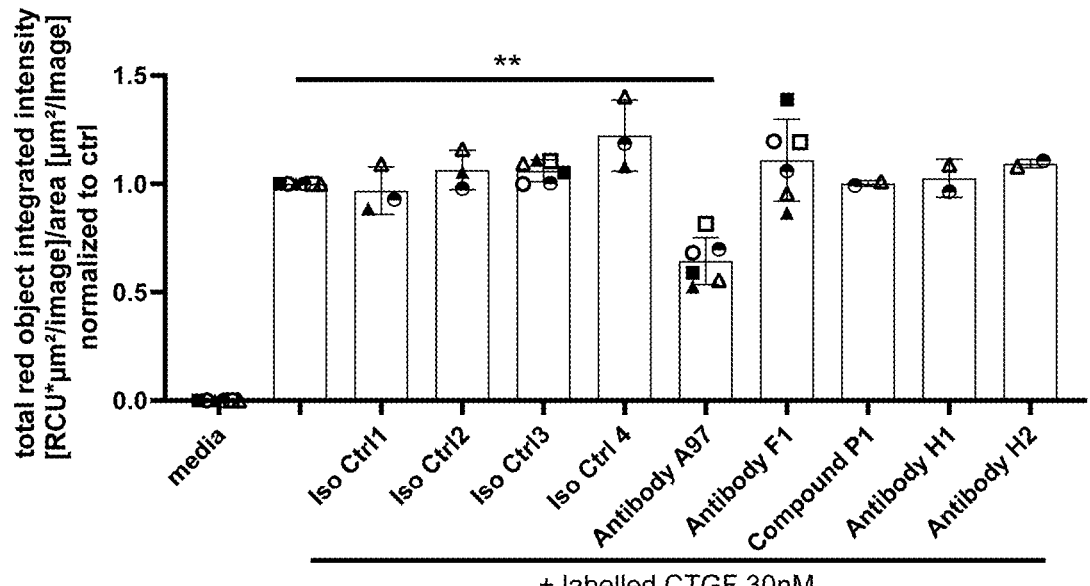
FIG. 10. Primary human lung fibroblasts (N=2-6; different shapes indicate distinct replicates) are exposed to either labeled CTGF or a mixture of labeled CTGF pre-incubated with isotype control or anti-CTGF antibodies as indicated on the X-axis (blank label indicates a no antibody control). After 1 hour incubation cells are washed 3 times with PBS and scanned with Incucyte for RPE signal. Results show the level of labeled CTGF binding to cells, normalized to cell density, and shown relatively to the control. Means were compared using One-way ANOVA; **p≤0.01.
Figure 11:
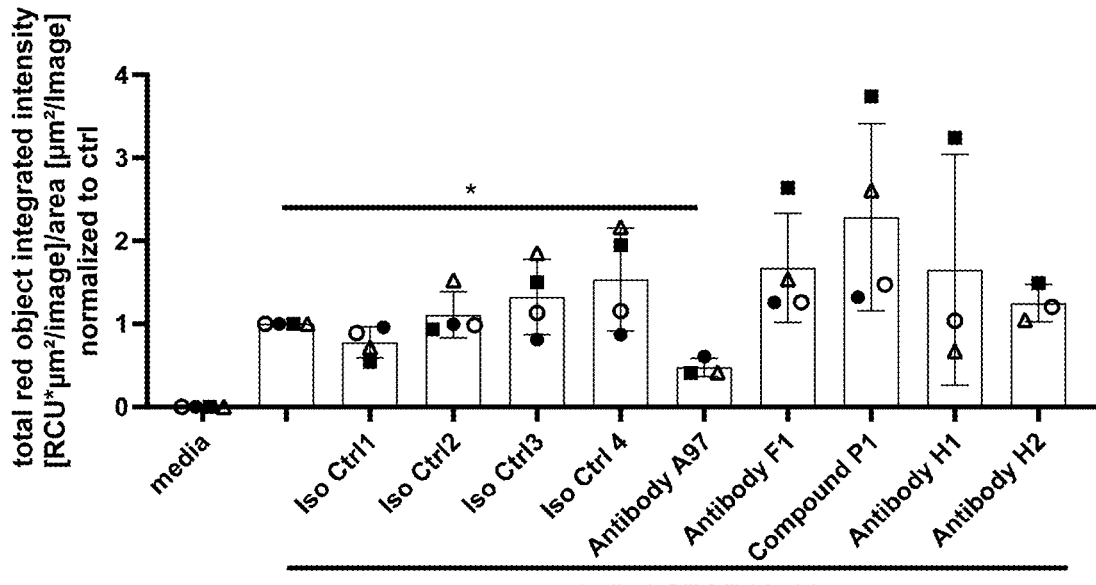
FIG. 11. Primary human alveolar type II cells (N=2-3; different shapes indicate distinct replicates) are exposed to either labeled CTGF or mixture of labeled CTGF pre-incubated with isotype control or anti-CTGF antibodies as indicated on the X-axis (blank label indicates a no antibody control). After 4 hours incubation cells are washed 3 times with PBS and scanned with Incucyte for RPE signal. Results show the level of labeled CTGF binding to cells, normalized to cell density, and shown relatively to the control. Means were compared using One-way ANOVA; *p≤0.05.
Figure 12:
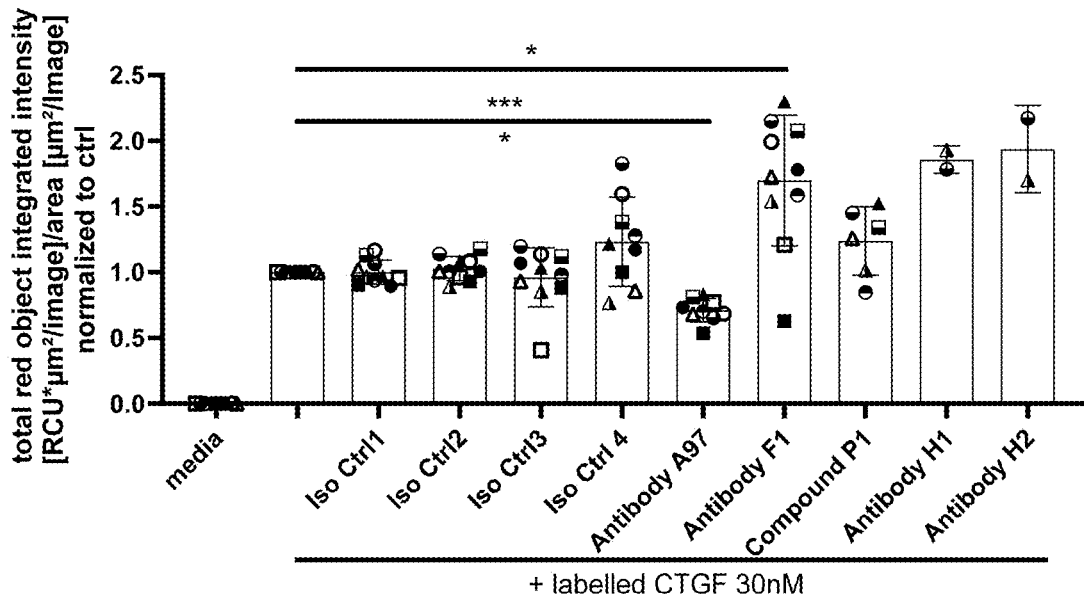
FIG. 12. A549 cells (n=2-10; different shapes indicate distinct replicates) are exposed to either labeled CTGF or mixture of labeled CTGF pre-incubated with isotype control or anti-CTGF antibodies as indicated on the X-axis (blank label indicates a no antibody control). After 1 hour incubation cells are washed 3 times with PBS and scanned with Incucyte for RPE signal. Results show the level of labeled CTGF binding to cells, normalized to cell density, and shown relatively to the control. Means were compared using One-way ANOVA; *p≤0.05, ****p≤0.0001

Impact of the anti-CTGF antibodies on the binding of the CTGF to the cell membrane was determined for primary human lung fibroblasts (phFb; FIG. 10; **p≤0.01), primary alveolar epithelial type II cells (ATII; FIG. 11; *p≤0.05) and A549 lung epithelial cells (FIG. 12; *p≤0.05, ****p≤0.0001). These results demonstrate that the A97 antibody could prevent binding of CTGF to the cell membrane in all tested cells, while antibodies F1, H1, H2, and compound P1 could not prevent binding of CTGF to the cell membrane in any tested cell.

Example 10. Macrophage Efferocytosis Effects of CTGF

This example shows that contacting homeostatic human macrophages (both iPSC-derived and blood-derived) with CTGF N-terminal fragment inhibited their ability to efferocytose dead cell bodies. This is accompanied by a raise in QPCT transcripts, a gene involved in efferocytosis suppression (Schloesser et al, 2022). The observed reduction in efferocytosis potential of macrophages may contribute to fibrotic disease progression, for example by allowing dead or senescent cells to accumulate and perpetuate profibrotic signaling.

Methods

Human induced pluripotent stem cell maintenance is done according to the protocol in Bitzer et al. (SLAS Discov. 2023; 28(4):149-62). In short, line 201B7 are cultivated in a 6 well format. Cells are split once per week, and twice per week a medium exchange is performed.

Differentiation of hiPSCs into macrophages is done according to the protocol in Bitzer et al. (id.). In short, cells are plated into T175 flask and are treated as in the maintenance for 1 week. In the second week differentiation is performed by adding the specified media and cytokines. From weeks 3 to 6 progenitor floating cells are collected. Those CD34+ precursor cells are used to differentiate into macrophages.

Primary macrophage cell culture is done according to the protocol in Schloesser D, et al. (J Cell Biol. 2022; 222(2): e202207097). In short, PBMCs are isolated from whole blood using LeucoSep™ tubes and monocytes are isolated by negative selection for CD14+.

Monocytes and CD34+ precursor cells are differentiated for 7 days by adding 50 ng/ml MCSF to monocytes for the generation of monocyte-derived macrophages (MDM) and 100 ng/ml MCS to CD34+ precursor cells for the generation of iPSC-derived macrophages (IDM).

Macrophage activation is done according to the protocol in Schloesser et al. (id.). Stimulation for RNA is made in 12-well plates (500,000 cells/well) and for the efferocytosis assay in 96 well plate (15,000 cells/well). Homeostatic macrophage phenotype is induced by IL-4 (10 ng/ml) and IL-13 (10 ng/ml) for 16-18 hours. Full length CTGF or NTF (4 nM) is added at the same time.

Apoptotic corpse generation and labelling is done according to the protocol in Schloesser et al. (id.). In brief, apoptotic Raji cells are generated by UV exposure. Afterwards cells are labeled using the pHrodo® dye from Sartorius and are added to macrophages in 96 well plate with a ratio of 1:3.3.

Efferocytosis Assay by IncuCtye S3 is done according to the protocol in Schloesser et al. (id.). In brief, 15,000 macrophages are plated per well and are stimulated overnight. After 16-18 hours, apoptotic Raji cells are added and the uptake is monitored for 24 hours.

RNA isolation and analysis is done according to the protocol in Schloesser et al. (id.). In brief, samples are lysed and RNA is isolated by using MagMax automated system. RNA is transcribed into cDNA and qPCR analysis is performed. Ct values or the fold change of untreated to stimulated are calculated ($2^{(-ddCT)}$) (dCt normalized to a housekeeping gene, ddCt unstimulated control).

Results

Figure 13:
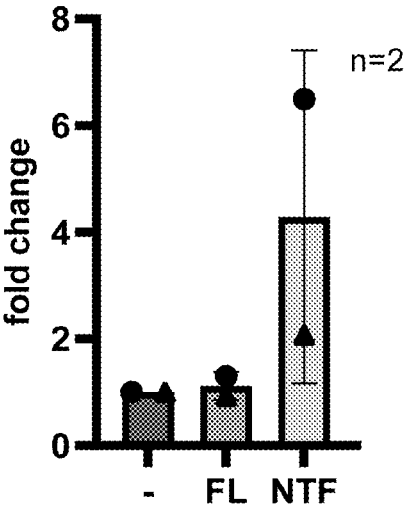
FIG. 13. QPCT gene expression in homeostatic (IL4/13) stimulated IDMs. Without fragments (−), FL CTGF and NTF CTGF fragment.
Figure 14A:
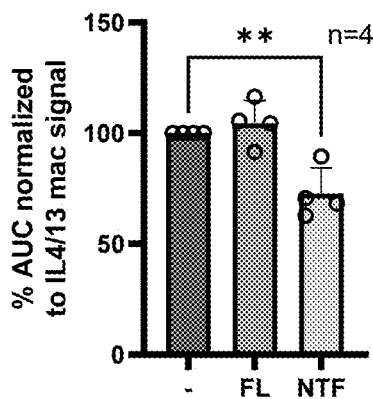
FIG. 14A-14B. Efferocytosis IDM (n=4, FIG. 14A) and MDM (n=2, FIG. 14B). One-way ANOVA with Tukey's multiple comparison test **p≤0.01.
Figure 14B:
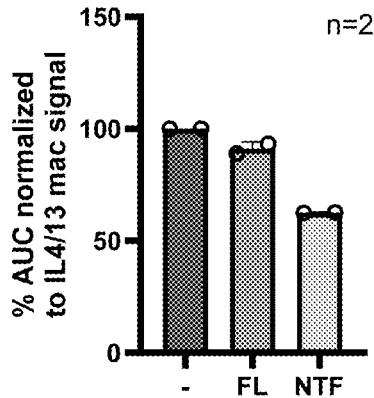

Full length (FL) CTGF didn't modify efferocytosis activity while CTGF N-terminal fragment leads to a significant reduction of efferocytotic capacity of homoestatic IL4/IL-13 activated macrophages, suggesting that abrogating cleavage may restore efferocytosis potential (FIG. 14A and FIG. 14B). CTGF N-terminal fragment (NTF) upregulated QPCT gene expression (FIG. 13). The findings were consistent in blood-derived macrophages and iPSC derived macrophages.

Example 11. Binding Affinity of Anti-CTGF Antibodies to CTGF

Binding affinity of anti-CTGF antibodies H1 (having the light chain of SEQ ID NO: 22 and the heavy chain of SEQ ID NO: 23), H2 (having the light chain of SEQ ID NO: 24 and the heavy chain of SEQ ID NO: 25), F1, and A97 for full length human CTGF or human CTGF N-terminal fragment are determined by surface plasmon resonance (SPR).

Surface plasmon resonance is conducted using a Biacore 8K+ (Cytiva). Protein A/G (Thermo Scientific) is amine coupled to CM5 Sensor S Chip (Cytiva). For binding to hCTGF N-terminal fragment (NTF), anti-CTGF antibody (1 μg/ml) is captured on the Protein A/G surface, followed by various concentrations of antigen (100 nM to 0.78 nM; 2-fold dilutions). For binding to hCTGF full length, anti-CTGF antibody (0.2 μg/ml) is captured followed by various concentrations of antigen (10 nM to 0.156 nM; 2-fold dilutions).

Results are shown in Tables 17 and 18 below.

TABLE 17

Binding affinity of anti-CTGF antibodies H1, H2, F1, and A97 for the human CTGF N-terminal fragment.

| mAb | $k_a$ (1/Ms) | $k_d$ (1/s) | $K_D$ (M) | $K_D$ (nM) |
|---|---|---|---|---|
| H1 | 1.22E+06 | 1.07E-02 | 8.82E-09 | 8.8 |
| H2 | 3.83E+05 | 1.75E-02 | 4.57E-08 | 46 |
| A97 | 2.90E+05 | 4.00E-05 | 1.40E-10 | 0.14 |
| F1 | 3.45E+05 | 1.05E-02 | 3.03E-08 | 30 |

TABLE 18

Binding affinity of anti-CTGF antibodies H1, H2, F1, and A97 for human full length CTGF.

| mAb | $K_a$ (1/Ms) | $K_d$ (1/s) | $K_D$ (M) | $K_D$ (PM) |
|---|---|---|---|---|
| H1 | 6.83E+06 | 6.71E-04 | 9.83E-11 | 98 |
| H2 | 2.70E+06 | 1.49E-03 | 5.54E-10 | 550 |
| A97 | 2.70E+06 | 4.80E-06 | 1.8E-12 | 1.8 |
| F1 | 1.37E+07 | 3.37E-03 | 2.47E-10 | 250 |

Example 12. Antibody Competition for CTGF Binding

This example shows the results of testing whether antibodies A97, H1, H2, and F1 compete with one another for binding to hCTGF.

Methods:

Surface plasmon resonance is conducted using a Biacore 8K+ (Cytiva). Protein A/G (Thermo Scientific) is amine coupled to CM5 Sensor S Chip (Cytiva). For each experiment, a first anti-CTGF antibody (100 nM) is captured on the Protein A/G, followed by blocking unused Protein A/G using an irrelevant IgG antibody (400 nM). Antigen (hCTGF N-terminal fragment (NTF) (100 nM) or hCTGF full length (20 nM)) and the second anti-CTGF antibody (100 nM) are injected in direct sequence using the dual command. Use of the "dual command" results in minimal to no intervening time between the end of antigen injection and start of mAb injection.

Results and Discussion:

Competitive binding results were obtained as shown in Table 18 and Table 19. Results were the same for full length hCTGF and hCTGF NTF. As expected, each anti-CTGF antibody competed with itself for binding to hCTGF NTF or full length hCTGF. Antibodies H1, H2, and F1 each competed with each other for binding to hCTGF NTF or to full length hCTGF. Antibody A97 did not compete with H1, H2 or F1 for binding to hCTGF NTF or to full length hCTGF.

The results indicate that the A97 does not compete with H1, H2, and F1 for binding to either hCTGF NTF or full length hCTGF.

TABLE 18

Anti-CTGF antibody competition for binding to hCTGF NTF. Each row is labeled with the first antibody, and each column is labeled with the second antibody. An "X" indicates that binding competition was observed between the first antibody and the second antibody, while an empty box indicates no competition was observed.

| | H1 | H2 | A97 | F1 |
|---|---|---|---|---|
| H1 | X | X | | X |
| H2 | X | X | | X |
| A97 | | | X | |
| F1 | X | X | | X |

TABLE 19

Anti-CTGF antibody competition for binding to full length hCTGF. Each row is labeled with the first antibody, and each column is labeled with the second antibody. An "X" indicates that binding competition was observed between the first antibody and the second antibody, while an empty box indicates no competition was observed.

| | H1 | H2 | A97 | F1 |
|---|---|---|---|---|
| H1 | X | X | | X |
| H2 | X | X | | X |
| A97 | | | X | |
| F1 | X | X | | X |

SEQUENCE LISTING

Sequence total quantity: 349
SEQ ID NO: 1              moltype = AA   length = 349
FEATURE                   Location/Qualifiers
source                    1..349
                          mol_type = protein
                          organism = Homo sapiens
SEQUENCE: 1
MTAASMGPVR VAFVVLLALC SRPAVGQNCS GPCRCPDEPA PRCPAGVSLV LDGCGCCRVC   60
AKQLGELCTE RDPCDPHKGL FCHFGSPANR KIGVCTAKDG APCIFGGTVY RSGESFQSSC   120
KYQCTCLDGA VGCMPLCSMD VRLPSPDCPF PRRVKLPGKC CEEWVCDEPK DQTVVGPALA   180
AYRLEDTFGP DPTMIRANCL VQTTEWSACS KTCGMGISTR VTNDNASCRL EKQSRLCMVR   240
PCEADLEENI KKGKKCIRTP KISKPIKFEL SGCTSMKTYR AKFCGVCTDG RCCTPHRTTT   300
LPVEFKCPDG EVMKKNMMFI KTCACHYNCP GDNDIFESLY YRKMYGDMA              349

SEQ ID NO: 2              moltype = AA   length = 323
FEATURE                   Location/Qualifiers
source                    1..323
                          mol_type = protein
                          organism = Synthetic construct
SEQUENCE: 2
QNCSGPCRCP DEPAPRCPAG VSLVLDGCGC CRVCAKQLGE LCTERDPCDP HKGLFCDFGS   60
PANRKIGVCT AKDGAPCIFG GTVYRSGESF QSSCKYQCTC LDGAVGCMPL CSMDVRLPSP   120
DCPFPRRVKL PGKCCEEWVC DEPKDQTVVG PALAAYRLED TFGPDPTMIR ANCLVQTTEW   180
SACSKTCGMG ISTRVTNDNA SCRLEKQSRL CMVRPCEADL EENIKKGKKC IRTPKISKPI   240
KFELSGCTSM KTYRAKFCGV CTDGRCCTPH RTTTLPVEFK CPDGEVMKKN MMFIKTCACH   300
YNCPGDNDIF ESLYYRKMYG DMA                                         323

SEQ ID NO: 3              moltype = AA   length = 160
FEATURE                   Location/Qualifiers
source                    1..160
                          mol_type = protein
                          organism = Homo sapiens
SEQUENCE: 3
QNCSGPCRCP DEPAPRCPAG VSLVLDGCGC CRVCAKQLGE LCTERDPCDP HKGLFCDFGS   60
PANRKIGVCT AKDGAPCIFG GTVYRSGESF QSSCKYQCTC LDGAVGCMPL CSMDVRLPSP   120
DCPFPRRVKL PGKCCEEWVC DEPKDQTVVG PALAENLYFQ                       160

SEQ ID NO: 4              moltype =    length =
SEQUENCE: 4
000

SEQ ID NO: 5              moltype =    length =
SEQUENCE: 5
000

SEQ ID NO: 6              moltype =    length =
SEQUENCE: 6
000

SEQ ID NO: 7              moltype =    length =
SEQUENCE: 7
000

SEQ ID NO: 8              moltype =    length =
SEQUENCE: 8
000

SEQ ID NO: 9              moltype =    length =
SEQUENCE: 9
000

SEQ ID NO: 10             moltype = AA   length = 16
FEATURE                   Location/Qualifiers
source                    1..16
                          mol_type = protein
                          organism = Synthetic construct
VARIANT                   1
                          note = K or R
VARIANT                   11
                          note = A, E, G, or T
VARIANT                   12
                          note = K or N
SEQUENCE: 10
XSSQSIVHYN XXTYLE                                                 16

SEQ ID NO: 11             moltype = AA   length = 7
FEATURE                   Location/Qualifiers
source                    1..7

-continued

```
                         mol_type = protein
                         organism = Synthetic construct
VARIANT                  4
                         note = N or S
VARIANT                  6
                         note = A or F
SEQUENCE: 11
KVSXRXS                                                              7

SEQ ID NO: 12            moltype = AA  length = 9
FEATURE                  Location/Qualifiers
source                   1..9
                         mol_type = protein
                         organism = Synthetic construct
SEQUENCE: 12
FQGSHFPLT                                                            9

SEQ ID NO: 13            moltype =   length =
SEQUENCE: 13
000

SEQ ID NO: 14            moltype =   length =
SEQUENCE: 14
000

SEQ ID NO: 15            moltype = AA  length = 5
FEATURE                  Location/Qualifiers
source                   1..5
                         mol_type = protein
                         organism = Synthetic construct
SEQUENCE: 15
DYYMA                                                                5

SEQ ID NO: 16            moltype = AA  length = 17
FEATURE                  Location/Qualifiers
source                   1..17
                         mol_type = protein
                         organism = Synthetic construct
VARIANT                  5
                         note = D, E, or Y
VARIANT                  13
                         note = A, D, or E
SEQUENCE: 16
NINYXGSRTD LLXSLKS                                                   17

SEQ ID NO: 17            moltype = AA  length = 10
FEATURE                  Location/Qualifiers
source                   1..10
                         mol_type = protein
                         organism = Synthetic construct
SEQUENCE: 17
DTSRGSYFDV                                                           10

SEQ ID NO: 18            moltype =   length =
SEQUENCE: 18
000

SEQ ID NO: 19            moltype =   length =
SEQUENCE: 19
000

SEQ ID NO: 20            moltype = AA  length = 214
FEATURE                  Location/Qualifiers
source                   1..214
                         mol_type = protein
                         organism = Synthetic construct
SEQUENCE: 20
DIQMTQSPSS LSASVGDRVT ITCRASQGIS SWLAWYQQKP EKAPKSLIYA ASSLQSGVPS    60
RFSGSGSGTD FTLTISSLQP EDFATYYCQQ YNSYPPTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 21            moltype = AA  length = 450
FEATURE                  Location/Qualifiers
source                   1..450
                         mol_type = protein
                         organism = Synthetic construct
SEQUENCE: 21
EGQLVQSGGG LVHPGGSLRL SCAGSGFTFS SYGMHWVRQA PGKGLEWVSG IGTGGGTYST    60
```

```
DSVKGRFTIS RDNAKNSLYL QMNSLRAEDM AVYYCARGDY YGSGSFFDCW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKRVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                     450

SEQ ID NO: 22              moltype = AA   length = 215
FEATURE                    Location/Qualifiers
source                     1..215
                           mol_type = protein
                           organism = Synthetic construct
SEQUENCE: 22
ETVVTQEPSL TVSPGGTVTL TCRSSIGAVT TSNYANWVQQ KPGQAFRGLI GGTSNRAPWT    60
PARFSGSLLG GKAALTLSGV QPEDEAEYYC ALWYSTHYVF GGGTKLTVLG QPKANPTVTL    120
FPPSSEELQA NKATLVCLIS DFYPGAVTVA WKADGSPVKA GVETTKPSKQ SNNKYAASSY    180
LSLTPEQWKS HRSYSCQVTH EGSTVEKTVA PTECS                              215

SEQ ID NO: 23              moltype = AA   length = 444
FEATURE                    Location/Qualifiers
source                     1..444
                           mol_type = protein
                           organism = Synthetic construct
SEQUENCE: 23
EVTLKESGPV LVKPTETLTL TCTVSGFSLS TFGVHWIRQP PGKGLEWLGV IWRRGGTDYN    60
AAFMSRLTIS KDTSKSQVVF TMTNMDPVDT ATYYCARDGG FDYWGQGTTV TVSSASTKGP    120
SVFPLAPSSK STSGGTAALG CLVKDYFPEP VTVSWNSGAL TSGVHTFPAV LQSSGLYSLS    180
SVVTVPSSSL GTQTYICNVN HKPSNTKVDK KVEPKSCDKT HTCPPCPAPE LLGGPSVFLF    240
PPKPKDTLYI TREPEVTCVV VDVSHEDPEV KFNWYVDGVE VHNAKTKPRE EQYNSTYRVV    300
SVLTVLHQDW LNGKEYKCKV SNKALPAPIE KTISKAKGQP REPQVYTLPP SRDELTKNQV    360
SLTCLVKGFY PSDIAVEWES NGQPENNYKT TPPVLDSDGS FFLYSKLTVD KSRWQQGNVF    420
SCSVMHEALH NHYTQKSLSL SPGK                                          444

SEQ ID NO: 24              moltype = AA   length = 213
FEATURE                    Location/Qualifiers
source                     1..213
                           mol_type = protein
                           organism = Synthetic construct
SEQUENCE: 24
EIVLTQSPAT LSLSPGERAT LSCSASSSVS YMHWFQQKPG QSPKLWIYST SNLASGVPAR    60
FSGSGSGTDY TLTISSLEPE DFAVYYCQQR SSYPLTFGQG TKLEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                213

SEQ ID NO: 25              moltype = AA   length = 445
FEATURE                    Location/Qualifiers
source                     1..445
                           mol_type = protein
                           organism = Synthetic construct
SEQUENCE: 25
EVQLVESGGG LVQPGGSLRL SCAASGFSFN TYAMNWVRQA PGKGLEWVAR IRTKSNNYAT    60
YYADSVKDRF TISRDDSESS LYLQMNSLKT EDTAVYYCVE TGFAYWDQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSRDELTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 26              moltype = AA   length = 188
FEATURE                    Location/Qualifiers
source                     1..188
                           mol_type = protein
                           organism = Synthetic construct
SEQUENCE: 26
QDSTSDLIPA PPLSKVPLQQ NFQDNQFQGK WYVVGVAGNA ILRPDKQPAK MFATIYELKE    60
DKSYDVTSVR FEAKSCKYTI KTFVPGSQPG EFTSGQIKSA PGQTSTLVRV VSTNYNQHAM    120
VFFKHVSQNR EIFVITLYGR TKELTSELKE NFIRFSKSLG LPENHIVFPV PIDQCIDGHH    180
HHHHHHH                                                             188

SEQ ID NO: 27              moltype =    length =
SEQUENCE: 27
000

SEQ ID NO: 28              moltype =    length =
SEQUENCE: 28
000
```

-continued

```
SEQ ID NO: 29         moltype =   length =
SEQUENCE: 29
000

SEQ ID NO: 30         moltype =   length =
SEQUENCE: 30
000

SEQ ID NO: 31         moltype =   length =
SEQUENCE: 31
000

SEQ ID NO: 32         moltype =   length =
SEQUENCE: 32
000

SEQ ID NO: 33         moltype =   length =
SEQUENCE: 33
000

SEQ ID NO: 34         moltype =   length =
SEQUENCE: 34
000

SEQ ID NO: 35         moltype =   length =
SEQUENCE: 35
000

SEQ ID NO: 36         moltype =   length =
SEQUENCE: 36
000

SEQ ID NO: 37         moltype =   length =
SEQUENCE: 37
000

SEQ ID NO: 38         moltype =   length =
SEQUENCE: 38
000

SEQ ID NO: 39         moltype =   length =
SEQUENCE: 39
000

SEQ ID NO: 40         moltype =   length =
SEQUENCE: 40
000

SEQ ID NO: 41         moltype =   length =
SEQUENCE: 41
000

SEQ ID NO: 42         moltype =   length =
SEQUENCE: 42
000

SEQ ID NO: 43         moltype =   length =
SEQUENCE: 43
000

SEQ ID NO: 44         moltype =   length =
SEQUENCE: 44
000

SEQ ID NO: 45         moltype =   length =
SEQUENCE: 45
000

SEQ ID NO: 46         moltype =   length =
SEQUENCE: 46
000

SEQ ID NO: 47         moltype =   length =
SEQUENCE: 47
000

SEQ ID NO: 48         moltype =   length =
SEQUENCE: 48
000
```

-continued

```
SEQ ID NO: 49            moltype =    length =
SEQUENCE: 49
000

SEQ ID NO: 50            moltype =    length =
SEQUENCE: 50
000

SEQ ID NO: 51            moltype =    length =
SEQUENCE: 51
000

SEQ ID NO: 52            moltype =    length =
SEQUENCE: 52
000

SEQ ID NO: 53            moltype =    length =
SEQUENCE: 53
000

SEQ ID NO: 54            moltype =    length =
SEQUENCE: 54
000

SEQ ID NO: 55            moltype =    length =
SEQUENCE: 55
000

SEQ ID NO: 56            moltype =    length =
SEQUENCE: 56
000

SEQ ID NO: 57            moltype =    length =
SEQUENCE: 57
000

SEQ ID NO: 58            moltype =    length =
SEQUENCE: 58
000

SEQ ID NO: 59            moltype =    length =
SEQUENCE: 59
000

SEQ ID NO: 60            moltype =    length =
SEQUENCE: 60
000

SEQ ID NO: 61            moltype =    length =
SEQUENCE: 61
000

SEQ ID NO: 62            moltype =    length =
SEQUENCE: 62
000

SEQ ID NO: 63            moltype =    length =
SEQUENCE: 63
000

SEQ ID NO: 64            moltype =    length =
SEQUENCE: 64
000

SEQ ID NO: 65            moltype =    length =
SEQUENCE: 65
000

SEQ ID NO: 66            moltype =    length =
SEQUENCE: 66
000

SEQ ID NO: 67            moltype =    length =
SEQUENCE: 67
000

SEQ ID NO: 68            moltype =    length =
SEQUENCE: 68
```

-continued

```
000

SEQ ID NO: 69          moltype =   length =
SEQUENCE: 69
000

SEQ ID NO: 70          moltype =   length =
SEQUENCE: 70
000

SEQ ID NO: 71          moltype =   length =
SEQUENCE: 71
000

SEQ ID NO: 72          moltype =   length =
SEQUENCE: 72
000

SEQ ID NO: 73          moltype =   length =
SEQUENCE: 73
000

SEQ ID NO: 74          moltype =   length =
SEQUENCE: 74
000

SEQ ID NO: 75          moltype =   length =
SEQUENCE: 75
000

SEQ ID NO: 76          moltype =   length =
SEQUENCE: 76
000

SEQ ID NO: 77          moltype =   length =
SEQUENCE: 77
000

SEQ ID NO: 78          moltype =   length =
SEQUENCE: 78
000

SEQ ID NO: 79          moltype =   length =
SEQUENCE: 79
000

SEQ ID NO: 80          moltype =   length =
SEQUENCE: 80
000

SEQ ID NO: 81          moltype =   length =
SEQUENCE: 81
000

SEQ ID NO: 82          moltype =   length =
SEQUENCE: 82
000

SEQ ID NO: 83          moltype =   length =
SEQUENCE: 83
000

SEQ ID NO: 84          moltype =   length =
SEQUENCE: 84
000

SEQ ID NO: 85          moltype =   length =
SEQUENCE: 85
000

SEQ ID NO: 86          moltype =   length =
SEQUENCE: 86
000

SEQ ID NO: 87          moltype =   length =
SEQUENCE: 87
000

SEQ ID NO: 88          moltype =   length =
```

```
SEQUENCE: 88
000

SEQ ID NO: 89          moltype =    length =
SEQUENCE: 89
000

SEQ ID NO: 90          moltype =    length =
SEQUENCE: 90
000

SEQ ID NO: 91          moltype =    length =
SEQUENCE: 91
000

SEQ ID NO: 92          moltype =    length =
SEQUENCE: 92
000

SEQ ID NO: 93          moltype =    length =
SEQUENCE: 93
000

SEQ ID NO: 94          moltype =    length =
SEQUENCE: 94
000

SEQ ID NO: 95          moltype =    length =
SEQUENCE: 95
000

SEQ ID NO: 96          moltype =    length =
SEQUENCE: 96
000

SEQ ID NO: 97          moltype =    length =
SEQUENCE: 97
000

SEQ ID NO: 98          moltype =    length =
SEQUENCE: 98
000

SEQ ID NO: 99          moltype =    length =
SEQUENCE: 99
000

SEQ ID NO: 100         moltype = AA  length = 16
FEATURE                Location/Qualifiers
source                 1..16
                       mol_type = protein
                       organism = Synthetic construct
SEQUENCE: 100
KSSQSIVHYN EKTYLE                                                    16

SEQ ID NO: 101         moltype = AA  length = 7
FEATURE                Location/Qualifiers
source                 1..7
                       mol_type = protein
                       organism = Synthetic construct
SEQUENCE: 101
KVSSRFS                                                             7

SEQ ID NO: 102         moltype = AA  length = 9
FEATURE                Location/Qualifiers
source                 1..9
                       mol_type = protein
                       organism = Synthetic construct
SEQUENCE: 102
FQGSHFPLT                                                           9

SEQ ID NO: 103         moltype = AA  length = 111
FEATURE                Location/Qualifiers
source                 1..111
                       mol_type = protein
                       organism = Synthetic construct
SEQUENCE: 103
VVMTQTPLSL SVSLGDQASI SCKSSQSIVH YNEKTYLEWY LQKPGQSPQL LIYKVSSRFS   60
GVPDRFSGSG SGTDFTLKIS RVEAEDLGVY YCFQGSHFPL TFGQGTKLEI K           111
```

-continued

```
SEQ ID NO: 104            moltype = AA  length = 218
FEATURE                   Location/Qualifiers
source                    1..218
                          mol_type = protein
                          organism = Synthetic construct
SEQUENCE: 104
VVMTQTPLSL SVSLGDQASI SCKSSQSIVH YNEKTYLEWY LQKPGQSPQL LIYKVSSRFS   60
GVPDRFSGSG SGTDFTLKIS RVEAEDLGVY YCFQGSHFPL TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 105            moltype = AA  length = 5
FEATURE                   Location/Qualifiers
source                    1..5
                          mol_type = protein
                          organism = Synthetic construct
SEQUENCE: 105
DYYMA                                                                5

SEQ ID NO: 106            moltype = AA  length = 17
FEATURE                   Location/Qualifiers
source                    1..17
                          mol_type = protein
                          organism = Synthetic construct
SEQUENCE: 106
NINYEGSRTD LLESLKS                                                  17

SEQ ID NO: 107            moltype = AA  length = 10
FEATURE                   Location/Qualifiers
source                    1..10
                          mol_type = protein
                          organism = Synthetic construct
SEQUENCE: 107
DTSRGSYFDV                                                          10

SEQ ID NO: 108            moltype = AA  length = 119
FEATURE                   Location/Qualifiers
source                    1..119
                          mol_type = protein
                          organism = Synthetic construct
SEQUENCE: 108
EVQLVESGGG LVQPGGSLRL SCAASGFTFS DYYMAWVRQA PGKGLEWVAN INYEGSRTDL   60
LESLKSRFTI SRDNAKNSVY LQMNSLRAED TAVYYCARDT SRGSYFDVWG AGTTVTVSS   119

SEQ ID NO: 109            moltype = AA  length = 448
FEATURE                   Location/Qualifiers
source                    1..448
                          mol_type = protein
                          organism = Synthetic construct
SEQUENCE: 109
EVQLVESGGG LVQPGGSLRL SCAASGFTFS DYYMAWVRQA PGKGLEWVAN INYEGSRTDL   60
LESLKSRFTI SRDNAKNSVY LQMNSLRAED TAVYYCARDT SRGSYFDVWG AGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                     448

SEQ ID NO: 110            moltype = AA  length = 16
FEATURE                   Location/Qualifiers
source                    1..16
                          mol_type = protein
                          organism = Synthetic construct
SEQUENCE: 110
KSSQSIVHYN EKTYLE                                                   16

SEQ ID NO: 111            moltype = AA  length = 7
FEATURE                   Location/Qualifiers
source                    1..7
                          mol_type = protein
                          organism = Synthetic construct
SEQUENCE: 111
KVSSRAS                                                              7

SEQ ID NO: 112            moltype = AA  length = 9
FEATURE                   Location/Qualifiers
source                    1..9
```

```
                          mol_type = protein
                          organism = Synthetic construct
SEQUENCE: 112
FQGSHFPLT                                                                   9

SEQ ID NO: 113           moltype = AA   length = 111
FEATURE                  Location/Qualifiers
source                   1..111
                         mol_type = protein
                         organism = Synthetic construct
SEQUENCE: 113
VVMTQTPLSL SVSLGDQASI SCKSSQSIVH YNEKTYLEWY LQKPGQSPQL LIYKVSSRAS    60
GVPDRFSGSG SGTDFTLKIS RVEAEDLGVY YCFQGSHFPL TFGQGTKLEI K             111

SEQ ID NO: 114           moltype = AA   length = 218
FEATURE                  Location/Qualifiers
source                   1..218
                         mol_type = protein
                         organism = Synthetic construct
SEQUENCE: 114
VVMTQTPLSL SVSLGDQASI SCKSSQSIVH YNEKTYLEWY LQKPGQSPQL LIYKVSSRAS    60
GVPDRFSGSG SGTDFTLKIS RVEAEDLGVY YCFQGSHFPL TFGQGTKLEI KRTVAAPSVF    120
IPPSDEQLK  SGTASVVCLL NNFYPREAKV QWKVDNALQS GNSQESVTEQ DSKDSTYSLS    180
STLTLSKADY EKHKVYACEV THQGLSSPVT KSFNRGEC                            218

SEQ ID NO: 115           moltype = AA   length = 5
FEATURE                  Location/Qualifiers
source                   1..5
                         mol_type = protein
                         organism = Synthetic construct
SEQUENCE: 115
DYYMA                                                                       5

SEQ ID NO: 116           moltype = AA   length = 17
FEATURE                  Location/Qualifiers
source                   1..17
                         mol_type = protein
                         organism = Synthetic construct
SEQUENCE: 116
NINYYGSRTD LLESLKS                                                          17

SEQ ID NO: 117           moltype = AA   length = 10
FEATURE                  Location/Qualifiers
source                   1..10
                         mol_type = protein
                         organism = Synthetic construct
SEQUENCE: 117
DTSRGSYFDV                                                                  10

SEQ ID NO: 118           moltype = AA   length = 119
FEATURE                  Location/Qualifiers
source                   1..119
                         mol_type = protein
                         organism = Synthetic construct
SEQUENCE: 118
EVQLVESGGG LVQPGGSLRL SCAASGFTFS DYYMAWVRQA PGKGLEWVAN INYYGSRTDL    60
LESLKSRFTI SRDNAKNSVY LQMNSLRAED TAVYYCARDT SRGSYFDVWG AGTTVTVSS     119

SEQ ID NO: 119           moltype = AA   length = 448
FEATURE                  Location/Qualifiers
source                   1..448
                         mol_type = protein
                         organism = Synthetic construct
SEQUENCE: 119
EVQLVESGGG LVQPGGSLRL SCAASGFTFS DYYMAWVRQA PGKGLEWVAN INYYGSRTDL    60
LESLKSRFTI SRDNAKNSVY LQMNSLRAED TAVYYCARDT SRGSYFDVWG AGTTVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKRVEPK SCDKTHTCPP CPAPEAAGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                       448

SEQ ID NO: 120           moltype = AA   length = 16
FEATURE                  Location/Qualifiers
source                   1..16
                         mol_type = protein
                         organism = Synthetic construct
SEQUENCE: 120
```

-continued

```
KSSQSIVHYN GKTYLE                                                        16

SEQ ID NO: 121          moltype = AA   length = 7
FEATURE                 Location/Qualifiers
source                  1..7
                        mol_type = protein
                        organism = Synthetic construct
SEQUENCE: 121
KVSSRFS                                                                  7

SEQ ID NO: 122          moltype = AA   length = 9
FEATURE                 Location/Qualifiers
source                  1..9
                        mol_type = protein
                        organism = Synthetic construct
SEQUENCE: 122
FQGSHFPLT                                                                9

SEQ ID NO: 123          moltype = AA   length = 111
FEATURE                 Location/Qualifiers
source                  1..111
                        mol_type = protein
                        organism = Synthetic construct
SEQUENCE: 123
VVMTQTPLSL SVSLGDQASI SCKSSQSIVH YNGKTYLEWY LQKPGQSPQL LIYKVSSRFS        60
GVPDRFSGSG SGTDFTLKIS RVEAEDLGVY YCFQGSHFPL TFGQGTKLEI K                111

SEQ ID NO: 124          moltype = AA   length = 218
FEATURE                 Location/Qualifiers
source                  1..218
                        mol_type = protein
                        organism = Synthetic construct
SEQUENCE: 124
VVMTQTPLSL SVSLGDQASI SCKSSQSIVH YNGKTYLEWY LQKPGQSPQL LIYKVSSRFS        60
GVPDRFSGSG SGTDFTLKIS RVEAEDLGVY YCFQGSHFPL TFGQGTKLEI KRTVAAPSVF        120
IFPPSDEQLK SGTASVVCLL NNFYPREAKV QWKVDNALQS GNSQESVTEQ DSKDSTYSLS        180
STLTLSKADY EKHKVYACEV THQGLSSPVT KSFNRGEC                                218

SEQ ID NO: 125          moltype = AA   length = 5
FEATURE                 Location/Qualifiers
source                  1..5
                        mol_type = protein
                        organism = Synthetic construct
SEQUENCE: 125
DYYMA                                                                    5

SEQ ID NO: 126          moltype = AA   length = 17
FEATURE                 Location/Qualifiers
source                  1..17
                        mol_type = protein
                        organism = Synthetic construct
SEQUENCE: 126
NINYEGSRTD LLASLKS                                                       17

SEQ ID NO: 127          moltype = AA   length = 10
FEATURE                 Location/Qualifiers
source                  1..10
                        mol_type = protein
                        organism = Synthetic construct
SEQUENCE: 127
DTSRGSYFDV                                                               10

SEQ ID NO: 128          moltype = AA   length = 119
FEATURE                 Location/Qualifiers
source                  1..119
                        mol_type = protein
                        organism = Synthetic construct
SEQUENCE: 128
EVQLVESGGG LVQPGGSLRL SCAASGFTFS DYYMAWVRQA PGKGLEWVAN INYEGSRTDL        60
LASLKSRFTI SRDNAKNSVY LQMNSLRAED TAVYYCARDT SRGSYFDVWG AGTTVTVSS         119

SEQ ID NO: 129          moltype = AA   length = 448
FEATURE                 Location/Qualifiers
source                  1..448
                        mol_type = protein
                        organism = Synthetic construct
SEQUENCE: 129
EVQLVESGGG LVQPGGSLRL SCAASGFTFS DYYMAWVRQA PGKGLEWVAN INYEGSRTDL        60
LASLKSRFTI SRDNAKNSVY LQMNSLRAED TAVYYCARDT SRGSYFDVWG AGTTVTVSSA        120
```

```
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                     448

SEQ ID NO: 130            moltype = AA   length = 16
FEATURE                   Location/Qualifiers
source                    1..16
                          mol_type = protein
                          organism = Synthetic construct
SEQUENCE: 130
KSSQSIVHYN GKTYLE                                                  16

SEQ ID NO: 131            moltype = AA   length = 7
FEATURE                   Location/Qualifiers
source                    1..7
                          mol_type = protein
                          organism = Synthetic construct
SEQUENCE: 131
KVSSRAS                                                            7

SEQ ID NO: 132            moltype = AA   length = 9
FEATURE                   Location/Qualifiers
source                    1..9
                          mol_type = protein
                          organism = Synthetic construct
SEQUENCE: 132
FQGSHFPLT                                                          9

SEQ ID NO: 133            moltype = AA   length = 111
FEATURE                   Location/Qualifiers
source                    1..111
                          mol_type = protein
                          organism = Synthetic construct
SEQUENCE: 133
VVMTQTPLSL SVSLGDQASI SCKSSQSIVH YNGKTYLEWY LQKPGQSPQL LIYKVSSRAS  60
GVPDRFSGSG SGTDFTLKIS RVEAEDLGVY YCFQGSHFPL TFGQGTKLEI K           111

SEQ ID NO: 134            moltype = AA   length = 218
FEATURE                   Location/Qualifiers
source                    1..218
                          mol_type = protein
                          organism = Synthetic construct
SEQUENCE: 134
VVMTQTPLSL SVSLGDQASI SCKSSQSIVH YNGKTYLEWY LQKPGQSPQL LIYKVSSRAS  60
GVPDRFSGSG SGTDFTLKIS RVEAEDLGVY YCFQGSHFPL TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 135            moltype = AA   length = 5
FEATURE                   Location/Qualifiers
source                    1..5
                          mol_type = protein
                          organism = Synthetic construct
SEQUENCE: 135
DYYMA                                                              5

SEQ ID NO: 136            moltype = AA   length = 17
FEATURE                   Location/Qualifiers
source                    1..17
                          mol_type = protein
                          organism = Synthetic construct
SEQUENCE: 136
NINYYGSRTD LLASLKS                                                 17

SEQ ID NO: 137            moltype = AA   length = 10
FEATURE                   Location/Qualifiers
source                    1..10
                          mol_type = protein
                          organism = Synthetic construct
SEQUENCE: 137
DTSRGSYFDV                                                         10

SEQ ID NO: 138            moltype = AA   length = 119
FEATURE                   Location/Qualifiers
source                    1..119
                          mol_type = protein
```

-continued

```
                         organism = Synthetic construct
SEQUENCE: 138
EVQLVESGGG LVQPGGSLRL SCAASGFTFS DYYMAWVRQA PGKGLEWVAN INYYGSRTDL    60
LASLKSRFTI SRDNAKNSVY LQMNSLRAED TAVYYCARDT SRGSYFDVWG AGTTVTVSS     119

SEQ ID NO: 139           moltype = AA   length = 448
FEATURE                  Location/Qualifiers
source                   1..448
                         mol_type = protein
                         organism = Synthetic construct
SEQUENCE: 139
EVQLVESGGG LVQPGGSLRL SCAASGFTFS DYYMAWVRQA PGKGLEWVAN INYYGSRTDL    60
LASLKSRFTI SRDNAKNSVY LQMNSLRAED TAVYYCARDT SRGSYFDVWG AGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPEAAGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                      448

SEQ ID NO: 140           moltype = AA   length = 16
FEATURE                  Location/Qualifiers
source                   1..16
                         mol_type = protein
                         organism = Synthetic construct
SEQUENCE: 140
KSSQSIVHYN ENTYLE                                                    16

SEQ ID NO: 141           moltype = AA   length = 7
FEATURE                  Location/Qualifiers
source                   1..7
                         mol_type = protein
                         organism = Synthetic construct
SEQUENCE: 141
KVSSRFS                                                               7

SEQ ID NO: 142           moltype = AA   length = 9
FEATURE                  Location/Qualifiers
source                   1..9
                         mol_type = protein
                         organism = Synthetic construct
SEQUENCE: 142
FQGSHFPLT                                                            9

SEQ ID NO: 143           moltype = AA   length = 111
FEATURE                  Location/Qualifiers
source                   1..111
                         mol_type = protein
                         organism = Synthetic construct
SEQUENCE: 143
VVMTQTPLSL SVSLGDQASI SCKSSQSIVH YNENTYLEWY LQKPGQSPQL LIYKVSSRFS    60
GVPDRFSGSG SGTDFTLKIS RVEAEDLGVY YCFQGSHFPL TFGQGTKLEI K            111

SEQ ID NO: 144           moltype = AA   length = 218
FEATURE                  Location/Qualifiers
source                   1..218
                         mol_type = protein
                         organism = Synthetic construct
SEQUENCE: 144
VVMTQTPLSL SVSLGDQASI SCKSSQSIVH YNENTYLEWY LQKPGQSPQL LIYKVSSRFS    60
GVPDRFSGSG SGTDFTLKIS RVEAEDLGVY YCFQGSHFPL TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 145           moltype = AA   length = 5
FEATURE                  Location/Qualifiers
source                   1..5
                         mol_type = protein
                         organism = Synthetic construct
SEQUENCE: 145
DYYMA                                                                5

SEQ ID NO: 146           moltype = AA   length = 17
FEATURE                  Location/Qualifiers
source                   1..17
                         mol_type = protein
                         organism = Synthetic construct
SEQUENCE: 146
NINYDGSRTD LLDSLKS                                                   17
```

```
SEQ ID NO: 147              moltype = AA   length = 10
FEATURE                     Location/Qualifiers
source                      1..10
                            mol_type = protein
                            organism = Synthetic construct
SEQUENCE: 147
DTSRGSYFDV                                                                10

SEQ ID NO: 148              moltype = AA   length = 119
FEATURE                     Location/Qualifiers
source                      1..119
                            mol_type = protein
                            organism = Synthetic construct
SEQUENCE: 148
EVQLVESGGG LVQPGGSLRL SCAASGFTFS DYYMAWVRQA PGKGLEWVAN INYDGSRTDL  60
LDSLKSRFTI SRDNAKNSVY LQMNSLRAED TAVYYCARDT SRGSYFDVWG AGTTVTVSS   119

SEQ ID NO: 149              moltype = AA   length = 448
FEATURE                     Location/Qualifiers
source                      1..448
                            mol_type = protein
                            organism = Synthetic construct
SEQUENCE: 149
EVQLVESGGG LVQPGGSLRL SCAASGFTFS DYYMAWVRQA PGKGLEWVAN INYDGSRTDL  60
LDSLKSRFTI SRDNAKNSVY LQMNSLRAED TAVYYCARDT SRGSYFDVWG AGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                     448

SEQ ID NO: 150              moltype = AA   length = 16
FEATURE                     Location/Qualifiers
source                      1..16
                            mol_type = protein
                            organism = Synthetic construct
SEQUENCE: 150
KSSQSIVHYN ENTYLE                                                  16

SEQ ID NO: 151              moltype = AA   length = 7
FEATURE                     Location/Qualifiers
source                      1..7
                            mol_type = protein
                            organism = Synthetic construct
SEQUENCE: 151
KVSSRAS                                                            7

SEQ ID NO: 152              moltype = AA   length = 9
FEATURE                     Location/Qualifiers
source                      1..9
                            mol_type = protein
                            organism = Synthetic construct
SEQUENCE: 152
FQGSHFPLT                                                          9

SEQ ID NO: 153              moltype = AA   length = 111
FEATURE                     Location/Qualifiers
source                      1..111
                            mol_type = protein
                            organism = Synthetic construct
SEQUENCE: 153
VVMTQTPLSL SVSLGDQASI SCKSSQSIVH YNENTYLEWY LQKPGQSPQL LIYKVSSRAS  60
GVPDRFSGSG SGTDFTLKIS RVEAEDLGVY YCFQGSHFPL TFGQGTKLEI K          111

SEQ ID NO: 154              moltype = AA   length = 218
FEATURE                     Location/Qualifiers
source                      1..218
                            mol_type = protein
                            organism = Synthetic construct
SEQUENCE: 154
VVMTQTPLSL SVSLGDQASI SCKSSQSIVH YNENTYLEWY LQKPGQSPQL LIYKVSSRAS  60
GVPDRFSGSG SGTDFTLKIS RVEAEDLGVY YCFQGSHFPL TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 155              moltype = AA   length = 5
FEATURE                     Location/Qualifiers
```

-continued

```
source                  1..5
                        mol_type = protein
                        organism = Synthetic construct
SEQUENCE: 155
DYYMA                                                       5

SEQ ID NO: 156          moltype = AA   length = 17
FEATURE                 Location/Qualifiers
source                  1..17
                        mol_type = protein
                        organism = Synthetic construct
SEQUENCE: 156
NINYEGSRTD LLDSLKS                                          17

SEQ ID NO: 157          moltype = AA   length = 10
FEATURE                 Location/Qualifiers
source                  1..10
                        mol_type = protein
                        organism = Synthetic construct
SEQUENCE: 157
DTSRGSYFDV                                                  10

SEQ ID NO: 158          moltype = AA   length = 119
FEATURE                 Location/Qualifiers
source                  1..119
                        mol_type = protein
                        organism = Synthetic construct
SEQUENCE: 158
EVQLVESGGG LVQPGGSLRL SCAASGFTFS DYYMAWVRQA PGKGLEWVAN INYEGSRTDL  60
LDSLKSRFTI SRDNAKNSVY LQMNSLRAED TAVYYCARDT SRGSYFDVWG AGTTVTVSS   119

SEQ ID NO: 159          moltype = AA   length = 448
FEATURE                 Location/Qualifiers
source                  1..448
                        mol_type = protein
                        organism = Synthetic construct
SEQUENCE: 159
EVQLVESGGG LVQPGGSLRL SCAASGFTFS DYYMAWVRQA PGKGLEWVAN INYEGSRTDL  60
LDSLKSRFTI SRDNAKNSVY LQMNSLRAED TAVYYCARDT SRGSYFDVWG AGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                               448

SEQ ID NO: 160          moltype = AA   length = 16
FEATURE                 Location/Qualifiers
source                  1..16
                        mol_type = protein
                        organism = Synthetic construct
SEQUENCE: 160
RSSQSIVHYN ENTYLE                                           16

SEQ ID NO: 161          moltype = AA   length = 7
FEATURE                 Location/Qualifiers
source                  1..7
                        mol_type = protein
                        organism = Synthetic construct
SEQUENCE: 161
KVSNRFS                                                     7

SEQ ID NO: 162          moltype = AA   length = 9
FEATURE                 Location/Qualifiers
source                  1..9
                        mol_type = protein
                        organism = Synthetic construct
SEQUENCE: 162
FQGSHFPLT                                                   9

SEQ ID NO: 163          moltype = AA   length = 111
FEATURE                 Location/Qualifiers
source                  1..111
                        mol_type = protein
                        organism = Synthetic construct
SEQUENCE: 163
VVMTQTPLSL PVSLGDQASI SCRSSQSIVH YNENTYLEWY LQKPGQSPQL LIYKVSNRFS  60
GVPDRFSGSG SGTDFTLKIS RVEAEDLGVY YCFQGSHFPL TFGQGTKLEI K           111
```

-continued

```
SEQ ID NO: 164          moltype = AA   length = 218
FEATURE                 Location/Qualifiers
source                  1..218
                        mol_type = protein
                        organism = Synthetic construct
SEQUENCE: 164
VVMTQTPLSL PVSLGDQASI SCRSSQSIVH YNENTYLEWY LQKPGQSPQL LIYKVSNRFS   60
GVPDRFSGSG SGTDFTLKIS RVEAEDLGVY YCFQGSHFPL TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 165          moltype = AA   length = 5
FEATURE                 Location/Qualifiers
source                  1..5
                        mol_type = protein
                        organism = Synthetic construct
SEQUENCE: 165
DYYMA                                                                5

SEQ ID NO: 166          moltype = AA   length = 17
FEATURE                 Location/Qualifiers
source                  1..17
                        mol_type = protein
                        organism = Synthetic construct
SEQUENCE: 166
NINYDGSRTD LLESLKS                                                  17

SEQ ID NO: 167          moltype = AA   length = 10
FEATURE                 Location/Qualifiers
source                  1..10
                        mol_type = protein
                        organism = Synthetic construct
SEQUENCE: 167
DTSRGSYFDV                                                          10

SEQ ID NO: 168          moltype = AA   length = 119
FEATURE                 Location/Qualifiers
source                  1..119
                        mol_type = protein
                        organism = Synthetic construct
SEQUENCE: 168
EVQLVESGGG LVQPGGSLRL SCAASGFTFS DYYMAWVRQA PGKGLEWVAN INYDGSRTDL   60
LESLKSRFTI SRDNAKNSVY LQMNSLRAED TAVYYCARDT SRGSYFDVWG AGTTVTVSS   119

SEQ ID NO: 169          moltype = AA   length = 448
FEATURE                 Location/Qualifiers
source                  1..448
                        mol_type = protein
                        organism = Synthetic construct
SEQUENCE: 169
EVQLVESGGG LVQPGGSLRL SCAASGFTFS DYYMAWVRQA PGKGLEWVAN INYDGSRTDL   60
LESLKSRFTI SRDNAKNSVY LQMNSLRAED TAVYYCARDT SRGSYFDVWG AGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                     448

SEQ ID NO: 170          moltype = AA   length = 16
FEATURE                 Location/Qualifiers
source                  1..16
                        mol_type = protein
                        organism = Synthetic construct
SEQUENCE: 170
RSSQSIVHYN ANTYLE                                                   16

SEQ ID NO: 171          moltype = AA   length = 7
FEATURE                 Location/Qualifiers
source                  1..7
                        mol_type = protein
                        organism = Synthetic construct
SEQUENCE: 171
KVSNRFS                                                              7

SEQ ID NO: 172          moltype = AA   length = 9
FEATURE                 Location/Qualifiers
source                  1..9
                        mol_type = protein
```

```
                         organism = Synthetic construct
SEQUENCE: 172
FQGSHFPLT                                                                  9

SEQ ID NO: 173          moltype = AA   length = 111
FEATURE                 Location/Qualifiers
source                  1..111
                        mol_type = protein
                        organism = Synthetic construct
SEQUENCE: 173
VVMTQTPLSL PVSLGDQASI SCRSSQSIVH YNANTYLEWY LQKPGQSPQL LIYKVSNRFS  60
GVPDRFSGSG SGTDFTLKIS RVEAEDLGVY YCFQGSHFPL TFGQGTKLEI K           111

SEQ ID NO: 174          moltype = AA   length = 218
FEATURE                 Location/Qualifiers
source                  1..218
                        mol_type = protein
                        organism = Synthetic construct
SEQUENCE: 174
VVMTQTPLSL PVSLGDQASI SCRSSQSIVH YNANTYLEWY LQKPGQSPQL LIYKVSNRFS  60
GVPDRFSGSG SGTDFTLKIS RVEAEDLGVY YCFQGSHFPL TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 175          moltype = AA   length = 5
FEATURE                 Location/Qualifiers
source                  1..5
                        mol_type = protein
                        organism = Synthetic construct
SEQUENCE: 175
DYYMA                                                                      5

SEQ ID NO: 176          moltype = AA   length = 17
FEATURE                 Location/Qualifiers
source                  1..17
                        mol_type = protein
                        organism = Synthetic construct
SEQUENCE: 176
NINYDGSRTD LLDSLKS                                                         17

SEQ ID NO: 177          moltype = AA   length = 10
FEATURE                 Location/Qualifiers
source                  1..10
                        mol_type = protein
                        organism = Synthetic construct
SEQUENCE: 177
DTSRGSYFDV                                                                 10

SEQ ID NO: 178          moltype = AA   length = 119
FEATURE                 Location/Qualifiers
source                  1..119
                        mol_type = protein
                        organism = Synthetic construct
SEQUENCE: 178
EVKLVESGGG LVQPGGSLRL SCAASGFTFS DYYMAWVRQA PGKGLEWVAN INYDGSRTDL  60
LDSLKSRFTI SRDNAKNSVY LQMNSLRAED TAVYYCARDT SRGSYFDVWG AGTTVTVSS   119

SEQ ID NO: 179          moltype = AA   length = 448
FEATURE                 Location/Qualifiers
source                  1..448
                        mol_type = protein
                        organism = Synthetic construct
SEQUENCE: 179
EVKLVESGGG LVQPGGSLRL SCAASGFTFS DYYMAWVRQA PGKGLEWVAN INYDGSRTDL  60
LDSLKSRFTI SRDNAKNSVY LQMNSLRAED TAVYYCARDT SRGSYFDVWG AGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                      448

SEQ ID NO: 180          moltype = AA   length = 16
FEATURE                 Location/Qualifiers
source                  1..16
                        mol_type = protein
                        organism = Synthetic construct
SEQUENCE: 180
RSSQSIVHYN TNTYLE                                                          16
```

-continued

```
SEQ ID NO: 181              moltype = AA   length = 7
FEATURE                     Location/Qualifiers
source                      1..7
                            mol_type = protein
                            organism = Synthetic construct
SEQUENCE: 181
KVSNRFS                                                             7

SEQ ID NO: 182              moltype = AA   length = 9
FEATURE                     Location/Qualifiers
source                      1..9
                            mol_type = protein
                            organism = Synthetic construct
SEQUENCE: 182
FQGSHFPLT                                                           9

SEQ ID NO: 183              moltype = AA   length = 111
FEATURE                     Location/Qualifiers
source                      1..111
                            mol_type = protein
                            organism = Synthetic construct
SEQUENCE: 183
VVMTQTPLSL PVSLGDQASI SCRSSQSIVH YNTNTYLEWY LQKPGQSPQL LIYKVSNRFS   60
GVPDRFSGSG SGTDFTLKIS RVEAEDLGVY YCFQGSHFPL TFGQGTKLEI K            111

SEQ ID NO: 184              moltype = AA   length = 218
FEATURE                     Location/Qualifiers
source                      1..218
                            mol_type = protein
                            organism = Synthetic construct
SEQUENCE: 184
VVMTQTPLSL PVSLGDQASI SCRSSQSIVH YNTNTYLEWY LQKPGQSPQL LIYKVSNRFS   60
GVPDRFSGSG SGTDFTLKIS RVEAEDLGVY YCFQGSHFPL TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 185              moltype =    length =
SEQUENCE: 185
000

SEQ ID NO: 186              moltype =    length =
SEQUENCE: 186
000

SEQ ID NO: 187              moltype =    length =
SEQUENCE: 187
000

SEQ ID NO: 188              moltype =    length =
SEQUENCE: 188
000

SEQ ID NO: 189              moltype =    length =
SEQUENCE: 189
000

SEQ ID NO: 190              moltype = AA   length = 16
FEATURE                     Location/Qualifiers
source                      1..16
                            mol_type = protein
                            organism = Synthetic construct
SEQUENCE: 190
RSSQSIVHYN GKTYLE                                                   16

SEQ ID NO: 191              moltype = AA   length = 7
FEATURE                     Location/Qualifiers
source                      1..7
                            mol_type = protein
                            organism = Synthetic construct
SEQUENCE: 191
KVSNRFS                                                             7

SEQ ID NO: 192              moltype = AA   length = 9
FEATURE                     Location/Qualifiers
source                      1..9
                            mol_type = protein
                            organism = Synthetic construct
SEQUENCE: 192
```

-continued

```
FQGSHFPLT                                                         9

SEQ ID NO: 193           moltype = AA  length = 111
FEATURE                  Location/Qualifiers
source                   1..111
                         mol_type = protein
                         organism = Synthetic construct
SEQUENCE: 193
VVMTQTPLSL PVSLGDQASI SCRSSQSIVH YNGKTYLEWY LQKPGQSPQL LIYKVSNRFS  60
GVPDRFSGSG SGTDFTLKIS RVEAEDLGVY YCFQGSHFPL TFGQGTKLEI K           111

SEQ ID NO: 194           moltype = AA  length = 218
FEATURE                  Location/Qualifiers
source                   1..218
                         mol_type = protein
                         organism = Synthetic construct
SEQUENCE: 194
VVMTQTPLSL PVSLGDQASI SCRSSQSIVH YNGKTYLEWY LQKPGQSPQL LIYKVSNRFS  60
GVPDRFSGSG SGTDFTLKIS RVEAEDLGVY YCFQGSHFPL TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 195           moltype =   length =
SEQUENCE: 195
000

SEQ ID NO: 196           moltype =   length =
SEQUENCE: 196
000

SEQ ID NO: 197           moltype =   length =
SEQUENCE: 197
000

SEQ ID NO: 198           moltype =   length =
SEQUENCE: 198
000

SEQ ID NO: 199           moltype =   length =
SEQUENCE: 199
000

SEQ ID NO: 200           moltype = AA  length = 16
FEATURE                  Location/Qualifiers
source                   1..16
                         mol_type = protein
                         organism = Synthetic construct
SEQUENCE: 200
RSSQSIVHYN EKTYLE                                                  16

SEQ ID NO: 201           moltype = AA  length = 7
FEATURE                  Location/Qualifiers
source                   1..7
                         mol_type = protein
                         organism = Synthetic construct
SEQUENCE: 201
KVSNRFS                                                            7

SEQ ID NO: 202           moltype = AA  length = 9
FEATURE                  Location/Qualifiers
source                   1..9
                         mol_type = protein
                         organism = Synthetic construct
SEQUENCE: 202
FQGSHFPLT                                                          9

SEQ ID NO: 203           moltype = AA  length = 111
FEATURE                  Location/Qualifiers
source                   1..111
                         mol_type = protein
                         organism = Synthetic construct
SEQUENCE: 203
VVMTQTPLSL PVSLGDQASI SCRSSQSIVH YNEKTYLEWY LQKPGQSPQL LIYKVSNRFS  60
GVPDRFSGSG SGTDFTLKIS RVEAEDLGVY YCFQGSHFPL TFGQGTKLEI K           111

SEQ ID NO: 204           moltype = AA  length = 218
FEATURE                  Location/Qualifiers
source                   1..218
                         mol_type = protein
```

-continued

```
                              organism = Synthetic construct
SEQUENCE: 204
VVMTQTPLSL PVSLGDQASI SCRSSQSIVH YNEKTYLEWY LQKPGQSPQL LIYKVSNRFS    60
GVPDRFSGSG SGTDFTLKIS RVEAEDLGVY YCFQGSHFPL TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 205          moltype =   length =
SEQUENCE: 205
000

SEQ ID NO: 206          moltype =   length =
SEQUENCE: 206
000

SEQ ID NO: 207          moltype =   length =
SEQUENCE: 207
000

SEQ ID NO: 208          moltype =   length =
SEQUENCE: 208
000

SEQ ID NO: 209          moltype =   length =
SEQUENCE: 209
000

SEQ ID NO: 210          moltype = AA  length = 16
FEATURE                 Location/Qualifiers
source                  1..16
                        mol_type = protein
                        organism = Synthetic construct
SEQUENCE: 210
KSSQSIVHYN GNTYLE                                                    16

SEQ ID NO: 211          moltype = AA  length = 7
FEATURE                 Location/Qualifiers
source                  1..7
                        mol_type = protein
                        organism = Synthetic construct
SEQUENCE: 211
KVSSRFS                                                               7

SEQ ID NO: 212          moltype = AA  length = 9
FEATURE                 Location/Qualifiers
source                  1..9
                        mol_type = protein
                        organism = Synthetic construct
SEQUENCE: 212
FQGSHFPLT                                                             9

SEQ ID NO: 213          moltype = AA  length = 111
FEATURE                 Location/Qualifiers
source                  1..111
                        mol_type = protein
                        organism = Synthetic construct
SEQUENCE: 213
VVMTQTPLSL SVSLGDQASI SCKSSQSIVH YNGNTYLEWY LQKPGQSPQL LIYKVSSRFS    60
GVPDRFSGSG SGTDFTLKIS RVEAEDLGVY YCFQGSHFPL TFGQGTKLEI K            111

SEQ ID NO: 214          moltype = AA  length = 218
FEATURE                 Location/Qualifiers
source                  1..218
                        mol_type = protein
                        organism = Synthetic construct
SEQUENCE: 214
VVMTQTPLSL SVSLGDQASI SCKSSQSIVH YNGNTYLEWY LQKPGQSPQL LIYKVSSRFS    60
GVPDRFSGSG SGTDFTLKIS RVEAEDLGVY YCFQGSHFPL TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 215          moltype =   length =
SEQUENCE: 215
000

SEQ ID NO: 216          moltype =   length =
SEQUENCE: 216
000
```

```
SEQ ID NO: 217          moltype =    length =
SEQUENCE: 217
000

SEQ ID NO: 218          moltype =    length =
SEQUENCE: 218
000

SEQ ID NO: 219          moltype =    length =
SEQUENCE: 219
000

SEQ ID NO: 220          moltype = AA   length = 16
FEATURE                 Location/Qualifiers
source                  1..16
                        mol_type = protein
                        organism = Synthetic construct
SEQUENCE: 220
KSSQSIVHYN GNTYLE                                                    16

SEQ ID NO: 221          moltype = AA   length = 7
FEATURE                 Location/Qualifiers
source                  1..7
                        mol_type = protein
                        organism = Synthetic construct
SEQUENCE: 221
KVSSRAS                                                              7

SEQ ID NO: 222          moltype = AA   length = 9
FEATURE                 Location/Qualifiers
source                  1..9
                        mol_type = protein
                        organism = Synthetic construct
SEQUENCE: 222
FQGSHFPLT                                                            9

SEQ ID NO: 223          moltype = AA   length = 111
FEATURE                 Location/Qualifiers
source                  1..111
                        mol_type = protein
                        organism = Synthetic construct
SEQUENCE: 223
VVMTQTPLSL SVSLGDQASI SCKSSQSIVH YNGNTYLEWY LQKPGQSPQL LIYKVSSRAS   60
GVPDRFSGSG SGTDFTLKIS RVEAEDLGVY YCFQGSHFPL TFGQGTKLEI K            111

SEQ ID NO: 224          moltype = AA   length = 218
FEATURE                 Location/Qualifiers
source                  1..218
                        mol_type = protein
                        organism = Synthetic construct
SEQUENCE: 224
VVMTQTPLSL SVSLGDQASI SCKSSQSIVH YNGNTYLEWY LQKPGQSPQL LIYKVSSRAS   60
GVPDRFSGSG SGTDFTLKIS RVEAEDLGVY YCFQGSHFPL TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 225          moltype =    length =
SEQUENCE: 225
000

SEQ ID NO: 226          moltype =    length =
SEQUENCE: 226
000

SEQ ID NO: 227          moltype =    length =
SEQUENCE: 227
000

SEQ ID NO: 228          moltype =    length =
SEQUENCE: 228
000

SEQ ID NO: 229          moltype =    length =
SEQUENCE: 229
000

SEQ ID NO: 230          moltype = AA   length = 16
FEATURE                 Location/Qualifiers
source                  1..16
```

-continued

```
                              mol_type = protein
                              organism = Synthetic construct
SEQUENCE: 230
KSSQSIVHYN GNTYLE                                                      16

SEQ ID NO: 231         moltype = AA   length = 7
FEATURE                Location/Qualifiers
source                 1..7
                       mol_type = protein
                       organism = Synthetic construct
SEQUENCE: 231
KVSSRAS                                                                7

SEQ ID NO: 232         moltype = AA   length = 9
FEATURE                Location/Qualifiers
source                 1..9
                       mol_type = protein
                       organism = Synthetic construct
SEQUENCE: 232
FQGSHFPLT                                                              9

SEQ ID NO: 233         moltype = AA   length = 112
FEATURE                Location/Qualifiers
source                 1..112
                       mol_type = protein
                       organism = Synthetic construct
SEQUENCE: 233
DIVMTQTPLS LSVSLGDQAS ISCKSSQSIV HYNGNTYLEW YLQKPGQSPQ LLIYKVSSRA     60
SGVPDRFSGS GSGTDFTLKI SRVEAEDLGV YYCFQGSHFP LTFGQGTKLE IK             112

SEQ ID NO: 234         moltype = AA   length = 219
FEATURE                Location/Qualifiers
source                 1..219
                       mol_type = protein
                       organism = Synthetic construct
SEQUENCE: 234
DIVMTQTPLS LSVSLGDQAS ISCKSSQSIV HYNGNTYLEW YLQKPGQSPQ LLIYKVSSRA     60
SGVPDRFSGS GSGTDFTLKI SRVEAEDLGV YYCFQGSHFP LTFGQGTKLE IKRTVAAPSV     120
FIFPPSDEQL KSGTASVVCL LNNFYPREAK VQWKVDNALQ SGNSQESVTE QDSKDSTYSL     180
SSTLTLSKAD YEKHKVYACE VTHQGLSSPV TKSFNRGEC                            219

SEQ ID NO: 235            moltype =    length =
SEQUENCE: 235
000

SEQ ID NO: 236            moltype =    length =
SEQUENCE: 236
000

SEQ ID NO: 237            moltype =    length =
SEQUENCE: 237
000

SEQ ID NO: 238            moltype =    length =
SEQUENCE: 238
000

SEQ ID NO: 239            moltype =    length =
SEQUENCE: 239
000

SEQ ID NO: 240         moltype = AA   length = 16
FEATURE                Location/Qualifiers
source                 1..16
                       mol_type = protein
                       organism = Synthetic construct
SEQUENCE: 240
KSSQSIVHYN EKTYLE                                                      16

SEQ ID NO: 241         moltype = AA   length = 7
FEATURE                Location/Qualifiers
source                 1..7
                       mol_type = protein
                       organism = Synthetic construct
SEQUENCE: 241
KVSSRAS                                                                7

SEQ ID NO: 242         moltype = AA   length = 9
FEATURE                Location/Qualifiers
```

-continued

```
source                  1..9
                        mol_type = protein
                        organism = Synthetic construct
SEQUENCE: 242
FQGSHFPLT                                                              9

SEQ ID NO: 243          moltype = AA  length = 112
FEATURE                 Location/Qualifiers
source                  1..112
                        mol_type = protein
                        organism = Synthetic construct
SEQUENCE: 243
DIVMTQTPLS LSVSLGDQAS ISCKSSQSIV HYNEKTYLEW YLQKPGQSPQ LLIYKVSSRA     60
SGVPDRFSGS GSGTDFTLKI SRVEAEDLGV YYCFQGSHFP LTFGQGTKLE IK             112

SEQ ID NO: 244          moltype = AA  length = 219
FEATURE                 Location/Qualifiers
source                  1..219
                        mol_type = protein
                        organism = Synthetic construct
SEQUENCE: 244
DIVMTQTPLS LSVSLGDQAS ISCKSSQSIV HYNEKTYLEW YLQKPGQSPQ LLIYKVSSRA     60
SGVPDRFSGS GSGTDFTLKI SRVEAEDLGV YYCFQGSHFP LTFGQGTKLE IKRTVAAPSV     120
FIFPPSDEQL KSGTASVVCL LNNFYPREAK VQWKVDNALQ SGNSQESVTE QDSKDSTYSL     180
SSTLTLSKAD YEKHKVYACE VTHQGLSSPV TKSFNRGEC                            219

SEQ ID NO: 245          moltype =    length =
SEQUENCE: 245
000

SEQ ID NO: 246          moltype =    length =
SEQUENCE: 246
000

SEQ ID NO: 247          moltype =    length =
SEQUENCE: 247
000

SEQ ID NO: 248          moltype =    length =
SEQUENCE: 248
000

SEQ ID NO: 249          moltype =    length =
SEQUENCE: 249
000

SEQ ID NO: 250          moltype = AA  length = 16
FEATURE                 Location/Qualifiers
source                  1..16
                        mol_type = protein
                        organism = Synthetic construct
SEQUENCE: 250
RSSQSIVHYN GNTYLE                                                     16

SEQ ID NO: 251          moltype = AA  length = 7
FEATURE                 Location/Qualifiers
source                  1..7
                        mol_type = protein
                        organism = Synthetic construct
SEQUENCE: 251
KVSNRDS                                                               7

SEQ ID NO: 252          moltype = AA  length = 9
FEATURE                 Location/Qualifiers
source                  1..9
                        mol_type = protein
                        organism = Synthetic construct
SEQUENCE: 252
FQGSHFPLT                                                             9

SEQ ID NO: 253          moltype = AA  length = 111
FEATURE                 Location/Qualifiers
source                  1..111
                        mol_type = protein
                        organism = Synthetic construct
SEQUENCE: 253
VVMTQTPLSL PVSLGDQASI SCRSSQSIVH YNGNTYLEWY LQKPGQSPQL LIYKVSNRDS     60
GVPDRFSGSG SGTDFTLKIS RVEAEDLGVY YCFQGSHFPL TFGQGTKLEI K              111
```

```
SEQ ID NO: 254          moltype = AA  length = 218
FEATURE                 Location/Qualifiers
source                  1..218
                        mol_type = protein
                        organism = Synthetic construct
SEQUENCE: 254
VVMTQTPLSL PVSLGDQASI SCRSSQSIVH YNGNTYLEWY LQKPGQSPQL LIYKVSNRDS  60
GVPDRFSGSG SGTDFTLKIS RVEAEDLGVY YCFQGSHFPL TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                           218

SEQ ID NO: 255          moltype =   length =
SEQUENCE: 255
000

SEQ ID NO: 256          moltype =   length =
SEQUENCE: 256
000

SEQ ID NO: 257          moltype =   length =
SEQUENCE: 257
000

SEQ ID NO: 258          moltype =   length =
SEQUENCE: 258
000

SEQ ID NO: 259          moltype =   length =
SEQUENCE: 259
000

SEQ ID NO: 260          moltype =   length =
SEQUENCE: 260
000

SEQ ID NO: 261          moltype =   length =
SEQUENCE: 261
000

SEQ ID NO: 262          moltype =   length =
SEQUENCE: 262
000

SEQ ID NO: 263          moltype =   length =
SEQUENCE: 263
000

SEQ ID NO: 264          moltype =   length =
SEQUENCE: 264
000

SEQ ID NO: 265          moltype =   length =
SEQUENCE: 265
000

SEQ ID NO: 266          moltype =   length =
SEQUENCE: 266
000

SEQ ID NO: 267          moltype =   length =
SEQUENCE: 267
000

SEQ ID NO: 268          moltype =   length =
SEQUENCE: 268
000

SEQ ID NO: 269          moltype =   length =
SEQUENCE: 269
000

SEQ ID NO: 270          moltype =   length =
SEQUENCE: 270
000

SEQ ID NO: 271          moltype =   length =
SEQUENCE: 271
000
```

-continued

```
SEQ ID NO: 272        moltype =    length =
SEQUENCE: 272
000

SEQ ID NO: 273        moltype =    length =
SEQUENCE: 273
000

SEQ ID NO: 274        moltype =    length =
SEQUENCE: 274
000

SEQ ID NO: 275        moltype =    length =
SEQUENCE: 275
000

SEQ ID NO: 276        moltype =    length =
SEQUENCE: 276
000

SEQ ID NO: 277        moltype =    length =
SEQUENCE: 277
000

SEQ ID NO: 278        moltype =    length =
SEQUENCE: 278
000

SEQ ID NO: 279        moltype =    length =
SEQUENCE: 279
000

SEQ ID NO: 280        moltype =    length =
SEQUENCE: 280
000

SEQ ID NO: 281        moltype =    length =
SEQUENCE: 281
000

SEQ ID NO: 282        moltype =    length =
SEQUENCE: 282
000

SEQ ID NO: 283        moltype =    length =
SEQUENCE: 283
000

SEQ ID NO: 284        moltype =    length =
SEQUENCE: 284
000

SEQ ID NO: 285        moltype =    length =
SEQUENCE: 285
000

SEQ ID NO: 286        moltype =    length =
SEQUENCE: 286
000

SEQ ID NO: 287        moltype =    length =
SEQUENCE: 287
000

SEQ ID NO: 288        moltype =    length =
SEQUENCE: 288
000

SEQ ID NO: 289        moltype =    length =
SEQUENCE: 289
000

SEQ ID NO: 290        moltype =    length =
SEQUENCE: 290
000

SEQ ID NO: 291        moltype =    length =
SEQUENCE: 291
000
```

```
SEQ ID NO: 292            moltype =    length =
SEQUENCE: 292
000

SEQ ID NO: 293            moltype =    length =
SEQUENCE: 293
000

SEQ ID NO: 294            moltype =    length =
SEQUENCE: 294
000

SEQ ID NO: 295            moltype =    length =
SEQUENCE: 295
000

SEQ ID NO: 296            moltype =    length =
SEQUENCE: 296
000

SEQ ID NO: 297            moltype =    length =
SEQUENCE: 297
000

SEQ ID NO: 298            moltype =    length =
SEQUENCE: 298
000

SEQ ID NO: 299            moltype =    length =
SEQUENCE: 299
000

SEQ ID NO: 300            moltype = AA   length = 16
FEATURE                   Location/Qualifiers
source                    1..16
                          mol_type = protein
                          organism = Synthetic construct
SEQUENCE: 300
KSSQSIVHYN EKTYLE                                                  16

SEQ ID NO: 301            moltype = AA   length = 16
FEATURE                   Location/Qualifiers
source                    1..16
                          mol_type = protein
                          organism = Synthetic construct
SEQUENCE: 301
KSSQSIVHYN GKTYLE                                                  16

SEQ ID NO: 302            moltype = AA   length = 16
FEATURE                   Location/Qualifiers
source                    1..16
                          mol_type = protein
                          organism = Synthetic construct
SEQUENCE: 302
KSSQSIVHYN ENTYLE                                                  16

SEQ ID NO: 303            moltype = AA   length = 16
FEATURE                   Location/Qualifiers
source                    1..16
                          mol_type = protein
                          organism = Synthetic construct
SEQUENCE: 303
RSSQSIVHYN ENTYLE                                                  16

SEQ ID NO: 304            moltype = AA   length = 16
FEATURE                   Location/Qualifiers
source                    1..16
                          mol_type = protein
                          organism = Synthetic construct
SEQUENCE: 304
RSSQSIVHYN ANTYLE                                                  16

SEQ ID NO: 305            moltype = AA   length = 16
FEATURE                   Location/Qualifiers
source                    1..16
                          mol_type = protein
                          organism = Synthetic construct
SEQUENCE: 305
```

-continued

```
RSSQSIVHYN TNTYLE                                             16

SEQ ID NO: 306        moltype = AA  length = 16
FEATURE               Location/Qualifiers
source                1..16
                      mol_type = protein
                      organism = Synthetic construct

SEQUENCE: 306
RSSQSIVHYN GKTYLE                                             16

SEQ ID NO: 307        moltype = AA  length = 16
FEATURE               Location/Qualifiers
source                1..16
                      mol_type = protein
                      organism = Synthetic construct

SEQUENCE: 307
RSSQSIVHYN EKTYLE                                             16

SEQ ID NO: 308        moltype = AA  length = 16
FEATURE               Location/Qualifiers
source                1..16
                      mol_type = protein
                      organism = Synthetic construct

SEQUENCE: 308
KSSQSIVHYN GNTYLE                                             16

SEQ ID NO: 309        moltype = AA  length = 16
FEATURE               Location/Qualifiers
source                1..16
                      mol_type = protein
                      organism = Synthetic construct

SEQUENCE: 309
RSSQSIVHYN GNTYLE                                             16

SEQ ID NO: 310        moltype = AA  length = 11
FEATURE               Location/Qualifiers
source                1..11
                      mol_type = protein
                      organism = Synthetic construct

SEQUENCE: 310
QSIVHYNEKT Y                                                  11

SEQ ID NO: 311        moltype = AA  length = 11
FEATURE               Location/Qualifiers
source                1..11
                      mol_type = protein
                      organism = Synthetic construct

SEQUENCE: 311
QSIVHYNGKT Y                                                  11

SEQ ID NO: 312        moltype = AA  length = 11
FEATURE               Location/Qualifiers
source                1..11
                      mol_type = protein
                      organism = Synthetic construct

SEQUENCE: 312
QSIVHYNENT Y                                                  11

SEQ ID NO: 313        moltype = AA  length = 11
FEATURE               Location/Qualifiers
source                1..11
                      mol_type = protein
                      organism = Synthetic construct

SEQUENCE: 313
QSIVHYNANT Y                                                  11

SEQ ID NO: 314        moltype = AA  length = 11
FEATURE               Location/Qualifiers
source                1..11
                      mol_type = protein
                      organism = Synthetic construct

SEQUENCE: 314
QSIVHYNTNT Y                                                  11

SEQ ID NO: 315        moltype = AA  length = 11
FEATURE               Location/Qualifiers
source                1..11
                      mol_type = protein
                      organism = Synthetic construct
```

-continued

```
SEQUENCE: 315
QSIVHYNGNT Y                                                        11

SEQ ID NO: 316        moltype = AA  length = 7
FEATURE               Location/Qualifiers
source                1..7
                      mol_type = protein
                      organism = Synthetic construct
SEQUENCE: 316
KVSSRFS                                                             7

SEQ ID NO: 317        moltype = AA  length = 7
FEATURE               Location/Qualifiers
source                1..7
                      mol_type = protein
                      organism = Synthetic construct
SEQUENCE: 317
KVSSRAS                                                             7

SEQ ID NO: 318        moltype = AA  length = 7
FEATURE               Location/Qualifiers
source                1..7
                      mol_type = protein
                      organism = Synthetic construct
SEQUENCE: 318
KVSNRFS                                                             7

SEQ ID NO: 319        moltype = AA  length = 7
FEATURE               Location/Qualifiers
source                1..7
                      mol_type = protein
                      organism = Synthetic construct
SEQUENCE: 319
KVSNRDS                                                             7

SEQ ID NO: 320        moltype =   length =
SEQUENCE: 320
000

SEQ ID NO: 321        moltype = AA  length = 9
FEATURE               Location/Qualifiers
source                1..9
                      mol_type = protein
                      organism = Synthetic construct
SEQUENCE: 321
FQGSHFPLT                                                           9

SEQ ID NO: 322        moltype =   length =
SEQUENCE: 322
000

SEQ ID NO: 323        moltype =   length =
SEQUENCE: 323
000

SEQ ID NO: 324        moltype =   length =
SEQUENCE: 324
000

SEQ ID NO: 325        moltype =   length =
SEQUENCE: 325
000

SEQ ID NO: 326        moltype =   length =
SEQUENCE: 326
000

SEQ ID NO: 327        moltype =   length =
SEQUENCE: 327
000

SEQ ID NO: 328        moltype =   length =
SEQUENCE: 328
000

SEQ ID NO: 329        moltype =   length =
SEQUENCE: 329
000
```

-continued

```
SEQ ID NO: 330          moltype = AA   length = 5
FEATURE                 Location/Qualifiers
source                  1..5
                        mol_type = protein
                        organism = Synthetic construct SEQUENCE: 330
DYYMA                                                              5

SEQ ID NO: 331          moltype = AA   length = 8
FEATURE                 Location/Qualifiers
source                  1..8
                        mol_type = protein
                        organism = Synthetic construct SEQUENCE: 331
GFTFSDYY                                                           8

SEQ ID NO: 332          moltype = AA   length = 10
FEATURE                 Location/Qualifiers
source                  1..10
                        mol_type = protein
                        organism = Synthetic construct SEQUENCE: 332
GFTFSDYYMA                                                         10

SEQ ID NO: 333          moltype = AA   length = 7
FEATURE                 Location/Qualifiers
source                  1..7
                        mol_type = protein
                        organism = Synthetic construct SEQUENCE: 333
GFTFSDY                                                            7

SEQ ID NO: 334          moltype = AA   length = 17
FEATURE                 Location/Qualifiers
source                  1..17
                        mol_type = protein
                        organism = Synthetic construct SEQUENCE: 334
NINYEGSRTD LLESLKS                                                 17

SEQ ID NO: 335          moltype = AA   length = 17
FEATURE                 Location/Qualifiers
source                  1..17
                        mol_type = protein
                        organism = Synthetic construct SEQUENCE: 335
NINYYGSRTD LLESLKS                                                 17

SEQ ID NO: 336          moltype = AA   length = 17
FEATURE                 Location/Qualifiers
source                  1..17
                        mol_type = protein
                        organism = Synthetic construct SEQUENCE: 336
NINYEGSRTD LLASLKS                                                 17

SEQ ID NO: 337          moltype = AA   length = 17
FEATURE                 Location/Qualifiers
source                  1..17
                        mol_type = protein
                        organism = Synthetic construct SEQUENCE: 337
NINYYGSRTD LLASLKS                                                 17

SEQ ID NO: 338          moltype = AA   length = 17
FEATURE                 Location/Qualifiers
source                  1..17
                        mol_type = protein
                        organism = Synthetic construct SEQUENCE: 338
NINYDGSRTD LLDSLKS                                                 17

SEQ ID NO: 339          moltype = AA   length = 17
FEATURE                 Location/Qualifiers
source                  1..17
                        mol_type = protein
                        organism = Synthetic construct SEQUENCE: 339
NINYEGSRTD LLDSLKS                                                 17
```

```
SEQ ID NO: 340            moltype = AA   length = 17
FEATURE                   Location/Qualifiers
source                    1..17
                          mol_type = protein
                          organism = Synthetic construct
SEQUENCE: 340
NINYDGSRTD LLESLKS                                                 17

SEQ ID NO: 341            moltype = AA   length = 8
FEATURE                   Location/Qualifiers
source                    1..8
                          mol_type = protein
                          organism = Synthetic construct
SEQUENCE: 341
INYEGSRT                                                           8

SEQ ID NO: 342            moltype = AA   length = 8
FEATURE                   Location/Qualifiers
source                    1..8
                          mol_type = protein
                          organism = Synthetic construct
SEQUENCE: 342
INYYGSRT                                                           8

SEQ ID NO: 343            moltype = AA   length = 8
FEATURE                   Location/Qualifiers
source                    1..8
                          mol_type = protein
                          organism = Synthetic construct
SEQUENCE: 343
INYDGSRT                                                           8

SEQ ID NO: 344            moltype = AA   length = 6
FEATURE                   Location/Qualifiers
source                    1..6
                          mol_type = protein
                          organism = Synthetic construct
SEQUENCE: 344
NYEGSR                                                             6

SEQ ID NO: 345            moltype = AA   length = 6
FEATURE                   Location/Qualifiers
source                    1..6
                          mol_type = protein
                          organism = Synthetic construct
SEQUENCE: 345
NYYGSR                                                             6

SEQ ID NO: 346            moltype = AA   length = 6
FEATURE                   Location/Qualifiers
source                    1..6
                          mol_type = protein
                          organism = Synthetic construct
SEQUENCE: 346
NYDGSR                                                             6

SEQ ID NO: 347            moltype = AA   length = 10
FEATURE                   Location/Qualifiers
source                    1..10
                          mol_type = protein
                          organism = Synthetic construct
SEQUENCE: 347
DTSRGSYFDV                                                         10

SEQ ID NO: 348            moltype = AA   length = 12
FEATURE                   Location/Qualifiers
source                    1..12
                          mol_type = protein
                          organism = Synthetic construct
SEQUENCE: 348
ARDTSRGSYF DV                                                      12
```

-continued

```
SEQ ID NO: 349      moltype = AA  length = 8
FEATURE             Location/Qualifiers
source              1..8
                    mol_type = protein
                    organism = Synthetic construct
SEQUENCE: 349
TSRGSYFD                                                        8
```

The invention claimed is:

1. An anti-CTGF antibody or an antigen-binding fragment thereof, comprising:

i. a light chain variable region comprising an L-CDR1 having the amino acid sequence of SEQ ID NO: 220, an L-CDR2 having the amino acid sequence of SEQ ID NO: 221, and an L-CDR3 having the amino acid sequence of SEQ ID NO: 222; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or ii. a light chain variable region comprising an L-CDR1 having the amino acid sequence of SEQ ID NO: 100, an L-CDR2 having the amino acid sequence of SEQ ID NO: 101, and an L-CDR3 having the amino acid sequence of SEQ ID NO: 102; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or iii. a light chain variable region comprising an L-CDR1 having the amino acid sequence of SEQ ID NO: 110, an L-CDR2 having the amino acid sequence of SEQ ID NO: 111, and an L-CDR3 having the amino acid sequence of SEQ ID NO: 112; and a heavy chain variable region comprising an H-CDR1 having the amino acid sequence of SEQ ID NO: 105, an H-CDR2 having the amino acid sequence of SEQ ID NO: 106, and an H-CDR3 having the amino acid sequence of SEQ ID NO: 107; or iv. a light chain variable region comprising an L-CDR1 having the amino acid sequence of SEQ ID NO: 100, an L-CDR2 having the amino acid sequence of SEQ ID NO: 101, and an L-CDR3 having the amino acid sequence of SEQ ID NO: 102; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or v. a light chain variable region comprising an L-CDR1 having the amino acid sequence of SEQ ID NO: 110, an L-CDR2 having the amino acid sequence of SEQ ID NO: 111, and an L-CDR3 having the amino acid sequence of SEQ ID NO: 112; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or vi. a light chain variable region comprising an L-CDR1 having the amino acid sequence of SEQ ID NO: 220, an L-CDR2 having the amino acid sequence of SEQ ID NO: 221, and an L-CDR3 having the amino acid sequence of SEQ ID NO: 222; and a heavy chain variable region comprising an H-CDR1 having the amino acid sequence of SEQ ID NO: 115, an H-CDR2 having the amino acid sequence of SEQ ID NO: 116, and an H-CDR3 having the amino acid sequence of SEQ ID NO: 117; or vii. a light chain variable region comprising an L-CDR1 having the amino acid sequence of SEQ ID NO: 100, an L-CDR2 having the amino acid sequence of SEQ ID NO: 101, and an L-CDR3 having the amino acid sequence of SEQ ID NO: 102; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or viii. a light chain variable region comprising an L-CDR1 having the amino acid sequence of SEQ ID NO: 110, an L-CDR2 having the amino acid sequence of SEQ ID NO: 111, and an L-CDR3 having the amino acid sequence of SEQ ID NO: 112; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147; or ix. a light chain variable region comprising an L-CDR1 having the amino acid sequence of SEQ ID NO: 220, an L-CDR2 having the amino acid sequence of SEQ ID NO: 221, and an L-CDR3 having the amino acid sequence of SEQ ID NO: 222; and a heavy chain variable region comprising an H-CDR1 having the amino acid sequence of SEQ ID NO: 145, an H-CDR2 having the amino acid sequence of SEQ ID NO: 146, and an H-CDR3 having the amino acid sequence of SEQ ID NO: 147.

2. The anti-CTGF antibody or an antigen-binding fragment thereof according to claim 1, wherein the anti-CTGF antibody or an antigen-binding fragment thereof comprises:

i. a light chain variable region comprising an amino acid sequence at least 90% identical to the amino acid sequence of SEQ ID NO: 223, and a heavy chain variable region comprising an amino acid sequence at least 90% identical to the amino acid sequence of SEQ ID NO: 108; or ii. a light chain variable region comprising an amino acid sequence at least 90% identical to the amino acid sequence of SEQ ID NO: 103, and a heavy chain variable region comprising an amino acid sequence at least 90% identical to the amino acid sequence of SEQ ID NO: 108; or iii. a light chain variable region comprising an amino acid sequence at least 90% identical to the amino acid sequence of SEQ ID NO: 113, and a heavy chain variable region comprising an amino acid sequence at least 90% identical to the amino acid sequence of SEQ ID NO: 108; or iv. a light chain variable region comprising an amino acid sequence at least 90% identical to the amino acid sequence of SEQ ID NO: 103, and a heavy chain variable region comprising an amino acid sequence at least 90% identical to the amino acid sequence of SEQ ID NO: 118; or v. a light chain variable region comprising an amino acid sequence at least 90% identical to the amino acid sequence of SEQ ID NO: 113, and a heavy chain variable region comprising an amino acid sequence at least 90% identical to the amino acid sequence of SEQ ID NO: 118; or vi. a light chain variable region comprising an amino acid sequence at least 90% identical to the amino acid sequence of SEQ ID NO: 223, and a heavy chain variable region comprising an amino acid sequence at least 90% identical to the amino acid sequence of SEQ ID NO: 118; or vii. a light chain variable region comprising an amino acid sequence at least 90% identical to the amino acid sequence of SEQ ID NO: 103, and a heavy chain variable region comprising an amino acid sequence at least 90% identical to the amino acid sequence of SEQ ID NO: 148; or viii. a light chain variable region comprising an amino acid sequence at least 90% identical to the amino acid sequence of SEQ ID NO: 113, and a heavy chain variable region comprising an amino acid sequence at least 90% identical to the amino acid sequence of SEQ ID NO: 148; or ix. a light chain variable region comprising an amino acid sequence at least 90% identical to the amino acid sequence of SEQ ID NO: 223, and a heavy chain variable region comprising an amino acid sequence at least 90% identical to the amino acid sequence of SEQ ID NO: 148.

3. The anti-CTGF antibody or an antigen-binding fragment thereof according to claim 1, wherein the anti-CTGF antibody or an antigen-binding fragment thereof comprises:

i. a light chain variable region comprising an amino acid sequence at least 95% identical to the amino acid sequence of SEQ ID NO: 223, and a heavy chain variable region comprising an amino acid sequence at least 95% identical to the amino acid sequence of SEQ ID NO: 108; or ii. a light chain variable region comprising an amino acid sequence at least 95% identical to the amino acid sequence of SEQ ID NO: 103, and a heavy chain variable region comprising an amino acid sequence at least 95% identical to the amino acid sequence of SEQ ID NO: 108; or iii. a light chain variable region comprising an amino acid sequence at least 95% identical to the amino acid sequence of SEQ ID NO: 113, and a heavy chain variable region comprising an amino acid sequence at least 95% identical to the amino acid sequence of SEQ ID NO: 108; or iv. a light chain variable region comprising an amino acid sequence at least 95% identical to the amino acid sequence of SEQ ID NO: 103, and a heavy chain variable region comprising an amino acid sequence at least 95% identical to the amino acid sequence of SEQ ID NO: 118; or v. a light chain variable region comprising an amino acid sequence at least 95% identical to the amino acid sequence of SEQ ID NO: 113, and a heavy chain variable region comprising an amino acid sequence at least 95% identical to the amino acid sequence of SEQ ID NO: 118; or vi. a light chain variable region comprising an amino acid sequence at least 95% identical to the amino acid sequence of SEQ ID NO: 223, and a heavy chain variable region comprising an amino acid sequence at least 95% identical to the amino acid sequence of SEQ ID NO: 118; or vii. a light chain variable region comprising an amino acid sequence at least 95% identical to the amino acid sequence of SEQ ID NO: 103, and a heavy chain variable region comprising an amino acid sequence at least 95% identical to the amino acid sequence of SEQ ID NO: 148; or viii. a light chain variable region comprising an amino acid sequence at least 95% identical to the amino acid sequence of SEQ ID NO: 113, and a heavy chain variable region comprising an amino acid sequence at least 95% identical to the amino acid sequence of SEQ ID NO: 148; or ix. a light chain variable region comprising an amino acid sequence at least 95% identical to the amino acid sequence of SEQ ID NO: 223, and a heavy chain variable region comprising an amino acid sequence at least 95% identical to the amino acid sequence of SEQ ID NO: 148.

4. The anti-CTGF antibody or an antigen-binding fragment thereof according to claim 1, wherein the anti-CTGF antibody or an antigen-binding fragment thereof comprises:

i. a light chain variable region comprising the amino acid sequence of SEQ ID NO: 223, and a heavy chain variable region comprising the amino acid sequence of SEQ ID NO: 108; or ii. a light chain variable region comprising the amino acid sequence of SEQ ID NO: 103, and a heavy chain variable region comprising the amino acid sequence of SEQ ID NO: 108; or iii. a light chain variable region comprising the amino acid sequence of SEQ ID NO: 113, and a heavy chain variable region comprising the amino acid sequence of SEQ ID NO: 108; or iv. a light chain variable region comprising the amino acid sequence of SEQ ID NO: 123, and a heavy chain variable region comprising the amino acid sequence of SEQ ID NO: 108; or v. a light chain variable region comprising the amino acid sequence of SEQ ID NO: 133, and a heavy chain variable region comprising the amino acid sequence of SEQ ID NO: 108; or vi. a light chain variable region comprising the amino acid sequence of SEQ ID NO: 103, and a heavy chain variable region comprising the amino acid sequence of SEQ ID NO: 118; or vii. a light chain variable region comprising the amino acid sequence of SEQ ID NO: 113, and a heavy chain variable region comprising the amino acid sequence of SEQ ID NO: 118; or viii. a light chain variable region comprising the amino acid sequence of SEQ ID NO: 223, and a heavy chain variable region comprising the amino acid sequence of SEQ ID NO: 118; or ix. a light chain variable region comprising the amino acid sequence of SEQ ID NO: 103, and a heavy chain variable region comprising the amino acid sequence of SEQ ID NO: 148; or x. a light chain variable region comprising the amino acid sequence of SEQ ID NO: 113, and a heavy chain variable region comprising the amino acid sequence of SEQ ID NO: 148; or xi. a light chain variable region comprising the amino acid sequence of SEQ ID NO: 223, and a heavy chain variable region comprising the amino acid sequence of SEQ ID NO: 148.

5. The anti-CTGF antibody or antigen-binding fragment thereof according to claim 1, comprising:

i. a light chain comprising an amino acid sequence at least 90% identical to the amino acid sequence of SEQ ID NO: 224, and a heavy chain comprising an amino acid sequence at least 90% identical to the amino acid sequence of SEQ ID NO: 109; or ii. a light chain comprising an amino acid sequence at least 90% identical to the amino acid sequence of SEQ ID NO: 104, and a heavy chain comprising an amino acid sequence at least 90% identical to the amino acid sequence of SEQ ID NO: 109; or iii. a light chain comprising an amino acid sequence at least 90% identical to the amino acid sequence of SEQ ID NO: 114, and a heavy chain comprising an amino acid sequence at least 90% identical to the amino acid sequence of SEQ ID NO: 109; or iv. a light chain comprising an amino acid sequence at least 90% identical to the amino acid sequence of SEQ ID NO: 104, and a heavy chain comprising an amino acid sequence at least 90% identical to the amino acid sequence of SEQ ID NO: 119; or v. a light chain comprising an amino acid sequence at least 90% identical to the amino acid sequence of SEQ ID NO: 114, and a heavy chain comprising an amino acid sequence at least 90% identical to the amino acid sequence of SEQ ID NO: 119; or vi. a light chain comprising an amino acid sequence at least 90% identical to the amino acid sequence of SEQ ID NO: 224, and a heavy chain comprising an amino acid sequence at least 90% identical to the amino acid sequence of SEQ ID NO: 119; or vii. a light chain comprising an amino acid sequence at least 90% identical to the amino acid sequence of SEQ ID NO: 104, and a heavy chain comprising an amino acid sequence at least 90% identical to the amino acid sequence of SEQ ID NO: 149; or viii. a light chain comprising an amino acid sequence at least 90% identical to the amino acid sequence of SEQ ID NO: 114, and a heavy chain comprising an amino acid sequence at least 90% identical to the amino acid sequence of SEQ ID NO: 149; or ix. a light chain comprising an amino acid sequence at least 90% identical to the amino acid sequence of SEQ ID NO: 224, and a heavy chain comprising an amino acid sequence at least 90% identical to the amino acid sequence of SEQ ID NO: 149.

6. The anti-CTGF antibody or antigen-binding fragment thereof according to claim 1, comprising:

i. a light chain comprising an amino acid sequence at least 95% identical to the amino acid sequence of SEQ ID NO: 224, and a heavy chain comprising an amino acid sequence at least 95% identical to the amino acid sequence of SEQ ID NO: 109; or ii. a light chain comprising an amino acid sequence at least 95% identical to the amino acid sequence of SEQ ID NO: 104, and a heavy chain comprising an amino acid sequence at least 95% identical to the amino acid sequence of SEQ ID NO: 109; or iii. a light chain comprising an amino acid sequence at least 95% identical to the amino acid sequence of SEQ ID NO: 114, and a heavy chain comprising an amino acid sequence at least 95% identical to the amino acid sequence of SEQ ID NO: 109; or iv. a light chain comprising an amino acid sequence at least 95% identical to the amino acid sequence of SEQ ID NO: 104, and a heavy chain comprising an amino acid sequence at least 95% identical to the amino acid sequence of SEQ ID NO: 119; or v. a light chain comprising an amino acid sequence at least 95% identical to the amino acid sequence of SEQ ID NO: 114, and a heavy chain comprising an amino acid sequence at least 95% identical to the amino acid sequence of SEQ ID NO: 119; or vi. a light chain comprising an amino acid sequence at least 95% identical to the amino acid sequence of SEQ ID NO: 224, and a heavy chain comprising an amino acid sequence at least 95% identical to the amino acid sequence of SEQ ID NO: 119; or vii. a light chain comprising an amino acid sequence at least 95% identical to the amino acid sequence of SEQ ID NO: 104, and a heavy chain comprising an amino acid sequence at least 95% identical to the amino acid sequence of SEQ ID NO: 149; or viii. a light chain comprising an amino acid sequence at least 95% identical to the amino acid sequence of SEQ ID NO: 114, and a heavy chain comprising an amino acid sequence at least 95% identical to the amino acid sequence of SEQ ID NO: 149; or ix. a light chain comprising an amino acid sequence at least 95% identical to the amino acid sequence of SEQ ID NO: 224, and a heavy chain comprising an amino acid sequence at least 95% identical to the amino acid sequence of SEQ ID NO: 149.

7. The anti-CTGF antibody or antigen-binding fragment thereof according to claim 1, comprising:

i. a light chain comprising the amino acid sequence of SEQ ID NO: 224, and a heavy chain comprising the amino acid sequence of SEQ ID NO: 109; or ii. a light chain comprising the amino acid sequence of SEQ ID NO: 104, and a heavy chain comprising the amino acid sequence of SEQ ID NO: 109; or iii. a light chain comprising the amino acid sequence of SEQ ID NO: 114, and a heavy chain comprising the amino acid sequence of SEQ ID NO: 109; or iv. a light chain comprising the amino acid sequence of SEQ ID NO: 104, and a heavy chain comprising the amino acid sequence of SEQ ID NO: 119; or v. a light chain comprising the amino acid sequence of SEQ ID NO: 114, and a heavy chain comprising the amino acid sequence of SEQ ID NO: 119; or vi. a light chain comprising the amino acid sequence of SEQ ID NO: 224, and a heavy chain comprising the amino acid sequence of SEQ ID NO: 119; or vii. a light chain comprising the amino acid sequence of SEQ ID NO: 104, and a heavy chain comprising the amino acid sequence of SEQ ID NO: 149; or viii. a light chain comprising the amino acid sequence of SEQ ID NO: 114, and a heavy chain comprising the amino acid sequence of SEQ ID NO: 149; or ix. a light chain comprising the amino acid sequence of SEQ ID NO: 224, and a heavy chain comprising the amino acid sequence of SEQ ID NO: 149.

8. An anti-CTGF antibody or antigen-binding fragment thereof, comprising a light chain variable region comprising the amino acid sequence of SEQ ID NO: 113, and a heavy chain variable region comprising the amino acid sequence of SEQ ID NO: 118.

9. An anti-CTGF antibody or antigen-binding fragment thereof, comprising a light chain variable region comprising the amino acid sequence of SEQ ID NO: 223, and a heavy chain variable region comprising the amino acid sequence of SEQ ID NO: 108.

10. An anti-CTGF antibody, comprising a light chain comprising the amino acid sequence of SEQ ID NO: 114, and a heavy chain comprising the amino acid sequence of SEQ ID NO: 149.

11. An anti-CTGF antibody, comprising a light chain comprising the amino acid sequence of SEQ ID NO: 224, and a heavy chain comprising the amino acid sequence of SEQ ID NO: 109.

12. The anti-CTGF antibody of claim 10, wherein said antibody comprises a light chain having an amino acid sequence consisting of SEQ ID NO: 114, and a heavy chain having an amino acid sequence consisting of SEQ ID NO: 149.

13. The anti-CTGF antibody of claim 11, wherein said antibody comprises a light chain having an amino acid sequence consisting of SEQ ID NO: 224, and a heavy chain having an amino acid sequence consisting of SEQ ID NO: 109.

14. A pharmaceutical composition comprising the antibody or an antigen-binding fragment thereof according to claim 1, and a pharmaceutically acceptable carrier.

15. A pharmaceutical composition comprising the antibody or an antigen-binding fragment thereof according to claim 10, and a pharmaceutically acceptable carrier.

16. A pharmaceutical composition comprising the antibody or an antigen-binding fragment thereof according to claim 11, and a pharmaceutically acceptable carrier.

17. An isolated polynucleotide or plurality of isolated polynucleotides that encodes a sequence comprising the heavy chain variable region and/or light chain variable region of the antibody or an antigen-binding fragment thereof according to claim 1.

18. An isolated polynucleotide or plurality of isolated polynucleotides that encodes a sequence comprising the heavy chain variable region and/or light chain variable region of the antibody or an antigen-binding fragment thereof according to claim 10.

19. An isolated polynucleotide or plurality of isolated polynucleotides that encodes a sequence comprising the heavy chain variable region and/or light chain variable region of the antibody or an antigen-binding fragment thereof according to claim 11.

20. A host cell comprising the polynucleotide or plurality of polynucleotides according to claim 17.

21. A host cell comprising the polynucleotide or plurality of polynucleotides according to claim 18.

22. A host cell comprising the polynucleotide or plurality of polynucleotides according to claim 19.

23. A method for the production of an anti-CTGF antibody or antigen-binding fragment thereof according to claim 1, comprising the steps:
   (a) cultivating a host cell comprising a polynucleotide or plurality of polynucleotides that encode said antibody or antigen-binding fragment thereof under conditions allowing the expression of the anti-CTGF antibody or antigen-binding fragment thereof; and
   (b) recovering said anti-CTGF antibody or antigen-binding fragment thereof.

24. A method for the production of an anti-CTGF antibody or antigen-binding fragment thereof according to claim 10, comprising the steps:
   (a) cultivating a host cell comprising a polynucleotide or plurality of polynucleotides that encode said antibody or antigen-binding fragment thereof under conditions allowing the expression of the anti-CTGF antibody or antigen-binding fragment thereof; and
   (b) recovering said anti-CTGF antibody or antigen-binding fragment thereof.

25. A method for the production of an anti-CTGF antibody or antigen-binding fragment thereof according to claim 11, comprising the steps:
   (a) cultivating a host cell comprising a polynucleotide or plurality of polynucleotides that encode said antibody or antigen-binding fragment thereof under conditions allowing the expression of the anti-CTGF antibody or antigen-binding fragment thereof; and
   (b) recovering said anti-CTGF antibody or antigen-binding fragment thereof.

26. An in-vitro method of inhibiting the interaction between human CTGF or human CTGF-NTF and a cell, comprising contacting said human CTGF with an effective amount of the anti-CTGF antibody or antigen-binding fragment thereof according to claim 1.

27. An in-vitro method of inhibiting the interaction between human CTGF or human CTGF-NTF and a cell, comprising contacting said human CTGF with an effective amount of the anti-CTGF antibody or antigen-binding fragment thereof according to claim 10.

28. An in-vitro method of inhibiting the interaction between human CTGF or human CTGF-NTF and a cell, comprising contacting said human CTGF with an effective amount of the anti-CTGF antibody or antigen-binding fragment thereof according to claim 11.

29. The anti-CTGF antibody or antigen binding fragment thereof of claim 1, wherein said anti-CTGF antibody or antigen binding fragment thereof:
   (a) is glycosylated; and/or
   (b) comprises a heavy chain constant region selected from IgG1, IgG2, IgG3, IgG4, IgM, IgA and IgE; and/or
   (c) comprises an IgG1 heavy chain constant region; and/or
   (d) comprises a heavy chain lacking a C-terminal lysine residue; and/or
   (e) comprises a light chain constant region selected from the group consisting of a kappa and a lambda light chain; and/or
   (f) is a monoclonal antibody; and/or
   (g) is a monospecific antibody; and/or
   (h) is a human, humanized, or chimeric antibody; and/or
   (i) binds human CTGF of SEQ ID NO: 2, with a KD of 5 pM or lower; and/or
   (j) binds the N-terminal fragment of human CTGF of SEQ ID NO: 3 with a KD of 500 pM or lower.

* * * * *